(12) United States Patent
Hacohen et al.

(10) Patent No.: US 11,452,768 B2
(45) Date of Patent: Sep. 27, 2022

(54) COMBINATION THERAPY WITH NEOANTIGEN VACCINE

(71) Applicants: The Broad Institute Inc., Cambridge, MA (US); DANA-FARBER CANCER INSTITUTE, INC, Boston, MA (US); THE GENERAL HOSPITAL CORPORATION, Boston, MA (US)

(72) Inventors: Nir Hacohen, Brookline, MA (US); Catherine J. Wu, Brookline, MA (US); Edward F. Fritsch, Concord, MA (US)

(73) Assignees: The Broad Institute, Inc., Cambridge, MA (US); Dana-Farber Cancer Institute, Inc., Boston, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 15/105,961

(22) PCT Filed: Dec. 19, 2014

(86) PCT No.: PCT/US2014/071707
§ 371 (c)(1),
(2) Date: Jun. 17, 2016

(87) PCT Pub. No.: WO2015/095811
PCT Pub. Date: Jun. 25, 2015

(65) Prior Publication Data
US 2016/0339090 A1    Nov. 24, 2016

Related U.S. Application Data

(60) Provisional application No. 61/976,274, filed on Apr. 7, 2014, provisional application No. 61/919,576, filed on Dec. 20, 2013.

(51) Int. Cl.
| | | |
|---|---|---|
| A61K 39/00 | (2006.01) | |
| C07K 16/28 | (2006.01) | |
| A61K 39/395 | (2006.01) | |
| A61K 45/06 | (2006.01) | |

(52) U.S. Cl.
CPC ...... *A61K 39/0011* (2013.01); *A61K 39/3955* (2013.01); *A61K 39/39558* (2013.01); *A61K 45/06* (2013.01); *C07K 16/2803* (2013.01); *C07K 16/2818* (2013.01); *A61K 2039/505* (2013.01); *A61K 2039/507* (2013.01); *A61K 2039/545* (2013.01); *A61K 2039/55561* (2013.01); *A61K 2039/70* (2013.01)

(58) Field of Classification Search
None
See application file for complete search history.

(56) References Cited

U.S. PATENT DOCUMENTS

| | | |
|---|---|---|
| 3,854,480 A | 12/1974 | Zaffaroni |
| 3,870,790 A | 3/1975 | Lowey et al. |
| 4,210,644 A | 7/1980 | Ewing et al. |
| 4,226,859 A | 10/1980 | Stach |
| 4,369,172 A | 1/1983 | Schor et al. |
| 4,379,454 A | 4/1983 | Campbell et al. |
| 4,452,775 A | 6/1984 | Kent |
| 4,554,101 A | 11/1985 | Hopp |
| 4,588,585 A | 5/1986 | Mark et al. |
| 4,603,112 A | 7/1986 | Paoletti et al. |
| 4,656,127 A | 4/1987 | Mundy |
| 4,675,189 A | 6/1987 | Kent et al. |
| 4,683,195 A | 7/1987 | Mullis et al. |
| 4,683,202 A | 7/1987 | Mullis |
| 4,690,915 A | 9/1987 | Rosenberg |
| 4,722,848 A | 2/1988 | Paoletti et al. |
| 4,743,249 A | 5/1988 | Loveland |
| 4,751,180 A | 6/1988 | Cousens et al. |
| 4,769,330 A | 9/1988 | Paoletti et al. |
| 4,816,540 A | 3/1989 | Onishi |
| 4,842,866 A | 6/1989 | Horder et al. |
| 4,844,893 A | 7/1989 | Honsik et al. |
| 4,906,169 A | 3/1990 | Chien et al. |
| 4,935,233 A | 6/1990 | Bell et al. |
| 4,973,468 A | 11/1990 | Chiang et al. |
| 5,023,084 A | 6/1991 | Chien et al. |
| 5,035,891 A | 7/1991 | Runkel et al. |
| 5,110,587 A | 5/1992 | Paoletti et al. |
| 5,133,974 A | 7/1992 | Paradissis et al. |
| 5,174,993 A | 12/1992 | Paoletti |
| 5,185,146 A | 2/1993 | Altenburger |
| 5,198,223 A | 3/1993 | Gale et al. |
| 5,204,253 A | 4/1993 | Sanford et al. |
| 5,217,720 A | 6/1993 | Sekigawa et al. |

(Continued)

FOREIGN PATENT DOCUMENTS

| | | |
|---|---|---|
| CN | 103180730 A | 6/2013 |
| EP | 1486567 A1 | 12/2004 |

(Continued)

OTHER PUBLICATIONS

Chianese-Bullock et al. (Vaccine, 2009, 27:1764-1770).*

(Continued)

*Primary Examiner* — Laura B Goddard
(74) *Attorney, Agent, or Firm* — Foley Hoag LLP

(57) ABSTRACT

The present invention relates to neoplasia vaccine or immunogenic composition administered in combination with other agents, such as checkpoint blockade inhibitors for the treatment or prevention of neoplasia in a subject.

32 Claims, 15 Drawing Sheets
Specification includes a Sequence Listing.

(56) References Cited

U.S. PATENT DOCUMENTS

| | | |
|---|---|---|
| 5,279,833 A | 1/1994 | Rose |
| 5,364,773 A | 11/1994 | Paoletti et al. |
| 5,407,686 A | 4/1995 | Patel et al. |
| 5,422,119 A | 6/1995 | Casper |
| 5,494,807 A | 2/1996 | Paoletti et al. |
| 5,541,171 A | 7/1996 | Rhodes et al. |
| 5,580,859 A | 12/1996 | Felgner et al. |
| 5,589,466 A | 12/1996 | Felgner et al. |
| 5,658,785 A | 8/1997 | Johnson |
| 5,686,281 A | 11/1997 | Roberts |
| 5,705,190 A | 1/1998 | Broad et al. |
| 5,736,152 A | 4/1998 | Dunn |
| 5,756,101 A | 5/1998 | Paoletti et al. |
| 5,762,938 A | 6/1998 | Paoletti et al. |
| 5,766,597 A | 6/1998 | Paoletti et al. |
| 5,766,882 A | 6/1998 | Falkner et al. |
| 5,770,212 A | 6/1998 | Falkner et al. |
| 5,811,104 A | 9/1998 | Dale et al. |
| 5,833,975 A | 11/1998 | Paoletti et al. |
| 5,843,728 A | 12/1998 | Seed et al. |
| 5,849,303 A | 12/1998 | Wasmoen et al. |
| 5,849,589 A | 12/1998 | Tedder et al. |
| 5,851,828 A | 12/1998 | Seed et al. |
| 5,858,358 A | 1/1999 | June et al. |
| 5,883,223 A | 3/1999 | Gray |
| 5,906,936 A | 5/1999 | Eshhar et al. |
| 5,912,170 A | 6/1999 | Seed et al. |
| 5,912,172 A | 6/1999 | Eshhar et al. |
| 5,942,235 A | 8/1999 | Paoletti |
| 5,989,562 A | 11/1999 | Wasmoen et al. |
| 5,990,091 A | 11/1999 | Tartaglia et al. |
| 5,994,136 A | 11/1999 | Naldini et al. |
| 6,004,777 A | 12/1999 | Tartaglia et al. |
| 6,004,811 A | 12/1999 | Seed et al. |
| 6,013,516 A | 1/2000 | Verma et al. |
| 6,090,393 A | 7/2000 | Fischer |
| 6,130,066 A | 10/2000 | Tartaglia et al. |
| 6,156,567 A | 12/2000 | Fischer |
| 6,159,477 A | 12/2000 | Audonnet et al. |
| 6,165,782 A | 12/2000 | Naldini et al. |
| 6,214,353 B1 | 4/2001 | Paoletti et al. |
| 6,228,846 B1 | 5/2001 | Audonnet et al. |
| 6,258,595 B1 | 7/2001 | Gao et al. |
| 6,265,189 B1 | 7/2001 | Paoletti et al. |
| 6,277,558 B1 | 8/2001 | Hudson |
| 6,284,240 B1 | 9/2001 | Seed et al. |
| 6,309,647 B1 | 10/2001 | Paoletti et al. |
| 6,312,682 B1 | 11/2001 | Kingsman et al. |
| 6,352,694 B1 | 3/2002 | June et al. |
| 6,392,013 B1 | 5/2002 | Seed et al. |
| 6,406,705 B1 | 6/2002 | Davis et al. |
| 6,410,014 B1 | 6/2002 | Seed et al. |
| 6,428,953 B1 | 8/2002 | Naldini et al. |
| 6,475,769 B1 | 11/2002 | Wilson et al. |
| 6,489,458 B2 | 12/2002 | Hackett et al. |
| 6,534,055 B1 | 3/2003 | June et al. |
| 6,537,540 B1 | 3/2003 | Burstein et al. |
| 6,537,594 B1 | 3/2003 | Paoletti et al. |
| 6,569,457 B2 | 5/2003 | Ullah et al. |
| 6,638,534 B1 | 10/2003 | Ishibashi et al. |
| 6,682,743 B2 | 1/2004 | Mayr |
| 6,713,068 B1 | 3/2004 | Audonnet et al. |
| 6,753,162 B1 | 6/2004 | Seed et al. |
| 6,761,893 B2 | 7/2004 | Chaplin et al. |
| 6,780,407 B1 | 8/2004 | Paoletti et al. |
| 6,780,417 B2 | 8/2004 | Kaslow et al. |
| 6,793,926 B1 | 9/2004 | Rasty et al. |
| 6,797,514 B2 | 9/2004 | Berenson et al. |
| 6,821,515 B1 | 11/2004 | Cleland et al. |
| 6,867,041 B2 | 3/2005 | Berenson et al. |
| 6,869,794 B2 | 3/2005 | Vogels et al. |
| 6,887,466 B2 | 5/2005 | June et al. |
| 6,893,865 B1 | 5/2005 | Lockert et al. |
| 6,905,680 B2 | 6/2005 | June et al. |
| 6,905,681 B1 | 6/2005 | June et al. |
| 6,905,874 B2 | 6/2005 | Berenson et al. |
| 6,913,752 B2 | 7/2005 | Chaplin et al. |
| 6,913,922 B1 | 7/2005 | Bout et al. |
| 6,923,973 B1 | 8/2005 | Cox et al. |
| 6,924,128 B2 | 8/2005 | Allen |
| 6,936,466 B2 | 8/2005 | Feldhaus |
| 6,943,019 B2 | 9/2005 | Wilson et al. |
| 6,953,690 B1 | 10/2005 | Gao et al. |
| 6,955,808 B2 | 10/2005 | Curiel |
| 6,974,695 B2 | 12/2005 | Vogels et al. |
| 6,991,797 B2 | 1/2006 | Andersen et al. |
| 7,029,848 B2 | 4/2006 | Vogels et al. |
| 7,045,313 B1 | 5/2006 | Moss et al. |
| 7,097,842 B2 | 8/2006 | Suter et al. |
| 7,115,391 B1 | 10/2006 | Chen et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,172,893 B2 | 2/2007 | Rabinowitz et al. |
| 7,175,843 B2 | 2/2007 | June et al. |
| 7,189,536 B2 | 3/2007 | Chaplin et al. |
| 7,198,784 B2 | 4/2007 | Kingsman et al. |
| 7,232,566 B2 | 6/2007 | June et al. |
| 7,255,862 B1 | 8/2007 | Tartaglia et al. |
| 7,259,015 B2 | 8/2007 | Kingsman et al. |
| 7,283,337 B2 | 10/2007 | Sakai et al. |
| 7,303,910 B2 | 12/2007 | Bebbington et al. |
| 7,335,364 B2 | 2/2008 | Chaplin et al. |
| 7,351,585 B2 | 4/2008 | Mitrophanous et al. |
| 7,384,644 B2 | 6/2008 | Chaplin et al. |
| 7,445,924 B2 | 11/2008 | Chaplin et al. |
| 7,459,270 B2 | 12/2008 | Chaplin et al. |
| 7,572,631 B2 | 8/2009 | Berenson et al. |
| 7,572,821 B2 | 8/2009 | Sun et al. |
| 7,608,279 B2 | 10/2009 | Parisot et al. |
| 7,628,980 B2 | 12/2009 | Suter et al. |
| 7,705,120 B2 | 4/2010 | Lillie et al. |
| 7,708,949 B2 | 5/2010 | Stone et al. |
| 7,741,465 B1 | 6/2010 | Eshhar et al. |
| 7,767,449 B1 | 8/2010 | Paoletti |
| 7,892,533 B2 | 2/2011 | Suter et al. |
| 7,897,156 B2 | 3/2011 | Ackermann et al. |
| 7,923,017 B2 | 4/2011 | Chaplin et al. |
| 7,939,086 B2 | 5/2011 | Chaplin et al. |
| 7,964,395 B2 | 6/2011 | Chaplin et al. |
| 7,964,396 B2 | 6/2011 | Chaplin et al. |
| 7,964,398 B2 | 6/2011 | Chaplin et al. |
| 7,985,739 B2 | 7/2011 | Kay et al. |
| 8,034,334 B2 | 10/2011 | Dudley et al. |
| 8,088,379 B2 | 1/2012 | Robbins et al. |
| 8,163,293 B2 | 4/2012 | Chaplin |
| 8,211,422 B2 | 7/2012 | Eshhar et al. |
| 8,227,432 B2 | 7/2012 | Hackett et al. |
| 8,236,560 B2 | 8/2012 | Chaplin et al. |
| 8,268,325 B2 | 9/2012 | Chaplin et al. |
| 8,268,329 B2 | 9/2012 | Chaplin et al. |
| 8,278,036 B2 | 10/2012 | Kariko et al. |
| 8,309,098 B2 | 11/2012 | Howley et al. |
| 8,372,622 B2 | 2/2013 | Suter et al. |
| 8,399,645 B2 | 3/2013 | Campana et al. |
| 8,404,658 B2 | 3/2013 | Hajjar et al. |
| 8,454,972 B2 | 6/2013 | Nabel et al. |
| 8,470,598 B2 | 6/2013 | Chaplin et al. |
| 8,557,779 B2 | 10/2013 | Sugiyama |
| 8,648,104 B2 | 2/2014 | Du et al. |
| 8,697,854 B2 | 4/2014 | Schendel et al. |
| 8,796,414 B2 | 8/2014 | Johnston |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,101,584 B2 | 8/2015 | June et al. |
| 9,102,760 B2 | 8/2015 | June et al. |
| 9,102,761 B2 | 8/2015 | June et al. |
| 9,115,402 B2 | 8/2015 | Hacohen et al. |
| 9,556,237 B2 | 1/2017 | Schmaljohn et al. |
| 9,909,159 B2 | 3/2018 | Marras et al. |
| 9,962,453 B2 | 5/2018 | Georges |
| 10,202,640 B2 | 2/2019 | Davis et al. |

(56) References Cited

U.S. PATENT DOCUMENTS

| | | |
|---|---|---|
| 10,426,824 B1 | 10/2019 | Hacohen et al. |
| 10,801,070 B2 | 10/2020 | Clement et al. |
| 10,835,585 B2 | 11/2020 | Fritsch et al. |
| 10,975,442 B2 | 4/2021 | Hacohen et al. |
| 10,993,997 B2 | 5/2021 | Hacohen et al. |
| 2003/0104008 A1 | 6/2003 | Loosmore et al. |
| 2004/0013648 A1 | 1/2004 | Kingsman et al. |
| 2004/0018971 A1 | 1/2004 | Fikes et al. |
| 2004/0053304 A1 | 3/2004 | Markowitz |
| 2006/0008468 A1 | 1/2006 | Chiang et al. |
| 2006/0163385 A1 | 7/2006 | Link et al. |
| 2006/0252077 A1 | 11/2006 | Buzby |
| 2006/0258607 A1 | 11/2006 | Jarosch et al. |
| 2007/0003442 A1 | 1/2007 | Link et al. |
| 2007/0025970 A1 | 2/2007 | Kingsman et al. |
| 2007/0055049 A1 | 3/2007 | Grey et al. |
| 2007/0083334 A1 | 4/2007 | Mintz et al. |
| 2007/0134197 A1 | 6/2007 | Eichner et al. |
| 2007/0184489 A1 | 8/2007 | Griffiths et al. |
| 2007/0195127 A1 | 8/2007 | Ahn et al. |
| 2008/0003142 A1 | 1/2008 | Link et al. |
| 2008/0014222 A1 | 1/2008 | Simmons |
| 2008/0014589 A1 | 1/2008 | Link et al. |
| 2008/0254008 A1 | 10/2008 | Dropulic et al. |
| 2009/0005254 A1 | 1/2009 | Griffiths et al. |
| 2009/0026082 A1 | 1/2009 | Rothberg et al. |
| 2009/0028888 A1 | 1/2009 | Bergeron et al. |
| 2009/0055944 A1 | 2/2009 | Korman et al. |
| 2009/0111106 A1 | 4/2009 | Mitrophanous et al. |
| 2009/0131543 A1 | 5/2009 | Weitz et al. |
| 2009/0136494 A1 | 5/2009 | Ponath et al. |
| 2009/0186042 A1 | 7/2009 | Johnston et al. |
| 2009/0220980 A1 | 9/2009 | Hoon et al. |
| 2009/0304711 A1 | 12/2009 | Pardoll et al. |
| 2010/0137143 A1 | 6/2010 | Rothberg et al. |
| 2010/0137163 A1 | 6/2010 | Link et al. |
| 2010/0158951 A1 | 6/2010 | Randolph et al. |
| 2010/0203531 A1 | 8/2010 | Sarkaria et al. |
| 2010/0210529 A1 | 8/2010 | van der Burg et al. |
| 2010/0282617 A1 | 11/2010 | Rothberg et al. |
| 2010/0286057 A1 | 11/2010 | Walensky et al. |
| 2010/0297071 A1 | 11/2010 | Ishibashi et al. |
| 2010/0304989 A1 | 12/2010 | Von Hoff et al. |
| 2011/0097312 A1 | 4/2011 | Molldrem |
| 2011/0223149 A1 | 9/2011 | Nash et al. |
| 2011/0257890 A1 | 10/2011 | Weinschenk et al. |
| 2011/0293571 A1 | 12/2011 | Widdowson et al. |
| 2011/0293637 A1* | 12/2011 | Hacohen ............... A61P 43/00 424/173.1 |
| 2012/0082691 A1 | 4/2012 | Rammensee et al. |
| 2012/0219947 A1 | 8/2012 | Yurkovetsky et al. |
| 2012/0244133 A1 | 9/2012 | Rosenberg et al. |
| 2012/0288539 A1 | 11/2012 | Eber |
| 2012/0295960 A1 | 11/2012 | Palfi et al. |
| 2013/0071414 A1 | 3/2013 | Dotti et al. |
| 2013/0210014 A1 | 8/2013 | Sharman |
| 2013/0295110 A1* | 11/2013 | Binder ............... A61K 31/7088 424/142.1 |
| 2014/0056986 A1 | 2/2014 | Desai et al. |
| 2014/0178438 A1 | 6/2014 | Sahin et al. |
| 2014/0256595 A1 | 9/2014 | Link et al. |
| 2014/0322716 A1 | 10/2014 | Robins |
| 2015/0079119 A1 | 3/2015 | Johnston |
| 2015/0125463 A1* | 5/2015 | Cogswell ............... A61P 35/00 424/142.1 |
| 2015/0140041 A1 | 5/2015 | Vitiello |
| 2015/0224182 A1* | 8/2015 | Hunt ............... A61K 39/0011 424/85.2 |
| 2015/0278441 A1 | 10/2015 | Min et al. |
| 2016/0008447 A1 | 1/2016 | Hacohen et al. |
| 2016/0101170 A1 | 4/2016 | Hacohen et al. |
| 2016/0130641 A1 | 5/2016 | Wang et al. |
| 2016/0213771 A1 | 7/2016 | Sampson et al. |
| 2016/0310584 A1 | 10/2016 | Fritsch et al. |
| 2016/0326593 A1 | 11/2016 | Clement et al. |
| 2016/0331822 A1 | 11/2016 | Hacohen et al. |
| 2016/0339090 A1 | 11/2016 | Hacohen et al. |
| 2017/0022251 A1 | 1/2017 | Rammensee et al. |
| 2017/0067090 A1 | 3/2017 | Zhang et al. |
| 2017/0160269 A1 | 6/2017 | Linnemann et al. |
| 2017/0199961 A1 | 7/2017 | Yelensky et al. |
| 2017/0233821 A1 | 8/2017 | Lianidou et al. |
| 2017/0298441 A1 | 10/2017 | Wu et al. |
| 2018/0000913 A1 | 1/2018 | Hacohen et al. |
| 2018/0055922 A1 | 3/2018 | Hacohen et al. |
| 2018/0127803 A1 | 5/2018 | Lei et al. |
| 2018/0153975 A1 | 6/2018 | Fritsch et al. |
| 2019/0060428 A1 | 2/2019 | Fritsch |
| 2019/0060432 A1 | 2/2019 | Hacohen et al. |
| 2019/0099475 A1 | 4/2019 | Benz et al. |
| 2019/0376147 A1 | 12/2019 | Fritsch |
| 2020/0016251 A1 | 1/2020 | Hacohen et al. |
| 2020/0069783 A1 | 3/2020 | Hacohen et al. |
| 2020/0101147 A1 | 4/2020 | Zeng |
| 2020/0330571 A1 | 10/2020 | Fritsch et al. |
| 2020/0368337 A1 | 11/2020 | Fritsch et al. |
| 2020/0407804 A1 | 12/2020 | Clement et al. |
| 2021/0220455 A1 | 7/2021 | Hacohen et al. |
| 2021/0262039 A1 | 8/2021 | Hacohen et al. |
| 2021/0379168 A1 | 12/2021 | Hacohen et al. |

FOREIGN PATENT DOCUMENTS

| | | |
|---|---|---|
| EP | 1680681 B1 | 11/2011 |
| EP | 2390363 A1 | 11/2011 |
| EP | 2569633 A2 | 3/2013 |
| EP | 2574346 | 4/2013 |
| FR | 2650840 A1 | 2/1991 |
| JP | 2003/517274 A | 5/2003 |
| JP | 2003/523365 A | 8/2003 |
| JP | 2003/535024 A | 11/2003 |
| JP | 2005/505271 A | 2/2005 |
| JP | 2005/529187 A | 9/2005 |
| JP | 2006/526628 A | 11/2006 |
| JP | 2009/532664 A | 9/2009 |
| JP | 2009532350 | 9/2009 |
| JP | 2010533184 A | 10/2010 |
| JP | 2012/522500 A | 9/2012 |
| JP | 2013-530943 A | 8/2013 |
| JP | 2013/530943 A | 8/2013 |
| WO | WO-9102087 A1 | 2/1991 |
| WO | WO-9106309 A1 | 5/1991 |
| WO | WO-92/15672 A1 | 9/1992 |
| WO | WO-9215322 A1 | 9/1992 |
| WO | WO-9215712 A1 | 9/1992 |
| WO | WO-9324640 A2 | 12/1993 |
| WO | WO-95/27780 A1 | 10/1995 |
| WO | WO-95/30018 A2 | 11/1995 |
| WO | WO-96/18372 A2 | 6/1996 |
| WO | WO-00/20587 A2 | 4/2000 |
| WO | WO-00/66153 A1 | 11/2000 |
| WO | WO-2001/89788 A2 | 11/2001 |
| WO | WO-2003020763 A2 | 3/2003 |
| WO | WO-2003/057171 A2 | 7/2003 |
| WO | 03086459 | 10/2003 |
| WO | WO-03/106692 A2 | 12/2003 |
| WO | WO-2004/002627 A2 | 1/2004 |
| WO | WO-2004/026897 A1 | 4/2004 |
| WO | WO-2004/030615 A2 | 4/2004 |
| WO | WO-2004033685 A1 | 4/2004 |
| WO | WO-2004044004 A2 | 5/2004 |
| WO | 2004058801 | 7/2004 |
| WO | WO-2004074322 A1 | 9/2004 |
| WO | WO-2004/091763 A2 | 10/2004 |
| WO | WO-2005/021151 A1 | 3/2005 |
| WO | WO-2005/087261 A2 | 9/2005 |
| WO | WO-2005113595 A2 | 12/2005 |
| WO | WO-2005114215 A2 | 12/2005 |
| WO | WO-2006000830 A2 | 1/2006 |
| WO | WO-2006/040551 A2 | 4/2006 |
| WO | WO-2006/040554 A1 | 4/2006 |
| WO | WO-2006/096571 A2 | 9/2006 |
| WO | WO-2006/121168 A1 | 11/2006 |
| WO | WO-2006125962 A2 | 11/2006 |

(56) References Cited

FOREIGN PATENT DOCUMENTS

| | | |
|---|---|---|
| WO | WO-2007/015540 A1 | 2/2007 |
| WO | WO-2007/059033 A1 | 5/2007 |
| WO | WO-2007/089541 A2 | 8/2007 |
| WO | WO-2007/095033 A2 | 8/2007 |
| WO | WO-2007/101227 A2 | 9/2007 |
| WO | WO-2007/124090 A2 | 11/2007 |
| WO | WO-2007/133710 A2 | 11/2007 |
| WO | 2008011344 | 1/2008 |
| WO | WO-2008038002 A2 | 4/2008 |
| WO | WO-2008039818 A2 | 4/2008 |
| WO | WO-2008063227 A2 | 5/2008 |
| WO | WO-2008/096831 A1 | 8/2008 |
| WO | WO-2008/109075 A2 | 9/2008 |
| WO | 2009014708 | 1/2009 |
| WO | WO-2009/025117 A1 | 2/2009 |
| WO | WO-2009/032477 A2 | 3/2009 |
| WO | WO-2009/043520 A1 | 4/2009 |
| WO | WO-2009/126306 A2 | 10/2009 |
| WO | WO-2010033949 A1 | 3/2010 |
| WO | WO-2010/045345 A2 | 4/2010 |
| WO | WO-2010/093784 A2 | 8/2010 |
| WO | WO-2011/051489 A2 | 5/2011 |
| WO | WO-2011/079176 A2 | 6/2011 |
| WO | 2011143656 | 11/2011 |
| WO | WO-2011146862 A1 | 11/2011 |
| WO | WO-2011/134944 A2 | 11/2011 |
| WO | WO-2012/027379 A2 | 3/2012 |
| WO | WO-2012/079000 A1 | 6/2012 |
| WO | WO-2012/095639 A2 | 7/2012 |
| WO | WO-2012/101112 A1 | 8/2012 |
| WO | 2012159754 | 11/2012 |
| WO | WO-2012/159643 A1 | 11/2012 |
| WO | WO-2012/159754 A2 | 11/2012 |
| WO | WO-2013/026027 A1 | 2/2013 |
| WO | WO-2013039889 A1 | 3/2013 |
| WO | WO-2013040371 A2 | 3/2013 |
| WO | WO-2013/036201 A1 | 3/2013 |
| WO | WO-2013/086464 A1 | 6/2013 |
| WO | WO-2013/123031 A2 | 8/2013 |
| WO | WO-2013/133405 A1 | 9/2013 |
| WO | WO-2013166321 A1 | 11/2013 |
| WO | WO-2013176915 A1 | 11/2013 |
| WO | WO-2013/173223 A1 | 11/2013 |
| WO | WO-2013164754 A2 | 11/2013 |
| WO | WO-2013176915 A1 | 11/2013 |
| WO | WO-2014018863 A1 | 1/2014 |
| WO | WO-2014/009535 A2 | 1/2014 |
| WO | WO-2014/012051 A1 | 1/2014 |
| WO | WO-2014011987 A1 | 1/2014 |
| WO | WO-2014047561 A1 | 3/2014 |
| WO | WO-2014/056986 A1 | 4/2014 |
| WO | WO-2014/059173 A2 | 4/2014 |
| WO | WO-2014085802 A1 | 6/2014 |
| WO | WO-2014/083173 A1 | 6/2014 |
| WO | WO-2014/133567 A1 | 9/2014 |
| WO | WO-2014134165 A1 | 9/2014 |
| WO | WO-2014/133568 A1 | 9/2014 |
| WO | WO-2014/150924 A2 | 9/2014 |
| WO | 2014168874 | 10/2014 |
| WO | WO-2014172606 A1 | 10/2014 |
| WO | WO-2014/183649 A1 | 11/2014 |
| WO | WO-2014184744 A1 | 11/2014 |
| WO | WO-2014191128 A1 | 12/2014 |
| WO | WO-2014/197369 A1 | 12/2014 |
| WO | WO-2015/094995 A2 | 6/2015 |
| WO | WO-2015/085233 A1 | 6/2015 |
| WO | WO-2015/095811 A2 | 6/2015 |
| WO | WO-2016/020710 A1 | 2/2016 |
| WO | WO-2016/100975 A1 | 6/2016 |
| WO | WO-2016/164833 A1 | 10/2016 |
| WO | WO-2016/201049 A2 | 12/2016 |
| WO | WO-2017/173321 A1 | 10/2017 |
| WO | WO-2017/184590 A1 | 10/2017 |
| WO | WO-2018/140391 A1 | 8/2018 |

OTHER PUBLICATIONS

Weber et al (Journal Clinical Oncology, 31:4311-4318, Dec. 1, 2013).*
Hodi etal (New England Journal of Medicine, 2010, 363:711-723).*
Kreiter et al (OncoImmunology, 2012, 1:768-769).*
Castle et al (Cancer Research, 2012, 72:1081-1091).*
Topalian et al (Current Opinion in Immunology, 2102, 24:207-212).*
Wolchok et al (NEJM, Jul. 2013, 36:122-133).*
Hamid et al (New England Journal of Medicine, Jul. 2013, 369:134-144).*
Gibney et al (Journal Clinical Oncology, 31; suppl (May 2013); abstract 9056).*
Haanen (European J Cancer Supplements, Sep. 2013, 11:97-105).*
Azvolinsky (Cancer Network, Nov. 19, 2013, 3 pages; http://www.cancernetwork.com/melanoma/pd-1-inhibitor-mk-3475-again-shows-promise-advanced-melanoma).*
Le at al (J Natl Compr Cancer Network, Jul. 2013; 11:766-772).*
Neon Therapeutics Press Release 2019, 5 pages.*
Ott et al (Nature, 2017, 547:217-221).*
NT-001 Clinical Trial, ClinicalTrials.gov, 2019, 11 pages.*
Mkrtichyan et al (Clinical Exp. Metastasis, 2011, 28:157-259, abstract#B 117, p. 247-248).*
History of changes for NCT01176461 ClinicalTrials.gov (posted Aug. 5, 2010).*
NCT01024231 ClinicalTrials.gov (Mar. 22, 2021).*
Callahan et al (Nivolumab Plus Ipilimumab in Patients With Advanced Melanoma: Updated Survival, Response, and Safety Data in a Phase I Dose-Escalation Study. J Clin Oncol. Feb. 1, 2018;36(4):391-398. doi: 10.1200/JCO.2017.72.2850. Epub Oct. 17, 2017).*
International Search Report dated Sep. 10, 2015, which issued during prosecution of International Application No. PCT/US2014/071707.
Sheng Yao, et al. "Advances in targeting cell surface signaling molecules for immune modulation" Nature Reviews Drug Discovery, 2013, 12:130-146.
"Monoclonal Antibody Therapy and Vaccine Therapy in treating patients with stage IV melanoma that has been removed by Surgery" National Library of Medicine, 2010, XP002738553, https:clinicaltrials.gov/archive/NCT011764/2010_08_05.
"CT-011 and p53 genetic vaccine for advance solid tumors" National Library of Medicine, 2011, XP002738554, https://clinicaltrials.gov/archive/NCT/01386502/2011_06_20.
Rajasagi Mohini, et al. "Systematic Identification of Personal Mutated Tumor-Specific Neoantigents in CLL" Biosis Database, XP002730782, Blood, 2012, 120:954, PREV201300232333.
Acevedo et al., "Analysis ofthe mechanisms mediating tumor-specific changes in gene expression in human liver tumors," Cancer Res, 68(8):2641-2651 (2008).
Akiyama et al., "GATA-4 and GATA-5 transcription factor genes and potential downstream antitumor target genes are epigenetically silenced in colorectal and gastric cancer," Mol Cell Biol, 23:8429-8439 (2003).
Alarcon et al., "DNA vaccines: technology and application as anti-parasite and anti-microbial agents," Advances in Parasitology, 42:343-410 (1999).
Ali et al., "In situ regulation of DC subsets and T cells mediates tumor regression in mice," Cancer Immunotherapy, 1(8):1-10 (2009).
Ali et al., "Infection-mimicking materials to program dendritic cells in situ," Nat Mater, 8:151-8 (2009).
Almeida et al., "CTdatabase: a knowledge-base of high-throughput and curated data on cancer-testis antigens," Nucleic acids research, 37:D816-819 (2008).
Altman et al., "Phenotypic analysis of antigen-specific T lymphocytes," Science, 274(5284):94-6 (1996).
Alvarez, "Present and future evolution of advanced breast cancer therapy," Breast Cancer Research, 12(Suppl 2):S1 (2010).
Amara et al., "Control of a mucosal challenge and prevention of AIDS by a multiprotein DNA/MVA vaccine," Science, 292(5514):69-74 (2001).

(56) References Cited

OTHER PUBLICATIONS

Amato et al., "Vaccination of metastatic renal cancer patients with MVA-5T4: a randomized, double-blind, placebo-controlled phase III study," Clin Can Res, 16(22):5539-47 (2010).
Amato et al., "Vaccination of renal cell cancer patients with modified vaccinia ankara delivering tumor antigen 5T4 (TroVax) administered with interleukin 2: a phase II trial," Clin Cancer Res, 14(22):7504-10 (2008).
Anders et al., "HTSeq-A Python framework to work with high-throughput sequencing data," Bioinformatics, 31(2):166-169 (2015).
Andersen et al., "Parallel detection of antigen-specific T cell responses by combinatorial encoding of MHC multimers," Nature protocols, 7(5):891-902 (2012).
Antoine et al., "The complete genomic sequence ofthe modified vaccinia Ankara strain: comparison with other orthopoxviruses," Virology, 244(2):365-96 (1998).
Antonis et al., "Vaccination with recombinant modified vaccinia virus Ankara expressing bovine respiratory syncytial virus (bRSV) proteins protects calves against RSV challenge," Vaccine, 25(25):4818-4827 (2007).
Aucouturier et al., "Adjuvants designed for veterinary and human vaccines," Vaccine, 19(17-19):2666-2672 (2001).
Ausubel, "A botanical macroscope," Proceedings of the National Academy of Sciences, 106(31):12569-12570 (2009).
Avogadri et al. "Modulation of CTLA-4 and GITR for Cancer Immunotherapy," Curr Top Microbiol Immunol, 344:211 (2011).
Bachem et al., "Superior antigen cross-presentation and XCR1 expression define human CD11c+ CD141+ cells as homologues of mouse CD8+ dendritic cells," Journal of Experimental Medicine, 207(6):1273-1281 (2010).
Baden et al., "First-in-human evaluation ofthe safety and immunogenicity of a recombinant adenovirus serotype 26 FflV-1 Env vaccine (IPCAVD 001)," J Infect Dis, 207(2):240-247 (2012).
Balagaan et al., "Stable and efficient intraocular gene transfer using pseudotyped EIAV lentiviral vectors," J Gene Med, 8:275-285 (2005).
Balazsi et al., "Cellular decision making and biological noise: from microbes to mammals," Cell, 144(6):910-925 (2011).
Balch et al., "Final version of 2009 AJCC melanoma staging and classification," Journal of clinical oncology, 27(36):6199-6206 (2009).
Barbie et al., "Systematic RNA interference reveals that oncogenic KRAS-driven cancers require TBK1," Nature, 462:108-112 (2009).
Barretina et al., "The Cancer Cell Line Encyclopedia enables predictive modelling of anticancer drug sensitivity," Nature, 483:603-607 (2012).
Baylin, "A decade of exploring the cancer epigenome-biological and translational implications," Nat Rev Cancer, 11:726-734 (2005).
Baylin, "DNA methylation and gene silencing in cancer," Nat Clin Pract Oncol 2, Suppl 1, S4-11 (2005).
Benson, "Tandem repeats finder: a program to analyze DNA sequences," Nucleic acids research, 27(2):573-580 (1999).
Benton et al., "Screening lambdagt recombinant clones by hybridization to single plaques in situ," Science, 196(4286):180-182 (1977).
Berger et al., "The genomic complexity of primary human prostate cancer," Nature, 470:214-220 (2011).
Berger et al.."Melanoma genome sequencing reveals frequent PREX2 mutations," Nature, 485(7399):502 (2012).
Berman et al., "Regions of focal DNA hypermethylation and long-range hypomethylation in colorectal cancer coincide with nuclear lamina-associated domains," Nat Genet, 44:40-46 (2012).
Bhardwaj et al., "TLR Agonists: Are They Good Adjuvants?," Cancer J, 16:382-391 (2010).
Bindea et al., "Spatiotemporal dynamics of intratumoral immune cells reveal the immune landscape in human cancer," Immunity, 39:782-795 (2013).
Bird, "DNA methylation patterns and epigenetic memory," Genes Dev, 16:6-21 (2002).

Birrell et al., "A genome-wide screen in *Saccharomyces cerevisiae* for genes affecting UV radiation sensitivity," Proceedings of the National Academy of Sciences 98(22):12608-12613 (2001).
Bishop et al., "APOBEC-mediated editing of viral RNA," Science, 305:645 (2004).
Bisht et al., "Severe acute respiratory syndrome coronavirus spike protein expressed by attenuated vaccinia virus protectively immunizes mice," Proc Natl Acad Sci, 101:6641-46 (2004).
Blanchard et al., "Modified vaccinia virus Ankara undergoes limited replication in human cells and lacks several immunomodulatory proteins: implications for use as a human vaccine," Journal of General Virology, 79(5): 1159-1167 (1998).
Bock et al., "BiQ Analyzer: visualization and quality control for DNA methylation data from bisulfite sequencing," Bioinformatics, 21:4067-4068 (2005).
Bock et al., "Reference Maps of human ES and iPS cell variation enable high-throughput characterization of pluripotent cell lines," Cell, 144:439-452 (2011).
Boller et al. "Characterization ofthe antibody response specific for the human endogenous retrovirus HTDV/HERV-K," Journal of virology, 71(6):4581-4588 (1997).
Boni et al. "Adoptive transfer of allogeneic tumor-specific T cells mediates effective regression of large tumors across major histocompatibility barriers," Blood, 112(12):4746-4754 (2008).
Boquest et al., "Isolation and transcription profiling of purified uncultured human stromal stem cells: alteration of gene expression after in vitro cell culture," Molecular biology of the cell, 16(3):1131-1141 (2005).
Boyle et al., "Gel-free multiplexed reduced representation bisulfite sequencing for large-scale DNA methylation profiling," Genome Biol, 13:R92 (2012).
Boyle et al., "Tapasin-related protein TAPBPR is an additional component ofthe MHC class I presentation pathway," Proceedings of the National Academy of Sciences, 110: 3465-3470 (2013).
Bozic et al., "Dynamics of targeted cancer therapy," Trends Mol Med, 18:311-316 (2012).
Bozic et al., "Evolutionary dynamics of cancer in response to targeted combination therapy," Elife, 2:e00747 (2013).
Brochier et al., "Large-scale eradication of rabies using recombinant vaccinia-rabies vaccine," Nature, 354:520-552 (1991).
Brown et al., "Integrative genomic analysis implicates gain of PIK3CA at 3g26 and MYC at 8q24 in chronic lymphocytic leukemia," Clin Cancer Res, 8:3791-802 (2012).
Buchschacher et al., "Human immunodeficiency virus vectors for inducible expression of foreign genes." Journal of virology, 66(5):2731-2739 (1992).
Buller et al., "Decreased virulence of recombinant vaccinia virus expression vectors is associated with a thymidine kinase-negative phenotype," Nature, 317:813-815 (1985).
Burger et al., "B cell receptor signaling in chronic lymphocytic leukemia," Trends Immunol, 34:592-601 (2013).
Burkhardt et al., "Autologous CLL cell vaccination early after transplant induces leukemia-specific T cells," The Journal of clinical investigation, 123(9):3756-3765 (2013).
Buser et al., "Unique composite hematolymphoid tumor consisting of a pro-T lymphoblastic lymphoma and an indeterminate dendritic cell tumor: evidence for divergent common progenitor cell differentiation," Pathobiology, 81:199-205 (2014).
Byrd et al., "Targeting BTK with ibrutinib in relapsed chronic lymphocytic leukemia," The New England journal of medicine, 369:32-42 (2013).
Bystryn et al., "Double-blind trial of a polyvalent, shed-antigen, melanoma vaccine," Clin Cancer Res, 7(7):1882-1887 (2001).
Böhm et al., DNA vector constructs that prime hepatitis B surface antigen-specific cytotoxic T lymphocyte and antibody responses in mice after intramuscular injection. Journal of immunological methods 193(1): 29-40 (1996).
Cahill et al., "450K-array analysis of chronic lymphocytic leukemia cells reveals global DNA methylation to be relatively stable over time and similar in resting and proliferative compartments," Leukemia, 27:150-158 (2013).
Cancer Genome Atlas Network, "Comprehensive molecular characterization of human colon and rectal cancer," Nature, 487:330-337 (2012).
Cancer Genome Atlas Network, "Comprehensive molecular portraits of human breast tumours," Nature, 490:61-70 (2012).

(56) References Cited

OTHER PUBLICATIONS

Cancer Genome Atlas Research Network, "Comprehensive genomic characterization defines human glioblastoma genes and core pathways," Nature, 455(7216):1061-1068 (2008).
Cancer Genome Atlas Research Network, "Comprehensive genomic characterization of squamous cell lung cancers," Nature, 489, 519-525 (2012).
Cancer Genome Atlas Research Network, "Comprehensive molecular characterization of clear cell renal cell carcinoma," Nature, 499:43-49 (2013).
Cancer Genome Atlas Research Network, "Comprehensive molecular characterization of gastric adenocarcinoma," Nature, 513:202-209 (2014).
Cancer Genome Atlas Research Network, "Genomic and epigenomic landscapes of adult de novo acute myeloid leukemia," New England Journal of Medicine, 368(22):2059-2074 (2013).
Cancer Genome Atlas Research Network, "Integrated genomic analyses of ovarian carcinoma," Nature, 474: 609-615 (2011).
Carreno et al., "IL-12p70-producing patient DC vaccine elicits Tcl-polarized immunity," Journal of Clinical Investigation, 123(8):3383-94 (2013).
Carter et al., "Absolute quantification of somatic DNA alterations in human cancer," Nat Biotechnol, 30:413-21 (2012).
Carter et al., "Accurate estimation of homologue-specific DNA concentration-ratios in cancer samples allows long-range haplotyping," Nature Precedings, 59-87 (2011).
CBOL Plant Working Group, "A DNA barcode for land plants," PNAS, 106(31):12794-12797 (2009).
Chang et al., "Immune selection of hot-spot beta 2-microglobulin gene mutations, HLA-A2 allospecificity loss, and antigen-processing machinery component down-regulation in melanoma cells derived from recurrent metastases following immunotherapy," Journal of immunology, 174:1462-1471 (2005).
Chapman et al., "Initial genome sequencing and analysis of multiple myeloma," Nature, 471:467-472 (2011).
Cheever, "Twelve immunotherapy drugs that could cure cancers," Immunological reviews, 222:357-368 (2008).
Chen et al., "Impact of replication timing on non-CpG and CpG substitution rates in mammalian genomes," Genome Res, 20:447-457 (2010).
Chen et al., "Langerhans Cell Sarcoma Arising from Chronic Lymphocytic Lymphoma/Small Lymphocytic Leukemia: Lineage Analysis and BRAF V600E Mutation Study," N Am J Sci, 5:386-91 (2013).
Chen et al., "Molecular mechanisms of T cell co-stimulation and co-inhibition," Nature reviews Immunology, 13:227-242 (2013).
Chen et al., "Recombinant modified vaccinia virus Ankara expressing the spike glycoprotein of severe acute respiratory syndrome coronavirus induces protective neutralizing antibodies primarily targeting the receptor binding region," Journal of virology, 79.5:2678-2688 (2005).
Chen et al.,"Induction of CD8+ T cell responses to dominant and subdominant epitopes and protective immunity to Sendai virus infection by DNA vaccination," The Journal of Immunology, 160(5):2425-2432 (1998).
Child et al., "Insertional inactivation of the large subunit of ribonucleotide reductase encoded by vaccinia virus is associated with reduced virulence in vivo," Virology, 174(2):625-629 (1990).
Chim et al., "Epigenetic dysregulation of the Wnt signalling pathway in chronic lymphocytic leukaemia," J Clin Pathol, 61:1214-1219 (2008).
Chiron et al., "Cell-cycle reprogramming for PI3K inhibition overrides a relapse-specific C4815 BTK mutation revealed by longitudinal functional genomics in mantle cell lymphoma," Cancer Discov, 4:1022-35 (2014).
Christian et al., "Targeting DNA double-strand breaks with TAL effector nucleases," Genetics, 186(2):757-761 (2010).
Chroboczek et al., "The Sequence of the Genome of Adenovirus Type 5 and Its Comparison with the Genome of Adenovirus Type 2," Virology, 186:280-285 (1992).

Church, "Genomes for all," Sci Am, 294(1):46-54 (2006).
Cibulskis et al., "ContEst: estimating cross-contamination of human samples in next-generation sequencing data," Bioinformatics, 27:2601-2602 (2011).
Cibulskis et al., "Sensitive detection of somatic point mutations in impure and heterogeneous cancer samples," Nat Biotechnol, 31:213-9 (2013).
Cleveland, "Lowess: A program for smoothing scatterplots by robust locally weighted regression," The American Statistician, 35:54 (1981).
Conlon et al., "Mouse, but not Human STING, Binds and Signals in Response to the Vascular Disrupting Agent 5,6-Dimethylxanthenone-4-Acetic Acid," Journal of Immunology, 190:5216-25 (2013).
Corbett et al., "Aerosol immunization with NYVAC and MVA vectored vaccines is safe, simple, and immunogenic," Proc Natl Acad Sci, 105(6):2046-51 (2008).
Cox et al., "Induction of cytotoxic T lymphocytes by recombinant canarypox (ALVAC) and attenuated vaccinia (NYVAC) viruses expressing the HIV-1 envelope glycoprotein," Virology, 195(2):845-850 (1993).
Crozat et al., "The XC chemokine receptor 1 is a conserved selective marker of mammalian cells homologous to mouse CD8α+ dendritic cells," Journal of Experimental Medicine, 207(6):1283-1292 (2010).
Daheshia et al., "Suppression of ongoing ocular inflammatory disease by topical administration of plasmid DNA encoding IL-10," The Journal of Immunology 159(4):1945-1952 (1997).
De et al., "Aberration in DNA methylation in B-cell lymphomas has a complex origin and increases with disease severity," PLoS Genet. 9:e1003137 (2013).
De Magalhaes et al., "Next-generation sequencing in aging research: emerging applications, problems, pitfalls and possible solutions," Ageing Research Reviews, 9(3):315-323 (2010).
DeLuca et al., "RNA-SeQC: RNA-seq metrics for quality control and process optimization," Bioinformatics, 28:1530-2 (2012).
DePristo et al., "A framework for variation discovery and genotyping using next-generation DNA sequencing data," Nature Genetics, 43:491-498 (2011).
Di Stasi et al., "Inducible apoptosis as a safety switch for adoptive cell therapy," New England Journal of Medicine, 365(18):1673-1683 (2011).
Didierlaurent et al., "Attenuated poxviruses expressing a synthetic HIV protein stimulate HLA-A2-restricted cytotoxic T-cell responses," Vaccine, 22(25-26):3395-3403 (2004).
Ding et al., "Somatic mutations affect key pathways in lung adenocarcinoma," Nature, 455:1069-1075 (2008).
Dohner et al., "Genomic aberrations and survival in chronic lymphocytic leukemia," The New England journal of medicine, 343:1910-1916 (2000).
Doody et al., "PRDMI/BLIMP-1 Modulates IFN—Dependent Control of the MHC Class I Antigen-Processing and Peptide-Loading Pathway," The Journal of Immunology, 179:7614-7623 (2007).
Earl et al., "Immunogenicity of a highly attenuated MVA smallpox vaccine and protection against monkeypox," Nature, 428:182 (2004).
Eckhardt et al., "DNA methylation profiling of human chromosomes 6, 20 and 22," Nat Genet, 38:1378-1385 (2006).
Eden et al., "Discovering motifs in ranked lists of DNA sequences," PLoS computational biology, 3, e39 (2007).
Eden et al., "GOrilla: a tool for discovery and visualization of enriched GO terms in ranked gene lists," BMC bioinformatics, 10:48 (2009).
Eggermont et al., "Ulceration and stage are predictive of interferon efficacy in melanoma: results of the phase III adjuvant trials EORTC 18952 and EORTC 18991," Eur J Cancer, 48(2):218-225 (2012).
Ehrlich, "DNA hypomethylation in cancer cells," Epigenomics, 1:239-259 (2009).
Engler et al., "A one pot, one step, precision cloning method with high throughput capability," PloS one 3(11):e3647 (2008).
Engler et al., "Golden gate shuffling: a one-pot DNA shuffling method based on type IIs restriction enzymes," PloS one, 4(5):e5553 (2009).

(56) References Cited

OTHER PUBLICATIONS

Escobar et al., "Bayesian density estimation and inference using mixtures," Journal of the American Statistical Association, 90:577-588 (1995).
Esteban, "Attenuated poxvirus vectors MVA and NYVAC as promising vaccine cadidates against HIV/AIDS," Human vaccines, 5(12):867-871 (2009).
Fais et al., "Chronic lymphocytic leukemia B cells express restricted sets of mutated and unmutated antigen receptors," The Journal of clinical investigation, 102:1515-25 (1998).
Fan et al., "The multi substrate adapter Gab1 regulates hepatocyte growth factor (scatter factor)-c-Met signaling for cell survival and DNA repair," Molecular and cellular biology, 21:4968-4984 (2001).
Fantom Consortium et al., "A promoter-level mammalian expression atlas," Nature, 507:462-470 (2014).
Farsaci et al., "Consequence of dose scheduling of sunitinib on host immune response elements and vaccine combination therapy," Int J Cancer, 130:1948-1959 (2012).
Felgner et al., "Lipofection: a highly efficient, lipid-mediated DNA-transfection procedure," PNAS, 84(21):7413-7414 (1987).
Ferrier-Rembert et al., "Short-and long-term immunogenicity and protection induced by non-replicating smallpox vaccine candidates in mice and comparison with the traditional 1st generation vaccine," Vaccine, 26(14):1794-1804 (2008).
Finke et al., "Sunitinib Reverses Type-1 Immune Suppression and Decreases T-Regulatory Cells in Renal Cell Carcinoma Patients," Clin Cancer Res, 14(20):6674-6682 (2008).
Fisher et al., "A scalable, fully automated process for construction of sequence-ready human exome targeted capture libraries," Genome Biol, 12:R1 (2011).
Flaherty et al., "From genes to drugs: targeted strategies for melanoma," Nat Rev Cancer, 12(5):349-361 (2012).
Flexner et al., "Prevention of vaccinia virus infection in imiminodeficient mice by vector-directed IL-2 expression," Nature, 330(6145):259-262 (1987).
Flynn et al., "Immunization with HIV Gag targeted to dendritic cells followed by recombinant New York vaccinia virus induces robust T-cell immunity in nonhuman primates," Proc Natl Acad Sci, 108(17):7131-7136 (2011).
Forconi et al., "Genome-wide DNA analysis identifies recurrent imbalances predicting outcome in chronic lymphocytic leukaemia with 17p deletion," British journal of haematology, 143:532-6 (2008).
Frederick et al., "BRAF inhibition is associated with enhanced melanoma antigen expression and a more favorable tumor microenvironment in patients with metastatic melanoma," Clin Cancer Res, 19:1225-1231 (2013).
Friedberg et al., "Inhibition of Syk with fostamatinib disodium has significant clinical activity in non-Hodgkin lymphoma and chronic lymphocytic leukemia," Blood, 115:2578-2585 (2011).
Fritsch et al., "Translational repression of MCL-1 couples stress-induced eIF2 alpha phosphorylation to mitochondrial apoptosis initiation," The Journal of biological chemistry, 282:22551-62 (2007).
Furman et al., "Ibrutinib resistance in chronic lymphocytic leukemia," The New England journal of medicine, 370(24):2352 (2014).
Furman et al., "Idelalisib and rituximab in relapsed chronic lymphocytic leukemia," The New England journal of medicine, 370:997-1007 (2014).
Fynan et al., "DNA vaccines: protective immunizations by parenteral, mucosal, and gene-gun inoculations," PNAS, 90 (24): 11478-82 (1993).
Gallego-Gomez et al., "Differences in virus-induced cell morphology and in virus maturation between MVA and other strains (WR, Ankara, and NYCBH) of vaccinia virus in infected human cells," Journal of virology, 77(19):10606-10622 (2003).
Gallois et al., "A needle in the 'cancer vaccine' haystack," Nature medicine, 16(8):854-856 (2010).
Gao et al., "Integrative analysis of complex cancer genomics and clinical profiles using the cBioPortal," Science signaling, 6(269):pi1 (2013).
Garimella et al., "Identification of novel molecular regulators of tumor necrosis factor-related apoptosis-inducing ligand (TRAIL)-induced apoptosis in breast cancer cells by RNAi screening," Breast cancer research, 16(2):R41 (2014).
Garofalo et al., "miR-221&222 regulate TRAIL resistance and enhance tumorigenicity through PTEN and TIMP3 downregulation," Cancer Cell, 16(6):498-509 (2009).
Garraway et al., "Lessons from the cancer genome," Cell, 153:17-37 (2013).
Gevaert et al., "Protein identification methods in proteomics," Electrophoresis: An International Journal, 21(6):1145-1154 (2000).
Gherardi et al., "Prime-boost immunization schedules based on influenza virus and vaccinia virus vectors potentiate cellular immune responses against human immunodeficiency virus Env protein systemically and in the genitorectal draining lymph nodes," Journal of virology, 77(12):7048-7057 (2003).
Ghiringhelli et al., "Metronomic cyclophosphamide regimen selectively depletes CD4+CD25+ regulatory T cells and restores T and NK effector functions in end stage cancer patients," Cancer Immunol Immunother, 56:641-648 (2007).
Giaever et al., "Functional profiling of the Saccharomyces cerevisiae genome," Nature, 418(6896):387-391 (2002).
Gibbs et al., "Abundant quantitative trait loci exist for DNA methylation and gene expression in human brain," PLoS genetics, 6:e1000952 (2010).
Gluzman, "SV40-transformed simian cells support the replication of early SV40 mutants," Cell, 23:175-182 (1981).
Goebel et al., "The complete DNA sequence of vaccinia virus," Virology, 179(1):247-266 (1990).
Gomez et al., "Efficient CD8+ T cell response to the HIV-env V3 loop epitope from multiple virus isolates by a DNA prime/vaccinia virus boost (rWR and rMVA strains) immunization regime and enhancement by the cytokine IFN-γ," Virus research, 105:11-22 (2004).
Gomez et al., "Head-to-head comparison on the immunogenicity of two HIV/AIDS vaccine candidates based on the attenuated poxvirus strains MVA and NYVAC co-expressing in a single locus the HIV-1BX08 gp120 and HIV-1IIIb Gag-Pol-Nef proteins of clade B," Vaccine, 25(15):2863-2885 (2007).
Gomez et al., "MVA and NYVAC as vaccines against emergent infectious diseases and cancer," Current gene therapy, 11(:3):189-217 (2011).
Gomez et al., "The poxvirus vectors MVA and NYVAC as gene delivery systems for vaccination against infectious diseases and cancer," Current gene therapy, 8(2):97-120 (2008).
Gomez et al., "Virus distribution of the attenuated MVA and NYVAC poxvirus strains in mice," Journal of General Virology, 88(9):2473-2478 (2007).
Greco et al., "Improving the safety of cell therapy with the TK-suicide gene," Front Pharmacol, 6:95 (2015).
Greenman et al., "Patterns of somatic mutation in human cancer genomes," Nature, 446:153-158 (2007).
Gregoriadis et al., "Improving the therapeutic efficacy of peptides and proteins: A role for polysialic acids," Int J Pharmaceutics, 300(1-2):125-30 (2005).
Grunstein et al., "Colony hybridization: a method for the isolation of cloned DNAs that contain a specific gene," PNAS, 72(10):3961-3965 (1975).
GTEx Consortium, The Genotype-Tissue Expression (GTEx) project, Nature genetics, 45:580-585 (2013).
Guo et al., "Droplet microfluidics for high-throughput biological assays," Lab Chip, 12:2146-55 (2012).
Guthals et al., "Shotgun Protein Sequencing with Meta-contig Assembly," Molecular and Cellular Proteomics, 1(10):1084-96 (2012).
Hadrup et al., "Parallel detection of antigen-specific T-eeil responses by multidimensional encoding of MHC multimers," Nature Methods, 6(7):520-26 (2009).
Halabi et al., "Prognostic model for predicting survival in men with hormone-refractory metastatic prostate cancer," Journal of Clinical Oncology, 21 (7):1232-1237 (2003).
Hall, "Advanced sequencing technologies and their wider impact in microbiology," Journal of experimental biology, 210(9):1518-1525 (2007).

(56) References Cited

OTHER PUBLICATIONS

Hanahan et al., "Hallmarks of cancer: the next generation," Cell, 144:646-674 (2011).
Hansen et al., "Increased methylation variation in epigenetic domains across cancer types," Nat Genet, 43:768-775 (2011).
Hanzelmann et al., "GSVA: gene set variation analysis for microarray and RNA-Seq data," BMC bioinformatics, 14:7 (2013).
Harris et al., "Comparison of sequencing-based methods to profile DNA methylation and identification of monoallelic epigenetic modifications," Nat Biotechnol, 28:1097-1105 (2010).
Harris et al., "RNA editing enzyme APOBECI and some of its homologs can act as DNA mutators," Molecular cell, 1095):1247-1253 (2002).
Heemskerk et al., "The cancer antigenome," EMBO Journal, 32(2):194-203 (2013).
Hel et al., "Potentiation of simian immunodeficiency virus (SIV)-specific CD4+ and CD8+ T cell responses by a DNA-SIV and NYVAC-SIV prime/boost regimen," The Journal of Immunology, 167(12):7180-7191 (2001).
Herbeuval et al., "HAART reduces death ligand but not death receptors in lymphoid tissue of HIV-infected patients and simian immunodeficiency virus-infected macaques," AIDS, 23:35-40 (2009).
Herman et al., "ibrutinib-induced lymphocytosis in patients with chronic lymphocytic leukemia: correlative analyses from a phase II study," Leukemia, 28:2188 (2014).
Hinrichs et al., "Exploiting the curative potential of adoptive T-cell therapy for cancer," Immunological reviews, 257:56-71 (2014).
Hombrink et al., "High-Throughput Identification of Potential Minor Histocompatibility Antigens by MHC Tetramer-Based Screening: Feasibility and Limitations," Plos One, 6(8):1-11 (2011).
Honigberg et al., "The Bruton tyrosine kinase inhibitor PCI-32765 blocks B-cell activation and is efficacious in models of autoimmune disease and B-cell malignancy," PNAS, 107:13075-13080 (2010).
Horig et al., "Phase 1 clinical trial of a recombinant canarypoxvirus (ALVAC) vaccine expressing human carcinoembryonic antigen and the B7.1 co-stimulatory molecule," Cancer Immunol Immunother, 49:504-514 (2000).
Huang et al., "Mucosal priming with replicative Tiantan vaccinia and systemic boosting with DNA vaccine raised strong mucosal and systemic HIV-specific immune responses," Vaccine, 25(52):8874-8884 (2007).
Hutchings et al., "Combination of protein and viral vaccines induces potent cellular and humoral immune responses and enhanced protection from murine malaria challenge," Infect Immun, 75(12):5819-26 (2007).
Illingworth et al., "Orphan CpG islands identify numerous conserved promoters in the mammalian genome," PLoS Genet, 6(9):e1001134 (2010).
Inokuchi et al., "DCC protein expression in hematopoietic cell populations and its relation to leukemogenesis," J Clin Invest, 97:852-857 (1996).
Itoh et al., "Personalized peptide vaccines: A new therapeutic modality for cancer," Cancer Sci, 97:970-976 (2006).
Izeradjene et al., "Casein kinase II (CK2) enhances death-inducing signaling complex (DISC) activity in TRAIL-induced apoptosis in human colon carcinoma cell lines," Oncogene, 24:2050-2058 (2005).
Jaatinen et al., "Global gene expression profile of human cord blood-derived CD133+ cells," Stem Cells, 24:631-641 (2006).
Jemal et al., "Cancer statistics, 2007," CA: a cancer journal for clinicians, 57:43-66 (2007).
Jennewein et al., "Sumoylation of peroxisome proliferator-activated receptor gamma by apoptotic cells prevents lipopolysaccharide-induced NCoR removal from kappaB binding sites mediating transrepression of proinflammatory cytokines," Journal of immunology, 181:5646-5652 (2008).
Jensen et al., "Design and implementation of adoptive therapy with chimeric antigen receptor-modified T cells," Immunol Rev, 257(1):127-144 (2014).
Johann et al., "GLVR1, a receptor for gibbon ape leukemia virus, is homologous to a phosphate permease of Neurospora crassa and is expressed at high levels in the brain and thymus," Journal of Virology, 66(3):1635-1640 (1992).
Johnson et al., "Single-cell perforin and granzyme expression reveals the anatomical localization of effector CD8+ T cells in influenza virus-infected mice," PNAS, 100:2657-2662 (2003).
Jones et al., "Functions of DNA methylation: islands, start sites, gene bodies and beyond," Nat Rev Genet, 13:484-492 (2012).
Jones et al., "InterProScan 5: genome-scale protein function classification," Bioinformatics, 30:1236-1240 (2014).
Jones et al., "The epigenomics of cancer," Cell, 128:683-692 (2007).
Kandoth et al., "Mutational landscape and significance across 12 major cancer types," Nature, 502:333-339 (2013).
Kantoff et al. "Overall survival analysis of a phase II randomized controlled trial of a Poxviral-based PSA-targeted immunotherapy in metastatic castration-resistant prostate cancer," Journal of Clinical Oncology, 28(7):1099-1105 (2010).
Karanikas et al., "High frequency of cytolytic T lymphocytes directed against a tumor-specific mutated antigen detectable with HLA tetramers in the blood of a lung carcinoma patient with long survival," Cancer Res, 61:3718-3724 (2001).
Karnani et al., "Pan-S replication patterns and chromosomal domains defined by genome-tiling arrays of ENCODE genomic areas," Genome research, 17:865-876 (2007).
Karolchik et al., "The UCSC Table Browser data retrieval tool," Nucleic acids research, 32:D493-496 (2004).
Kaufman et al., "Phase II randomized study of vaccine treatment of advanced prostate cancer (E7897): a trial of the Eastern Cooperative Oncology Group," Journal of Clinical Oncology, 22(11):2122-2132 (2004).
Khong et al., "Natural selection of tumor variants in the generation of "tumor escape" phenotypes," Nature immunology, 3:999-1005 (2002).
Kim et al., "A Myc network accounts for similarities between embryonic stem and cancer cell transcription programs," Cell, 143:313-324 (2010).
Kim et al., "Anticancer flavonoids are mouse-selective STING agonists," ACS chemical biology, 8(7):1396-1401 (2013).
Kim et al., "TopHat2: accurate alignment of transcriptomes in the presence of insertions, deletions and gene fusions," Genome biology, 14:R36 (2013).
Kim et al., "TroVax, a recombinant modified vaccinia Ankara virus encoding 5T4: lessons learned and future development," Human vaccines, 6(10):784-791 (2010).
Kimmel et al., "[54] Identification and characterization of specific clones: Strategy for confirming the validity of presumptive clones," Methods in enzymology, 152:507-511 (1987).
Kirkwood et al., "High- and Low-dose Interferon Alpha-2b in High-isk Melanoma: First Analysis of Intergroup Trial E1690/S9111/C9190," J Clin Oncol, 18:2444-2458 (2000).
Kirkwood et al., "Interferon alfa-2b Adjuvant Therapy of High-Risk Resected Cutaneous Melanoma: The Eastern Cooperative Oncology Group Trial EST 1684," J Clin Oncol, 14:7-17 (1996).
Klein et al., "Droplet Barcoding for Single-Cell Transcriptomics Applied to Embryonic Stem Cells," Cell, 161:1187-1201 (2015).
Kloor et al., "Immune evasion of microsatellite unstable colorectal cancers," International journal of cancer, 127:1001-1010 (2010).
Kobayashi et al., "Peptide epitope identification for tumor-reactive CD4 T cells," Current opinion in immunology, 20(2):221-227 (2008).
Koch, "Combining morphology and DNA barcoding resolves the taxonomy of Western Malagasy Liotrigona Moure, 1961," African Invertebrates, 51 (2):413-421 (2010).
Kotwal et al., "Vaccinia virus encodes two proteins that are structurally related to members of the plasma serine protease inhibitor superfamily," Journal of virology, 63(2):600-606 (1989).
Kreiter et al., "Mutant MHC Class II epitopes drive therapeutic immune responses to cancer," Nature, 520:692 (2015).
Kreso et al., "Variable clonal repopulation dynamics influence chemotherapy response in colorectal cancer," Science, 339:543-548 (2013).
Kress et al., "DNA barcodes: Genes, genomics, and bioinformatics," PNAS, 105(8):2761-2762 (2008).

(56) References Cited

OTHER PUBLICATIONS

Kress et al., "Use of DNA barcodes to identify flowering plants," PNAS, 102(23):8369-8374 (2005).
Krieg, "Therapeutic potential of Toll-like receptor 9 activation," Nature reviews Drug discovery, 5(6):471-484 (2006).
Kulis et al., "Epigenomic analysis detects widespread gene-body DNA hypomethylation in chronic lymphocytic leukemia," Nat Genet, 44:1236-1242 (2012).
Kyte et al., "Telomerase Peptide Vaccination Combined with Temozolomide: A Clinical Trial in Stage IV Melanoma Patients," Clin Cancer Res, 17(13):4568-4580 (2011).
Lahaye et al., "DNA barcoding the floras of biodiversity hotspots," PNAS, 105(8):2923-2928 (2008).
Landan et al., "Epigenetic polymorphism and the stochastic formation of differentially methylated regions in normal and cancerous tissues," Nat Genet, 44:1207-1214 (2012).
Landau et al., "Clonal evolution in hematological malignancies and therapeutic implications," Leukemia, 28:34-43 (2014).
Landau et al., "Evolution and impact of subclonal mutations in chronic lymphocytic leukemia," Cell, 152(4):714-726 (2013).
Langmead et al., "Fast gapped-read alignment with Bowtie 2," Nature methods, 9:357-359 (2012).
Langmead et al., "Ultrafast and memory-efficient alignment of short DNA sequences to the human genome," Genome Biology, 10:R25 (2009).
Lawrence et al., "Discovery and saturation analysis of cancer genes across 21 tumour types," Nature, 505:495-501 (2014).
Lawrence et al., "Mutational heterogeneity in cancer and the search for new cancer-associated genes," Nature, 499:214-218 (2013).
Le Mercier et al., "Beyond CTLA-4 and PD-1, the generation Z of negative checkpoint regulators," Front Immunol, 6:418 (2015).
Lee et al., "Sequential amplification of cloned DNA as tandem multimers using class-IIS restriction enzymes," Genetic Analysis: Biomolecular Engineering, 13(6):139-145 (1996).
Leitner et al., "Immune responses induced by intramuscular or gene gun injection of protective deoxyribonucleic acid vaccines that express the circumsporozoite protein from *Plasmodium berghei* malaria parasites," J Immunol, 159(12):6112-6119 (1997).
Lemay et al., "Dok-3, a Novel Adapter Molecule Involved in the Negative Regulation of Immunoreceptor Signaling," Mol Cell Biol, 20:2743-2754 (2000).
Lennerz et al., "The response of autologous T cells to a human melanoma is dominated by mutated neoantigens," PNAS, 102(44):16013-16018 (2005).
Lewintre et al., "Analysis of chronic lymphotic leukemia transcriptomic profile: differences between molecular subgroups," Leuk Lymphoma, 50:68-79 (2009).
Lewis et al., "DNA Vaccines: A Review," Advances in Virus Research, 54:129-88 (1999).
Li et al., "Fast and accurate short read alignment with Burrows-Wheeler Transform," Bioinformatics, 25(14):1754-1760 (2009).
Li et al., "Inactivating mutations of the chromatin remodeling gene ARID2 in hepatocellular carcinoma," Nature Genetics, 43:828-829 (2011).
Li et al., "Mapping short DNA sequencing reads and calling variants using mapping quality scores," Genome Res, 18:1851-1858 (2008).
Li et al., "RSEM: accurate transcript quantification from RNA-Seq data with or without a reference genome," BMC Bioinformatics,12:323 (2011).
Li et al., "The Sequence Alignment/Map format and SAMtools," Bioinformatics, 25(16):2078-2079 (2009).
Li et al.."Fast and accurate long-read alignment with Burrows-Wheeler transform," Bioinformatics, 26(5):589-595 (2010).
Liggins et al., "MORC4, a novel member of the MORC family, is highly expressed in a subset of diffuse large B-cell lymphomas," Brit J Haematol, 138:479-486 (2007).
Lim et al., "Transcriptome analyses of mouse and human mammary cell subpopulations reveal multiple conserved genes and pathways," Breast Cancer Res, 12:R21 (2010).
Lin et al., "Relevance of the immunoglobulin VH somatic mutation status in patients with chronic lymphocytic leukemia treated with fludarabine, cyclophosphamide, and rituximab (FCR) or related chemoimmunotherapy regimens," Blood, 113:3168-71 (2009).
Lindhout et al., "Site-specific enzymatic polysialylation of therapeutic proteins using bacterial enzymes," PNAS, 108(18):7397-7402 (2011).
Link et al., "Electric control of droplets in microfluidic devices," Angew Chem Int Ed Engl, 45(16):2556-2560 (2006).
Liu et al., "Systematic identification of type I and type II interferon-induced antiviral factors," PNAS, 109(11):4239-4244 (2012).
Livak et al. "Methods for qPCR gene expression profiling applied to 1440 lymphoblastoid single cells," Methods, 59(1):71-79 (2013).
Llobet et al., "CK2 controls TRAIL and Fas sensitivity by regulating FLIP levels in endometrial carcinoma cells," Oncogene, 27:2513-2524 (2008).
Lohr et al., "Discovery and prioritization of somatic mutations in diffuse large B-cell lymphoma (DLBCL) by whole-exome sequencing," PNAS, 109(10):3879-3884 (2012).
Lu et al., "Mutated regions of nucleophosmin 1PPP1R3B Is Recognized by T Cells Used to Treat a Melanoma Patient Who Experienced a Durable Complete Tumor Regression," J Immunol, 190(12):6034-6042 (2013).
Luckow et al.,"Trends in the Development of Baculovirus Expression Vectors," Nat Biotechnol, 6:47-55 (1988).
Lund et al., "Coordination of early protective immunity to viral infection by regulatory T cells," Science, 320(5880):1220-1224 (2008).
Mackett et al., "Vaccinia virus: a selectable eukaryotic cloning and expression vector," PNAS, 79:7415-7419 (1982).
Macosko et al., "Highly Parallel Genome-wide Expression Profiling of Individual Cells Using Nanoliter Droplets," Cell, 161(5):1202-1214 (2015).
Maegawa et al., "Age-related epigenetic drift in the pathogenesis of MDS and AML," Genome Res, 24:580-591 (2014).
Mandl et al., "Immunotherapy with MVA-BN®-HER2 induces HER-2-specific Th1 immunity and alters the intratumoral balance of effector and regulatory T cells," Cancer Immunol Immunother, 61(1):19-29 (2012).
Manghera et al., "Endogenous retrovirus-K promoter: a landing strip for inflammatory transcription factors?," Retrovirol, 10:16 (2013).
Maratea et al. "Deletion and fusion analysis of the phage φX174 lysis gene E," Gene 40(1):39-46 (1985).
Marcais et al., "A fast, lock-free approach for efficient parallel counting of occurrences of k-mers," Bioinformatics, 27(6):764-770 (2011).
Mark et al., "Site-specific mutagenesis of the human fibroblast interferon gene," PNAS, 81(18):5662-5666 (1984).
Marshall et al., "Phase I Study in Cancer Patients of a Replication-Defective Avipox Recombinant Vaccine That Expresses Human Carcinoembryonic Antigen," J Clin Oncol, 17:332-337 (1999).
Maus et al., "Adoptive Immunotherapy for Cancer or Viruses," Annual Review of Immunology, 32:189-225 (2014).
Mayer et al., "A revised nomenclature for transcribed human endogenous retroviral loci," Mobile DNA, 2:7 (2011).
Mayr et al., "Abstammung, Eigenschaften und Verwendung des attenuierten Vaccinia-Stammes MVA (Translated Summary)," Infection, 3(1):6-14 (1975).
Mayr, "The smallpox vaccination strain MVA: marker, genetic structure, experience gained with the parenteral vaccination and behavior in organisms with a debilitated defence mechanism (author's transl)," Zentralbl Bakteriol 167(5-6):375-9 (1978).
Mazutis et al., "Single-cell analysis and sorting using droplet-based microfluidics," Nat Protoc, 8:870-891 (2013).
McCormack et al., "HLA-A*3101 and Carbamazepine-Induced Hypersensitivity Reactions in Europeans," New Engl J Med, 364:1134-1143 (2011).
McCurdy et al., "Modified Vaccinia Ankara: Potential as an Alternative Smallpox Vaccine," Clin Infect Dis, 38:1749-1753 (2004).
McFadden et al., "Genetic and clonal dissection of murine small cell lung carcinoma progression by genome sequencing," Cell, 156(6):1298-1311 (2014).

(56) References Cited

OTHER PUBLICATIONS

McKenna et al., "The Genome Analysis Toolkit: a MapReduce framework for analyzing next-generation DNA sequencing data," Genome Res, 20(9):1297-1303 (2010).
Medema et al., "Immune Escape of Tumors in Vivo by Expression of Cellular Flice-Inhibitory Protein," J Exp Med, 190:1033-1038 (1999).
Meissner et al., "Genome-scale DNA methylation maps of pluripotent and differentiated cells," Nature, 454:766-770 (2008).
Melief et al., "Immunotherapy of established (pre)malignant disease by synthetic long peptide vaccines," Nature Rev Cancer, 8:351-360 (2008).
Menke et al., "Genetic interactions between the Wilms' tumor 1 gene and the p53 gene," Cancer Res, 62(22):6615-6620 (2002).
Mermel et al., "GISTIC2.0 facilitates sensitive and confident localization of the targets of focal somatic copy-number alteration in human cancers," Genome Biol, 12:R41 (2011).
Merrifield, "Solid Phase Peptide Synthesis. I. The Synthesis of a Tetrapeptide," J Am Chem Soc, 85(14):2149-2154 (1963).
Messmer et al., "In vivo measurements document the dynamic cellular kinetics of chronic lymphocytic leukemia B cells," J Clin Invest, 115(3):755-764 (2005).
Meyer et al., "Mapping of deletions in the genome of the highly attenuated vaccinia virus MVA and their influence on virulence," J Gen Virol, 72:1031-1038 (1991).
Midgley, "Vaccinia virus strain NYVAC induces substantially lower and qualitatively different human antibody responses compared with strains Lister and Dryvax," J Gen Virol, 89:2992-2997 (2008).
Miller et al., "Construction and properties of retrovirus packaging cells based on gibbon ape leukemia virus," Virol, 65:2220-2224 (1991).
Missale et al., "HLA-A31- and HLA-Aw68-restricted cytotoxic T cell responses to a single hepatitis B virus nucleocapsid epitope during acute viral hepatitis," J Exp Med, 177(3):751-762 (1993).
Mocellin et al., "Interferon Alpha Adjuvant Therapy in Patients With High-Risk Melanoma: A Systematic Review and Meta-analysis," JNCI, 102(7):493-501 (2010).
Mooij, "Differential CD4+ versus CD8+ T-Cell Responses Elicited by Different Poxvirus-Based Human Immunodeficiency Virus Type 1 Vaccine Candidates Provide Comparable Efficacies in Primates," J Virol, 82(6):2975-2988 (2008).
Mor et al., "Complexity of the cytokine and antibody response elicited by immunizing mice with Plasmodium yoelii circumsporozoite protein plasmid DNA," J Immunol, 155(4):2039-2046 (1995).
Morison et al., "A census of mammalian imprinting," Trends Genet, 21(8):457-465 (2005).
Morozov et al., "The Transmembrane Protein of the Human Endogenous Retrovirus—K (HERV-K) Modulates Cytokine Release and Gene Expression," PloS one 8(8):e70399 (2013).
Moss, "Reflections on the early development of poxvirus vectors," Vaccine, 31(39): 4220-4222 (2013).
Murphy et al., "Genetic construction, expression, and melanoma-selective cytotoxicity of a diphtheria toxin-related alpha-melanocyte-stimulating hormone fusion protein," PNAS, 83:8258-8262 (1986).
Musey et al., "HIV-1 Vaccination Administered Intramuscularly Can Induce Both Systemic and Mucosal T Cell Immunity in HIV-1-Uninfected Individuals," J Immunol, 171(2):1094-1101 (2003).
Najera et al., "Cellular and Biochemical Differences between Two Attenuated Poxvirus Vaccine Candidates (MVA and NYVAC) and Role of the C7L Gene," J Virol, 80(12):6033-6047 (2006).
Nam et al., "Different contribution of co-stimulatory molecules B7.1 and B7.2 to the immune response to recombinant modified vaccinia virus ankara vaccine expressing prM/E proteins of Japanese encephalitis virus and two hepatitis B virus vaccines," Acta Virol, 51:125-30 (2007).
Nielsen et al., "NetMHCpan, a Method for Quantitative Predictions of Peptide Binding to Any HLA-A and -B Locus Protein of Known Sequence," PloS one, 2:e796 (2007).
Nishimura et al., "Distinct Role of Antigen-Specific T Helper Type 1 (Th1) and Th2 Cells in Tumor Eradication in Vivo," J Ex Med, 190(5):617-27 (1999).
Nocentini et al., "A new member of the tumor necrosis factor/nerve growth factor receptor family inhibits T cell receptor-induced apoptosis," PNAS, 94(12):6216-6221 (1997).
Oh et al., "Neutrophil isolation protocol," J Vis Exp (2008).
Ohnishi et al., "Premature Termination of Reprogramming In Vivo Leads to Cancer Development through Altered Epigenetic Regulation," Cell, 156(4):663-677 (2014).
Oshiumi et al., "Dead/H Box 3 (DDX3) helicase binds the RIG-I adaptor IPS-1 to up-regulate IFN-beta-inducing potential," Eur J Immunol, 40:940-948 (2010).
Oudard et al., "A phase II study of the cancer vaccine TG4010 alone and in combination with cytokines in patients with metastatic renal clear-cell carcinoma: clinical and immunological findings," Cancer Immunol Immunother, 60(2):261-71 (2011).
Padgett et al., "Creating seamless junctions independent of restriction sites in PCR cloning," Gene, 168:31-35 (1996).
Page et al., "Immune Modulation in Cancer with Antibodies," Annu Rev Med, 65:185-202 (2014).
Pages, et al., "Effector Memory T Cells, Early Metastasis, and Survival in Colorectal Cancer," New Engl J Med, 353:2654-2666 (2005).
Panicali et al., "Construction of live vaccines by using genetically engineered poxviruses: biological activity of recombinant vaccinia virus expressing influenza virus hemagglutinin," PNAS, 80(17):5364-5368 (1983).
Panicali et al., "Construction of poxviruses as cloning vectors: insertion of the thymidine kinase gene from herpes simplex virus into the DNA of infectious vaccinia virus," 79(16):4927-4931 (1982).
Pantaleo et al., "Poxvirus vector-based HIV vaccines," Curr Opin HIV-AIDS, 5:391-396 (2010).
Paoletti, "Applications of pox virus vectors to vaccination: an update," PNAS, 93(21):11349-53 (1996).
Pei et al., "Genome-wide DNA methylation analysis reveals novel epigenetic changes in chronic lymphocytic leukemia," Epigenetics, 7:567-578 (2012).
Peng et al., "DOK3 Negatively Regulates LPS Responses and Endotoxin Tolerance," PloS one7:e39967 (2012).
Perez et al., "A new era in anticancer peptide vaccines," Cancer, 116(9):2071-2080 (2010).
Perez et al., "p63 consensus DNA-binding site: identification, analysis and application into a p63MH algorithm," Oncogene, 26:7363-7370 (2007).
Perkvs et al., "Poxvirus based vaccine candidates for cancer, AIDS, and other infectious diseases," J Leukocyte Biol, 58(1):1-13 (1995).
Perreau et al., "DNA/NYVAC Vaccine Regimen Induces HIV-Specific CD4 and CD8 T-Cell Responses in Intestinal Mucosa," J Virol, 85(19):9854-9862 (2011).
Petsch et al., "Protective efficacy of in vitro synthesized, specific mRNA vaccines against influenza A virus infection," Nat Biotechnol, 30(12):1210-1216 (2012).
Pieters et al., "On guard: coronin proteins in innate and adaptive immunity," Nat Rev Immunol, 13:510-518 (2013).
Pirard et al., "Interferon Alpha as Adjuvant Postsurgical Treatment of Melanoma: A Meta-Analysis," Dermatology, 208(1):43-48 (2004).
Poirot et al., "Multiplex genome edited T-cell manufacturing platform for "off-the-shelf" adoptive T-cell immunotherapies," Cancer Res, 75(18):3853 (2015).
Poulet, "Development and registration of recombinant veterinary vaccines: The example of the canarypox vector platform," Vaccine, 25(30):5606-5612 (2007).
Powell et al., "NCoR1 Mediates Papillomavirus E8E2C Transcriptional Repression," J Virol, 84:4451-4460 (2010).
Pujadas et al., "Regulated noise in the epigenetic landscape of development and disease," Cell, 148(6):1123-1131 (2012).
Qin et al., "Soft lithography for micro- and nanoscale patterning," Nat Protoc, 5:491-502 (2010).
Quesada et al., "Exome sequencing identifies recurrent mutations of the splicing factor SF3B1 gene in chronic lymphocytic leukemia," Nat Genet, 44:47-52 (2012).

(56) References Cited

OTHER PUBLICATIONS

Ramos et al., "An Inducible Caspase 9 Suicide Gene to Improve the Safety of Mesenchymal Stromal Cell Therapies," Stem Cells, 28(6):1107-1115 (2010).

Ramskold et al., "Full-length mRNA-Seq from single-cell levels of RNA and individual circulating tumor cells," Nat Biotechnol, 30:777-782 (2012).

Rassenti et al., "Relative value of ZAP-70, CD38, and immunoglobulin mutation status in predicting aggressive disease in chronic lymphocytic leukemia," Blood, 112:1923-1930 (2008).

Raval et al., "Downregulation of Death-Associated Protein Kinase 1 (DAPK1) in Chronic Lymphocytic Leukemia," Cell, 129(5):879-890 (2007).

Ravi et al., "Sensitization of Tumor Cells to Apo2 Ligand/TRAIL-induced Apoptosis by Inhibition of Casein Kinase II," Cancer Res, 62(15):4180-4185 (2002).

Restifo et al., "Adoptive immunotherapy for cancer: harnessing the T cell response," Nat Rev Immunol, 12(4):269-281 (2015).

Robinson et al., "DNA vaccines for viral infections: Basic studies and applications," Adv Virus Res, 55:1-74 (2000).

Robinson et al., "edgeR: a Bioconductor package for differential expression analysis of digital gene expression data," Bioinformatics, 26(1):139-140 (2010).

Robinson et al., "Integrative genomics viewer," Nat Biotechnol, 29:24-26 (2011).

Rolph et al., "Recombinant viruses as vaccines and immunological tools," Curr Opin Immunol, 9(4):517-524 (1997).

Ronchetti et al., "Frontline:GITR, a member ofthe TNF receptor superfamily,is costimulatory to mouse T lymphocytesubpopulations," Eur J Immunol, 34(3):613-622 (2004).

Rosenberg, "Raising the Bar: The Curative Potential of Human Cancer Immunotherapy," Sci Transl Med, 4(127):127ps128 (2012).

Rossi et al., "Integrated mutational and cytogenetic analysis identifies new prognostic subgroups in chronic lymphocytic leukemia," Blood, 121:1403-1412 (2013).

Rubio-Moscardo et al., "Characterization of 8p21.3 chromosomal deletions in B-cell lymphoma: TRAIL-R1 and TRAIL-R2 as candidate dosage-dependent tumor suppressor genes," Blood, 106:3214-3222 (2005).

Rupprecht et al., "Oral immunization and protection of raccoons (*Procyon lotor*) with a vaccinia-rabies glycoprotein recombinant virus vaccine," PNAS, 83:7947-7950 (1986).

Rutledge et al., "Tumor-Infiltrating Lymphocytes in Glioblastoma Are Associated with Specific Genomic Alterations and Related to Transcriptional Class," Clin Cancer Res, 19:4951-4960 (2013).

Sabado et al., "Preparation of Tumor Antigen-loaded Mature Dendritic Cells for Immunotherapy," J Vis Exp, 78:50085 (2013).

Sadelain, "Eliminating Cells Gone Astray," New Engl J Med, 365:1735-1737 (2011).

Samuels et al., "Oncogenic PI3K and its role in cancer," Curr Opin Oncol, 18:77-82n (2006).

Sancho, "The Block in Assembly of Modified Vaccinia Virus Ankara in HeLa Cells Reveals New Insights into Vaccinia Virus Morphogenesis," J Virol, 76(16):8313-8334 (2002).

Sato et al., "Discovery of Novel Targets for Aberrant Methylation in Pancreatic Carcinoma Using High-Throughput Microarrays," Cancer Res, 63(13):3735-3742 (2003).

Saturno et al., "Combining TRAIL with PI3 Kinase or HSP90 inhibitors enhances apoptosis in colorectal cancer cells via suppression of survival signaling," Oncotarget, 4(8):1185-1198 (2013).

Saunders et al., "Strelka: accurate somatic small-variant calling from sequenced tumor-normal sample pairs," Bioinformatics, 28(14):1811-1817 (2012).

Schmitt et al., "Transcriptional Profiling of Human Endogenous Retrovirus Group HERV-K(HML-2) Loci in Melanoma," Genome Biol Evol, 5(2):307-328 (2013).

Schneider et al., "Induction of CD8+ T cells using heterologous prime-boost immunisation strategies," Immunol Rev, 170(1):29-38 (1999).

Schreiber et al., "Cancer Immunoediting: Integrating Immunity's Roles in Cancer Suppression and Promotion," Science, 331 (6024):1565-1570 (2011).

Schumacher et al., "Prognostic Significance of Activated CD8+ T Cell Infiltrations within Esophageal Carcinomas," Cancer Res, 61(10):3932-3936 (2001).

Scriba et al., "Modified vaccinia Ankara expressing Ag85A, a novel tuberculosis vaccine, is safe in adolescents and children, and induces polyfunctional CD4+ T cells," Eur J Immunol, 40(1):279-290 (2010).

Seberg et al., "How Many Loci Does it Take to DNA Barcode a Crocus?," PLoS One 4(2):e4598 (2009).

Secchiero et al., "Aberrant expression of TRAIL in B chronic lymphocytic leukemia (B-CLL) cells," J Cell Physiol, 205(2):246-252 (2005).

Sedegah et al., "Protection against malaria by immunization with plasmid DNA encoding circumsporozoite protein," PNAS, 91(21):9866-9870 (1994).

Sensi et al., "Unique tumor antigens: evidence for immune control of genome integrity and immunogenic targets forT cell-mediated patient-specific immunotherapy," Clin Cancer, Res 12:5023-5032 (2006).

Shah et al., "Multiple BCR-ABL kinase domain mutations confer polyclonal resistance to the tyrosine kinase inhibitor imatinib (STI571) in chronic phase and blast crisis chronic myeloid leukemia," Cancer Cell, 2(2):117-125 (2002).

Shalek et al., "Single-cell RNA-seq reveals dynamic paracrine control of cellular variation," Nature, 510(7505):363-369 (2014).

Shannon, "A Mathematical Theory of Communication," Bell System Technical Journal, 27(3):379-423 (1948).

Shao et al., "Clonally related histiocytic/dendritic cell sarcoma and chronic lymphocytic leukemia/small lymphocytic lymphoma: a study of seven cases," Mod Pathol, 24:1421-1432 (2011).

Sharei et al., "Ex Vivo Cytosolic Delivery of Functional Macromolecules to Immune Cells," PLOS ONE, 10(4):e0118803 (2015).

Shendure et al., "Next-generation DNA sequencing," Nat Biotechnol, 26(10):1135-1145 (2008).

Shida, "Effects and virulences of recombinant vaccinia viruses derived from attenuated strains that express the human T-cell leukemia virus type I envelope gene," J Virol, 62(12):4474-4480 (1988).

Shipony et al., "Dynamic and static maintenance of epigenetic memory in pluripotent and somatic cells," Nature, 513:115-119 (2014).

Sidney et al., "HLA class I supertypes: a revised and updated classification," BMC Immunol, 9:1 (2008).

Siegel et al., "Cancer statistics, 2013," CA, 63(1):11-30 (2013).

Simpson et al., "Cancer/testis antigens, gametogenesis and cancer," Nat Rev Cancer, 5:615-625 (2005).

Sizemore, "Attenuated Shigella as a DNA Delivery Vehicle for DNA-Mediated Immunization," Science, 270(5234):299-303 (1995).

Slingluff et al., "Immunologic and Clinical Outcomes of a Randomized Phase II Trial of Two Multipeptide Vaccines for Melanoma in the Adjuvant Setting," Clin Cancer Res, 13(21):6386-6395 (2007).

Smith et al., "Comparison of biosequences," Adv Appl Math, 2(4):482-489 (1981).

Smith et al., "Construction and characterization of an infectious vaccinia virus recombinant that expresses the influenza hemagglutinin gene and induces resistance to influenza virus infection in hamsters," PNAS, 80(23):7155-7159 (1983).

Smith et al., "Infectious vaccinia virus recombinants that express hepatitis B virus surface antigen," Nature, 302:490-495 (1983).

Smoley et al., "Standardization of fluorescence in situ hybridization studies on chronic lymphocytic leukemia (CLL) blood and marrow cells by the CLL Research Consortium," Cancer Genet Cytogenet, 203(2):141-148 (2010).

Soininen et al., "Analysing diet of small herbivores: the efficiency of DNA barcoding coupled with high-throughput pyrosequencing for deciphering the composition of complex plant mixtures," Front Zool, 6:16 (2009).

Sommerfelt et al., "Receptor interference groups of 20 retroviruses plating on human cells," Virol, 176:58-69 (1990).

(56) References Cited

OTHER PUBLICATIONS

Song et al., "c-Cbl acts as a mediator of Src-induced activation of the PI3K-Akt signal transduction pathway during TRAIL treatment," Cellular Signalling, 22(3):377-385 (2010).
Sosman et al., "A phase 2 trial of complete resection for stage IV melanoma: results of Southwest Oncology Group Clinical Trial S9430," Cancer, 117(20):4740-4706 (2011).
Speiser et al., "Molecularly defined vaccines for cancer immunotherapy, and protective T cell immunity," Semin Immunol, 22(3):144-154 (2010).
Spencer et al., "Non-genetic origins of cell-to-cell variability in TRAIL-induced apoptosis," Nature, 459:428-432 (2009).
Spranger et al., "Up-regulation of PD-LI, IDO, and Tregs in the melanoma tumor microenvironment is driven by CD8+ T cells," Sci Transl Med, 5(200):200ra116 (2013).
Staehler et al., "An open label study to evaluate the safety and immunogenicity of the peptide based cancer vaccine IMA901," ASCO meeting 2007; Abstract No. 3017.
Stransky et al., "The Mutational Landscape of Head and Neck Squamous Cell Carcinoma," Science, 333:1157-1160 (2011).
Su et al., "Next-generation sequencing and its applications in molecular diagnostics" Exp Rev Mol Diagn, 11 (3):333-343 (2011).
Subramanian et al., "Gene set enrichment analysis: a knowledge-based approach for interpreting genome-wide expression profiles," PNAS, 102:15545-15550 (2005).
Sullivan et al., "Expression and Characterization of Herpes Simplex Virus Type 1 (HSV-1) Glycoprotein G (gG) by Recombinant Vaccinia Virus: Neutralization of HSV-1 Infectivity with Anti-gG Antibody," Gen Vir, 68:2587-2598 (1987).
Suzuki et al., "A Novel Glycosylphosphatidyl Inositol-Anchored Protein on Human Leukocytes: A Possible Role for Regulation of Neutrophil Adherence and Migration," J Immunol, 162(7):4277-4284 (1999).
Sykulev et al., "Evidence that a Single Peptide-MHC Complex on a Target Cell Can Elicit a Cytolytic T Cell Response," Immunity, 4:565-571 (1996).
Tang et al., "The landscape of viral expression and host gene fusion and adaptation in human cancer," Nat Commun, 4:2513 (2013).
Tartaglia et al., "NYVAC: A highly attenuated strain of vaccinia virus," Virology, 188(1):217-232 (1992).
Ten Bosch et al., "Keeping Up With the Next Generation: Massively Parallel Sequencing in Clinical Diagnostics," J Mol Diagn, 10(6):484-492 (2008).
Teng et al., "A human TAPBP (TAPASIN)-related gene, TAPBP-R," Eur J Immunol, 32:1059-1068 (2002).
Textor et al., "Human NK cells are alerted to induction of p53 in cancer cells by upregulation of the NKG2D ligands ULBPI and ULBP2," Cancer Res, 71:5998-6009 (2011).
Timp et al., "Cancer as a dysregulated epigenome allowing cellular growth advantage at the expense of the host," Nat Rev Cancer, 13:497-510 (2013).
Tjoa et al., "Follow-up evaluation of prostate cancer patients infused with autologous dendritic cells pulsed with PSMA peptides," The Prostate, 32(4):272-278 (1997).
Tucker et al., "Massively Parallel Sequencing: The Next Big Thing in Genetic Medicine," Am J Hum Genet, 85(2):142-154 (2009).
Uderhardt et al., "12/15-lipoxygenase orchestrates the clearance of apoptotic cells and maintains immunologic tolerance," Immunity, 36(5):834-846 (2012).
Ushijima et al., "Fidelity of the methylation pattern and its variation in the genome," Genome research, 13:868-874 (2005).
Uyttenhove et al., "Evidence for a tumoral immune resistance mechanism based on tryptophan degradation by indoleamine 2,3-di oxygenase," Nature medicine, 9:1269-1274 (2003).
Van Rooij et al., "Tumor exome analysis reveals neoantigen-specific T-cell reactivity in an ipilimumab-responsive melanoma," Journal of clinical oncology: official journal of the American Society of Clinical Oncology, 31:32 (2013).

Verardi et al., "A vaccinia virus renaissance: new vaccine and immunotherapeutic uses after smallpox eradication," Human vaccines & immunotherapeutics, 8(7):961-970 (2012).
Von Krempelhuber et al., "A randomized, double-blind, dose-finding Phase II study to evaluate immunogenicity and safety of the third generation smallpox vaccine candidate IMVAMUNE®," Vaccine, 28(5):1209-1216 (2010).
Von Mehren et al., "Pilot study of a dual gene recombinant avipox vaccine containing both carcinoembryonic antige (CEA.) and B7.1 transgenes in patients with, recurrent CEA-expressing adenocarcinomas," Clin Cancer Res, 6:2219-28 (2000).
Wahl et al., "[43] Molecular hybridization of immobilized nucleic acids: Theoretical concepts and practical considerations," Methods in enzymology, Academic Press, 152:399-407 (1987).
Walter et al., "Multipeptide immune response to cancer vaccine IMA901 after single-dose cyclophosphamide associates with longer patient survival," Nature medicine, 18(8):1254 (2012).
Wang et al., "Role of protein kinase CK2 in the regulation of tumor necrosis factor-related apoptosis inducing ligand-induced apoptosis in prostate cancer cells," Cancer research, 66:2242-2249 (2006).
Wang et al., "SF3B1 and other novel cancer genes in chronic lymphocytic leukemia," N Engl J Med, 365:2497-2506 (2011).
Wang et al., "Widespread plasticity in CTCF occupancy linked to DNA methylation," Genome Res, 22:1680-1688 (2012).
Watson et al., "SHP-1: the next checkpoint target for cancer immunotherapy?," Biochem Soc Trans, 44(2):356-362 (2016).
Weber et al., "Assembly of Designer TAL Effectors by Golden Gate Cloning," PLoS ONE, 6:e19722 (2001).
Webster et al., "Enhanced T cell-mediated protection against malaria in human challenges by using the recombinant poxviruses FP9 and modified vaccinia virus Ankara," Proceedings of the National Academy of Sciences, 102(13):4836-4841 (2005).
Weiner et al., "Genetic vaccines," Scientific American, 281(1):50-57 (1999).
Weyer et al., "Generation and evaluation of a recombinant modified vaccinia virus Ankara vaccine for rabies," Vaccine, 25(21):4213-4222 (2007).
Weyer et al., "Poxvirus-vectored vaccines for rabies—a review," Vaccine, 27(51):7198-7201 (2009).
Wheatley et al., "Does adjuvant interferon-alpha for high-risk melanoma provide a worthwhile benefit?A meta-analysis of the randomised trials," Cancer treatment reviews, 29(4):241-252 (2003).
Whelan et al., "Safety and immunogenicity of boosting BCG vaccinated subjects with BCG: comparison with boosting with a new TB vaccine, MVA85A," PLoS One, 4(6):e5934 (2009).
Widschwendter et al., "Epigenetic stem cell signature in cancer," Nat Genet, 39:157-158 (2007).
Wierda et al., "Multivariable model for time to first treatment in patients with chronic lymphocytic leukemia," J Clin Oncol, 29:4088-4095 (2011).
Wiktor et al., "Protection from rabies by a vaccinia virus recombinant containing the rabies virus glycoprotein gene," Proceedings of the National Academy of Sciences, 81(22):7194-7198 (1984).
Wilson et al., "Formation of infectious hybrid virions with gibbon ape leukemia virus and human T-cell leukemia virus retroviral envelope glycoproteins and the gag and pol proteins of Moloney murine leukemia virus," Journal of virology, 63(5):2374-2378 (1989).
Winzeler et al., "Functional characterization of the S. cerevisiae genome by gene deletion and parallel analysis," science, 285(5429):901-906 (1999).
Wong et al., "Module map of stem cell genes guides creation of epithelial cancer stem cells," Cell Stem Cell, 2:333-344 (2008).
Woodfine et al., "Quantitative analysis of DNA methylation at all human imprinted regions reveals preservation of epigenetic stability in adult somatic tissue," Epigenetics & chromatin, 4:1 (2011).
Woyach et al., "Resistance mechanisms for the Bruton's tyrosine kinase inhibitor ibrutinib," The New England journal of medicine, 370:2286-94 (2014).
Wyatt et al., "Marker rescue of the host range restriction defects of modified vaccinia virus Ankara," Virology, 251(2):334-342 (1998).

(56) References Cited

OTHER PUBLICATIONS

Wyatt et al., "Multiprotein HIV type 1 clade B DNA and MVA vaccines: construction, expression, and immunogenicity in rodents of the MVA component," AIDS research and human retroviruses, 20(6):645-653 (2004).
Xi et al., "BSMAP: whole genome bisulfite sequence MAPping program," BMC bioinformatics, 10:232 (2009).
Xie et al., "Stepwise reprogramming of B cells into macrophages," Cell, 117(5):663-676 (2004).
Xu et al., "Design of 240,000 orthogonal 25mer DNA barcode probes," Proceedings of the National Academy of Sciences, pnas-0812506106 (2009).
Yan et al., "PBAF chromatin-remodeling complex requires a novel specificity subunit, BAF200, to regulate expression of selective interferon-responsive genes," Genes & development, 19(14):1662-1667 (2005).
Yang et al., "Meta-analysis followed by replication identifies loci in or near CDKN1B, TET3, CD80, DRAM1, and ARID5B as associated with systemic lupus erythematosus in Asians," American journal of human genetics, 92:41-51 (2013).
Yilma, "Prospects for the total eradication of rinderpest," Vaccine, 7(6):484-485 (1989).
Yoshihara et al., Inferring tumour purity and stromal and immune cell admixture from expression data,: Nature communications 4:2612 (2013).
Yoshitake et al., "Cross☐linking of GPI☐80, a possible regulatory molecule of cell adhesion, induces up☐regulation of CD11b/CD18 expression on neutrophil surfaces and shedding of L☐ selectin," Journal of leukocyte biology, 71(2):205-211 (2002).
Young et al., "Resurrection of endogenous retroviruses in antibody-deficient mice," Nature, 491(7426)774 (2012).
Yu et al., "Nucleic acid-sensing Toll-like receptors are essential for the control of endogenous retrovirus viremia and ERV-induced tumors," Immunity, 37(5):867-879 (2012).
Yuille et al., "TCL1 is activated by chromosomal rearrangement or by hypomethylation," Genes, Chromosomes and Cancer, 30(4):336-341 (2001).
Zhang et al., "Machine learning competition in immunology-prediction of HLA class I binding peptides," J Immunol Methods 374:1-4 (2009).
Zhang et al., "The impact of next-generation sequencing on genomics," J Genet Genomics, 38(3):95-109 (2011).
Zhou et al., "A hypermorphic missense mutation in PLCG2, encoding phospholipase Cgamma2, causes a dominantly inherited autoinflammatory disease with immunodeficiency," Am J Hum Genet, 91:713-20 (2012).
Zhou et al., "Long-term outcome after haploidentical stem cell transplant and infusion of T cells expressing the inducible caspase 9 safety transgene," Blood, 123(25):3895-3905 (2014).
Ziller et al., "Charting a dynamic DNA methylation landscape ofthe human genome," Nature, 500:477-481 (2013).
Zitvogel et al., "Immunological aspects of cancer chemotherapy," Nature reviews immunology, 8:59 (2008).
Zorn et al., "A natural cytotoxic T cell response in a spontaneously regressing human melanoma targets a neoantigen resulting from a somatic point mutation," Eur J Immunol, 29(2):592-601 (1999).
Acknowledgment of Receipt dated Jun. 28, 2017 for Response to Notices of Opposition of EP2569633.
Adams, "Toll-like receptor agonists in cancer therapy," Immunotherapy, 1(6):949-964 (2009).
Albert et al., "Direct Selection of Human Genomic Loci by Microarray Hybridization," Nat Methods, 4(11): 903-905 (2007).
Allison, "The Mode of Action of Immunological Adjuvants," Dev Biol Stand, 92: 3-11 (1998).
Alyea et al., "Toxicity and Efficacy of Defined Doses of CD4+ Donor Lymphocytes for Treatment of Relapse After Allogeneic Bone Marrow Transplant," Blood, 91(10):3671-3680 (1998).
Anderson et al., "Next Generation DNA Sequencing and the Future of Genomic Medicine," Genes, 1: 38-69 (2010).
Annunziata et al., "Frequent Engagement of the Classical and Alternative NF-KB Pathways by Diverse Genetic Abnormalities in Multiple Myeloma," Cancer Cell, 12(2):115-130 (2007).
Applicant's Authorization and Release Form of the Massachusetts General Hospital, Aug. 12, 2008; and Supplemental Release to Applicant ofthe Partners Healthcare System, Aug. 13, 2008.
Attia et al., "Autoimmunity Correlates With Tumor Regression in Patients With Metastatic Melanoma Treated with Anti-Cytotoxic T-Lymphocyte Antigen-4," J Clin Oncol, 23.(25): 6043-6053 (2005).
Austen et al., "Mutations in the ATM Gene Lead to Impaired Overall and Treatment-Free Survival that is Independent of IGVH Mutation Status in Patients with B-CLL," Blood, 106(9): 3175-3182 (2005).
Bachireddy et al., "Reversal of in situ T cell exhaustion during effective human anti-leukemia responses to donor lymphocyte infusion," Blood, 123(9):1412-1421 (2013).
Balakrishnan et al., "Novel Somatic and Germline Mutations in Cancer Candidate Genes in Glioblastoma, Melanoma, and Pancreatic Carcinoma," Cancer Res, 67: 3545-3550 (2007).
Baskar et al., "Autologous Lymphoma Vaccines Induce Human T Cell Responses Against Multiple, Unique Epitopes," J Clin Invest, 113:1498-1510 (2004).
Baurain et al., "High Frequency of Autologous Anti-Melanoma CTL Directed Against an Antigen Generated by a Point Mutation in a New Helicase Gene," J Immunol, 164: 6057-6066 (2000).
Beck et al., "Enterocolitis in Patients With Cancer After Antibody Blockade of Cytotoxicity TLymphocyte-Associated Antigen 4," J Clin Oncol, 24(15): 2283-2289 (2006).
Bellucci et al., "Complete Response to Donor Lymphocyte Infusion in Multiple Myeloma is Associated with Antibody Responses to Highly Expressed Antigens," Blood, 103: 656-663 (2004).
Bentley et al., "Accurate Whole Human Genome Sequencing using Reversible Terminator Chemistry," Nature, 456(7218): 53-59 (2008).
Bettelli et al., "TH-17 cells in the circle of immunity and autoimmunity," Nat Immunol, 8:345-350 (2007).
Bogunovic et al., "TLR4 engagement during TLR3-induced proinflammatory signaling in dendritic cells promotes IL-10-mediated suppression of antitumor immunity," Cancer Res, 71(16):5467-5476 (2011).
Boisguerin et al., "Translation of genomis-guided RNA-based personalised cancer vaccaines: towards the bedside," British J Cancer, 111:1469-1475 (2014).
Boon et al., "Human T Cell Responses Against Melanoma," Annu Rev Immunol, 24:175-208 (2006).
Boon, "Toward a Genetic Analysis of Tumor Rejection Antigens," Adv Cancer Res, 58:177-210 (1992).
Boscardin et al., "Antigen targeting to dendritic cells elicits long-lived T cell help for antibody responses," Journal of Experimental Medicine, 203(3):599-606 (2006).
Bowerman et al., "Engineering the binding properties ofthe T cell receptor:peptide:MHC ternary complex that governs T cell activity," Mol Immunol, 46(15):3000-3008 (2009).
Brahmer et al., "Safety and activity of anti-PD-L1 antibody in patients with advanced cancer," N Engl J Med, 366(26):2455-2465 (2012).
Brandle et al., "A Mutated HLA-A2 Molecule Recognized by Autologous Cytotoxic T Lymphocytes on a Human Renal Cell Carcinoma," J Exp Med, 183: 2501-2508 (1996).
Brinckerhoff et al., "Melanoma Vaccines," Curr Opin Oncol, 12:163-173 (2000).
Broad Institute Article, Jan. 29, 2009, "Turning Cancer's Strength Into Weakness," (2009).
Brown et al., "Neo-antigens predicted by tumor genome meta-analysis correlate with increased patient survival," Genome Res, 24(5):743-750 (2014).
Brunsvig et al., "Telomerase Peptide Vaccination: A Phase I/II Study in Patients with Non-Small Cell Lung Cancer," Cancer Immunol Immunother, 55(12): 1553-1564 (2006).
Buckwaiter et al., "'It is the antigen(s), stupid' and other lessons from over a decade of vaccitherapy of human cancer," Seminar in Immunology, 20(5):296-300 (2008).

(56) References Cited

OTHER PUBLICATIONS

Burger et al., "Safety and activity of ibrutinib plus rituximab for patients with high-risk chronic lymphocytic leukaemia: a single-arm, phase 2 study," Lancet Oncology, 15(10):1090-1099 (2014).
Cai et al., "Mutated BCR-ABL Generates Immunogenic T-Cell Epitopes in CML Patients," Clinical Cancer Research, 18(20):5761-5772 (2012).
Cai et al., "Peptides Derived From Mutated BCR-ABL Elicit T Cell Immunity In CML Patients," Blood, 116(21): 388-388 (2010).
Carpten et al., "A transforming mutation in the pleckstrin homology domain of AKT1 in cancer," Nature, 448(26):439-444 (2004).
Carter et al., "Identification and validation of cell surface antigens for antibody targeting in oncology," Endocrine-Related Cancer, 11:659-687 (2004).
Caskey et al., "Synthetic double-stranded RNA induces innate immune responses similar to a live viral vaccine in humans," The Journal of experimental medicine, 208(12):2357-2366 (2011).
Castle et al., "Exploiting the mutanome for tumor vaccination," Cancer research, 72(5):1081-1091 (2012).
Certified Priority Document for U.S. Appl. No. 61/334,866, filed May 14, 2010.
Chang et al., "Peptide length-based prediction of peptide-MHC class II binding," Bioinformatics, 22(22): 2761-2767 (2006).
Chatila, "The Regulatory T Cell Transcriptosome: E Pluribus Unum," Immunity, 27(5):693-695 (2007).
Chiari et al., "Two Antigens Recognized by Autologous Cytolytic T Lymphocytes on a Melanoma Result from a Single Point Mutation in an Essential Housekeeping Gene," Cancer Res, 59: 5785-5792 (1999).
Chinese Office Action dated Jun. 12, 2017 in corresponding CN Application No. 2014800322910.
Ciofani et al., "A Validated Regulatory Network for Th17 Cell Specification," Cell, 151(2):289-303 (2012).
Clinical trial NCT 01970358, Patrick Ott, A Phase I Study With a Personalized NeoAntigen Cancer Vaccine in Melanoma, p. 1-6, Retrieved from https://clinicaltrials.gov/ct2/show/NCT01970358 downloaded Jun. 20, 2017.
Coffman et al., "Vaccine Adjuvants: Putting Innate Immunity to Work," Immunity 33:492-503 (2010).
Consolidated Table of Documents filed in Opposition to date in Response to Notices of Opposition of EP2569633 dated Jun. 28, 2017.
Coulie et al., "A mutated intron sequence codes for an antigenic peptide recognized by cytolytic T lymphocytes on a human melanoma," Proc Natl Acad Sci USA, 92(17):7976-7980 (1995).
De Plaen et al., "Immunogenic (tum-) Variants of Mouse Tumor P815: Cloning of the Gene of Tum-Antigen P91A and Identification of the Tum-Mutation," PNAS, 85: 2274-2278 (1988).
Declaration by Stephen Johnston filed during the prosecution of granted U.S. Pat. No. 8,796,414 Nov. 20, 2013.
Declaration of Dr Nir Hacohen on Feb. 16, 2014.
Declaration of Dr. John C. Castle executed on Nov. 9, 2016.
Dengjel et al., "Glycan side chains on naturally presented MHC class II ligands," J. Mass Spectrom, 40:100-104 (2005).
Dermer et al., "Another Anniversary for the War on Cancer," Biotech, 12:320 (1994).
Ding et al., "Genome remodelling in a basal-like breast cancer metastasis and xenograft," Nature, 464:999-1005 (2010).
Dubey et al., "The immunodominant antigen of an ultraviolet-induced regressor tumor is generated by a somatic point mutation in the Dead (Seq Id No. 62) box helicase p68," The Journal of experimental medicine, 185(4):695-705 (1997).
Dudley et al., "Cancer Regression and Autoimmunity in Patients After Clonal Repopulation with Antitumor Lymphocytes," Science, 298: 850-854 (2002).
DuPage et al., "Expression of tumour-specific antigens underlies cancer immunoediting," Nature, 482(7385):405-409 (2012).
Dupuis et al., "Dendritic Cells Internalize Vaccine Adjuvant after Intramuscular Injection," Cell Immunol, 186(1): 18-27 (1998).

Engelhard, "Structure of peptides associated with MHC class I molecules," Curr Opin Immunol, 6(1):13-23 (1994).
Erlich et al., "Next-generation sequencing for HLA typing of class I loci," BMC Genomics, 12:42 (2011).
Estep et al., "Mutation Analysis of BRAF, MEK1 and MEK2 in 15 Ovarian Cancer Cell Lines: Implications for Therapy," PLOS ONE, 12:e1279 (2007).
Extended European Search Report dated Apr. 11, 2016, which issued during prosecution of EP Application No. 15198284.0.
Extended European Search Report received for EP patent application No. EP11781409, dated Apr. 10, 2014.
Extended Search Report in Corresponding European Application No. 11781409.5, dated Apr. 14, 2014.
Extracts from the USPTO patent register.
Ezzell, "Cancer 'Vaccines': An idea whose time has come?," J NIH Res, 7:46 (1995).
Feigner et al., "Lipofection: A Highly Efficient, Lipid-Mediated DNA-Transfection Procedure," PNAS, 84(21): 7413-7417 (1987).
Fransen et al., "Controlled local delivery of CTLA-4 blocking antibody induces CD8+ T-cell-dependent tumor eradication and decreases risk of toxic side effects," Clin Cancer Res, 19(19):5381-5389 (2013).
Fritsch et al., "HLA-Binding Properties of Tumor Neoepitopes in Humans," Cancer Immunol Res, 2(6):522-529 (2014).
Fritsch et al., "Personal neoantigen cancer vaccines: The momentum builds," Oncoimmunology, 3(6):e29311 (2014).
Gabrilovich et al., "IL-12 and Mutant P53 Peptide-Pulsed Dendritic Cells for the Specific Immunotherapy of Cancer," J Immunother Emphasis Tumor Immunol, 19(6): 414-418 (1996).
Garcia-Marco et al., "Frequent Somatic Deletion of the 13q12.3 locus Encompassing BRCA2 in Chronic Lymphocytic Leukemia," Blood, 88:1568-1575 (1996).
Gaucher et al., "Yellow fever vaccine induces integrated multilineage and polyfunctional immune responses," The Journal of experimental medicine, 205(13):3119-3131 (2008).
Giannopoulos et al., "Peptide vaccination elicits leukemia-associated antigen-specific cytotoxic CD8+ T-cell responses in patients with chronic lymphocytic leukemia," Leukemia, 24(4):798-805 (2010).
Gilboa, "The Makings of a Tumor Rejection Antigen," Immunity, 11: 263-270 (1999).
Gnirke et al., "Solution Hybrid Selection with Ultra-Long Oligonucleotides for Massively Parallel Targeted Sequencing," Nat Biotechnol, 27(2): 182-189 (2009).
Gotter et al., "Medullary Epithelial Cells of the Human Thymus Express a Highly Diverse Selection of Tissue-specific Genes Colocalized in Chromosomal Clusters," J Exp Med, 199(2): 155-166 (2004).
Goya et al., "SNVMix:predicting single nucleotide variants from next-generation sequencing of tumors," Bioinformatics, Original Paper, 26(6): 730-736 (2010).
Gros et al., "PD-1 identifies the patient-specific CD8+ tumor-reactive repertoire infiltrating human tumors," The Journal of clinical investigation, 124(5):2246-2259 (2014).
Gubin et al., "Checkpoint blockade cancer immunotherapy targets tumor-specific mutant antigens," Nature, 515:577-581 (2014).
Gueguen et al., "An Antigen Recognized by Autologous CTLs on a Human Bladder Carcinoma," J Immunol, 160(12): 6188-6194 (1998).
Guo et al., "Different length peptides bind to HLA-Aw68 similarity at their ends but bulge on in the middle," Nature, 360:364-366 (1992).
Hacohen et al., "Getting Personal with Neoantigen-Based Therapeutic Cancer Vaccines," Cancer Immunol. Res, 1(1):11-15 (2013).
Herbst et al., "Predictive Correlates of Response to the Anti-PD-L1 Antibody MPDL3280A in Cancer Patients," Nature, 515(7528):563-567 (2014).
Herman et al., "Differences in the Recognition by CTL of Peptides Presented by the HLAB* 4402 and the HLA-B*4403 Molecules Which Differ by a Single Amino Acid," Tissue Antigens, 53: 111-121 (1999).
Hersey et al., "Phase I/II study of treatment with dendritic cell vaccines in patient with disseminated melanoma," Cancer Immunol Immunoother, 53:125-134 (2004).

(56) References Cited

OTHER PUBLICATIONS

Hocker et al., "Ultraviolet Radiation and Melanoma: A Systematic Review and Analysis of Reported Sequence Variants," Hum Mutat, 28(6): 578-588 (2007).
Hodi et al., "Biologic Activity of Cytotoxic T Lymphocyte-Associated Antigen 4 Antibody Blockade in Previously Vaccinated Metastatic Melanoma and Ovarian Carcinoma Patients," PNAS, 100: 4712-4717 (2003).
Hodi et al., "Immunologic and Clinical Effects of Antibody Blockade of Cytotoxic T Lymphocyte-Associated Antigen 4 in Previously Vaccinated Cancer Patients," PNAS, 105: 3005-3010 (2008).
Huang et al., "T Cells Associated With Tumor Regression Recognize Frameshifted Products of the CDKN2A Tumor Suppressor Gene Locus and a Mutated HLA Class I Gene Product," J Immunol, 172(10):6057-6064 (2004).
Humphries et al., "Lineage tracing reveals multipotent stem cells maintain human adenomas and the pattern of clonal expansion in tumor evolution," PNAS, 110(27):e2490-e2499 (2013).
Intellectual Property Policy for Partners-Affiliated Hospitals and Institutions, Aug. 15, 2002.
International Preliminary Report on Patentability for International Application No. PCT/US2011/036665 dated Nov. 20, 2012.
International Preliminary Report on Patentability for International Application No. PCT/US2014/033185 dated Oct. 22, 2015.
International Preliminary Report on Patentability for International Application No. PCT/US2014/067146 dated May 31, 2016.
International Preliminary Report on Patentability for International Application No. PCT/US2014/068746 dated Jun. 7, 2016.
International Preliminary Report on Patentability for International Application No. PCT/US2014/068893 dated Jun. 7, 2016.
International Preliminary Report on Patentability for International Application No. PCT/US2014/071707 dated Jun. 21, 2016.
International Preliminary Report on Patentability for International Application No. PCT/US2015/067143 dated Jun. 20, 2017.
International Search Report and Written Opinion for International Application No. PCT/US/2015/051340 dated Dec. 21, 2015.
International Search Report and Written Opinion for International Application No. PCT/US/2016/033452 dated May 20, 2016.
International Search Report and Written Opinion for International Application No. PCT/US/2016/036605 dated Jan. 16, 2017.
International Search Report and Written Opinion for International Application No. PCT/US2011/036665 dated Jul. 2, 2012.
International Search Report and Written Opinion for International Application No. PCT/US2014/033185 dated Nov. 5, 2014.
International Search Report and Written Opinion for International Application No. PCT/US2014/067146 dated Mar. 31, 2015.
International Search Report and Written Opinion for International Application No. PCT/US2015/067143 dated Apr. 12, 2016.
International Search Report for International Application No. PCT/US2014/068746 dated Mar. 23, 2015.
International Search Report for International Application No. PCT/US2014/068893 dated Apr. 9, 2015.
Invention Agreement of the Dana-Farber Cancer Institute, Jul. 1, 1997.
Japanese Office Action dated Jan. 22, 2018, which issured during prosecution of JP 2016-507587.
Japanese Office Action from Application No. 2013-510360 dated Apr. 28, 2015.
Ji et al., "An immune-active tumor microenvironment favors clinical response to ipilimumab," Cancer Immunol Immunother, 61(7):1019-1031 (2011).
Jocham et al., "Adjuvant Autologous Renal Tumour Cell Vaccine and Risk of Tumour Progression in Patients with Renal-Cell Carcinoma After Radical Nephrectomy: Phase III, Randomised Controlled Trial," Lancet, 363: 594-599 (2004).
Kanduri et al., "Differential genome-wide array-based methylation profiles in prognostic subsets of chronic lymphocytic leukemia," Blood, 115(2):296-305 (2010).
Kannan et al., "Vaccination strategies in follicular lymphoma," Current hematologic malignancy reports, 4(4):189-195 (2009).

Kanzler et al., "Therapeutic Targeting of Innate Immunity with Toll-like Receptor Agonists and Antagonists," Nat Med, 13: 552-559 (2007).
Kawai et al., "TLR signaling," Seminars in immunology, 19(1):24-32 (2007).
Kawakami et al., "Identification of human tumor antigens and its implications for diagnosis and treatment of cancer," Cancer Sci, 95(10): 784-791 (2004).
Keats et al., "Promiscuous Mutations Activate the Noncanonical NF-KB Pathway in Multiple Myeloma," Cancer Cell, 12: 131-144 (2007).
Kenter et al., "Phase I Immunotherapeutic Trial with Long Peptides Spanning the E6 and E7 Sequences of High-Risk Human Papillomavirus 16 in End-Stage Cervical Cancer Patients Show Low Toxicity and Robust Immunogenicity," Clin. Cancer Research, 14(1):169-177 (2008).
Kenter et al., "Vaccination against HPV-16 oncoproteins for vulvar intraepithelial neoplasia," New England Journal of Medicine, 361(19):1838-1847 (2009).
Keogh et al., "Identification of New Epitopes from Four Different Tumor-Associated Antigens: Recognition of Naturally Processed Epitopes Correlates with HLA-A☐0201-Binding Affinity," J Immunol, 167:787-796 (2001).
Kessler et al., "Identification of T-cell epitopes for cancer immunotherapy," Leukemia, 21:1859-1874 (2007).
Khalili et al., "In silico prediction of tumor antigens derived from functional missense mutations of the cancer gene census," Oncoimmunology, 1(8):1281-1289 (2012).
Klebanoff et al., "Therapeutic cancer vaccines:are we there yet?," Immunol Rev, 239(1):27-44 (2011).
Koh et al., "Immunological consequences of using three different clinical/laboratory techniques of emulsifying peptide-based vaccines in incomplete Freund's adjuvant," J Translational Med, 4:42 (2006).
Komarova et al., "Evolution of Ibrutinib Resistance in Chronic Lymphcytic Leukemia (CLL)," Proceedings of the National Academy of Sciences, 111(38):13906-13911 (2014).
Kornher et al., "Mutation Detection Using Nucleotide Analogs That Alter Electrophoretic Mobility," Nucleic Acids Res, 17(19): 7779-7784 (1989).
Kronenberger et al., "A Polyvalent Cellular Vaccine Induces T-cell Responses Against Specific Self-antigens Overexpressed in Chronic Lymphocytic B-cell Leukemia," J Immunother, 31(8): 723-730 (2008).
Kuppuswamy et al., "Single Nucleotide Primer Extension to Detect Genetic Diseases: Experimental Application to Hemophilia B (Factor IX) and Cystic Fibrosis Genes," PNAS, 88(4): 1143-1147 (1991).
Ladetto et al., "Real-Time Polymerase Chain Reaction in Multiple Myeloma: Quantitative Analysis of Tumor Contamination of Stem Cell Harvests," Exp Hematol, 30: 529-536 (2002).
Landau et al., "Chronic lymphocytic leukemia: molecular heterogeneity revealed by high-throughput genomics," Genome Med, 5:47 (2013).
Landau et al., "Evolution and Impact of Subclonal Mutations in Chronic Lymphocytic Leukemia," Cell, 152:714-726 (2013).
Landau et al., "Increased Local Disorder of DNA Methylation Forms the Basis of High Intra-Leukemic Epigenetic Heterogeneity and Enhances CLL Evolution," Blood, 122:596 (2013).
Le et al., "Evaluation of Ipilimumab in combination with allogeneic pancreatic tumor cells transfected with a GM-CSF gene in previously treated pancreatic cancer," J Immunother, 36(7):382-389 (2013).
Leffers et al., "Immunization with a P53 synthetic long peptide vaccine induces P53☐specific immune responses in ovarian cancer patients, a phase II trial," Int J Cancer, 125(9):2104-2113 (2009).
Leffers et al., "Long☐term clinical and immunological effects of p53☐SLP® vaccine in patients with ovarian cancer," Int J Cancer, 130(1):105-112 (2012).
Lemmel et al., "Differential quantitative analysis of MHC ligands by mass spectrometry using stable isotope labeling," Nature Biotechnology, 22(4):450-454 (2004).

(56) References Cited

OTHER PUBLICATIONS

Lennerz et al., "The Response of Autologous T Cells to a Human Melanoma is Dominated by Mutated Neoantigens," PNAS, 102(44):16013-10618 (2005).
Letter from Mathys & Squire dated Jun. 28, 2017 accompanying Response to Notices of Opposition of EP2569633.
Letter from Mathys & Squire dated Jun. 29, 2017+B245:B256.
Lewin et al., "DNA is the Genetic Material: Mutations Change the Sequence of DNA," Genes IV, 4:68-69 (1990).
Ley et al., "DNA sequencing of a cytogenetically normal acute myeloid leukaemia genome," Nature, 456: 66-72 (2008).
Ley et al., "DNMT3A Mutations in Acute Myeloid Leukemia", The New England Journal of Medicine, 363: 2423-2433 (2010).
Li et al., "Cancer Genome Sequencing and Its Implications for Personalized Cancer Vaccines," Cancers 3(4):4191-4211 (2011).
Lin et al., "Evaluation of MHC-II Peptide Binding Prediction Servers: Applications for Vaccine Research," BMC Bioinformatics, 9: S22 (2008).
Linard et al., "A ras-Mutated Peptide Targeted by CTL Infiltrating a Human Melanoma Lesion," J Immunol, 168:4802-4808 (2002).
Linnemann et al., "High-throughput identification of antigen-specific TCRs by TCR gene capture," Nat Med, 19(11):1534-1541 (2013).
Liu et al., "Athlates:accurate typing of human leukocyte antigen through exome sequencing," Nucleic Acids Res, 41(14):e142 (2013).
Lundegaard et al., "NetMHC-3.0: accurate web accessible predictions of human, mouse and monkey MHC class I affinities for peptides of length 8-11," Nucleic Acids Research, 36: W509.W512 (2008).
Lundegaard et al., "Prediction of epitopes using neural network based methods," J Immunol Methods, 374(1-2):26-34 (2011).
Lundegaard et al., "State of the art and challenges in sequence based T-cell epitope prediction," Immunome Research, 6(Suppl 2): S3 (2010).
Macconaill et al., Profiling Critical Cancer Gene Mutations in Clinical Tumor Samples, PLoS One, 4(11):e7887 (2009).
Machiels et al., "Peptide-Based Cancer Vaccines," Seminars in Oncology, 29(5):494-502 (2002).
Maeurer et al., "New treatment options for patients with melanoma: review of melanoma-derived T-cell epitopebased peptide vaccines," Melanom Research, 6:11-24 (1996).
Maker et al., "Intrapatient Dose Escalation of Anti-CTLA-4 Antibody in Patients With Metastatic Melanoma," J Immunother, 29: 455-463 (1997).
Malavota et al., "Interpretation of the dissolution of insoluble peptide sequences based on the acid☐base properties of the solvent," Protein Sci, 15(6):1476-1488 (2006).
Malcikova et al., "Identification of somatic hypermutations in the TP53 gene in B-cell chronic lymphocytic leukemia," Molecular Immunol, 45(5):1525-1529 (2008).
Mandruzzato et al., "A CASP-8 Mutation Recognized by Cytolytic T Lymphocytes on a Human Head and Neck Carcinoma," J Exp Med, 186: 785-793 (1997).
Mannino et al., "Liposome Mediated Gene Transfer," Biotechniques, 6(7): 682-690 (1988).
Marabelle et al., "Depleting tumor-specific Tregs at a single site eradicates disseminated tumors," J Clin Invest, 1123(6):2447-2463(2013).
Mardis et al., "Cancer genome sequencing: a review," Human Molecular Genetics, 18(2): R163-R168 (2009).
Mardis et al., "Recurring Mutations Found by Sequencing an Acute Myeloid Leukemia Genome," New Engl J Med, 361:1058-1066 (2009).
Margulies et al., "Genome Sequencing in Open Microfabricated High Density Picoliter Reactors," Nature, 15:437(7057): 376-380 (2005).
Marijt et al., "Hematopoiesis-Restricted Minor Histocompatibility Antigens HA-1- or HA -2-specific T Cells can Induce Complete Remissions of Relapsed Leukemia," PNAS, 100: 2742-2747 (2003).

Marina et al., "Serologic Markers of Effective Tumor Immunity Against Chronic Lymphocytic Leukemia Include Nonmutated B-Cell Antigens," Cancer Res, 70(4): 1344-1355 (2010).
Matsushita et al., "Cancer Exome Analysis Reveals a T Cell Dependent Mechanism of Cancer Immunoediting," Nature, 482(7385):400-404 (2012).
McDermott et al., "Immune Therapy for Kidney Cancer: A Second Dawn?," Semin Oncol, 40(4):492-498 (2013).
Men et al., "Assessment of Immunogenicity of Human Melan-A Peptide Analogues in HLA-A*0201/Kb Transgenic Mice," J Immunol, 162:3566-3573 (1999).
Meyerson et al., "Advances in understanding cancer genomes through second-generation sequencing," Nat Rev Genetics, 11:685-696 (2010).
Morton et al., "Prolonged Survival of Patients Receiving Active Immunotherapy With Canvaxin Therapeutic Polyvalent Vaccine After Complete Resection of Melanoma Metastatic to Regional Lymph Nodes," Ann Surg, 236(4):438-448 (2002).
Mullally et al., "Beyond HLA: The Significance of Genomic Variation for Allogeneic Hematopoietic Stem Cell Transplantation," Blood, 109:1355-1362 (2007).
Murphy et al., "Antigen Presentation to T Lymphocytes," Janeway's Immunobiology, 7th Edition, 5:182-83 & 197 (2008).
Murphy et al., "Phase I Clinical Trial: T-Cell Therapy for Prostate Cancer Using Autologous Dendritic Cells Pulsed with HLA-A0201-Specific Peptides from Prostate-Specific Membrane Antigen," Prostate, 29(6): 371-380 (1996).
Notice of Opposition to European Patent No. EP2569633-Agenus Inc. (Opponent) dated Nov. 9, 2016.
Notice of Opposition to European Patent No. EP2569633-Dr. Christian Muller (Opponent) dated Nov. 9, 2016.
Notice of Opposition to European Patent No. EP2569633-Gritstone Oncology, Inc. (Opponent) dated Nov. 9, 2016.
Notice of Opposition to European Patent No. EP2569633-James Poole Limited (Opponent) dated Nov. 9, 2016.
Notice of Opposition to European Patent No. EP2569633-Strawman Limited (Opponent) dated Nov. 10, 2016.
Novellino et al., "A listing of human tumor antigens recognized by T cells: Mar. 2004 update," Cancer Immunol Immunother, 54(3):187-207 (2005).
Nyren et al., "Solid Phase DNA Minisequencing by an Enzymatic Luminometric Inorganic Pyrophosphate Detection Assay," Anal Biochem, 208(1): 171-175 (1993).
O'Shea et al., "Signal transduction and Th17 cell differentiation," Microbes Infect, 11(5):599-611 (2009).
Oakes et al., "Evolution of DNA Methylation Is Linked to Genetic Aberrations in Chronic Lymphocytic Leukemia," Cancer Discov, 4(3):348-361 (2014).
Oakes et al., "Heterogeneity and Evolution of DNA Methylation in Chronic Lymphocytic Leukemia," Blood, 122(21):1626 (2013).
Ofran et al., "Identification of Human Minor Histocompatibility Antigens (MHA) by Combining Bioinformatic Prediction of Peptide Epitopes with Validation of T Cell Reactivity in Patient Blood Samples after Allogeneic Hematopoietic Stem Cell Transplantation," Biol Bone Marrow Transplant, 14:1 (Abstract #2) (2008).
Okada et al., "Induction of CD8+ T-Cell Responses Against Novel Glioma-Associated Antigen Peptides and Clinical Activity by Vaccinations With α-Type 1 Polarized Dendritic Cells and Polyinosinic-Polycytidylic Acid Stabilized by Lysine and Carboxymethylcellulose in Patients With Recurrent Malignant Glioma," J Clin Oncol, 29(3):330-336 (2011).
Opavsky et al., CpG Island Methylation in a Mouse Model of Lymphoma Is Driven by the Genetic Configuration of Tumor Cells, PLOS Genetics, 3(9):e167 (2007).
Opposition Letter—Agenus Inc. (Opponent) in European Patent 2569633, dated Nov. 9, 2016.
Opposition Letter—Dr. Christian Muller (Opponent) in European Patent No. 2569633, dated Nov. 9, 2016.
Opposition Letter—Gritstone Oncology Inc. (Opponent) in European Application No. 11781409.5 dated Nov. 7, 2016.
Opposition Letter—James Poole Limited (Opponent) in European Patent No. 2569633, dated Nov. 9, 2016.

(56) References Cited

OTHER PUBLICATIONS

Opposition Letter—Strawman Limited (Opponent) in European Patent No. 2569633 dated Nov. 10, 2016.
Ott et al., "An Immunogenic personal neoantigen vaccine for patients with melanoma," Nature, 547:217-221 (2017).
Ott et al., "CTLA-4 and PD-1/PD-L1 Blockade: New Immunotherapeutic Modalities with Durable Clinical Benefit in Melanoma Patients," Clin Cancer Res, 19(19):5300-5309 (2013).
Ott et al., "Vaccines and Melanoma," Hematol Oncol Clin N Am, 28(3):559-569 (2014).
Screenshot Patent Assignment Abstract of Title of U.S. Appl. No. 13/108,610, filed May 16, 2011.
Pan et al., "Epigenomic Evaluation in diffuse Large B-Cell Lymphomas," Blood, Nov. 15, 2013, 122(21) XP55174946.
Parker et al., "Scheme for Ranking Potential HLA-A2 Binding Peptides Based on Independent Binding of Individual Peptide Side-Chains," J Immunol, 152(1): 163-175 (1994).
Parkhurst et al., "Improved induction of melanoma-reactive CTL with peptides from the melanoma antigen gp100 modified at HLA-A*0201-binding residues", The Journal of Immunology, 157: 2539-2548 (1996).
Parmiani et al., "Unique Human Tumor Antigens: Immunobiology and Use in Clinical Trials," J Immunol, 178: 1975-1979 (2007).
Pasmant et al., "Characterization of a Germ-Line Deletion, Including the Entire INK4/ARF Locus, in a Melanoma-Neural System Tumor Family: Identification of ANRIL, an Antisense Noncoding RNA Whose Expression Coclusters with ARF," Cancer Res, 67(8):3963-3969 (2007).
Peters et al., "The Immune Epitope Database and Analysis Resource: From Vision to Blueprint," PLoS Biol, 3(3): e91 (2005).
Peters et al., "The many faces of TH-17 Cells," Curr Opin Immunol, 23(6):702-706 (2011).
Phan et al., "Cancer regression and autoimmunity induced by cytotoxic T lymphocyte-associated antigen 4 blockade in patients with metastatic melanoma," PNAS, 100(14):8372-8377 (2003).
Pilla et al., "Multipeptide vaccination in cancer patient," Expert Opin Biol Ther, 9(8):1043-1055 (2009).
Piros et al., "Market Opportunity for Molecular Diagnostics in Personalized Cancer Therapy," Handbook of Clinical Nanomedicine: Law, Business, Regulation, Safety and Risk, Chapter 14: 1-29 (2016).
Pleasance et al., "A comprehensive catalogue of somatic mutations from a human cancer genome," Nature, 463:191-196 (2010).
Pleasance et al., "A small-cell lung cancer genome with complex signatures of tobacco exposure," Nature, 463: 184-190 (2010).
Policy Reallocating Ownership of Intellectual Property Covered by the Intellectual Property Policy, Sep. 18, 2002.
Prezant et al., "Trapped-Oligonucleotide Nucleotide Incorporation (TONI) Assay, a Simple Method for Screening Point Mutations," Hum Mutat, 1(2): 159-164 (1992).
Provan et al., "Eradication of Polymerase Chain Reaction-Detectable Chronic Lymphocytic Leukemia Cells is Associated with Improved Outcome After Bone Marrow Transplantation," Blood, 88: 2228-2235 (1996).
Assignment Data Screenshot of U.S. Appl. No. 61/334,866, filed May 14, 2010.
Quezada et al.,"CTLA4 blockade and GM-CSF combination immunotherapy alters the intratumor balance of effector and regulatory T cells," J Clin Invest, 116(7):1935-1945 (2006).
Rajasagi et al., "Systematic identification of personal tumor-specific neoantigens in chronic lymphocytic leukemia," Blood, 124(3): 453 (2014).
Rammensee et al., "Cancer Vaccines: Some Basic Considerations," Genomic and Personalized Medicine, 5:573-589 (2009).
Rammensee et al., "MHC ligands and peptide motifs: first listing," Immunogenetics, 41:178 (1995).
Rammensee et al., "SYFPEITHI: Database for MHC Ligands and Peptide Motifs," Immunogenetics, 50(3-4): 213-219 (1999).
Rammensee et al., "Towards Patient-Specific Tumor Antigen Selection for Vaccination," Immunological Reviews, Blackwell Publishing Munksgaard, 188:164-176 (2002).
Reifenberger et al., "Frequent Alterations of Ras Signaling Pathway Genes in Sporadic Malignant Melanomas," Int J Cancer, 109: 377-384 (2004).
Response to Notices of Opposition of EP2569633, dated Jun. 28, 2017.
Ressing et al., "Human CTL epitopes encoded by human papillomavirus type 16 E6 and E7 identified through in vivo and in vitro immunogenicity studies of HLA-A*0201-binding peptides.," J Immunol, 154(11):5934-5943 (1995).
Ribas et al., "Antitumor Activity in Melanoma and Anti-Self Responses in a Phase I Trial with the Anti-Cytotoxic T Lymphocyte-Associated Antigen 4 Monoclonal Antibody CP-675,206," J Clin Oncol, 23(35): 8968-8977 (2005).
Richter et al., "Mechanistic Determinants of Biotherapeutics Absorption Following SC Administration," The AAPS Journal, 14(3):559-568 (2012).
Rifenberger et al., "Frequent Alterations of Ras Signaling Pathway Genes in Sporadic Malignant Melanomas," Int J Cancer, 109:377-384 (2004).
Rini et al., "Biology and Treatment of Advanced Renal Cell Carcinoma: A Global Perspective," Semin Oncol, 40(4):419-420 (2013).
Rizvi et al., "Mutational landscape determines sensitivity to PD-1 blockade in non-small cell lung cancer," Science, 348(6230):124-128 (2015).
Robbins et al., "A mutated beta-catenin gene encodes a melanoma-specific antigen recognized by tumor infiltrating lymphocytes," J Exp Med, 183(3):1185-1192 (1996).
Robbins et al., "Mining exomic sequencing data to identify mutated antigens recognized by adoptively transferred tumor-reactive T cells," Nat Med, 19(6):747-752 (2013).
Robinson et al., "A phase I-II trial of multiple-dose polyriboinosic-polyribocytidylic acid in patieonts with leukemia or solid tumors," J Natl Cancer Inst, 57(3):599-602 (1976).
Rondon et al., "Graft-versus-Leukemia Effect After Allogeneic Bone Marrow Transplantation for Chronic Lymphocytic Leukemia," Bone Marrow Transplant, 18: 669-672 (1996).
Rooney et al., "Molecular and Genetic Properties of Tumors Associated with Local Immune Cytolytic Activity," Cell, 160(1-2):48-61 (2015).
Rosenberg et al., "Adoptive cell transfer as personalized immunotherapy for human cancer," Science, 348(6230):62-68 (2015).
Rosenberg et al., "Cancer Immunotherapy: Moving Beyond Current Vaccines," Nat Med, 10: 909-915 (2004).
Rubinfeld et al., "Stabilization of Beta-Catenin by Genetic Defects in Melanoma Cell Lines," Science, 275(5307):1790-1792 (1997).
Sabbatini et al., "Phase I trial of overlapping long peptides from a tumor self-antigen and Poly-ICLC shows rapid induction of integrated immune response in ovarian cancer patients," Clin Cancer Res, 18:6497-6508 (2012).
Salem et al., "Defining the Antigen-Specific T-Cell Response to Vaccination and Poly(I:C)/TLR3 Signaling: Evidence of Enhanced Primary and Memory CD8 T-Cell Responses and Antitumor Immunity," J Immunother, 28(3):220-228 (2005).
Sampson et al., "An epidermal growth receptor variant III-targeted vaccine is safe and immunogenic in patients with glioblastomas multiforme," Mol Cancer Ther, 8(10):2773-2779 (2009).
Sampson et al., "Greater chemotherapy-induced lymphopenia enhances tumor-specific immune responses that eliminate EGFRvIII-expressing tumor cells in patients with glioblastoma," Neuro-Oncology, 13(3):324-333 (2011).
Sampson et al., "Immunologic Escape After Prolonged Progression-Free Survival With Epidermal Growth Factor Receptor Variant III Peptide Vaccination in Patients With Newly Diagnosed Glioblastoma," J Clin Oncol, 28(31):4722-4729 (2010).
Sanderson et al., "Autoimmunity in a Phase I Trial of a Fully Human Anti-Cytotoxic T-Lymphocyte Antigen-4 Monoclonal Antibody With Multiple Melanoma Peptides and Montanide ISA 51 for Patients With Resected Stages III and IV Melanoma," J Clin Oncol, 23(4):741-750 (2005).

(56) References Cited

OTHER PUBLICATIONS

Saterdal et al., "Frameshift-mutation-derived peptides as tumor-specific antigens in inherited and spontaneous colorectal cancer," Proceedings of the National Academy of Sciences 98(23): 13255-13260 (2001).
Sato et al., "Intraepithelial CD8+ tumor-infiltrating lymphocytes and a high CD8+/regulatory T cell ratio are associated with favorable prognosis in ovarian cancer," PNAS, 102(51):1838-18543 (2005).
Schaffner et al., "Somatic ATM Mutations Indicate a Pathogenic Role of ATM in B-Cell Chronic Lymphocytic Leukemia," Blood, 94: 748-753 (1999).
Scheibenbogen et al., "Analysis of the T Cell Response To Tumor and Viral Peptide Antigens by an IFNy-ELISPOT assay," Int. J. Cancer, 71:932-936 (1997).
Schietinger et al., "Specificity in cancer immunotherapy," Semin. Immunol, 20(5)276-285 (2008).
Schuh et al., "Monitoring chronic lymphocytic leukemia progression by whole genome sequencing reveals heterogeneous clonal evolution patterns," Blood, 120(20):4191-4196 (2012).
Schuster et al., "Vaccination With Patient-Specific Tumor-Derived Antigen in First Remission Improves Disease-Free Survival in Follicular Lymphoma," J Clin Oncol, 29(20):2787-2794 (2011).
Schwitalle et al., "Immunogenic peptides generated by frameshift mutations in DNA mismatch repair-deficient cancer cells," Cancer Immunity, 4(1):14 (2004).
Segal et al., "Epitope Landscape in Breast and Colorectal Cancer," Cancer Res, 68: 889-892 (2008).
Sensi et al., "Unique Tumor Antigenesis: Evidence for Immune Control of Genome Integrity and Immunogenic for T Cell-Mediated Patient-Specific Immunotherapy," Clin Cancer Res, 12(7): :5023-5032 (2006).
Sette et al., "Peptide binding to the most frequent HLA-A class I alleles measured by quantitative molecular binding assays," Molecular Immunology, 31 (11): 813-822 (1994).
Sette et al., "The relationship between class I binding affinity and immunogenicity of potential cytotoxic T cell epitopes," The Journal of Immunology, 153: 5586-5592 (1994).
Shames et al., "A Genome-Wide Screen for Promoter Methylation in Lung Cancer Identifies Novel Methylation Markers for Multiple Malignancies," PLOS Med, 3(12):e486 (2006).
Sharma et al., "Novel cancer immunotherapy agents with survival benefit: recent successes and next steps," Nat Rev Cancer, 11(11):805-812 (2011).
Shastri et al., "Presentation of endogenous peptide/MHC class I complexes is profoundly influenced by specific C-terminal flanking residues," J Immunol, 155:4339 (1995).
Shukla et al., "Topics in Cancer Genomics," Graduate Theses and Dissertations, Paper 13796 (2014). [accessed online] https://search.proquest.com/docview/1558874754.
Sidney et al., "Measurement of MHC/Peptide Interactions by Gel Filtration or Monoclonal Antibody Capture," Curr Protoc Immunol: 18.3.1-18.3.36 (2013).
Siegmund et al., "Inferring clonal expansion and cancer stem cell dynamics from DNA methylation patterns in colorectal cancers," PNAS, 106(12):4828-4833 (2009).
Simmons et al., "Local secretion of anti-CTLA-4 enhances the therapeutic efficacy of a cancer immunotherapy with reduced evidence of systemic autoimmunity," Cancer Immunol Immunother, 57(8):1263-1270 (2008).
Simpson et al., "Fc-dependent depletion of tumor-infiltrating regulatory T cells co-defines the efficacy of anti-CTLA-4 therapy against melanoma," J Exp Med, 210(9):1695-1710 (2013).
Slingluff et al., "Randomized Multicenter Trial ofthe Effects of Melanoma-Associated Helper Peptides and Cyclophosphamide on the Immunogenicity of a Multipeptide Melanoma Vaccine," J Clin Oncol, 29(21):2924-2932 (2011).
Snyder et al., "Genetic Basis for Clinical Response to CTLA-4 Blockade in Melanoma," New Engl J Med, 371 (23):2189-2199 (2014).

Snyder et al., "Immunogenic peptide discovery in cancer genomes," Cuff Opin Genet Dev, 30:7-16 (2015).
Soares et al. "A subset of dendritic cells induces CD4+ T cells to produce IFN-gamma by an IL-12-independent but CD70-dependent mechanism in vivo," J Exp Med, 2215(11):1095-1106 (2007).
Soiffer et al., "Vaccination with irradiated autologous melanoma cells engineered to secrete human granulocyte-macrophage colony-stimulating factor generates potent antitumor immunity in patients with metastatic melanoma," PNAS, 95(22):13141-13146 (1998).
Soiffer et al., "Vaccination With Irradiated, Autologous Melanoma Cells Engineered to Secrete Granulocyte-Macrophage Colony-Stimulating Factor by Adenoviral-Mediated Gene Transfer Augments Antitumor Immunity in Patients With Metastatic Melanoma," J Clin Oncol, 21(17):3343-3350 (2003).
Sokolov., "Primer Extension Technique for the Detection of Single Nucleotide in Genomic DNA," Nucleic Acids Res. 18(12): 3671 (1990).
Speetjens et al., "Induction of p53-Specific Immunity by a p53 Synthetic Long Peptide Vaccine in Patients Treated for Metastatic Colorectal Cancer," Clin Cancer Res, 15(3):1086-1095 (2009).
Spitler, "Cancer Vaccines: The Interferon Analogy," Cancer Biother, 10:1-3 (1995).
Srivastava et al., "Modeling the Repertoire of True Tumor-Specific MHC I Epitopes in a Human Tumor," Plos One, 4(7):e6094 (2009).
Srivastava, "Therapeutic Cancer Vaccines," Curr Opin Immunol, 18: 201-205 (2006).
Stahl-Hennig et al., "Synthetic double-stranded RNAs are adjuvants for the induction of T helper 1 and humoral immune responses to human papillomavirus in rhesus macaques," PLoS pathogens, 5(4):e1000373 (2009).
Stankovic et al., "Microarray Analysis Reveals that TP53- and ATM-Mutant B-CLLs Share a Defect in Activating Proapoptotic Responses after DNA Damage but are Distinguished byMajor Differences in Activating Prosurvival Responses," Blood, 103: 291-300 (2004).
Stover et al., "New Use of BCG for Recombinant Vaccines," Nature, 351 (6326): 456-460 (1991).
Stratton et al., "The Cancer Genome," Nature, 458(7239):719-724 (2009).
Su et al., "Immunological and Clinical Responses in Metastatic Renal Cancer Patients Vaccinated with Tumor RNA-Transfected Dendritic Cells," Cancer Res, 63: 2127-2133 (2003).
Submission in opposition proceedings of EP 2569633, dated Jun. 28, 2017.
Syvanen et al., "A Primer-Guided Nucleotide Incorporatiopn Assay in the Genotyping of Apolipoprotein E," Genomics, 8(4): 684-692 (1990).
Syvanen et al., "Identification of Individuals by Analysis of Biallelic DNA Markers, Using PCR and Solid-Phase Minisequencing," Am J Hum Genet, 52(1): 46-59 (1993).
Table S4 Somatic mutations Identified in Breast or Colorectal Cancers filed on Nov. 7, 2016 in Notice of Opposition by Gritstone Oncology Inc. to EP 2569633.
Table S5 Breast CAN-genes, filed on Nov. 7, 2016, in Notice of Opposition by Gritstone Oncology Inc., to EP Patent No. 2569633.
Table S6 Colorectal CAN-genes, filed on Nov. 7, 2016 in Notice of Opposition by Gritstone Oncology Inc, to EP Patent No. 2569633.
Testori et al., "Phase III comparison of vitespen, an autologous tumor-derived heat shock protein gp96 peptide complex vaccine, with physician's choice of treatment for stage IV melanoma: the C-100-21 Study Group," J Clin Oncol, 26(6):955-962 (2008).
Thomas et al., "High-Throughput Oncogene Mutation Profiling in Human Cancer," Nat Genet, 39: 347-351 (2007).
Thompson et al., "Aberrations ofthe B-Cell Receptor B29 (CD79b) Gene in Chronic Lymphocytic Leukemia," Blood, 90(4):1387-1394 (1997).
Thornton et al., "Characterisation of TP53 Abnormalities in Chronic Lymphocytic Leukaemia," Hematol J, 5: 47-54 (2004).
Timmerman et al., "Idiotype-Pulsed Dendritic Cell Vaccination for B-Cell Lymphoma: Clinical and Immune Responses in 35 Patients," Blood, 99: 1517-1526 (2002).

(56) References Cited

OTHER PUBLICATIONS

Tjoa et al., "Follow-Up Evaluation of Prostate Cancer Patients Infused with Autologous Dendritic Cells Pulsed with PSMA Peptides," Prostate, 32(4): 272-278 (1997).
Tong et al., "Methods and protocols for prediction of immunogenic epitopes", Briefings In Bioinformatics, 8(2): 96-108 (2008).
Topalian et al., "Safety, Activity, and Immune Correlates of Anti-PD-1 Antibody in Cancer," N Engl J Med, 366(26):2443-2454 (2012).
Topalian et al., "Survival, Durable Tumor Remission, and Long-Term Safety in Patients With Advanced Melanoma Receiving Nivolumab," J Clin Oncol, 32(10):1020-1030 (2014).
Tough et al., "Induction of bystander T cell proliferation by viruses and type I interferon in vivo," Science, 272(5270):1947-1950 (1996).
Tourdot et al., "A general strategy to enhance immunogenicity of low-affinity HLA-A2.1-associated peptides: implication in the identificatiioonn of cryptic tumor epitopes," Eur. J. Immunol, 30:3411-3421 (2000).
Toze et al., "Myeloablative Allografting for Chronic Lymphocytic Leukemia: Evidence for Potent Graft-versus-Leukemia Effect Associated with Graft-versus-Host Disease," Bone Marrow Transplant, 36: 825-830 (2005).
Tran et al., "Cancer Immunotherapy Based on Mutation-Specific CD4+ T Cells in a Patient with Epithelial Cancer," Science, 344(6184):641-645 (2014).
Trumpfheller et al., "Intensified and protective CD4+ T cell immunity in mice with anti-dendritic cell HIV gag fusion antibody vaccine," J Exp Med, 203(3):607-617 (2006).
Trumpfheller et al., "The microbial mimic poly IC induces durable and protective CD4+ T cell immunity together with a dendritic cell targeted vaccine," PNAS, 105(7):2574-2579 (2008).
Tumeh et al., "PD-1 blockade induces responses by inhibiting adaptive immune resistance," Nature, 515(7528):568-571 (2014).
U.S. Final Office Action dated May 25, 2017 and issued in U.S. Appl. No. 15/187,174.
U.S. Final Rejection dated Sep. 13, 2017 and issued in U. S. U.S. Appl. No. 14/794,449.
U.S. Non-Final Office Action dated Jan. 22, 2018 and issued in U.S. Appl. No. 15/187,174.
U.S. Non-Final Office Action dated Dec. 5, 2016 and issued in U.S. Appl. No. 15/187,174.
U.S. Non-Final Office Action dated Dec. 29, 2016 and issued in U.S. Appl. No. 14/794,449.
Ueda et al., "Germ Line and Somatic Mutations of BRAF V599E in Ovarian Carcinoma," Int J Gynecol Cancer, 17: 794-797 (2007).
Ugozzoli et al., "Detection of Specific Alleles by Using Allele-Specific Primer Extension Followed by Capture on Solid Support," Genet Anal Tech AppL, 9(4): 107-112 (1992).
UniProtKB Printouts- Q5SW79 filed on Nov. 2016 in Muller Opposition to EP 2569633.
Vaishampayan et al., "Active immunotherapy of metastatic melanoma with allogeneic melanoma lysates and interferon alpha," Clin Cancer Res, 8(12):3696-3701 (2002).
Van de Roemer et al., "P1737:IVAC: Individualized vaccines for cancer," Immunology 137(SuppL 1):715, Sep. 2012.
Van Den Broeke et al., "Identification and Eiptope Enhancement of a PAX-FKHR Fusion Protein Breakpoint Epitope in Alveolar Rhabdomyosarcoma Cells Created by a Tumorigenic Chromosomal Translocation Inducing CTL Capable of Lysing Human Tumors," American Association for Cancer Research, 66(3):1818-1823 (2006).
Van der Bruggen et al., "A Gene Encoding an Antigen Recognized by Cytolytic T Lymphocytes on a Human Melanoma," Science, 254:1643-1647 (1991).
Van Elsas et al., "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation," Journal of Experimental Medicine, 190(3):355-366 (1999).
Van Pel et al., "Tumor Cell Variants Obtained by a Mutageneis of a Lewis Lung Carcinoma Cell Line: Immune Rejection by Syngeneic Mice," PNAS, 76(10): 5282-5285 (1979).
Van Poelgeest et al., "HPV16 synthetic long peptide (HPV16-SLP) vaccination therapy of patients with advanced or recurrent HPV16-induced gynecological carcinoma, a phase II trial," J Transl Med, 11:88 (2013).
Van Rooij et al., "Tumor Exome Analysis Reveals Neoantigen-Specific T-Cell Reactivity in an 1pilimumab-Responsive Melanoma," Journal of Clinical Oncology, 31(32):e439-e442 (2013).
Van Trappen et al., "Somatic Mitochondrial DNA Mutations in Primary and Metastatic Ovarian Cancer," Gynecol Oncol, 104: 129-133 (2007).
Verhoef et al., "Des-enkephalin-γ-endorphin (DEγE): Biotransformation in rat, dog and human plasma," Eur J Drug Metab Ph, 11(4):291-302 (1986).
Vermeij et al., "Potentiation of a p53-SLP vaccine by cyclophosphamide in ovarian cancer: a single-arm phase II study," Int J Cancer, 131(5):E670-680 (2012).
Vogelstein et al., "Cancer Genome Landscapes," Science, 339(6127): 1546-1558 (2013).
Volpe et al., "Alternative BCR/ABL Splice Variants in Philadelphia Chromosome-Positive Leukemias Result in Novel Tumor-Specific Fusion Proteins that May Represent Potential Targets for Immunotherapy Approaches," Cancer Res, 67(11):5300-5307 (2007).
Walter et al., "DNA Methylation Profiling Defines Clinically Relevant Biological Subsets of Non-small Cell Lung Cancer," Clin Cancer Res, 18(8):2360-2373 (2012).
Wang, "Tumor Antigens Discovery: Perspectives for Cancer Therapy", Molecular Medicine, 3(11): 716-731 (1997).
Weinschenk et al., "Integrated Functional Genomics Approach for the Design of Patientindividual Antitumor Vaccines," Cancer Res, 62: 5818-5827 (2002).
Welters et al., "Induction of tumor-specific CD4+ and CD8+ T-cell immunity in cervical cancer patients by a human papillomavirus type 16 E6 and E7 long peptides vaccine," Clinical cancer research, 14(1):178-187 (2008).
Welters et al., "Success or failure of vaccination for HPV16-positive vulvar lesions correlates with kinetics and phenotype of induced T-cell responses," PNAS, 107(26):11895-11899 (2010).
Willmore-Payne et al., "Human Malignant Melanoma: Detectection of BRAF- and c-kit-Activating Mutations by High-Resolution Amplicon Melting Analysis," Hum Pathol, 36: 486-493 (2005).
Wolchok et al., "Nivolumab plus ipilimumab in advanced melanoma," N Engl J Med, 369(2):122-133 (2013).
Wolfel et al., "A p16INK4a-insensitive CDK4 mutant targeted by cytolytic T lymphocytes in a human melanoma," Science, 269(5228):1281-1284 (1995).
Wolff et al., "Direct Gene Transfer into Mouse Muslce in Vivo," Science, 247(4949):1465-1468 (1990).
Wood et al., "The Genomic Landscapes of Human Breast and Colorectal Cancers," Science, 318:1108-1113 (2007).
Woodbury et al., "Introduction to Macromolecular Binding Equilibria," CRC Press, 13:978 (2007).
Wu et al., "Detection of a potent humoral response asscoiated with immune-induced remission of chronic myelogenous leukemia," J Clin Invest, 106(5):705-714 (2000).
Wu et al., "Graft-versus-Leukemia Target Antigens in Chronic Myelogenous Leukemia Are Expressed on Myeloid Progenitor Cells," Clin Cancer Res, 11(12):4504-4511 (2005).
Wu et al., "Induction of Tumor Immunity Following Allogeneic Stem Cell Transplantation," Adv Immunol, 90:133-173 (2006).
Wu et al., "Mouse Model of Human Ovarian Endometrioid Adenocarcinoma Based on Somatic Defects in the Wnt/6-Catenin and PI3K/Pten Signaling Pathways," Cancer Cell, 11: 321-333 (2007).
Wu et al., "Reconstitution of T-Cell Receptor Repertoire Diversity Following T-Cell Depleted Allogeneic Bone Marrow Transplantation is Related to Hematopoietic Chimerism," Blood, 95: 352-359 (2000).
Yang et al. "CML66, a broadly immunogenic tumor antigen, elicits a humoral immune response associated with remission of chronic myelogenous leukemia," PNAS, 98(13):7492-7497 (2001).

(56) References Cited

OTHER PUBLICATIONS

Yokoyama et al., "Matrilysin (MMP-7) Is a Novel Broadly Expressed Tumor Antigen Recognized by Antigen-Specific T Cells," Clin Cancer Res, 14(17): 5503-5511 (2008).
Yosef et al., "Dynamic regulatory network controlling TH17 cell differentiation," Nature, 496(7446):461-468 (2013).
Zeestraten et al., "Addition of interferon-alpha to the p53-SLP(R) vaccine results in increased production of interferon-gamma in vaccinated colorectal cancer patients: a phase I/11 clinical trial," Int J Cancer, 132(7):1581-1591 (2013).
Zhang et al., "Graft-versus-Leukemia Antigen CML66 Elicits Coordinated B-Cell and T-Cell Immunity after Donor Lymphocyte Infusion," Clin Cancer Res, 16: 2729-2739 (2010).
Zhang et al., "Intratumoral T Cells, recurrence, and survival in epithelial ovarian cancer," New Engl J Med, 348(3):203-213 (2003).
Zhou et al., "Diverse CD8+ T-Cell Responses to Renal Cell Carcinoma Antigens in Patients Treated with an Autologous Granulocyte-Macrophage Colony-Stimulating Factor Gene-Transduced Renal Tumor Cell Vaccine," Cancer Res, 65:1079-1088 (2005).
Zhou et al., "Transcriptional regulatory networks in Th17 cell differentiation," Curr Opin Immunol, 21(2):146-152 (2009).
Zhou et al., Persistance of Multiple Tumor-Specific T-Cell Clones is Associated with Complete Tumor Regression in a Melanoma Patient Receiving Adoptive Cell transfer Therapy, J Immunother, 28(1):53-62 (2005).
Zhu et al., "Toll like receptor-3 ligand poly-ICLC promotes the efficacy of peripheral vaccinations with tumor antigen-derived peptide epitopes in murine CNS tumor models," Journal of translational medicine, 5:10 (2007).
Zwaveling et al., "Established human papillomavirus type 16-expressing tumors are effectively eradicated following vaccination with long peptides," J Immunol, 169(1):350-358 (2002).
Andreatta et al., "Gapped sequence alignment using artificial neural networks: application to the MHC class I system," Bioinformatics 32(4):511-517 (2016).
Bassani-Sternberg et al., "Mass Spectrometry of Human Leukocyte Antigen Class I Peptidomes Reveals Strong Effects of Protein Abundance and Turnover on Antigen Presentation," Mol Cell Proteomics, 14:658-673 (2015).
Behrends et al., "Network organization of the human autophagy system," Nature, 466(7302):68-76 (2010).
Berg et al., "Detection of artifacts and peptide modifications in liquid chromatography/mass spectrometry data using two-dimensional signal intensity map data visualization," Rapid Commun Mass Spectrom, 20(10):1558-1562 (2006).
Boen et al., "Identification of T Cell Ligands in a Library of Peptides Covalently Attached to HLA-DR4," J Immunol, 165:2040-2047 (2000).
Boisgerault et al., "Definition of the HLA-A29 peptide ligand motif allows prediction of potential T-cell epitopes from the retinal soluble antigen, a candidate autoantigen in birdshot retinopathy," PNAS, 93:3466-3470 (1996).
Bourdetsky et al., The nature and extent of contributions by defective ribosome products to the HLA peptidome, Pnas, III, E1591-E1599 (2014).
Bremel et al., "An integrated approach to epitope analysis I: Dimensional reduction, visualization and prediction of MHC binding using amino acid principal components and regression approaches," Immunome Res, 6:7 (2010).
Caron et al., "Analysis of MHC immunopeptidomes using mass spectrometry," Mol Cell Proteomics (2015), doi: 10.1074/mcp.OI 15.052431.
Chowell et al., "TCR contact residue hydrophobicity is a hallmark of immunogenic CD8(+) T cell epitopes," PNAS, 112:E1754-E1762 (2015).
Christianson et al., "Defining human ERAD networks through an integrative mapping strategy," Nat Cell Biol, 14:93-105 (2012).

Eichmann et al., "Identification and characterisation of peptide binding motifs of six autoimmune disease-associated human leukocyte antigen-class I molecules including HLA-B*39:06," Tissue Antigens 84(4):378-388 (2014).
Elias et al., Target-decoy search strategy for increased confidence in large-scale protein identifications by mass spectrometry, Nat Meth, 4:207-214 (2007).
Eyers et al., "CONSeQuence: prediction of reference peptides for absolute quantitative proteomics using consensus machine learning approaches," Mol Cell Proteomics (2011); 10(11):M110.003384. doi: 10.1074/mcp.MI 10.003384. Epub Aug. 3, 2011.
Fruci et al., "Altered expression of endoplasmic reticulum aminopeptidases ERAPI and ERAP2 in transformed non-lymphoid human tissues," J Cell Physiol, 216(3):742-749 (2008).
Fusaro et al., "Prediction of high-responding peptides for targeted protein assays by mass spectrometry" Nat Biotechnol, 27(2):190-198 (2009).
Guasp et al., "The Peptidome of Behcet's Disease-Associated HLA-B*51 :01 Includes Two Subpeptidomes Differentially Shaped by Endoplasmic Reticulum Aminopeptidase 1," Arthritis Rheumatol, 68:505-515 (2016).
Guruprasad et al., "Correlation between stability of a protein and its dipeptide composition: a novel approach for predicting in vivo stability of a protein from its primary sequence," Protein Eng, 4(2):155-161 (1990).
Harndahl et al., "Peptide-MHC class I stability is a better predictor than peptide affinity of CTL immunogenicity," Eur J Immunol, 42:1405-1416 (2012).
Harndahl et al., "Real-time, High-Throughput Measurements of Peptide-MHC-I Dissociation Using a Scintillation Proximity Assay," J Immunol Methods, 374:5-12 (2011).
Hickman et al., "Toward a Definition of Self: Proteomic Evaluation of the Class I Peptide Repertoire," J Immunol, 172:2944-2952 (2004).
Hoof et al., "NetMHCpan, a method for MHC class I binding prediction beyond humans," Immunogenetics, 61:1-13 (2009).
Hunt et al., "Characterization of peptides bound to the class I MHC molecule HLA-A2.1 by mass spectrometry," Science, 255:1261-1263 (1992).
Ishihama et al., "Exponentially Modified Protein Abundance Index (emPAI) for Estimation of Absolute Protein Amount in Proteomics by the Number of Sequenced Peptides per Protein," Mol Cell Proteomics, 4:1265-1272 (2005).
Jeffery et al., "The Influence of HLA Class I Alleles and Heterozygosity on the Outcome of Human T Cell Lymphotropic Virus Type I Infection," J Immunol, 165:7278-7284 (2000).
Jorgensen et al., "NetMHC stab—predicting stability of peptide-MHC-1 complexes; impacts for cytotoxic T lymphocyte epitope discovery," Immunology 141:18-26 (2014).
Keskin et al., "Direct identification of an HPV-16 tumor antigen from cervical cancer biopsy specimens," Front Immunol, 2:75 (2011).
Keskin et al., "Physical detection of influenza A epitopes identifies a stealth subset on human lung epithelium evading natural CD8 immunity," PNAS, 112(7):2151-2156 (2015).
Kesmir et al., "Prediction of proteasome cleavage motifs by neural networks," Protein Eng, 15(4):287-296 (2002).
Kim et al., "Derivation of an amino acid similarity matrix for peptide:MHC binding and its application as a Bayesian prior," BMC Bioinformatics, 10:1-11 (2009).
Kim et al., "Positional Bias of MHC Class I Restricted T-Cell Epitopes in Viral Antigens Is Likely due to a Bias in Conservation," PLoS Comput Biol, 9:el002884 (2013).
Kronke et al. "Lenalidomide causes selective degradation of IKZFI and IKZF3 in multiple myeloma cells," Science, 343(6168): 301-305 (2014).
Kronke et al. "Lenalidomide induces ubiquitination and degradation of CKla in del(5q) MDS," Nature, 523(7559):183-188 (2015).
Larsen et al., "Large-scale validation of methods for cytotoxic T-lymphocyte epitope prediction," BMC Bioinformatics, 8:424-424 (2007).

(56) References Cited

OTHER PUBLICATIONS

Linnemann et al., "High-throughput epitope discovery reveals frequent recognition of neo-antigens by CD4+ T cells in human melanoma," Nat Med, 21:81-85 (2015).
Llano et al., "Best-Characterized HIV-1 CTL Epitopes: The 2013 Update," HIV Mol Immunol , 3-25 (2013).
Lorente et al., "Diversity of Natural Self-Derived Ligands Presented by Different HLA Class I Molecules in Transporter Antigen Processing-Deficient Cells," PLoS ONE 8:e59118 (2013).
Ma, "Novor: Real-Time Peptide de Novo Sequencing Software," J Am Soc Mass Spectrom, 26:1885-1894 (2015).
McMurtrey et al., "Toxoplasma gondii peptide ligands open the gate of the HLA class I binding groove," eLife 5:el2556 (2016).
Milner et al., "The Effect of Proteasome Inhibition on the Generation of the Human Leukocyte Antigen (HLA) Peptidome," Mol Cell Proteomics, 12:1853-1864 (2013).
Milner et al., "The Turnover Kinetics of Major Histocompatibility Complex Peptides of Human Cancer Cells*," Mol Cell Proteomics, 5:357-365 (2006).
Mommen et al., "Expanding the detectable HLA peptide repertoire using electron-transfer/higher-energy collision dissociation (EThcD)," PNAS III, 4507-4512 (2014).
Mommen et al., "Sampling From the Proteome to the Human Leukocyte Antigen-DR (HLA-DR) Ligandome Proceeds Via High Specificity," Mol Cell Proteomics MCP, 15:1412-1423 (2016).
Muntel et al., "Abundance-based Classifier for the Prediction of Mass Spectrometric Peptide Detectability Upon Enrichment (PPA)," Mol Cell Proteomics, 14:430-440 (2015).
Ng et al., "Dereplication and de novo sequencing of nonribosomal peptides," Nat Meth, 6:596-599 (2009).
Nielsen et al., "The role of the proteasome in generating cytotoxic T-cell epitopes: insights obtained from improved predictions of proteasomal cleavage," Immunogenetics, 57:33-41 (2005).
Oates et al., "D(2)P(2): database of disordered protein predictions," Nucleic Acids Res, 41:D508-D516(2013).
Osorio et al., "Stability Analysis of Antimicrobial Peptides in Solvation Conditions by Molecular Dynamics," Adv Comp Bio, 232:127-131 (2014).
Pritchard et al., "Exome Sequencing to Predict Neoantigens in Melanoma," Cancer Immunol Res, 3:992-998 (2015).
Rappsilber et al., "Protocol for micro-purification, enrichment, pre-fractionation and storage of peptides for proteomics using StageTips," Nat Protoc, 2(8):1896-1906 (2007).
Reche et al., "Elicitation from virus-naive individuals of cytotoxic T lymphocytes directed against conserved HIV-1 epitopes," Med Immunol, 5:1 (2006).
Robinson et al., "The IPD and FMGT/HLA database: allele variant databases," Nucleic Acids Res, 43:D423-D431 (2015).
Rock et al., "Re-examining class-I presentation and the DRiP hypothesis," Trends Immunol, 35(4):144-152 (2014).
Ruggles et al., "An analysis of the sensitivity of proteogenomic mapping of somatic mutations and novel splicing events in cancer," Cell Proteomics, 15(3):1060-1071 (2015).
Saveanu et al., "Concerted peptide trimming by human ERAPI and ERAP2 aminopeptidase complexes in the endoplasmic reticulum," Nat Immunol, 6:689-697 (2005).
Saxova et al., "Predicting proteasomal cleavage sites: a comparison of available methods," Int Immunol, 15:781-787 (2003).
Schumacher et al., "Neoantigens in cancer immunotherapy," Science, 348:69-74 (2015).
Searle et al., "Using Data Independent Acguisition (DIA) to Model High-responding Peptides for Targeted Proteomics Experiments," Mol Cell Proteomics, 14:2331-2340 (2015).
Shimizu et al., "Production of human cells expressing individual transferred HLA-A,-B,-C genes using an HLA-A,-B,-C null human cell line," J Immunol, 142(9):3320-3328 (1989).
Shimizu et al., "Transfer of cloned human class I major histocompatibility complex genes into HLA mutant human lymphoblastoid cells," Mol Cell Biol, 6(4):1074-1087 (1986).
Sidney et al., "Measurement of MHC/Peptide Interactions by Gel Filtration" Curr Prot Immunol, 31(1):18.3.1-18.3.19 (1999).
Sowa et al., "Defining the Human Deubiguitinating Enzyme Interaction Landscape," Cell, 138(2):389-403 (2009).
Trolle et al., "The Length Distribution of Class I-Restricted T Cell Epitopes Is Determined by Both Peptide Supply and MHC Allele-Specific Binding Preference," J Immunol (2016), doi: 10.4049/iimmunol.1501721.
Tynan et al., "T cell receptor recognition of a "super-bulged" major histocompatibility complex class I-bound peptide," Nat Immunol, 6:1114-1122 (2005).
Udeshi et al., "Methods for guantification of in vivo changes in protein ubiguitination following proteasome and deubiguitinase inhibition," Mol Cell Proteomics, 11:148-159 (2012).
Vita et al., "The immune epitope database (IEDB) 3.0," Nucleic Acids Res, 43:D405-D412 (2015).
Walz et al., "The antigenic landscape of multiple myeloma: mass spectrometry (re)defines targets for T-cell-based immunotherapy," Blood 126:1203-1213 (2015).
Yewdell, "DRiPs solidify: progress in understanding endogenous MHC class I antigen processing," Trends Immunol, 32(11):548-558 (2011).
Zhang et al., "Dana-Farber repository for machine learning in immunology," J Immunol Methods, 374(1-2):18-25 (2011).
Backert et al., "Immunoinformatics and epitope prediction in the age of genomic medicine," Genome Medicine, 7:119 (2015).
Buller et al., "Deletion of the vaccinia virus growth factor gene reduces virus virulence," Journal of virology, 62(3):866-874 (1988).
Carreno et al., "A dendritic cell vaccine increases the breadth and diversity of melanoma neoantigen-specific T cells," Science, 348(6239):803-808 (2015).
Chen et al., Molecular Pharmaceutics, 3:109-111 (2010).
Declaration by Professor John Haanen, M.D., Ph.D.
Dreicer et al., "MVA-MUC1-IL2 vaccine immunotherapy (TG4010) improves PSA doubling time in patients with prostate cancer with biochemical failure," Investigational new drugs, 27(4):379-386 (2009).
Dössinger et al., "MHC multimer-guided and cell culture-independent isolation of functional T cell receptors from single cells facilitates TCR identification for immunotherapy," PloS one, 8(4):e61384 (2013).
Final Rejection for U.S. Appl. No. 13/108,610, "Compositions and Methods of Identifying Tumor Specific Neoantigens," dated May 12, 2014.
Final Rejection for U.S. Appl. No. 14/794,449, "Compositions and Methods of Identifying Tumor Specific Neoantigens," dated Sep. 13, 2017.
Final Rejection for U.S. Appl. No. 14/877,125, "Compositions and Methods for Personalized Neoplasia Vaccines," dated Oct. 25, 2017.
Final Rejection for U.S. Appl. No. 15/038,504 , "Compositions and Methods for Diagnosing, Evaluating and Treating Cancer By Means of the DNA Methyl," dated Apr. 30, 2018.
Final Rejection for U.S. Appl. No. 15/038,504 , "Compositions and Methods for Diagnosing, Evaluating and Treating Cancer By Means of the Dna Methyl," dated Dec. 21, 2018.
Final Rejection for U.S. Appl. No. 15/102,129, "Formulations for Neoplasia Vaccines," dated Sep. 14, 2018.
Final Rejection for U.S. Appl. No. 15/105,961, "Combination Therapy With Neoantigen Vaccine," dated Jul. 5, 2018.
Final Rejection for U.S. Appl. No. 15/187,174, "Compositions and Methods of Identifying Tumor Specific Neoantigens," dated May 25, 2017.
Final Rejection for U.S. Appl. No. 15/187,174, "Compositions and Methods of Identifying Tumor Specific Neoantigens," dated Oct. 12, 2018.
Gazdar, "Activating and resistance mutations of EGFR in non-small-cell lung cancer: role in clinical response to EGFR tyrosine kinase inhibitors," Oncogene, 28:S24-S31 (2009).
Han et al., "Linking T-Cell Receptor Sequence to Fucntional Phenotype at the Single-Cell Level," Nat Biotechnol, 32:684-692 (2014).

(56) References Cited

OTHER PUBLICATIONS

Hombrink et al., "Identification of Biological Relevant Minor Histocompatibility Antigens within the B-lymphocyte-Derived HLA-Ligandome Using a Reverse Immunology Approach," Clin Cancer Res, 21(9):2177-2186 (2015).
Illumina, "Immunotherapy, the Next Generation of Cancer Treatment, NGS-guided assessment of interactions between tumors and the immune system leads to new discoveries in immuno-oncology," (2016).
Jarmalavicius et al., "High Immunogenicity of the Human Leukocyte Antigen Peptidomes of Melanoma Tumor Cells," J Biol Chem, 287(40):33401-33411 (2012).
Johnson et al., "Discovery of Naturally Processed and HLA-Presented Class I Peptides from Vaccinia Virus Infection using Mass Spectrometry for Vaccine Development," Vaccine, 28(1):38-47 (2009).
Jun et al., "Progress in T cell adoptive Immunotherapy for Malignant Solid Tumors," Chin Med Biotechnol, 3(1):1-7 (2008).
Kalaora et al., "Use of HLA peptidomics and whole exome sequencing to identify human immunogenic neo-antigens," Oncotarget, 7(5):5110-5117 (2016).
Keskin et al., "Neoantigen vaccine generates intratumoral T cell responses in phase Ib glioblastoma trial," Nature, 565(7738):234-239 (2019).
Kim et al., "mTOR inhibitors radiosensitize PTEN-deficient non-small-cell lung cancer cells harboring an EGFR activating mutation by inducing autophagy," J Cell Biochem, 114(6):1248-1256 (2013).
Klug et al., "Characterization of MHC Ligands for Peptide Based Tumor Vaccination," Current Pharmaceutical Design, 15(28): 3221-3236 (2009).
Lata et al., "MHCBN 4.0: A database of MHC/TAP binding peptides and T-cell epitopes," BMC Research Notes, 2(1): 61 (2009).
Linardou et al., "Assessment of somatic k-RAS mutations as a mechanism associated with resistance to EGFR-targeted agents: a systematic review and meta-analysis of studies in advanced non-small-cell lung cancer and metastatic colorectal cancer," Lancet Oncol, 9(10):962-972 (2008).
Linardou et al., "Somatic EGFR mutations and efficacy of tyrosine kinase inhibitors in NSCLC," Nat Rev Clin Oncol, 6(6):352-366 (2009).
Lucas et al., "About human tumor antigens to be used in immunotherapy," Semin Immunol, 20(5):301-307 (2008).
Luo et al. "Machine learning methods for Predicting hla-Peptide Binding activity," Bioinformatics and Biology Insights, 9(s3):21-29 (2015).
Mosmann et al., "TH1 and TH2 Cells: Different Patterns of Lymphokine Secretion Lead to Different Functional Properties," Ann Rev Immunol, 7:145-173 (1989).
Nielsen et al., "NetMHCpan-3.0; improved prediction of binding to MHC class I molecules integrating information from multiple receptor and peptide length datasets," Genome Medicine, 8:33 (2016).
Non-Final Office Action for U.S. Appl. No. 13/108,610, "Compositions and Methods of Identifying Tumor Specific Neoantigens," dated Aug. 15, 2013.
Non-Final Office Action for U.S. Appl. No. 13/108,610, "Compositions and Methods of Identifying Tumor Specific Neoantigens," dated Dec. 3, 2014.
Non-Final Office Action for U.S. Appl. No. 14/794,449, "Compositions and Methods of Identifying Tumor Specific Neoantigens," dated Dec. 29, 2016.
Non-Final Office Action for U.S. Appl. No. 14/794,449, "Compositions and Methods of Identifying Tumor Specific Neoantigens," dated Jul. 24, 2018.
Non-Final Office Action for U.S. Appl. No. 14/877,125, "Compositions and Methods for Personalized Neoplasia Vaccines," dated Mar. 27, 2017.
Non-Final Office Action for U.S. Appl. No. 14/877,125, "Compositions and Methods for Personalized Neoplasia Vaccines," dated Nov. 2, 2018.
Non-Final Office Action for U.S. Appl. No. 15/038,504, "Compositions and Methods for Diagnosing, Evaluating and Treating Cancer By Means of the DNA Methyl," dated Sep. 6, 2017.
Non-Final Office Action for U.S. Appl. No. 15/102,129, "Formulations for Neoplasia Vaccines," dated Dec. 17, 2018.
Non-Final Office Action for U.S. Appl. No. 15/102,129, "Formulations for Neoplasia Vaccines," dated Jul. 28, 2017.
Non-Final Office Action for U.S. Appl. No. 15/102,129, "Formulations for Neoplasia Vaccines," dated Mar. 7, 2018.
Non-Final Office Action for U.S. Appl. No. 15/105,961, "Combination Therapy With Neoantigen Vaccine," dated Jan. 8, 2019.
Non-Final Office Action for U.S. Appl. No. 15/105,961, "Combination Therapy With Neoantigen Vaccine," dated Nov. 20, 2017.
Non-Final Office Action for U.S. Appl. No. 15/187,174, "Compositions and Methods of Identifying Tumor Specific Neoantigens," dated Dec. 5, 2016.
Non-Final Office Action for U.S. Appl. No. 15/187,174, "Compositions and Methods of Identifying Tumor Specific Neoantigens," dated Jan. 22, 2018.
Non-Final Office Action for U.S. Appl. No. 15/513,127, "Use of Clonal Evolution Analysis for Ibrutinib Resistance in Chronic Lymphocytic Leukemia Patients," dated Nov. 26, 2018.
Non-Final Office Action for U.S. Appl. No. 15/537,785, "Methods for Profiling the T Cell Repertoire," dated Dec. 21, 2018.
Non-Final Office Action for U.S. Appl. No. 16/181,098, "Compositions and Methods of Identifying Tumor Specific Neoantigens," dated Jan. 31, 2019.
Notice of Allowance for U.S. Appl. No. 13/108,610, "Compositions and Methods of Identifying Tumor Specific Neoantigens," dated Jun. 11, 2015.
Notice of Allowance for U.S. Appl. No. 13/108,610, "Compositions and Methods of Identifying Tumor Specific Neoantigens," dated May 12, 2015.
Notice of Allowance for U.S. Appl. No. 15/102,129, "Formulations for Neoplasia Vaccines," dated Oct. 12, 2018.
Novershtern et al., "Densely Interconnected Transcriptional Circuits Control Cell States in Human Hematopoiesis," Cell, 144(2):296-309 (2011).
Assignment Register extract (accessed Oct. 20, 2016).
Prints-outs from the UniProtKB database concerning the CEP170, Parva and FLT3 genes.
Restriction Requirement for U.S. Appl. No. 13/108,610, "Compositions and Methods of Identifying Tumor Specific Neoantigens," dated Mar. 7, 2013.
Restriction Requirement for U.S. Appl. No. 14/794,449, "Compositions and Methods of Identifying Tumor Specific Neoantigens," dated Oct. 26, 2016.
Restriction Requirement for U.S. Appl. No. 14/877,125, "Compositions and Methods for Personalized Neoplasia Vaccines," dated Nov. 18, 2016.
Restriction Requirement for U.S. Appl. No. 15/038,504, "Compositions and Methods for Diagnosing, Evaluating and Treating Cancer By Means of the DNA Methyl," dated Jun. 22, 2017.
Restriction Requirement for U.S. Appl. No. 15/102,129, "Formulations for Neoplasia Vaccines," dated May 8, 2017.
Restriction Requirement for U.S. Appl. No. 15/105,961, "Combination Therapy With Neoantigen Vaccine," dated Jul. 13, 2017.
Restriction Requirement for U.S. Appl. No. 15/187,174, "Compositions and Methods of Identifying Tumor Specific Neoantigens," dated Sep. 9, 2016.
Restriction Requirement for U.S. Appl. No. 15/513,127, "Use of Clonal Evolution Analysis for Ibrutinib Resistance in Chronic Lymphocytic Leukemia Patients," dated Aug. 13, 2018.
Restriction Requirement for U.S. Appl. No. 15/537,785, "Methods for Profiling the T Cell Repertoire," dated Mar. 22, 2018.
Restriction Requirement for U.S. Appl. No. 15/575,328, "Shared Neoantigens," dated Feb. 7, 2019.
Rubin et al., "Mutation patterns in cancer genomes," PNAS, 106(51):21766-21770 (2009).
Sahin et al., "Personalized RNA mutanome vaccines mobilize poly-specific therapeutic immunity against cancer," Nature, 547(7662):222-226 (2017).

(56) References Cited

OTHER PUBLICATIONS

Singh-Jasuga et al., "Correlation of T-cell response, clinical activity and regulatory T-cell levels in renal cell carcinoma patients treated with IMA901, a novel multi-peptide vaccine," J Clin Conology, 25:18S, Abstract #3017 (2007).
Sjoblom et al., "The Consensus Coding Sequences of Human Breast and Colorectal Cancers," Science, 314(5797):268-274 (2006).
Stranzl et al., "NetCTLpan: pan-specific MHC class I pathway epitope predictions," Immunogenetics, 62(6):357-368 (2010).
Sun et al., Material bionics and Thinking Innovation, 176-177 (2012).
Tang et al., "NeoantigenR: An annotation based pipeline for tumor neoantigen identification from seguencing data," bioRxiv preprint first posted online Aug. 8, 2017.
Trolle et al., "Automated benchmarking of peptide-MHC class I binding predictions," Bioinformatics, 31(13):2174-2181 (2015).
Turchaninova et al., "Pairing of T-cell receptor chains via emulsion PCR," Eur J Immunol, 43:2507-2515 (2013).
Van Buuren et al., "High sensitivity of cancer exome-based CD8 T cell neo-antigen identification," OncoImmunology, 3(5):e28836 (2014).
Vogel et al., "Mass Spectrometry Reveals Changes in Mhc I Antigen Presentation After Lentivector Expression of a Gene Regulation System," Molecular Therapy-Nucleic Acids, 2:e75 (2013).
Wang et al., Functional Polymeric Material, 1-44 (2010).
Wraith, "The Future of Immunotherapy: A 20-Year Perspective," Front Immunol, 8:1668 (2017).
You et al., "Understanding Prediction Systems for HLA-Binding Peptides and T-Cell Epitope Identification," Pattern Recognition in Bioinformatics, Lecture Notes in Computer Science, 4474: 337-348 (2007).
Zhang et al., Oncology, 1-44 (2005).
U.S. Appl. No. 16/094,786, filed Oct. 18, 2018, Pending.
U.S. Appl. No. 14/794,449, filed Jul. 8, 2015, 2016-00008447, Published.
U.S. Appl. No. 16/188,737, filed Nov. 13, 2018, Pending.
U.S. Appl. No. 16/381,791, filed Apr. 11, 2019, Pending.
U.S. Appl. No. 14/877,125, filed Oct. 7, 2015, 2016-0101170, Published.
U.S. Appl. No. 15/102,129, filed Jun. 6, 2016, 2016-0310584, Published.
U.S. Appl. No. 15/038,504, filed May 23, 2016, 2016-0326593, Published.
U.S. Appl. No. 15/575,328, filed Nov. 17, 2017, 2018-0153975, Published.
PCT/US18/14831, Jan. 23, 2018 WO2018/140391, Published.
11781409.5 (opposition therein), May 16, 2011, 2569633 Granted-opposition pending.
U.S. Appl. No. 16/094,786, filed Oct. 18, 2018, 2019-0346442, Pending.
U.S. Appl. No. 13/108,610, filed May 16, 2011, 2011-0293637, U.S. Pat. No. U.S. Pat. No. 9,115,402, Granted.
U.S. Appl. No. 14/877,125, filed Oct. 7, 2015, 2016-0101170, Allowed.
U.S. Appl. No. 16/813,371, filed Mar. 9, 2020, Pending.
U.S. Appl. No. 17/017,045, filed Sep. 10, 2020, Pending.
U.S. Appl. No. 15/537,785, filed Jun. 19, 2017, 2018-0000913, Published.
U.S. Appl. No. 15/537,839, filed Jun. 19, 2017, 2019-0127803, Allowed.
U.S. Appl. No. 16/859,252, filed Apr. 27, 2020, Pending.
U.S. Appl. No. 15/513,127, Mar. 21, 2017, 2017-0298441, Published.
"Neon Therapeutics' Personal Neoantigen Vaccine Study Demonstrates Prolonged Progress ion-Free Survival in Advanced or Metastatic Melanoma, Non-Small Cell Lung and Bladder Cancers," published by Globe Newswire on Jul. 15, 2019 ("Neon Press Release 2019").
Bediaga et al., "DNA methylation epigenotypes in breast cancer molecular subtypes," Breast Cancer Research, 12:R77 (2010).
Cardarella et al., "Clinical, Pathologic, and Biologic Features Associated with BRAF Mutations in Non-Small Cell Lung Cancer," Clin Cancer Res, 19(16):4532-4540 (2013).
Chang et al., "Use of tumor genomic profiling to reveal mechanisms of resistance to the BTK inhibitor ibrutinib in chronic lymphocytic leukemia (CLL)," J Clin Oncol, 31(15S):Abstract 7014 (2013).
Dai et al., "Prediction of soluble heterologous protein expression levels in *Escherichia coli* from sequence-based features and its potential in biopharmaceutical process development," Pharmaceutical Bioprocessing, 2(3): 253-266 (2014).
DeKosky et al., "High-throughput sequencing of the paired human immunoglobulin heavy and light chain repertoire," Nature Biotech 166-170 (2013).
Di Nicolantonio et al., "Wild-Type Is Required for Response to Panitumumab or Cetuximab in Metastatic Colorectal Cancer," Journal of Clinical Oncology, 26(35):5705-5712 (2008).
Donkena et al., "Oxidative Stress and DNA Methylation in Prostate Cancer," Obstetrics and Gynecology International, 2010(Article ID 302051):14 pages (2010).
Dressman et al., "Gene expression profiles of multiple breast cancer phenotypes and response to neoadjuvant chemotherapy," Clin Cancer Res, 12(3):819-826 (2006).
Du et al., "The Significance and Therapeutic Potential of GATA3 Expression and Mutation in Breast Cancer: A Systematic Review," Med Res Rev, 35(6):1300-1315 (2015).
Extended European Search Report for EP Application No. 19219395.1 dated Jul. 23, 2020.
Extended European Search Report for EP Application No. EP 20179960 dated Nov. 9, 2020.
Filatreau et al., "Technische Universitat Berlin, Fakultat III—Prozesswissenschaften Direct comparasion of T cell receptor avidity of auto-antigen specific conventional and regulatory T cells," Abstract, 1-6.
Final Rejection for U.S. Appl. No. 14/794,449, "Compositions and Methods of Identifying Tumor Specific Neoantigens," dated Apr. 5, 2019.
Final Rejection for U.S. Appl. No. 14/877,125, "Compositions and Methods for Personalized Neoplasia Vaccines," dated May 24, 2019.
Final Rejection for U.S. Appl. No. 15/102,129, "Formulations for Neoplasia Vaccines," dated Aug. 15, 2019.
Final Rejection for U.S. Appl. No. 15/105,961, "Combination Therapy With Neoantigen Vaccine," dated Aug. 23, 2019.
Final Rejection for U.S. Appl. No. 15/513,127, "Use of Clonal Evolution Analysis for Ibrutinib Resistance in Chronic Lymphocytic Leukemia Patients," dated May 17, 2019.
Final Rejection for U.S. Appl. No. 15/537,785, "Methods for Profiling the T Cell Repertoire," dated Jul. 18, 2019.
Final Rejection for U.S. Appl. No. 15/537,839, "Molecular Biomarkers for Cancer Immunotherapy," dated May 1, 2020.
Final Rejection for U.S. Appl. No. 15/575,328,"Shared Neoantigens," dated Oct. 23, 2019.
Final Rejection for U.S. Appl. No. 16/181,098, "Compositionsand Methods of Identifying Tumor Specific Neoantigens," dated Jun. 17, 2019.
Ganesan et al., "Tumor-Infiltrating Regulatory T Cells Inhibit Endogenous Cytotoxic T Cell Responses to Lung Adenocarcinoma," The Journal of Immunology, 191(4): 2009-2017 (2013).
Gascoigne et al., "Allelic exclusion of the T cell receptor a-chain: developmental regulation of post-translational event," Semin Immunol, 11:337-347 (1999).
Goh et al., "Mining the Structural Genomics Pipeline: Identification of Protein Properties that Affect High-throughput Experimental Analysis," Journal of Molecular Biology, 336(1): 115-130 (2004).
IEDB Analysis Resource for MHC-I binding predictions (printed Oct. 2019).
IEDB Analysis Resource for MHC-II binding predictions (printed Oct. 2019).
Jiang et al., "GATA3 Mutations Define a Unique Subtype of Luminal-Like Breast Cancer With Improved Survival," Canc 120:1329-1337 (2014).

(56) References Cited

OTHER PUBLICATIONS

Khammari et al., "Treatment of metastatic melanoma with autologous melan-A/mart-1-specific cytotoxic t lymphocyte clones," Journal of Investigative Dermatology, 129(12): 2835-2842 (2009).
Kim et al., "Inactivating mutations of caspase-8 in colorectal carcinomas," Gastroenterology, 125:708-715 (2003).
Kobayashi et al., "DNA methylation profiling reveals novel biomarkers and important roles for DNA methyltransferases in prostate cancer," Genome Research, 21:1017-1027 (2011).
Landau et al., "The evolutionary landscape of chronic lymphocytic leukemia treated with ibrutinib targeted therapy," Nat Commun, 8(1):2185 (2017).
Lee, "Identification of Neo-antigens for a Cancer Vaccine by Transcriptome Analysis", PhD Thesis, Arizona State University (2012).
Loveridge et al., "The genetic contribution to human T-cell receptor repertoire," Immunology, 74:246-250 (1991).
Mackall et al., "Targeting tumor specific translocations in sarcomas in pediatric patients for immunotherapy," Clinical Orthopaedics and Related Research, 373:25-31 (2000).
Mardis, "The impact of next-generation sequencing technology on genetics," Trends in Genetics, 24(3):133-141 (2007).
McCleskey et al., "GATA-3 Expression in Advanced Breast Cancer: Prognostic Value and Organ-Specific Relapse," Amer J Clin Pathol 144:756-763 (2015).
Mikeska et al., "The implications of heterogeneous DNA methylation for the accurate quantification of methylation," Epigenomics, 2(4):561-573 (2010).
Niwa et al., "Bimodal protein solubility distribution revealed by an aggregation analysis of the entire ensemble of *Escherichia coli* proteins," PNAS, 106(11): 4201-4206 (2009).
Non-Final Office Action for U.S. Appl. No. 15/102,129, "Formulations for Neoplasia Vaccines," dated Apr. 26, 2019.
Non-Final Office Action for U.S. Appl. No. 15/575,328, "Shared Neoantigens," dated Jun. 27, 2019.
Non-Final Rejection for U.S. Appl. No. 14/877,125, "Compositions and Methods for Personalized Neoplasia Vaccines," dated Feb. 3, 2020.
Non-Final Rejection for U.S. Appl. No. 15/038,504, "Compositions and Methods for Diagnosing, Evaluating and Treating Cancer By Means of the DNA Methylation Status," dated Feb. 4, 2020.
Non-Final Rejection for U.S. Appl. No. 15/105,961, "Combination Therapy With Neoantigen Vaccine," dated Jun. 2, 2020.
Non-Final Rejection for U.S. Appl. No. 15/513,127, "Use of Clonal Evolution Analysis for Ibrutinib Resistance in Chronic Lymphocytic Leukemia Patients," dated Oct. 29, 2019.
Non-Final Rejection for U.S. Appl. No. 15/537,785, "Methods for Profiling the T Cell Repertoire," dated May 11, 2020.
Non-Final Rejection for U.S. Appl. No. 15/537,839, "Molecular Biomarkers for Cancer Immunotherapy," dated Oct. 8, 2019.
Non-Final Rejection for U.S. Appl. No. 15/735,566, "Formulations for Neoplasia Vaccines and Methods of Preparing Thereof," dated May 28, 2020.
Non-Final Rejection for U.S. Appl. No. 15/800,732, "Compositions and Methods of Identifying Tumor Specific Neoantigens," dated Apr. 10, 2020.
Notice of Allowance for U.S. Appl. No. 15/575,328, "Shared Neoantigens," dated Jan. 23, 2020.
Notice of Allowance for U.S. Appl. No. 16/188,737, "Compositions and Methods of Identifying Tumor Specific Neoantigens," dated Jul. 25, 2019.
O'Mahony et al., "A Pilot Study of CTLA-4 Blockade after Cancer Vaccine Failure in Patients with Advanced Malignancy" Clin Canc Res 13(3):958-964 (2007).
Ohashi et al., "Lung cancers with aquired resistance to EGFR inhibitors occasionally harbor BRAF gene mutations but lack mutations in KRAS, NRAS, or MEK1," PNAS, E2127-E2133 (2012).
Ott et al., "A Phase lb Trial of Personalized Neoantigen Therapy Plus Anti-PD-1 in Patients with Advanced Melanoma, Non-small Cell Lung Cancer, or Bladder Cancer," Cell, 183(2):347-362 (2020).
Peters et al., "Accurate whole-genome sequencing and haplotyping from 10 to 20 human cells," Nature 487:190-195 (2012).
Pietras, "Biologic Basis of Sequential and Combination Therapies for Hormone-Responsive Breast Cancer," Oncologist, 11:704-717 (2006).
Poster entitled "Disease-related biomarkers are associated with extended progression-free survival after treatment with Neo-PV-01 in combination with anti-PD1 in patients with metastatic cancers" presented at The Society for Immunotherapy of Cancer Annual Meeting Nov. 6-10, 2019 ("SITC 2019 poster").
Restriction Requirement for U.S. Appl. No. 15/537,839, "Molecular Biomarkers for Cancer Immunotherapy," dated Jun. 20, 2019.
Sharma et al., "A Chromatin-Mediated Reversible Drug-Tolerant State in Cancer Cell Subpopulations," Cell, 141:69-80 (2010).
Shen et al., "Integrated genetic and epigenetic analysis identifies three different subclasses of colon cancer," PNAS, 104(47):18654-18659 (2007).
Smialowsky et al., "Protein solubility: sequence based prediction and experimental verification," Bioinformatics, 23(19):2356-3542 (2007).
Song et al., "Full screening and accurate subtyping of HLA-A*02 alleles through group-specific amplification and mono-allelic sequencing," Cell Mol Immunol, 10:490-496 (2013).
Soung et al., "Capase-8 gene is frequently inactivated by the frameshift somatic mutation 1225_1226delTG in hepatocellular carcinomas," Oncogene, 24:141-147 (2005).
Supplementary Materials from Third Party Observation in EP Application No. 15198284.0.
Thon et al., "Personalized treatment strategies in glioblastoma: MGMT promoter methylation status," Onco Targets and Therapy, 6:1363-1372 (2013).
Vandrovcova et al., :Somatic BRAF-V600E Mutations in Familial Colorectal Cancer, Cancer Epidemio Biomarkers Prev, 15(11):2270-2273 (2006).
Varley et al., "Intra-tumor heterogeneity of MLH1 promoter methylation revealed by deep single molecule bisulfite sequencing," Nucleic Acids Research, 37(14):4603-4612 (2009).
Vita et al., "The Immune Epitope Database 2.0," Nucleic Acids Res, 38:D854-D862 (2010).
Yee et al., "Adoptive T cell therapy using antigen-specific CD8 T cell clones for the treatment of patients with metastatic melanoma: In vivo persistence, migration, and antitumor effect of transferred T cells," PNAS, 99(25): 16168-16173 (2002).
"A Phase 1 Study of Nivolumab in Subjects With Advanced or Recurrent Malignancies (MDX1106-03)," National Library of Medicine, First posted: Aug. 8, 2008 and last updated Mar. 24, 2020. https://clinicaltrials.gov/ct2/show/NCT00730639. Clinical Trials Identifier NCT00730639.
"Dose-escalation Study of Combination BMS-936558 (MDX-1106) and Ipilimumab in Subjects With Unresectable Stage III or Stage IV Malignant Melanoma," National Library of Medicine, First posted: Dec. 2, 2009 and last updated Mar. 22, 2021. https://www.clinicaltrials.gov/ct2/show/NCT01024231, Clinical Trials Identifier NCT01024231.
"Single-cell sequencing: A brief overview of how to derive a genome or transcriptome from a single cell," Nature Methods, 18(11) (2014).
"Study of Pembrolizumab (MK-3475) in Participants With Progressive Locally Advanced or Metastatic Carcinoma, Melanoma, or Non-small Cell Lung Carcinoma (P07990/MK-3475-001/KEYNOTE-001) (KEYNOTE-001)," National Library of Medicine, First posted: Feb. 15, 2011 and last updated Dec. 13, 2019 https://clinicaltrials.gov/ct2/show/NCT01295827, Clinical Trials Identifier NCT01295827.
Allocca et al., "Novel adeno-associated virus serotypes efficiently transduce murine Photoreceptors," Journal of Virology, 81 (20): 11372-11380 (2007).
Final Office Action for U.S. Appl. No. 15/735,566, "Formulations for Neoplasia Vaccines and Methods of Preparing Thereof," dated Feb. 3, 2021.

(56) References Cited

OTHER PUBLICATIONS

Final Office Action for U.S. Appl. No. 15/800,732, "Compositions and Methods of Identifying Tumor Specific Neoantigens," dated Dec. 17, 2020.
Final Office Action for U.S. Appl. No. 16/813,371, "Formulations for Neoplasia Vaccines," dated Oct. 13, 2020.
Fritsch et al., "Personal Neoantigen Cancer Vaccines: A Road Not Fully Paved," Cancer Immunology Research, 8: 1465-9 (2020).
Mandelboim et al., "Regression of Established Murine Carcinoma Metastases Following Vaccination with Tumor-Associated Antigen Peptides," Nature Medicine, 1(11):1179-1183 (1995).
Miyamoto et al., "GATA binding protein 3 is down-regulated in bladder cancer yet strong expression is an independent predictor of poor prognosis in invasive tumor," Human Pathology, 43:2033-2040 (2012).
Non-Final Office Action for U.S. Appl. No. 15/105,961, "Combination Therapy With Neoantigen Vaccine," dated Jan. 21, 2021.
Non-Final Office Action for U.S. Appl. No. 15/513,127, "Use of Clonal Evolution Analysis for Ibrutinib Resistance in Chronic Lymphocytic Leukemia Patients," dated Dec. 4, 2020.
Non-Final Office Action for U.S. Appl. No. 16/181,098, "Compositions and Methods of Identifying Tumor Specific Neoantigens," dated Oct. 29, 2020.
Topalian et al., "Five-Year Survival and Correlates Among Patients With Advanced Melanoma, Renal Cell Carcinoma, or Non-Small Cell Lung Cancer Treated With Nivolumab," JAMA Oncol., 5(10): 1411-1420 (2019).
U.S. Non-Final Office Action dated Mar. 7, 2019 and issued in U.S. Appl. No. 15/037,394.
U.S. Non-Final Office Action dated Oct. 2, 2020 and issued in U.S. Appl. No. 15/037,394.
Vandenberghe et al., "Heparin binding directs activation of T cells against adeno-associated virus serotype 2 capsid," Nature Medicine, 12(8): 967-971 (2006).
U.S. Appl. No. 16/094,786, filed Oct. 18, 2018, 2019-0346442, Published.
U.S. Appl. No. 13/108,610, filed May 16, 2011, 2011-0293637, U.S. Pat. No. 9,115,402, Granted.
U.S. Appl. No. 14/794,449, filed Jul. 8, 2015, 2016-00008447, Abandoned.
U.S. Appl. No. 15/187,174, filed Jun. 20, 2016, 2016-0331822, Abandoned.
U.S. Appl. No. 15/800,732, filed Nov. 1, 2017, 2018-0055922, Published.
U.S. Appl. No. 16/181,098, filed Nov. 5, 2018, 2019-0060432, Published.
U.S. Appl. No. 16/188,737, filed Nov. 13, 2018, 2016-0101170, U.S. Pat. No. 10426824, Granted.
U.S. Appl. No. 16/381,791, filed Apr. 11, 2019, 2020-0069783, Published.
U.S. Appl. No. 16/528,195, filed Jul. 31, 2019, 2020-0016251, Published.
U.S. Appl. No. 15/037,394, filed May 18, 2016, 2016-0298185, Published.
U.S. Appl. No. 14/877,125, filed Oct. 7, 2015, 2016-0101170, Pending.
U.S. Appl. No. 17/089,408, filed Nov. 4, 2020, 2021-0220455, Published.
U.S. Appl. No. 15/102,129, filed Jun. 6, 2016, 2016-0310584, Abandoned.
U.S. Appl. No. 16/813,371, filed Mar. 9, 2020, 2020-0330571, Published.
U.S. Appl. No. 15/038,504, filed May 23, 2016, 2016-0326593, U.S. Pat. No. 10,801,070, Granted.
U.S. Appl. No. 17/017,045, filed Sep. 10, 2020, 2020-0407804, Published.
U.S. Appl. No. 15/537,785, filed Jun. 19, 2017, 2018-0000913, U.S. Pat. No. 10,993,997, Granted.
U.S. Appl. No. 17/217,864, filed Mar. 30, 2021, 2021-0379168, Published.
U.S. Appl. No. 15/537,839, filed Jun. 19, 2017, 2019-0127803, Published.
U.S. Appl. No. 17/179,956, filed Feb. 19, 2021, 2021-0262039, Published.
U.S. Appl. No. 15/575,328, filed Nov. 17, 2017, 2018-0153975, U.S. Pat. No. 10,835,585, Granted.
U.S. Appl. No. 16/856,252, filed Apr. 27, 2020, 2020-0368337, Published.
U.S. Appl. No. 15/513,127, filed Mar. 21, 2017, 2017-0298441, Published.
U.S. Appl. No. 15/735,566, filed Dec. 11, 2017, 2019-0060428, Published.
U.S. Appl. No. 16/480,535, filed Jul. 24, 2019, 2019-0376147, Published.
11781409.5 (Opposition therein), May 16, 2011, 2,56,9633, 2,569,633, Granted-opposition pending.
15198284.0, May 16, 2011, 3,023,788, 3,023,788, Granted-opposition pending.
Adam Piore., "Custom Cancer Vaccines," Feb. 27, 2019 edition of MIT Technology Review.
Alderton G. "Research Highlights" from vol. 13 of *Nature Reviews, Cancer* (Apr. 2013).
Aranda et al. "Motely Malignancies" p. 1565 from vol. 19, No. 12 of *Nature Medicine* (Dec. 2013), entitled "Notable advances 2013".
Blackwell HE, Grubbs RH (1998). "Highly Efficient Synthesis of Covalently Cross-Linked Peptide Helices by Ring-Closing Metathesis". Angewandte Chemie International Edition. 37 (23): 3281-3284.
CNBC news article posted online on Mar. 1, 2019 entitled "Bill Gates: These breakthrough technologies are going to profoundly change the world".
Dana-Farber Cancer Institute; Feb. 20, 2013 publication of the Dana-Farber Cancer Institute entitled, Inside the Institute'; and the article "Study tracks evolution of leukemia."
Datasheet for the decision of May 31, 2007, Boards of Appeal of The European Patent Office, T 1396/06.
Duarte "Milestone 21 Individualized neoantigen vaccines" Nature Milestones, Nov. 2020: S3-S25.
Kyte et al., "A Simple Method for Displaying the Hydropathic Character of a Protein," J. Mol. Biol., 157: 105-132 (1982).
Lee et al., "Monocyte-derived dendritic cells from HLA-matched allogenic donors showed a greater ability to induce leukemic cell-specific T cells in comparison to leukemic cell-derived dendritic cells or monocyte-derived dendritic cells from AML patients," Leukemia Research, 32: 1653-1660 (2008).
Peters et al., "A Community Resource Benchmarking Predictions of Peptide Binding to MHC-I Molecules," PLoS Computational Biology, 2(6): e65 (2006).
Singh et al., "CIMT 2010: Report on the eighth annual meeting of the association for cancer immunotherapy, May 26-28, 2010, Mainz, Germany," Cancer Immunol. Immunother., 60:443-450 (2011).
Somasundaram et al., "Human Leukocyte Antigen-A2-Restricted CTL Responses to Mutated BRAF Peptides in Melanoma Patients," Cancer Res, 66(6): 3287-3293 (2006).
Tjernberg et al., "DMSO-Related Effects in Protein Characterization," Journal of Biomolecular Screening, 11(2): 131-137 (2006).
Vonderheide et al, "Immunotherapy at Large: The road to personalized cancer vaccines," Nature Medicine 19(9) 1098-1100 (2013).
Wu et al., "Structure-based engineering of a monoclonal antibody for improved solubility," Protein Engineering, Design & Selection, 23(8): 643-651 (2010).
U.S. Appl. No. 17/089,408, filed Nov. 4, 2020, Pending.
U.S. Appl. No. 17/217,864, filed Mar. 30, 2021, Pending.
U.S. Appl. No. 15/537,839, filed Jun. 19, 2017, 2019-0127803, U.S. Pat. No. 10,975,442, Granted.
U.S. Appl. No. 17/179,956, filed Feb. 19, 2021, Pending.
U.S. Appl. No. 16/859,252, filed Apr. 27, 2020, 2020-0368337, Published.
15198284.0 (opposition therein), May 16, 2011, 3023788, 3023788, Granted-opposition pending.

\* cited by examiner

Study 1: Nivolumab vs Nivolumab and NeoVax following AHSCT in Non-Hodgkins Lymphoma Study 2: Nivolumab and NeoVax in metastatic melanoma and metastatic RCC.

Study 3a: Dose escalation of reduced intensity intravenous Ipilimumab in metastatic melanoma Study 3B: Dose escalation of sub-cutaneous Ipilimumab (Local) in metastatic melanoma Study 4: Study combining NeoVax and Ipilimumab to Treat high-risk Renal Cell Carcinoma

SEQUENCE LISTING

<160> NUMBER OF SEQ ID NOS: 62

<210> SEQ ID NO 1
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Pro Pro Tyr Pro Tyr Ser Ser Pro Ser Leu Val Leu Pro Thr Glu Pro
1               5                   10                  15

His Thr Pro Lys Ser Leu Gln Gln Pro Gly Leu Pro Ser
            20                  25

<210> SEQ ID NO 2
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Asn Pro Glu Lys Tyr Lys Ala Lys Ser Arg Ser Pro Gly Ser Pro Val
1               5                   10                  15

Val Glu Gly Thr Gly Ser Pro Pro Lys Trp Gln Ile Gly Glu Gln Glu
            20                  25                  30

Phe

<210> SEQ ID NO 3
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gly Thr Tyr Leu Gln Gly Thr Ala Ser Ala Leu Ser Gln Ser Gln Glu
1               5                   10                  15

Arg Pro Pro Ser Val Asn Arg Val Pro Pro Ser Ser Pro Ser Ser Gln
            20                  25                  30

Glu

<210> SEQ ID NO 4
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ala Glu Ser Ala Gln Arg Gln Gly Pro Asn Gly Gly Gly Glu Gln Ser
1               5                   10                  15

Ala Asn Glu Phe
            20

```
<210> SEQ ID NO 5
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Glu Pro Asp Gln Glu Ala Val Gln Ser Ser Thr Tyr Lys Asp Cys Asn
1               5                   10                  15

Thr Leu His Leu Pro Thr Glu Arg Phe Ser Pro Val Arg
            20                  25

<210> SEQ ID NO 6
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Leu Lys Asp Ser Asn Ser Trp Pro Pro Ser Asn Lys Arg Gly Phe Asp
1               5                   10                  15

Thr Glu Asp Ala His Lys Ser Asn Ala Thr Pro Val Pro
            20                  25

<210> SEQ ID NO 7
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Ala Ser Arg Arg Ser Ser Ala Ser Gln Gly Ala Gly Ser Leu Gly
1               5                   10                  15

Leu Ser Glu Glu Lys Thr Leu Arg Ser Gly Gly Gly Pro
            20                  25

<210> SEQ ID NO 8
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Lys Lys Glu Lys Ala Glu Lys Leu Glu Lys Glu Arg Gln Arg His Ile
1               5                   10                  15

Ser Lys Pro Leu Leu Gly Gly Pro Phe Ser Leu Thr Thr His Thr Gly
            20                  25                  30

Glu

<210> SEQ ID NO 9
<211> LENGTH: 33
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 9

Ser Pro Thr Glu Pro Ser Thr Lys Leu Pro Gly Phe Asp Ser Cys Gly
1               5                   10                  15

Asn Thr Glu Ile Ala Glu Arg Lys Ile Lys Arg Ile Tyr Gly Gly Phe
            20                  25                  30

Lys

<210> SEQ ID NO 10
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Glu Cys Gly Lys Ala Phe Thr Arg Gly Ser Gln Leu Thr Gln His Gln
1               5                   10                  15

Gly Ile His Ile Ser Glu Lys Ser Phe Glu Tyr Lys Glu Cys Gly Ile
            20                  25                  30

Asp

<210> SEQ ID NO 11
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ser His Val Glu Lys Ala His Ile Thr Ala Glu Ser Ala Gln Arg Gln
1               5                   10                  15

Gly Pro Asn Gly Gly Gly Glu Gln Ser Ala Asn Glu Phe
            20                  25

<210> SEQ ID NO 12
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Pro Ile Glu Arg Val Lys Lys Asn Leu Leu Lys Lys Glu Tyr Asn Val
1               5                   10                  15

Ser Asp Asp Ser Met Lys Leu Gly Gly Asn Asn Thr Ser Glu Lys Ala
            20                  25                  30

Asp

<210> SEQ ID NO 13
<211> LENGTH: 32
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 13

His Lys Ser Ile Gly Gln Pro Lys Leu Ser Thr His Pro Phe Leu Cys
1               5                   10                  15

Pro Lys Pro Gln Lys Met Asn Thr Ser Leu Gly Gln His Leu Thr Leu
            20                  25                  30

<210> SEQ ID NO 14
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ala Glu Ser Ala Gln Arg Gln Gly Pro Leu Gly Gly Gly Glu Gln Ser
1               5                   10                  15

Ala Asn Glu Phe
            20

<210> SEQ ID NO 15
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Lys Pro Lys Lys Val Ala Gly Ala Ala Thr Pro Lys Lys Ser Ile Lys
1               5                   10                  15

Arg Thr Pro Lys Lys Val Lys Lys Pro Ala Thr Ala Ala Gly Thr Lys
            20                  25                  30

Lys

<210> SEQ ID NO 16
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Ser Lys Leu Pro Tyr Pro Val Ala Lys Ser Gly Lys Arg Ala Leu Ala
1               5                   10                  15

Arg Gly Pro Ala Pro Thr Glu Lys Thr Pro His Ser Gly Ala Gln Leu
            20                  25                  30

Gly

<210> SEQ ID NO 17
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 17

Glu Gln Gly Pro Trp Gln Ser Glu Gly Gln Thr Trp Arg Ala Ala Gly
1               5                   10                  15

Gly Arg Val Pro Val Pro Cys Pro Ala Ala Gly Pro Gly
            20                  25

<210> SEQ ID NO 18
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Ser Gly Ala Arg Ile Gly Ala Pro Pro His Ala Thr Ala Thr Ser
1               5                   10                  15

Ser Ser Ser Phe Met Pro Gly Thr Trp Gly Arg Glu Asp Leu
            20                  25                  30

<210> SEQ ID NO 19
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Lys Leu Ala Trp Arg Gly Arg Ile Ser Ser Ser Gly Cys Pro Ser Met
1               5                   10                  15

Thr Ser Pro Pro Ser Pro Met Phe Gly Met Thr Leu His Thr
            20                  25                  30

<210> SEQ ID NO 20
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Asp Ser Ala Val Asp Lys Gly His Pro Asn Arg Ser Ala Leu Ser Leu
1               5                   10                  15

Thr Pro Gly Leu Arg Ile Gly Pro Ser Gly Ile Pro Gln Ala Gly Leu
            20                  25                  30

Gly

<210> SEQ ID NO 21
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Leu Leu Thr Asp Arg Asn Thr Ser Gly Thr Thr Phe Thr Leu Leu Gly
1               5                   10                  15
```

```
Val Ser Asp Tyr Pro Glu Leu Gln Val Pro
            20                  25

<210> SEQ ID NO 22
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Leu Thr Asp Leu Pro Gly Arg Ile Arg Val Ala Pro Gln Gln Asn Asp
1               5                   10                  15

Leu Asp Ser Pro Gln Gln Ile Ser Ile Ser Asn Ala Glu
            20                  25

<210> SEQ ID NO 23
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Lys Gly Ala Ser Leu Asp Ala Gly Trp Gly Ser Pro Arg Trp Thr Thr
1               5                   10                  15

Thr Arg Met Thr Ser Ala Ser Ala Gly Arg Ser Thr Arg Ala
            20                  25                  30

<210> SEQ ID NO 24
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Phe Arg Leu Ile Trp Arg Ser Val Lys Asn Gly Lys Ser Ser Arg Glu
1               5                   10                  15

Gln Glu Leu Ser Trp Asn Cys Ser His Gln Val Pro Ser Leu Gly Ala
            20                  25                  30

<210> SEQ ID NO 25
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gly Lys Ser Arg Gly Gln Gln Ala Gln Asp Arg Ala Arg His Ala Ala
1               5                   10                  15

Gly Ala Ala Pro Ala Arg Pro Leu Gly Ala Leu Arg Glu Gln
            20                  25                  30

<210> SEQ ID NO 26
<211> LENGTH: 33
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Leu Leu Thr Asp Arg Asn Thr Ser Gly Thr Thr Phe Thr Leu Leu Gly
1               5                   10                  15

Val Ser Asp Tyr Pro Glu Leu Gln Val Pro Ile Pro Gln Ala Gly Leu
            20                  25                  30

Gly

<210> SEQ ID NO 27
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Arg Gly Leu His Ser Gln Gly Leu Gly Arg Gly Arg Ile Ala Met Ala
1               5                   10                  15

Gln Thr Ala Gly Val Leu Arg Ser Leu Glu Gln Glu Glu
            20                  25

<210> SEQ ID NO 28
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Pro Gln Leu Ala Gly Gly Gly Ser Gly Ala Pro Gly Glu His Pro
1               5                   10                  15

Leu Leu Pro Gly Gly Ala Pro Leu Pro Ala Gly Leu Phe
            20                  25

<210> SEQ ID NO 29
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Thr Trp Ala Gly His Val Ser Thr Ala Leu Ala Arg Pro Leu Gly Ala
1               5                   10                  15

Pro Trp Ala Glu Pro Gly Ser Cys Gly Pro Gly Thr Asn
            20                  25

<210> SEQ ID NO 30
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 30

Lys Lys Asn Ile Thr Asn Leu Ser Arg Leu Val Val Arg Pro Asp Thr
1               5                   10                  15

Asp Ala Val Tyr
            20

<210> SEQ ID NO 31
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Trp Asp Gly Pro Pro Glu Asn Asp Met Leu Leu Lys Glu Ile Cys Gly
1               5                   10                  15

Ser Leu Ile Pro
            20

<210> SEQ ID NO 32
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Leu Ala Ala Ser Gly Leu His Gly Ser Ala Trp Leu Val Pro Gly Glu
1               5                   10                  15

Gln Pro Val Ser Gly Pro His His Gly Lys Gln Pro Ala Gly Val
            20                  25                  30

<210> SEQ ID NO 33
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Pro Ile Gln Val Phe Tyr Thr Lys Gln Pro Gln Asn Asp Tyr Leu His
1               5                   10                  15

Val Ala Leu Val Ser Val Phe Gln Ile His Gln Glu Ala Pro Ser Ser
            20                  25                  30

Gln

<210> SEQ ID NO 34
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Val Ala Gly Leu Ala Ala Ser Gly Leu His Gly Ser Ala Trp Leu Val
1               5                   10                  15
```

Pro Gly Glu Gln Pro Val Ser Gly Pro His His Gly Lys Gln
            20                  25                  30

<210> SEQ ID NO 35
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Ser Lys Arg Gly Val Gly Ala Lys Thr Leu Leu Pro Asp Pro Phe
1               5                   10                  15

Leu Phe Trp Pro Cys Leu Glu Gly Thr Arg Arg Ser Leu
            20                  25

<210> SEQ ID NO 36
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Ser Tyr Lys Lys Leu Pro Leu Leu Ile Phe Pro Ser His Arg Arg Ala
1               5                   10                  15

Pro Leu Leu Ser Ala Thr Gly Asp Arg Gly Phe Ser Val
            20                  25

<210> SEQ ID NO 37
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Gly Leu Leu Ser Asp Gly Ser Gly Leu Gly Gln Ile Thr Trp Ala Ser
1               5                   10                  15

Ala Glu His Leu Gln Arg Pro Gly Ala Gly Ala Glu Leu Ala
            20                  25                  30

<210> SEQ ID NO 38
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Asp Leu Cys Ile Cys Pro Arg Ser His Arg Gly Ala Phe Gln Leu Leu
1               5                   10                  15

Pro Ser Ala Leu Leu Val Arg Val Leu Glu Gly Ser Asp Ser
            20                  25                  30

<210> SEQ ID NO 39
<211> LENGTH: 30

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Asp Ala Ser Asp Phe Leu Pro Asp Thr Gln Leu Phe Pro His Phe Thr
1               5                   10                  15
Glu Leu Leu Leu Pro Leu Asp Pro Leu Glu Gly Ser Ser Val
            20                  25                  30

<210> SEQ ID NO 40
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Asp Met Ala Trp Arg Arg Asn Ser Arg Leu Tyr Trp Leu Ile Lys Met
1               5                   10                  15
Val Glu Gln Trp Gln Glu Gln His Leu Pro Ser Leu Ser Ser
            20                  25                  30

<210> SEQ ID NO 41
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Leu Ser Val Pro Phe Thr Cys Gly Val Asn Phe Gly Asp Ser Ile Glu
1               5                   10                  15
Asp Leu Glu Ile
            20

<210> SEQ ID NO 42
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Pro Leu Met Gln Thr Glu Leu His Gln Leu Val Pro Glu Ala Asp Pro
1               5                   10                  15
Glu Glu Met Ala
            20

<210> SEQ ID NO 43
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 43

Glu Asp Leu His Leu Leu Ser Val Pro Cys Pro Ser Tyr Lys Lys Leu
1               5                   10                  15

Pro Leu Leu Ile Phe Pro Ser His Arg Arg Ala Pro Leu Leu Ser Ala
            20                  25                  30

<210> SEQ ID NO 44
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Ala His Arg Gln Gly Glu Lys Gln His Leu Leu Pro Val Phe Ser Arg
1               5                   10                  15

Leu Ala Leu Arg Leu Pro Trp Arg His Ser Val Gln Leu
            20                  25

<210> SEQ ID NO 45
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Ala Leu Ser Leu Thr Pro Gly Leu Arg Ile Gly Pro Ser Gly Leu Phe
1               5                   10                  15

Leu Val Phe Leu Ala Glu Ser Ala Val Asp Lys Gly His Pro Asn Arg
            20                  25                  30

Ser

<210> SEQ ID NO 46
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Asp Ser Ala Val Asp Lys Gly His Pro Asn Arg Ser Ala Leu Ser Leu
1               5                   10                  15

Thr Pro Gly Leu Arg Ile Gly Pro Ser Gly Leu Phe Leu Val Phe Leu
            20                  25                  30

Ala

<210> SEQ ID NO 47
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Leu Arg Val Phe Ile Gly Asn Ile Ala Val Asn His Ala Pro Val Ser
```

```
1               5                   10                  15
Leu Arg Pro Gly Leu Gly Leu Pro Pro Gly Ala Pro Pro Gly Thr Val
                20                  25                  30
Pro
```

<210> SEQ ID NO 48
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

```
Leu Pro Val Phe Ile Gly Asn Ile Ala Val Asn His Ala Pro Val Ser
1               5                   10                  15
Leu Arg Pro Gly Leu Gly Leu Pro Pro Gly Ala Pro Pro Gly Thr Val
                20                  25                  30
Pro
```

<210> SEQ ID NO 49
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

```
Val Ser Trp Gly Lys Lys Val Gln Pro Ile Asp Ser Ile Leu Ala Asp
1               5                   10                  15
Trp Asn Glu Asp Ile Glu Ala Phe Glu Met Met Glu Lys Asp
                20                  25                  30
```

<210> SEQ ID NO 50
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

```
Gly Thr Lys Ala Leu Gln Leu His Ser Ile Ala Gly Arg Trp Pro Arg
1               5                   10                  15
Met Glu Pro Trp Val Val Glu Ser Met Ser Leu Gly Val Pro
                20                  25                  30
```

<210> SEQ ID NO 51
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

```
Ser Gly Gln Pro Ala Pro Glu Glu Thr Val Leu Phe Leu Gly Leu Leu
1               5                   10                  15
His Gly Leu Leu Leu Ile Leu Arg Arg Leu Arg Gly Gly
```

```
                        20                  25

<210> SEQ ID NO 52
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Tyr Leu Leu Pro Lys Thr Ala Val Val Leu Arg Cys Pro Ala Leu Arg
1               5                   10                  15

Val Arg Lys Pro
            20

<210> SEQ ID NO 53
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Ile Gly Ala Leu Asn Pro Lys Arg Ala Ala Phe Phe Ala Glu His Tyr
1               5                   10                  15

Glu Ser Trp Glu
            20

<210> SEQ ID NO 54
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Ser Tyr Asp Ser Val Ile Arg Glu Leu Leu Gln Lys Pro Asn Val Arg
1               5                   10                  15

Val Val Val Leu
            20

<210> SEQ ID NO 55
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Val Glu Gln Gly His Val Arg Val Gly Pro Asp Val Val Thr His Pro
1               5                   10                  15

Ala Phe Leu Val
            20

<210> SEQ ID NO 56
<211> LENGTH: 31
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 56

Ala Pro Ala Leu Gly Pro Gly Ala Ala Ser Val Ala Ser Arg Cys Gly
1               5                   10                  15

Leu Asp Pro Ala Leu Ala Pro Gly Gly Ser His Met Leu Arg Ala
            20                  25                  30

<210> SEQ ID NO 57
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Leu Leu Thr Asp Arg Asn Thr Ser Gly Thr Thr Phe Thr Leu Leu Gly
1               5                   10                  15

Val Ser Asp Tyr Pro Glu Leu Gln Val Pro Leu Phe Leu Val Phe Leu
            20                  25                  30

Ala

<210> SEQ ID NO 58
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Glu Glu Gly Leu Leu Pro Glu Val Phe Gly Ala Gly Val Pro Leu Ala
1               5                   10                  15

Leu Cys Pro Ala Val Pro Ser Ala Ala Lys Pro His Arg Pro Arg Val
            20                  25                  30

Leu

<210> SEQ ID NO 59
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Val Gln Leu Ser Ile Gln Asp Val Ile Arg Arg Ala Arg Leu Ser Thr
1               5                   10                  15

Val Pro Thr Ala Gln Arg Val Ala Leu Arg Ser Gly Trp Ile
            20                  25                  30

<210> SEQ ID NO 60
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 60

Leu Pro Val Phe Ile Gly Asn Ile Ala Val Asn His Ala Pro Val Ser
1               5                   10                  15

Leu Arg Pro Gly Leu Gly Leu Pro Pro Gly Ala Pro Pro Leu Val Val
            20                  25                  30

Pro

<210> SEQ ID NO 61
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 61

His His His His His His
1               5

<210> SEQ ID NO 62
<211> LENGTH: 4
<212> TYPE: PRT
<213> ORGANISM: Homo sapiens

<400> SEQUENCE: 62

Asp Glu Ala Asp
1

COMBINATION THERAPY WITH NEOANTIGEN VACCINE

RELATED APPLICATIONS AND INCORPORATION BY REFERENCE

The present application is filed pursuant to 35 U.S.C. § as an U.S. National Phase Application of International Patent Application No. PCT/US2014/071707, which was filed on Dec. 19, 2014. This application claims benefit of and priority to U.S. provisional patent applications 61/919,576, filed Dec. 20, 2013 and 61/976,274, filed on Apr. 7, 2014.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was made with government support under R01 CA155010 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 13, 2016, is named 47608.02.2001_SL.txt and is 26,057 bytes in size.

FIELD OF THE INVENTION

The present invention relates to methods for the treatment of neoplasia, and more particularly tumors, by administering to a subject a neoplasia vaccine comprising a plurality of neoplasia/tumor specific neoantigens and at least one checkpoint inhibitor.

BACKGROUND OF THE INVENTION

Approximately 1.6 million Americans are diagnosed with neoplasia every year, and approximately 580,000 people in the United States are expected to die of the disease in 2013. Over the past few decades there been significant improvements in the detection, diagnosis, and treatment of neoplasia, which have significantly increased the survival rate for many types of neoplasia. However, only about 60% of people diagnosed with neoplasia are still alive 5 years after the onset of treatment, which makes neoplasia the second leading cause of death in the United States.

Currently, there are a number of different existing cancer therapies, including ablation techniques (e.g., surgical procedures, cryogenic/heat treatment, ultrasound, radiofrequency, and radiation) and chemical techniques (e.g., pharmaceutical agents, cytotoxic/chemotherapeutic agents, monoclonal antibodies, and various combinations thereof). Unfortunately, such therapies are frequently associated with serious risk, toxic side effects, and extremely high costs, as well as uncertain efficacy.

There is a growing interest in cancer therapies that seek to target cancerous cells with a patient's own immune system (e.g., cancer vaccines) because such therapies may mitigate/eliminate some of the herein-described disadvantages. Cancer vaccines are typically composed of tumor antigens and immunostimulatory molecules (e.g., cytokines or TLR ligands) that work together to induce antigen-specific cytotoxic T cells that target and destroy tumor cells. Current cancer vaccines typically contain shared tumor antigens, which are native proteins (i.e.—proteins encoded by the DNA of all the normal cells in the individual) that are selectively expressed or over-expressed in tumors found in many individuals. While such shared tumor antigens are useful in identifying particular types of tumors, they are not ideal as immunogens for targeting a T-cell response to a particular tumor type because they are subject to the immune dampening effects of self-tolerance. Vaccines containing tumor-specific and patient-specific neoantigens can overcome some of the disadvantages of vaccines containing shared tumor antigens.

Described in the present application is combination therapy for achieving a desirable therapeutic result, and in particular in treating cancer.

Citation or identification of any document in this application is not an admission that such document is available as prior art to the present invention.

SUMMARY OF THE INVENTION

The present invention relates to neoplasia vaccines or immunogenic compositions administered in combination with one or more other agents, such as one or more checkpoint blockade inhibitors for the treatment or prevention of neoplasia in a subject.

In one aspect, the invention features a method of treating or preventing a neoplasia in a subject in need thereof that may comprise administering to a subject in need thereof (a) a neoplasia vaccine or immunogenic composition; and (b) at least one checkpoint inhibitor. The administering can be serially or sequentially or at substantially the same time or substantially simultaneously. For example, the administering of the neoplasia vaccine or immunogenic composition and the administering of the at least one checkpoint inhibitor can be at about the same time or substantially simultaneously. Alternatively, the administering of the neoplasia vaccine or immunogenic composition can be on one time schedule, e.g., weekly, biweekly, every three weeks, monthly, bimonthly, every quarter year (every three months), every third of a year (every four months), every five months, twice yearly (every six months), every seven months, every eight months, every nine months, every ten months, every eleven months, annually or the like, and the administering of the at least one checkpoint blockade inhibitor can be on a different schedule, typical for the checkpoint blockade inhibitor such that the subject or patient has two different treatment schedules running concomitantly and the administering of the neoplasia vaccine or immunogenic composition and the administering of the at least one checkpoint inhibitor can be sequentially or serially. The neoplasia vaccine or immunogenic composition advantageously comprises at least four different neoantigens (and by different antigens it is intended that each antigen has a different neoepitope), e.g., at least 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33 or 34 or 35 or 36 or 37 or 38 or 39 or 40 or more different neoantigens can be in the neoplasia vaccine or immunogenic composition. The neoplasia vaccine or immunogenic composition can be administered via subcompositions, each containing a portion of the neoantigens, and sub-compositions can be administered to different places on the subject or patient; for instance, a composition comprising 20 different neoantigens, can be administered in four (4) subcompositions, each containing 5 of the 20 different neoantigens, and the four (4) subcompositions can be administered so as to endeavor to deliver each subcomposition at or near a draining lymph node of the patient, e.g., to each of the arms and legs (e.g., thigh or upper thigh or near buttocks or lower back on each side of the patient) so as to endeavor to deliver each subcomposition at or near a draining lymph node of the patient or subject. Of course, the number of locations and hence number of subcompositions can vary, e.g., the skilled practitioner could consider administration at or near the spleen to have a fifth point of administration, and the skilled practitioner can vary the locations such that only one, two or three are used (e.g., each arm and a leg, each of legs and one arm, each of the legs and no arms, or only both arms). The vaccine or immunogenic composition administered at the aforementioned various intervals can be different formulations, and the subcompositions administered at different places on the subject or patient during a single administration can be different compositions. For instance, a first administration can be of a whole antigen vaccine or immunogenic composition and a next or later administration can be of a vector (e.g., viral vector or plasmid) that has expression of antigen(s) in vivo. Likewise, in the administration of different subcompositions to different locations on the patient or subject, some of the subcompositions can comprise a whole antigen and some of the subcompositions can comprise a vector (e.g., viral vector or plasmid) that has expression of antigen(s) in vivo. And some compositions and subcompositions can comprise both vector(s) (e.g., viral vector or plasmid) that has/have expression of antigen(s) in vivo and whole antigens. Some vectors (e.g., poxvirus) that have expression of antigen(s) in vivo can have an immunostimulatory or adjuvanting effect, and hence compositions or subcompositions that contain such vectors can be self-adjuvanting. Also, by changing up the nature of how the antigens are presented to the immune system, the administrations can "prime" and then "boost" the immune system. And in this text, when there is mention of a "vaccine" it is intended that the invention comprehends immunogenic compositions, and when there is mention of a patient or subject it is intended that such an individual is a patient or subject in need of the herein disclosed treatments, administrations, compositions, and generally the subject invention.

In one embodiment, the neoplasia vaccine or immunogenic composition comprises at least two, at least three, at least four or at least five neoantigenic peptides. In another embodiment, the neoantigenic peptide ranges from about 5 to about 50 amino acids in length. In another related embodiment, the neoantigenic peptide ranges from about 15 to about 35 amino acids in length. Typically, the length is greater than about 15 or 20 amino acids, e.g., from 15 to 50 or about 75 amino acids.

In one embodiment, the neoplasia vaccine or immunogenic composition further comprises a pH modifier and a pharmaceutically acceptable carrier.

In one embodiment, the method further comprises administration of an immunomodulator or adjuvant (and hence the vaccine or immunogenic composition can include an immunomodulator or adjuvant). In another related embodiment, the immunomodulator or adjuvant is selected from the group consisting of poly-ICLC, 1018 ISS, aluminum salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PEPTEL, vector system, PLGA microparticles, resiquimod, SRL172, Virosomes and other Virus-like particles, YF-17D, VEGF trap, R848, beta-glucan, Pam3Cys, and Aquila's QS21 stimulon. In another further embodiment, the immunomodulator or adjuvant is poly-ICLC.

The dissolution of these polymers in water leads to an acid solution which is neutralized, preferably to physiological pH, in order to give the adjuvant solution into which the vaccine or immunogenic composition or antigen(s) or vector(s) thereof is incorporated. The carboxyl groups of the polymer are then partly in COO$^-$.

Preferably, a solution of adjuvant according to the invention, especially of carbomer, is prepared in distilled water, preferably in the presence of sodium chloride, the solution obtained being at acidic pH. This stock solution is diluted by adding it to the required quantity (for obtaining the desired final concentration), or a substantial part thereof, of water charged with salt such as NaCl, preferably physiological saline (NaCl 9 g/l), all at once or in several portions with concomitant or subsequent neutralization (pH 7.3 to 7.4), preferably with a base such as NaOH. This solution at physiological pH is used as is to reconstitute the vaccine, especially stored in freeze-dried or lyophilized form.

The polymer concentration in the final vaccine composition is 0.01% to 2% w/v, more particularly 0.06 to 1% w/v, preferably 0.1 to 0.6% w/v.

Moreover, the invention applies to the use of any type of expression vector, such as a viral expression vector, e.g., poxvirus (e.g., orthopoxvirus or avipoxvirus such as vaccinia virus, including Modified Vaccinia Ankara or MVA, MVA-BN, NYVAC according to WO-A-92/15672, fowlpox, e.g., TROVAX, canarypox, e.g., ALVAC (WO-A-95/27780 and WO-A-92/15672) pigeonpox, swinepox and the like), adenovirus, AAV herpesvirus, and lentivirus; or a plasmid or DNA or nucleic acid molecule vector. Some vectors that are cytoplasmic, such as poxvirus vectors, may be advantageous. However adenovirus, AAV and lentivirus can also be advantageous to use in the practice of the invention.

In a ready-for-use, especially reconstituted, vaccine or immunogenic composition, the vector, e.g., viral vector, is present in the quantities within the ambit of the skilled person from this disclosure and the knowledge in the art (such as in patent and scientific literature cited herein).

Whole antigen or vector, e.g., recombinant live vaccines generally exist in a freeze-dried form allowing their storage and are reconstituted immediately before use in a solvent or excipient, which can include an adjuvant as herein discussed.

The subject of the invention is therefore also a vaccination or immunization set or kit comprising, packaged separately, freeze-dried vaccine and a solution, advantageously including an adjuvant compound as herein discussed for the reconstitution of the freeze-dried vaccine.

The subject of the invention is also a method of vaccination or immunization comprising or consisting essentially of or consisting of administering, e.g., by the parenteral, preferably subcutaneous, intramuscular or intradermal, route or by the mucosal route a vaccine or immunogenic composition in accordance with the invention at the rate of one or more administrations. Optionally this method includes a preliminary step of reconstituting the freeze-dried vaccine or immunogenic composition (e.g., if lyophilized whole antigen or vector) in a solution, advantageously also including an adjuvant.

In one embodiment, the checkpoint inhibitor is an inhibitor of the programmed death-1 (PD-1) pathway. In another embodiment, the inhibitor of the PD-1 pathway is an anti-PD1 antibody. In a related embodiment, the inhibitor of the PD-1 pathway is Nivolumab.

In one embodiment, the checkpoint inhibitor is an anti-cytotoxic T-lymphocyte-associated antigen 4 (CTLA4) antibody. In a related embodiment, the anti-CTLA4 antibody is Ipilumumab or Tremelimumab.

In one embodiment, the subject is suffering from a neoplasia selected from the group consisting of: Non-Hodgkin's Lymphoma (NHL), clear cell Renal Cell Carcinoma (ccRCC), melanoma, sarcoma, leukemia or a cancer of the bladder, colon, brain, breast, head and neck, endometrium, lung, ovary, pancreas or prostate. In another embodiment, the neoplasia is metastatic. In a further embodiment, the subject has no detectable neoplasia but is at high risk for disease recurrence. In a further related embodiment, the subject has previously undergone autologous hematopoietic stem cell transplant (AHSCT).

In one embodiment, administration of the checkpoint inhibitor is initiated before initiation of administration of the neoplasia vaccine or immunogenic composition. In one embodiment, administration of the checkpoint inhibitor is initiated after initiation of administration of the neoplasia vaccine or immunogenic composition. In one embodiment, administration of the checkpoint inhibitor is initiated simultaneously with the initiation of administration of the neoplasia vaccine or immunogenic composition.

In another embodiment, administration of the checkpoint inhibitor continues every 2-8 or more weeks after the first administration of the checkpoint inhibitor. In a further embodiment, administration of the checkpoint inhibitor continues every 2, 3 or 4, 6 or 8 weeks after the first administration of the checkpoint inhibitor. In another further embodiment, the administration of the checkpoint inhibitor is withheld during the week prior to administration of the neoplasia vaccine or immunogenic composition. In still another further embodiment, the administration of the checkpoint inhibitor is withheld during administration of the neoplasia vaccine or immunogenic composition.

In one embodiment, the administration of the checkpoint inhibitor is initiated following tumor resection. In another embodiment, administration of the neoplasia vaccine or immunogenic composition is initiated 1-15 weeks after tumor resection. In another further embodiment, administration of the neoplasia vaccine or immunogenic composition is initiated 4-12 weeks after tumor resection.

In one embodiment, administration of the neoplasia vaccine or immunogenic composition is in a prime/boost dosing regimen. In another embodiment, administration of the neoplasia vaccine or immunogenic composition is at weeks 1, 2, 3 or 4 as a prime. In another further embodiment, administration of the neoplasia vaccine or immunogenic composition is at months 2, 3, 4 or 5 as a boost.

In one embodiment, the vaccine or immunogenic composition is administered at a dose of about 10 μg-1 mg per 70 kg individual as to each neoantigenic peptide. In another embodiment, the vaccine or immunogenic composition is administered at an average weekly dose level of about 10 μg-2000 μg per 70 kg individual as to each neoantigenic peptide. In another further embodiment, the checkpoint inhibitor is administered at a dose of about 0.1-10 mg/kg. In another related embodiment, the administration is intravenous.

In one embodiment, the anti-CTLA4 antibody is administered at a dose of about 1 mg/kg-3 mg/kg.

In one embodiment, the vaccine or immunogenic composition is administered intravenously or subcutaneously.

In another embodiment, the checkpoint inhibitor is administered intravenously or subcutaneously.

In another embodiment, the checkpoint inhibitor is administered subcutaneously within about 2 cm of the site of administration of the neoplasia vaccine or immunogenic composition.

In one embodiment, the checkpoint inhibitor is administered at a dose of about 0.1-1 mg per site of administration of the neoplasia vaccine or immunogenic composition, per 70 kg individual.

In one embodiment, the method further comprises administration of one or more additional agents. In another embodiment, the additional agents are selected from the group consisting of: chemotherapeutic agents, anti-angiogenesis agents and agents that reduce immune-suppression. In a further embodiment, the one or more additional agents are one or more anti-glucocorticoid induced tumor necrosis factor family receptor (GITR) agonistic antibodies.

In one embodiment the method may comprise administering the combination therapy within a standard of care for a particular cancer. In another embodiment the combination therapy is administered within a standard of care where addition of the combination therapy is synergistic with the steps in the standard of care.

The invention comprehends performing methods as in U.S. patent application No. 20110293637, incorporated herein by reference, e.g., a method of identifying a plurality of at least 4 subject-specific peptides and preparing a subject-specific immunogenic composition that upon administration presents the plurality of at least 4 subject-specific peptides to the subject's immune system, wherein the subject has a tumor and the subject-specific peptides are specific to the subject and the subject's tumor, said method comprising:

(i) identifying, including through
  nucleic acid sequencing of a sample of the subject's tumor and
  nucleic acid sequencing of a non-tumor sample of the subject,
a plurality of at least 4 tumor-specific non-silent mutations not present in the non-tumor sample; and (ii) selecting from the identified non-silent mutations the plurality of at least 4 subject-specific peptides, each having a different tumor neo-epitope that is an epitope specific to the tumor of the subject, from the identified plurality of tumor specific mutations, wherein each neo-epitope is an expression product of a tumor-specific non-silent mutation not present in the non-tumor sample, each neo-epitope binds to a HLA protein of the subject, and selecting includes
  determining binding of the subject-specific peptides to the HLA protein, and (iii) formulating the subject-specific immunogenic composition for administration to the subject so that upon administration the plurality of at least 4 subject-specific peptides are presented to the subject's immune system, wherein the selecting or formulating comprises at least one of:

including in the subject-specific immunogenic composition a subject-specific peptide that includes an expression product of an identified neo-ORF, wherein a neo-ORF is a tumor-specific non-silent mutation not present in the non-tumor sample that creates a new open reading frame, and including in the subject-specific immunogenic composition a subject-specific peptide that includes an expression product of an identified point mutation and has a determined binding to the HLA protein of the subject with an IC50 less than 500 nM, whereby, the plurality of at least 4 subject-specific peptides are identified, and the subject-specific immunogenic composition that upon administration presents the plurality of at least 4 subject-specific peptides to the subject's immune system, wherein the subject-specific peptides are specific to the subject and the subject's tumor, is prepared; or a method of identifying a neoantigen comprising:

a. identifying a tumor specific mutation in an expressed gene of a subject having cancer;
b. wherein when said mutation identified in step (a) is a point mutation:
   i. identifying a mutant peptide having the mutation identified in step (a), wherein said mutant peptide binds to a class I HLA protein with a greater affinity than a wild-type peptide; and has an IC50 less than 500 nm;
c. wherein when said mutation identified in step (a) is a splice-site, frameshift, read-through or gene-fusion mutation:
   i. identifying a mutant polypeptide encoded by the mutation identified in step (a), wherein said mutant polypeptide binds to a class I HLA protein; or a method of inducing a tumor specific immune response in a subject comprising administering one or more peptides or polypeptides identified and an adjuvant; or a method of vaccinating or treating a subject for cancer comprising:
a. identifying a plurality of tumor specific mutations in an expressed gene of the subject wherein when said mutation identified is a:
   i. point mutation further identifying a mutant peptide having the point mutation; and/or
   ii. splice-site, frameshift, read-through or gene-fusion mutation further identifying a mutant polypeptide encoded by the mutation;
b. selecting one or more mutant peptides or polypeptides identified in step (a) that binds to a class I HLA protein;
c. selecting the one or more mutant peptides or polypeptides identified in step (b) that is capable of activating anti-tumor CD8 T-cells; and
d. administering to the subject the one or more peptides or polypeptides, autologous dendritic cells or antigen presenting cells pulsed with the one or more peptides or polypeptides selected in step (c); or preparing a pharmaceutical composition comprising one identified peptide(s), and performing method(s) as herein discussed. Thus, the neoplasia vaccine or immunogenic composition herein can be as in U.S. patent application No. 20110293637.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) is provided by the Office upon request and payment of the necessary fee.

The following detailed description, given by way of example, but not intended to limit the invention solely to the specific embodiments described, may best be understood in conjunction with the accompanying drawings, incorporated herein by reference, wherein.

DETAILED DESCRIPTION OF THE INVENTION

Definitions

Figure 1:
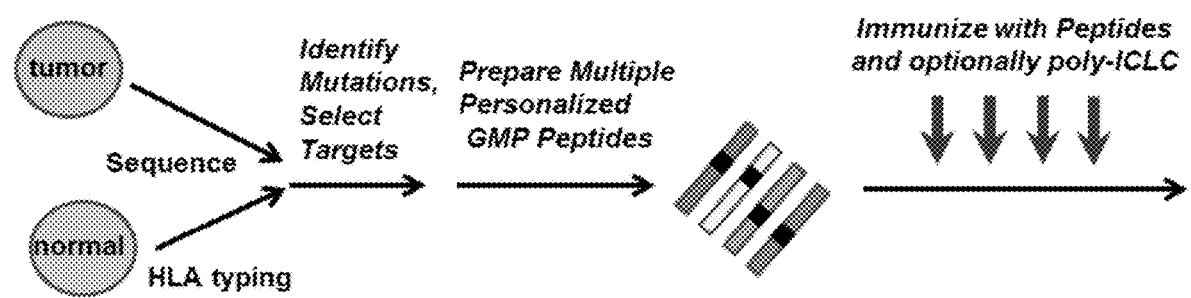
FIG. 1 depicts a flow process for making a personalized cancer vaccine or immunogenic composition.

To facilitate an understanding of the present invention, a number of terms and phrases are defined herein:

Unless specifically stated or obvious from context, as used herein, the term "about" is understood as within a range of normal tolerance in the art, for example within 2 standard deviations of the mean. About can be understood as within 50%, 45%, 40%, 35%, 30%, 25%, 20%, 15%, 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Unless specifically stated or obvious from context, as used herein, the term "or" is understood to be inclusive. Unless specifically stated or obvious from context, as used herein, the terms "a," "an," and "the" are understood to be singular or plural.

By "agent" is meant any small molecule chemical compound, antibody, nucleic acid molecule, or polypeptide, or fragments thereof.

Immune checkpoints are inhibitory pathways that slow down or stop immune reactions and prevent excessive tissue damage from uncontrolled activity of immune cells. By "checkpoint inhibitor" is meant to refer to any small molecule chemical compound, antibody, nucleic acid molecule, or polypeptide, or fragments thereof, that inhibits the inhibitory pathways, allowing more extensive immune activity. In certain embodiments, the checkpoint inhibitor is an inhibitor of the programmed death-1 (PD-1) pathway, for example an anti-PD1 antibody, such as, but not limited to Nivolumab. In other embodiments, the checkpoint inhibitor is an anti-cytotoxic T-lymphocyte-associated antigen (CTLA-4) antibody. In additional embodiments, the checkpoint inhibitor is targeted at another member of the CD28CTLA4 Ig superfamily such as BTLA, LAG3, ICOS, PDL1 or KIR Page et al., Annual Review of Medicine 65:27 (2014)). In further additional embodiments, the checkpoint inhibitor is targeted at a member of the TNFR superfamily such as CD40, OX40, CD137, GITR, CD27 or TIM-3. In some cases targeting a checkpoint inhibitor is accomplished with an inhibitory antibody or similar molecule. In other cases, it is accomplished with an agonist for the target; examples of this class include the stimulatory targets OX40 and GITR.

The term "combination" embraces the administration of a neoplasia vaccine or immunogenic composition (e.g. a pooled sample of neoplasia/tumor specific neoantigens) and one or more checkpoint inhibitors, as part of a treatment regimen intended to provide a beneficial (additive or synergistic) effect from the co-action of one or more of these therapeutic agents. The combination may also include one or more additional agents, for example, but not limited to, chemotherapeutic agents, anti-angiogenesis agents and agents that reduce immune-suppression. The beneficial effect of the combination includes, but is not limited to, pharmacokinetic or pharmacodynamic co-action resulting from the combination of therapeutic agents. Administration of these therapeutic agents in combination typically is carried out over a defined time period (for example, minutes, hours, days, or weeks depending upon the combination selected).

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. For example, one combination of the present invention may comprise a pooled sample of tumor specific neoantigens and a checkpoint inhibitor administered at the same or different times, or they can be formulated as a single, co-formulated pharmaceutical composition comprising the two compounds. As another example, a combination of the present invention (e.g., a pooled sample of tumor specific neoantigens and a checkpoint inhibitor and/or an anti-CTLA4 antibody) may be formulated as separate pharmaceutical compositions that can be administered at the same or different time. As used herein, the term "simultaneously" is meant to refer to administration of one or more agents at the same time. For example, in certain embodiments, a neoplasia vaccine or immunogenic composition and a checkpoint inhibitor are administered simultaneously. Simultaneously includes administration contemporaneously, that is during the same period of time. In certain embodiments, the one or more agents are administered simultaneously in the same hour, or simultaneously in the same day. Sequential or substantially simultaneous administration of each therapeutic agent can be effected by any appropriate route including, but not limited to, oral routes, intravenous routes, sub-cutaneous routes, intramuscular routes, direct absorption through mucous membrane tissues (e.g., nasal, mouth, vaginal, and rectal), and ocular routes (e.g., intravitreal, intraocular, etc.). The therapeutic agents can be administered by the same route or by different routes. For example, one component of a particular combination may be administered by intravenous injection while the other component(s) of the combination may be administered orally. The components may be administered in any therapeutically effective sequence. The phrase "combination" embraces groups of compounds or non-drug therapies useful as part of a combination therapy.

The term "neoantigen" or "neoantigenic" means a class of tumor antigens that arises from a tumor-specific mutation(s) which alters the amino acid sequence of genome encoded proteins.

By "neoplasia" is meant any disease that is caused by or results in inappropriately high levels of cell division, inappropriately low levels of apoptosis, or both. For example, cancer is an example of a neoplasia. Examples of cancers include, without limitation, leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

The term "neoplasia vaccine" is meant to refer to a pooled sample of neoplasia/tumor specific neoantigens, for example at least two, at least three, at least four, at least five, or more neoantigenic peptides. A "vaccine" is to be understood as meaning a composition for generating immunity for the prophylaxis and/or treatment of diseases (e.g., neoplasia/tumor). Accordingly, vaccines are medicaments which comprise antigens and are intended to be used in humans or animals for generating specific defense and protective substance by vaccination. A "neoplasia vaccine composition" can include a pharmaceutically acceptable excipient, carrier or diluent.

The term "pharmaceutically acceptable" refers to approved or approvable by a regulatory agency of the Federal or a state government or listed in the U.S. Pharmacopeia or other generally recognized pharmacopeia for use in animals, including humans.

A "pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

A "pharmaceutically acceptable salt" of pooled tumor specific neoantigens as recited herein may be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH2)n-COOH where n is 0-4, and the like. Similarly, pharmaceutically acceptable cations include, but are not limited to sodium, potassium, calcium, aluminum, lithium and ammonium. Those of ordinary skill in the art will recognize from this disclosure and the knowledge in the art that further pharmaceutically acceptable salts for the pooled tumor specific neoantigens provided herein, including those listed by Remington's Pharmaceutical Sciences, 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

By a "polypeptide" or "peptide" is meant a polypeptide that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide. An isolated polypeptide may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

As used herein, the terms "prevent," "preventing," "prevention," "prophylactic treatment," and the like, refer to reducing the probability of developing a disease or condition in a subject, who does not have, but is at risk of or susceptible to developing a disease or condition.

The term "prime/boost" or "prime/boost dosing regimen" is meant to refer to the successive administrations of a vaccine or immunogenic or immunological compositions. The priming administration (priming) is the administration of a first vaccine or immunogenic or immunological composition type and may comprise one, two or more administrations. The boost administration is the second administration of a vaccine or immunogenic or immunological composition type and may comprise one, two or more administrations, and, for instance, may comprise or consist essentially of annual administrations. In certain embodiments, administration of the neoplasia vaccine or immunogenic composition is in a prime/boost dosing regimen.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

A "receptor" is to be understood as meaning a biological molecule or a molecule grouping capable of binding a ligand. A receptor may serve, to transmit information in a cell, a cell formation or an organism. The receptor comprises at least one receptor unit and frequently contains two or more receptor units, where each receptor unit may consist of a protein molecule, in particular a glycoprotein molecule.

The receptor has a structure that complements the structure of a ligand and may complex the ligand as a binding partner. Signaling information may be transmitted by conformational changes of the receptor following binding with the ligand on the surface of a cell. According to the invention, a receptor may refer to particular proteins of MHC classes I and II capable of forming a receptor/ligand complex with a ligand, in particular a peptide or peptide fragment of suitable length.

The term "subject" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

The terms "treat," "treated," "treating," "treatment," and the like are meant to refer to reducing or ameliorating a disorder and/or symptoms associated therewith (e.g., a neoplasia or tumor). "Treating" may refer to administration of the combination therapy to a subject after the onset, or suspected onset, of a cancer. "Treating" includes the concepts of "alleviating", which refers to lessening the frequency of occurrence or recurrence, or the severity, of any symptoms or other ill effects related to a cancer and/or the side effects associated with cancer therapy. The term "treating" also encompasses the concept of "managing" which refers to reducing the severity of a particular disease or disorder in a patient or delaying its recurrence, e.g., lengthening the period of remission in a patient who had suffered from the disease. It is appreciated that, although not precluded, treating a disorder or condition does not require that the disorder, condition, or symptoms associated therewith be completely eliminated.

The term "therapeutic effect" refers to some extent of relief of one or more of the symptoms of a disorder (e.g., a neoplasia or tumor) or its associated pathology. "Therapeutically effective amount" as used herein refers to an amount of an agent which is effective, upon single or multiple dose administration to the cell or subject, in prolonging the survivability of the patient with such a disorder, reducing one or more signs or symptoms of the disorder, preventing or delaying, and the like beyond that expected in the absence of such treatment. "Therapeutically effective amount" is intended to qualify the amount required to achieve a therapeutic effect. A physician or veterinarian having ordinary skill in the art can readily determine and prescribe the "therapeutically effective amount" (e.g., ED50) of the pharmaceutical composition required. For example, the physician or veterinarian could start doses of the compounds of the invention employed in a pharmaceutical composition at levels lower than that required in order to achieve the desired therapeutic effect and gradually increase the dosage until the desired effect is achieved.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

The combination therapy disclosed herein constitutes a new method for treating various types of cancer. The combination therapy described herein also provides a method of therapy for achieving clinical benefit without an unacceptable level of side effects.

The present invention relates to methods for the treatment of neoplasia, and more particularly tumors, by administering to a subject a neoplasia vaccine or immunogenic composition comprising a plurality of neoplasia/tumor specific neoantigens and at least one checkpoint inhibitor.

As described in more detail herein, whole genome/exome sequencing may be used to identify all, or nearly all, mutated neoantigens that are uniquely present in a neoplasia/tumor of an individual patient, and that this collection of mutated neoantigens may be analyzed to identify a specific, optimized subset of neoantigens for use as a personalized cancer vaccine or immunogenic composition for treatment of the patient's neoplasia/tumor. For example, a population of neoplasia/tumor specific neoantigens may be identified by sequencing the neoplasia/tumor and normal DNA of each patient to identify tumor-specific mutations, and the patient's HLA allotype can be identified. The population of neoplasia/tumor specific neoantigens and their cognate native antigens may then be subject to bioinformatic analysis using validated algorithms to predict which tumor-specific mutations create epitopes that could bind to the patient's HLA allotype. Based on this analysis, a plurality of peptides corresponding to a subset of these mutations may be designed and synthesized for each patient, and pooled together for use as a cancer vaccine or immunogenic composition in immunizing the patient.

The immune system can be classified into two functional subsystems: the innate and the acquired immune system. The innate immune system is the first line of defense against infections, and most potential pathogens are rapidly neutralized by this system before they can cause, for example, a noticeable infection. The acquired immune system reacts to molecular structures, referred to as antigens, of the intruding organism. There are two types of acquired immune reactions, which include the humoral immune reaction and the cell-mediated immune reaction. In the humoral immune reaction, antibodies secreted by B cells into bodily fluids bind to pathogen-derived antigens, leading to the elimination of the pathogen through a variety of mechanisms, e.g. complement-mediated lysis. In the cell-mediated immune reaction, T-cells capable of destroying other cells are activated. For example, if proteins associated with a disease are present in a cell, they are fragmented proteolytically to peptides within the cell. Specific cell proteins then attach themselves to the antigen or peptide formed in this manner and transport them to the surface of the cell, where they are presented to the molecular defense mechanisms, in particular T-cells, of the body. Cytotoxic T cells recognize these antigens and kill the cells that harbor the antigens.

The molecules that transport and present peptides on the cell surface are referred to as proteins of the major histocompatibility complex (MHC). MHC proteins are classified into two types, referred to as MHC class I and MHC class II. The structures of the proteins of the two MHC classes are very similar; however, they have very different functions. Proteins of MHC class I are present on the surface of almost all cells of the body, including most tumor cells. MHC class I proteins are loaded with antigens that usually originate from endogenous proteins or from pathogens present inside cells, and are then presented to naïve or cytotoxic T-lymphocytes (CTLs). MHC class II proteins are present on dendritic cells, B-lymphocytes, macrophages and other antigen-presenting cells. They mainly present peptides, which are processed from external antigen sources, i.e. outside of the cells, to T-helper (Th) cells. Most of the peptides bound by the MHC class I proteins originate from cytoplasmic proteins produced in the healthy host cells of an organism itself, and do not normally stimulate an immune reaction. Accordingly, cytotoxic T-lymphocytes that recognize such self-peptide-presenting MHC molecules of class I are deleted in the thymus (central tolerance) or, after their release from the thymus, are deleted or inactivated, i.e. tolerized (peripheral tolerance). MHC molecules are capable of stimulating an immune reaction when they present peptides to non-tolerized T-lymphocytes. Cytotoxic T-lymphocytes have both T-cell receptors (TCR) and CD8 molecules on their surface. T-Cell receptors are capable of recognizing and binding peptides complexed with the molecules of MHC class I. Each cytotoxic T-lymphocyte expresses a unique T-cell receptor which is capable of binding specific MHC/peptide complexes.

The peptide antigens attach themselves to the molecules of MHC class I by competitive affinity binding within the endoplasmic reticulum, before they are presented on the cell surface. Here, the affinity of an individual peptide antigen is directly linked to its amino acid sequence and the presence of specific binding motifs in defined positions within the amino acid sequence. If the sequence of such a peptide is known, it is possible to manipulate the immune system against diseased cells using, for example, peptide vaccines.

One of the critical barriers to developing curative and tumor-specific immunotherapy is the identification and selection of highly specific and restricted tumor antigens to avoid autoimmunity. Tumor neoantigens, which arise as a result of genetic change (e.g., inversions, translocations, deletions, missense mutations, splice site mutations, etc.) within malignant cells, represent the most tumor-specific class of antigens. Neoantigens have rarely been used in cancer vaccine or immunogenic compositions due to technical difficulties in identifying them, selecting optimized neoantigens, and producing neoantigens for use in a vaccine or immunogenic composition. These problems may be addressed by:

identifying all, or nearly all, mutations in the neoplasia/tumor at the DNA level using whole genome, whole exome (e.g., only captured exons), or RNA sequencing of tumor versus matched germline samples from each patient;

analyzing the identified mutations with one or more peptide-MHC binding prediction algorithms to generate a plurality of candidate neoantigen T cell epitopes that are expressed within the neoplasia/tumor and may bind patient HLA alleles; and synthesizing the plurality of candidate neoantigen peptides selected from the sets of all neoORF peptides and predicted binding peptides for use in a cancer vaccine or immunogenic composition.

As described herein, there is a large body of evidence in both animals and humans that mutated epitopes are effective in inducing an immune response and that cases of spontaneous tumor regression or long term survival correlate with CD8+ T-cell responses to mutated epitopes (Buckwalter and Srivastava PK. "It is the antigen(s), stupid" and other lessons from over a decade of vaccitherapy of human cancer. Seminars in immunology 20:296-300 (2008); Karanikas et al, High frequency of cytolytic T lymphocytes directed against a tumor-specific mutated antigen detectable with HLA tetramers in the blood of a lung carcinoma patient with long survival. Cancer Res. 61:3718-3724 (2001); Lennerz et al, The response of autologous T cells to a human melanoma is dominated by mutated neoantigens. Proc Natl Acad Sci USA. 102:16013 (2005)) and that "immunoediting" can be tracked to alterations in expression of dominant mutated antigens in mice and man (Matsushita et al, Cancer exome analysis reveals a T-cell-dependent mechanism of cancer immunoediting Nature 482:400 (2012); DuPage et al, Expression of tumor-specific antigens underlies cancer immunoediting Nature 482:405 (2012); and Sampson et al, Immunologic escape after prolonged progression-free survival with epidermal growth factor receptor variant III peptide vaccination in patients with newly diagnosed glioblastoma J Clin Oncol. 28:4722-4729 (2010)). In one embodiment, the mutated epitopes of a cancer patient are determined.

In one embodiment mutated epitopes are determined by sequencing the genome and/or exome of tumor tissue and healthy tissue from a cancer patient using next generation sequencing technologies. In another embodiment genes that are selected based on their frequency of mutation and ability to act as a neoantigen are sequenced using next generation sequencing technology. Next-generation sequencing applies to genome sequencing, genome resequencing, transcriptome profiling (RNA-Seq), DNA-protein interactions (ChIP-sequencing), and epigenome characterization (de Magalhies J P, Finch C E, Janssens G (2010). "Next-generation sequencing in aging research: emerging applications, problems, pitfalls and possible solutions". Ageing Research Reviews 9 (3): 315-323; Hall N (May 2007). "Advanced sequencing technologies and their wider impact in microbiology". J. Exp. Biol. 209 (Pt 9): 1518-1525; Church G M (January 2006). "Genomes for all". Sci. Am. 294 (1): 46-54; ten Bosch J R, Grody W W (2008). "Keeping Up with the Next Generation". The Journal of Molecular Diagnostics 10 (6): 484-492; Tucker T, Marra M, Friedman J M (2009). "Massively Parallel Sequencing: The Next Big Thing in Genetic Medicine". The American Journal of Human Genetics 85 (2): 142-154). Next-generation sequencing can now rapidly reveal the presence of discrete mutations such as coding mutations in individual tumors, most commonly single amino acid changes (e.g., missense mutations) and less frequently novel stretches of amino acids generated by frame-shift insertions/deletions/gene fusions, read-through mutations in stop codons, and translation of improperly spliced introns (e.g., neoORFs). NeoORFs are particularly valuable as immunogens because the entirety of their sequence is completely novel to the immune system and so are analogous to a viral or bacterial foreign antigen. Thus, neoORFs: (1) are highly specific to the tumor (i.e. there is no expression in any normal cells); (2) can bypass central tolerance, thereby increasing the precursor frequency of neoantigen-specific CTLs. For example, the power of utilizing analogous foreign sequences in a therapeutic anti-cancer vaccine or immunogenic composition was recently demonstrated with peptides derived from human papilloma virus (HPV). ~50% of the 19 patients with pre-neoplastic, viral-induced disease who received 3-4 vaccinations of a mix of HPV peptides derived from the viral oncogenes E6 and E7 maintained a complete response for ≥24 months (Kenter et a, Vaccination against HPV-16 Oncoproteins for Vulvar Intraepithelial Neoplasia NEJM 361:1838 (2009)).

Sequencing technology has revealed that each tumor contains multiple, patient-specific mutations that alter the protein coding content of a gene. Such mutations create altered proteins, ranging from single amino acid changes (caused by missense mutations) to addition of long regions of novel amino acid sequence due to frame shifts, read-through of termination codons or translation of intron regions (novel open reading frame mutations; neoORFs).

These mutated proteins are valuable targets for the host's immune response to the tumor as, unlike native proteins, they are not subject to the immune-dampening effects of self-tolerance. Therefore, mutated proteins are more likely to be immunogenic and are also more specific for the tumor cells compared to normal cells of the patient.

An alternative method for identifying tumor specific neoantigens is direct protein sequencing. Protein sequencing of enzymatic digests using multidimensional MS techniques (MSn) including tandem mass spectrometry (MS/MS)) can also be used to identify neoantigens of the invention. Such proteomic approaches permit rapid, highly automated analysis (see, e.g., K. Gevaert and J. Vandekerckhove, Electrophoresis 21:1145-1154 (2000)). It is further contemplated within the scope of the invention that high-throughput methods for de novo sequencing of unknown proteins may be used to analyze the proteome of a patient's tumor to identify expressed neoantigens. For example, meta shotgun protein sequencing may be used to identify expressed neoantigens (see e.g., Guthals et al. (2012) Shotgun Protein Sequencing with Meta-contig Assembly, Molecular and Cellular Proteomics 11(10):1084-96).

Tumor specific neoantigens may also be identified using MHC multimers to identify neoantigen-specific T-cell responses. For example, high-throughput analysis of neoantigen-specific T-cell responses in patient samples may be performed using MHC tetramer-based screening techniques (see e.g., Hombrink et al. (2011) High-Throughput Identification of Potential Minor Histocompatibility Antigens by MHC Tetramer-Based Screening: Feasibility and Limitations 6(8):1-11; Hadrup et al. (2009) Parallel detection of antigen-specific T-cell responses by multidimensional encoding of MHC multimers, Nature Methods, 6(7):520-26; van Rooij et al. (2013) Tumor exome analysis reveals neoantigen-specific T-cell reactivity in an Ipilimumab-responsive melanoma, Journal of Clinical Oncology, 31:1-4; and Heemskerk et al. (2013) The cancer antigenome, EMBO Journal, 32(2):194-203). Such tetramer-based screening techniques may be used for the initial identification of tumor specific neoantigens, or alternatively as a secondary screening protocol to assess what neoantigens a patient may have already been exposed to, thereby facilitating the selection of candidate neoantigens for the invention.

In one embodiment the sequencing data derived from determining the presence of mutations in a cancer patient is analysed to predict personal mutated peptides that can bind to HLA molecules of the individual. In one embodiment the data is analysed using a computer. In another embodiment the sequence data is analysed for the presence of neoantigens. In one embodiment neoantigens are determined by their affinity to MHC molecules. Efficiently choosing which particular mutations to utilize as immunogen requires identification of the patient HLA type and the ability to predict which mutated peptides would efficiently bind to the patient's HLA alleles. Recently, neural network based learning approaches with validated binding and non-binding peptides have advanced the accuracy of prediction algorithms for the major HLA-A and -B alleles. Utilizing the recently improved algorithms for predicting which missense mutations create strong binding peptides to the patient's cognate MHC molecules, a set of peptides representative of optimal mutated epitopes (both neoORF and missense) for each patient may be identified and prioritized (Zhang et al, Machine learning competition in immunology—Prediction of HLA class I binding peptides J Immunol Methods 374:1 (2011); Lundegaard et al Prediction of epitopes using neural network based methods J Immunol Methods 374:26 (2011)).

Targeting as many mutated epitopes as practically possible takes advantage of the enormous capacity of the immune system, prevents the opportunity for immunological escape by down-modulation of a particular immune targeted gene product, and compensates for the known inaccuracy of epitope prediction approaches. Synthetic peptides provide a particularly useful means to prepare multiple immunogens efficiently and to rapidly translate identification of mutant epitopes to an effective vaccine or immunogenic composition. Peptides can be readily synthesized chemically and easily purified utilizing reagents free of contaminating bacteria or animal substances. The small size allows a clear focus on the mutated region of the protein and also reduces irrelevant antigenic competition from other components (unmutated protein or viral vector antigens).

In one embodiment the drug formulation is a multi-epitope vaccine or immunogenic composition of long peptides. Such "long" peptides undergo efficient internalization, processing and cross-presentation in professional antigen-presenting cells such as dendritic cells, and have been shown to induce CTLs in humans (Melief and van der Burg, Immunotherapy of established (pre) malignant disease by synthetic long peptide vaccines Nature Rev Cancer 8:351 (2008)). In one embodiment at least 1 peptide is prepared for immunization. In a preferred embodiment 20 or more peptides are prepared for immunization. In one embodiment the neoantigenic peptide ranges from about 5 to about 50 amino acids in length. In another embodiment peptides from about 15 to about 35 amino acids in length is synthesized. In preferred embodiment the neoantigenic peptide ranges from about 20 to about 35 amino acids in length.

Production of Tumor Specific Neoantigens

The present invention is based, at least in part, on the ability to present the immune system of the patient with a pool of tumor specific neoantigens. One of skill in the art from this disclosure and the knowledge in the art will appreciate that there are a variety of ways in which to produce such tumor specific neoantigens. In general, such tumor specific neoantigens may be produced either in vitro or in vivo. Tumor specific neoantigens may be produced in vitro as peptides or polypeptides, which may then be formulated into a personalized neoplasia vaccine or immunogenic composition and administered to a subject. As described in further detail herein, such in vitro production may occur by a variety of methods known to one of skill in the art such as, for example, peptide synthesis or expression of a peptide/polypeptide from a DNA or RNA molecule in any of a variety of bacterial, eukaryotic, or viral recombinant expression systems, followed by purification of the expressed peptide/polypeptide. Alternatively, tumor specific neoantigens may be produced in vivo by introducing molecules (e.g., DNA, RNA, viral expression systems, and the like) that encode tumor specific neoantigens into a subject, whereupon the encoded tumor specific neoantigens are expressed. The methods of in vitro and in vivo production of neoantigens is also further described herein as it relates to pharmaceutical compositions and methods of delivery of the combination therapy.

In Vitro Peptide/Polypeptide Synthesis

Proteins or peptides may be made by any technique known to those of skill in the art, including the expression of proteins, polypeptides or peptides through standard molecular biological techniques, the isolation of proteins or peptides from natural sources, in vitro translation, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and Gen-Pept databases located at the National Institutes of Health website. The coding regions for known genes may be amplified and/or expressed using the techniques disclosed herein or as would be known to those of ordinary skill in the art. Alternatively, various commercial preparations of proteins, polypeptides and peptides are known to those of skill in the art.

Peptides can be readily synthesized chemically utilizing reagents that are free of contaminating bacterial or animal substances (Merrifield R B: Solid phase peptide synthesis. I. The synthesis of a tetrapeptide. J. Am. Chem. Soc. 85:2149-54, 1963). In certain embodiments, neoantigenic peptides are prepared by (1) parallel solid-phase synthesis on multichannel instruments using uniform synthesis and cleavage conditions; (2) purification over a RP-HPLC column with column stripping; and re-washing, but not replacement, between peptides; followed by (3) analysis with a limited set of the most informative assays. The Good Manufacturing Practices (GMP) footprint can be defined around the set of peptides for an individual patient, thus requiring suite changeover procedures only between syntheses of peptides for different patients.

Alternatively, a nucleic acid (e.g., a polynucleotide) encoding a neoantigenic peptide of the invention may be used to produce the neoantigenic peptide in vitro. The polynucleotide may be, e.g., DNA, cDNA, PNA, CNA, RNA, either single- and/or double-stranded, or native or stabilized forms of polynucleotides, such as e.g. polynucleotides with a phosphorothiate backbone, or combinations thereof and it may or may not contain introns so long as it codes for the peptide. In one embodiment in vitro translation is used to produce the peptide. Many exemplary systems exist that one skilled in the art could utilize (e.g., Retic Lysate IVT Kit, Life Technologies, Waltham, Mass.).

An expression vector capable of expressing a polypeptide can also be prepared. Expression vectors for different cell types are well known in the art and can be selected without undue experimentation. Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host (e.g., bacteria), although such controls are generally available in the expression vector. The vector is then introduced into the host bacteria for cloning using standard techniques (see, e.g., Sambrook et al. (1989) Molecular Cloning, A Laboratory Manual, Cold Spring Harbor Laboratory, Cold Spring Harbor, N.Y.).

Expression vectors comprising the isolated polynucleotides, as well as host cells containing the expression vectors, are also contemplated. The neoantigenic peptides may be provided in the form of RNA or cDNA molecules encoding the desired neoantigenic peptides. One or more neoantigenic peptides of the invention may be encoded by a single expression vector.

The term "polynucleotide encoding a polypeptide" encompasses a polynucleotide which includes only coding sequences for the polypeptide as well as a polynucleotide which includes additional coding and/or non-coding sequences. Polynucleotides can be in the form of RNA or in the form of DNA. DNA includes cDNA, genomic DNA, and synthetic DNA; and can be double-stranded or single-stranded, and if single stranded can be the coding strand or non-coding (anti-sense) strand.

In embodiments, the polynucleotides may comprise the coding sequence for the tumor specific neoantigenic peptide fused in the same reading frame to a polynucleotide which aids, for example, in expression and/or secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide.

In embodiments, the polynucleotides can comprise the coding sequence for the tumor specific neoantigenic peptide fused in the same reading frame to a marker sequence that allows, for example, for purification of the encoded polypeptide, which may then be incorporated into the personalized neoplasia vaccine or immunogenic composition. For example, the marker sequence can be a hexa-histidine tag (SEQ ID NO: 61) supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. Additional tags include, but are not limited to, Calmodulin tags, FLAG tags, Myc tags, S tags, SBP tags, Softag 1, Softag 3, V5 tag, Xpress tag, Isopeptag, SpyTag, Biotin Carboxyl Carrier Protein (BCCP) tags, GST tags, fluorescent protein tags (e.g., green fluorescent protein tags), maltose binding protein tags, Nus tags, Strep-tag, thioredoxin tag, TC tag, Ty tag, and the like.

In embodiments, the polynucleotides may comprise the coding sequence for one or more of the tumor specific neoantigenic peptides fused in the same reading frame to create a single concatamerized neoantigenic peptide construct capable of producing multiple neoantigenic peptides.

In certain embodiments, isolated nucleic acid molecules having a nucleotide sequence at least 60% identical, at least 65% identical, at least 70% identical, at least 75% identical, at least 80% identical, at least 85% identical, at least 90% identical, at least 95% identical, or at least 96%, 97%, 98% or 99% identical to a polynucleotide encoding a tumor specific neoantigenic peptide of the present invention, can be provided.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80% identical, at least 85% identical, at least 90% identical, and in some embodiments, at least 95%, 96%, 97%, 98%, or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482-489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

The isolated tumor specific neoantigenic peptides described herein can be produced in vitro (e.g., in the laboratory) by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In embodiments, a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest is produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (e.g., by synthesis, site-directed mutagenesis, or another method), the polynucleotide sequences encoding a particular isolated polypeptide of interest is inserted into an expression vector and optionally operatively linked to an expression control sequence appropriate for expression of the protein in a desired host. Proper assembly can be confirmed by nucleotide sequencing, restriction mapping, and expression of a biologically active polypeptide in a suitable host. As well known in the art, in order to obtain high expression levels of a transfected gene in a host, the gene can be operatively linked to transcriptional and translational expression control sequences that are functional in the chosen expression host.

Recombinant expression vectors may be used to amplify and express DNA encoding the tumor specific neoantigenic peptides. Recombinant expression vectors are replicable DNA constructs which have synthetic or cDNA-derived DNA fragments encoding a tumor specific neoantigenic peptide or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail herein. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous, and in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

Useful expression vectors for eukaryotic hosts, especially mammals or humans include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR 1, pBR322, pMB9 and their derivatives, wider host range plasmids, such as M13 and filamentous single-stranded DNA phages.

Suitable host cells for expression of a polypeptide include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin. Cell-free translation systems could also be employed. Appropriate cloning and expression vectors for use with bacterial, fungal, yeast, and mammalian cellular hosts are well known in the art (see Pouwels et al., Cloning Vectors: A Laboratory Manual, Elsevier, N.Y., 1985).

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese hamster ovary (CHO), 293, HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography, and the like), centrifugation, differential solubility, or by any other standard technique for protein purification. Affinity tags such as hexahistidine (SEQ ID NO: 61), maltose binding domain, influenza coat sequence, glutathione-S-transferase, and the like can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a cancer stem cell protein-Fc composition. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

In Vivo Peptide/Polypeptide Synthesis

The present invention also contemplates the use of nucleic acid molecules as vehicles for delivering neoantigenic peptides/polypeptides to the subject in need thereof, in vivo, in the form of, e.g., DNA/RNA vaccines (see, e.g., WO2012/159643, and WO2012/159754, hereby incorporated by reference in their entirety).

In one embodiment neoantigens may be administered to a patient in need thereof by use of a plasmid. These are plasmids which usually consist of a strong viral promoter to drive the in vivo transcription and translation of the gene (or complementary DNA) of interest (Mor, et al., (1995). The Journal of Immunology 155 (4): 2039-2046). Intron A may sometimes be included to improve mRNA stability and hence increase protein expression (Leitner et al. (1997). The Journal of Immunology 159 (12): 6112-6119). Plasmids also include a strong polyadenylation/transcriptional termination signal, such as bovine growth hormone or rabbit beta-globulin polyadenylation sequences (Alarcon et al., (1999). Adv. Parasitol. Advances in Parasitology 42: 343-410; Robinson et al., (2000). Adv. Virus Res. Advances in Virus Research 55: 1-74; Böhm et al., (1996). Journal of Immunological Methods 193 (1): 29-40.). Multicistronic vectors are sometimes constructed to express more than one immunogen, or to express an immunogen and an immunostimulatory protein (Lewis et al., (1999). Advances in Virus Research (Academic Press) 54: 129-88).

Because the plasmid is the "vehicle" from which the immunogen is expressed, optimising vector design for maximal protein expression is essential (Lewis et al., (1999). Advances in Virus Research (Academic Press) 54: 129-88). One way of enhancing protein expression is by optimising the codon usage of pathogenic mRNAs for eukaryotic cells. Another consideration is the choice of promoter. Such promoters may be the SV40 promoter or Rous Sarcoma Virus (RSV).

Plasmids may be introduced into animal tissues by a number of different methods. The two most popular approaches are injection of DNA in saline, using a standard hypodermic needle, and gene gun delivery. A schematic outline of the construction of a DNA vaccine plasmid and its subsequent delivery by these two methods into a host is illustrated at Scientific American (Weiner et al., (1999) Scientific American 281 (1): 34-41). Injection in saline is normally conducted intramuscularly (IM) in skeletal muscle, or intradermally (ID), with DNA being delivered to the extracellular spaces. This can be assisted by electroporation by temporarily damaging muscle fibres with myotoxins such as bupivacaine; or by using hypertonic solutions of saline or sucrose (Alarcon et al., (1999). Adv. Parasitol. Advances in Parasitology 42: 343-410). Immune responses to this method of delivery can be affected by many factors, including needle type, needle alignment, speed of injection, volume of injection, muscle type, and age, sex and physiological condition of the animal being injected (Alarcon et al., (1999). Adv. Parasitol. Advances in Parasitology 42: 343-410).

Gene gun delivery, the other commonly used method of delivery, ballistically accelerates plasmid DNA (pDNA) that has been adsorbed onto gold or tungsten microparticles into the target cells, using compressed helium as an accelerant (Alarcon et al., (1999). Adv. Parasitol. Advances in Parasitology 42: 343-410; Lewis et al., (1999). Advances in Virus Research (Academic Press) 54: 129-88).

Alternative delivery methods may include aerosol instillation of naked DNA on mucosal surfaces, such as the nasal and lung mucosa, (Lewis et al., (1999). Advances in Virus Research (Academic Press) 54: 129-88) and topical administration of pDNA to the eye and vaginal mucosa (Lewis et al., (1999) Advances in Virus Research (Academic Press) 54: 129-88). Mucosal surface delivery has also been achieved using cationic liposome-DNA preparations, biodegradable microspheres, attenuated *Shigella* or *Listeria* vectors for oral administration to the intestinal mucosa, and recombinant adenovirus vectors.

The method of delivery determines the dose of DNA required to raise an effective immune response. Saline injections require variable amounts of DNA, from 10 µg-1 mg, whereas gene gun deliveries require 100 to 1000 times less DNA than intramuscular saline injection to raise an effective immune response. Generally, 0.2 µg-20 µg are required, although quantities as low as 16 ng have been reported. These quantities vary from species to species, with mice, for example, requiring approximately 10 times less DNA than primates. Saline injections require more DNA because the DNA is delivered to the extracellular spaces of the target tissue (normally muscle), where it has to overcome physical barriers (such as the basal lamina and large amounts of connective tissue, to mention a few) before it is taken up by the cells, while gene gun deliveries bombard DNA directly into the cells, resulting in less "wastage" (See e.g., Sedegah et al., (1994). Proceedings of the National Academy of Sciences of the United States of America 91 (21): 9866-9870; Daheshiaet al., (1997). The Journal of Immunology 159 (4): 1945-1952; Chen et al., (1998). The Journal of Immunology 160 (5): 2425-2432; Sizemore (1995) Science 270 (5234): 299-302; Fynan et al., (1993) Proc. Natl. Acad. Sci. U.S.A. 90 (24): 11478-82).

In one embodiment, a neoplasia vaccine or immunogenic composition may include separate DNA plasmids encoding, for example, one or more neoantigenic peptides/polypeptides as identified in according to the invention. As discussed herein, the exact choice of expression vectors can depend upon the peptide/polypeptides to be expressed, and is well within the skill of the ordinary artisan. The expected persistence of the DNA constructs (e.g., in an episomal, non-replicating, non-integrated form in the muscle cells) is expected to provide an increased duration of protection.

One or more neoantigenic peptides of the invention may be encoded and expressed in vivo using a viral based system (e.g., an adenovirus system, an adeno associated virus (AAV) vector, a poxvirus, or a lentivirus). In one embodiment, the neoplasia vaccine or immunogenic composition may include a viral based vector for use in a human patient in need thereof, such as, for example, an adenovirus (see, e.g., Baden et al. First-in-human evaluation of the safety and immunogenicity of a recombinant adenovirus serotype 26 HIV-1 Env vaccine (IPCAVD 001). J Infect Dis. 2013 Jan. 15; 207(2):240-7, hereby incorporated by reference in its entirety). Plasmids that can be used for adeno associated virus, adenovirus, and lentivirus delivery have been described previously (see e.g., U.S. Pat. Nos. 6,955,808 and 6,943,019, and U.S. Patent application No. 20080254008, hereby incorporated by reference).

Among vectors that may be used in the practice of the invention, integration in the host genome of a cell is possible with retrovirus gene transfer methods, often resulting in long term expression of the inserted transgene. In a preferred embodiment the retrovirus is a lentivirus. Additionally, high transduction efficiencies have been observed in many different cell types and target tissues. The tropism of a retrovirus can be altered by incorporating foreign envelope proteins, expanding the potential target population of target cells. A retrovirus can also be engineered to allow for conditional expression of the inserted transgene, such that only certain cell types are infected by the lentivirus. Cell type specific promoters can be used to target expression in specific cell types. Lentiviral vectors are retroviral vectors (and hence both lentiviral and retroviral vectors may be used in the practice of the invention). Moreover, lentiviral vectors are preferred as they are able to transduce or infect non-dividing cells and typically produce high viral titers. Selection of a retroviral gene transfer system may therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the desired nucleic acid into the target cell to provide permanent expression. Widely used retroviral vectors that may be used in the practice of the invention include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., (1992) J. Virol. 66:2731-2739; Johann et al., (1992) J. Virol. 66:1635-1640; Sommnerfelt et al., (1990) Virol. 176:58-59; Wilson et al., (1998) J. Virol. 63:2374-2378; Miller et al., (1991) J. Virol. 65:2220-2224; PCT/US94/05700). Zou et al. administered about 10 µl of a recombinant lentivirus having a titer of $1 \times 10^9$ transducing units (TU)/ml by an intrathecal catheter. These sort of dosages can be adapted or extrapolated to use of a retroviral or lentiviral vector in the present invention.

Also useful in the practice of the invention is a minimal non-primate lentiviral vector, such as a lentiviral vector based on the equine infectious anemia virus (EIAV) (see, e.g., Balagaan, (2006) J Gene Med; 8: 275-285, Published online 21 Nov. 2005 in Wiley InterScience (www.interscience.wiley.com). DOI: 10.1002/jgm.845). The vectors may have cytomegalovirus (CMV) promoter driving expression of the target gene. Accordingly, the invention contemplates amongst vector(s) useful in the practice of the invention: viral vectors, including retroviral vectors and lentiviral vectors.

Also useful in the practice of the invention is an adenovirus vector. One advantage is the ability of recombinant adenoviruses to efficiently transfer and express recombinant genes in a variety of mammalian cells and tissues in vitro and in vivo, resulting in the high expression of the transferred nucleic acids. Further, the ability to productively infect quiescent cells, expands the utility of recombinant adenoviral vectors. In addition, high expression levels ensure that the products of the nucleic acids will be expressed to sufficient levels to generate an immune response (see e.g., U.S. Pat. No. 7,029,848, hereby incorporated by reference).

In an embodiment herein the delivery is via an adenovirus, which may be at a single booster dose containing at least $1 \times 10^5$ particles (also referred to as particle units, pu) of adenoviral vector. In an embodiment herein, the dose preferably is at least about $1 \times 10^6$ particles (for example, about $1 \times 10^6 - 1 \times 10^{12}$ particles), more preferably at least about $1 \times 10^7$ particles, more preferably at least about $1 \times 10^8$ particles (e.g., about $1 \times 10^8 - 1 \times 10^{11}$ particles or about $1 \times 10^8 - 1 \times 10^{12}$ particles), and most preferably at least about $1 \times 10^9$ particles (e.g., about $1 \times 10^9 - 1 \times 10^{10}$ particles or about $1 \times 10^9 - 1 \times 10^{12}$ particles), or even at least about $1 \times 10^{10}$ particles (e.g., about $1 \times 10^{10} - 1 \times 10^{12}$ particles) of the adenoviral vector. Alternatively, the dose comprises no more than about $1 \times 10^{14}$ particles, preferably no more than about $1 \times 10^{13}$ particles, even more preferably no more than about $1 \times 10^{12}$ particles, even more preferably no more than about $1 \times 10^{11}$ particles, and most preferably no more than about $1 \times 10^{10}$ particles (e.g., no more than about $1 \times 10^9$ articles). Thus, the dose may contain a single dose of adenoviral vector with, for example, about $1 \times 10^6$ particle units (pu), about $2 \times 10^6$ pu, about $4 \times 10^6$ pu, about $1 \times 10^7$ pu, about $2 \times 10^7$ pu, about $4 \times 10^7$ pu, about $1 \times 10^8$ pu, about $2 \times 10^8$ pu, about $4 \times 10^8$ pu, about $1 \times 10^9$ pu, about $2 \times 10^9$ pu, about $4 \times 10^9$ pu, about $1 \times 10^{10}$ pu, about $2 \times 10^{10}$ pu, about $4 \times 10^{10}$ pu, about $1 \times 10^{11}$ pu, about $2 \times 10^{11}$ pu, about $4 \times 10^{11}$ pu, about $1 \times 10^{12}$ pu, about $2 \times 10^{12}$ pu, or about $4 \times 10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In terms of in vivo delivery, AAV is advantageous over other viral vectors due to low toxicity and low probability of causing insertional mutagenesis because it doesn't integrate into the host genome. AAV has a packaging limit of 4.5 or 4.75 Kb. Constructs larger than 4.5 or 4.75 Kb result in significantly reduced virus production. There are many promoters that can be used to drive nucleic acid molecule expression. AAV ITR can serve as a promoter and is advantageous for eliminating the need for an additional promoter element. For ubiquitous expression, the following promoters can be used: CMV, CAG, CBh, PGK, SV40, Ferritin heavy or light chains, etc. For brain expression, the following promoters can be used: SynapsinI for all neurons, CaMKIIalpha for excitatory neurons, GAD67 or GAD65 or VGAT for GABAergic neurons, etc. Promoters used to drive RNA synthesis can include: Pol III promoters such as U6 or H1. The use of a Pol II promoter and intronic cassettes can be used to express guide RNA (gRNA).

As to AAV, the AAV can be AAV1, AAV2, AAV5 or any combination thereof. One can select the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The above promoters and vectors are preferred individually.

In an embodiment herein, the delivery is via an AAV. A therapeutically effective dosage for in vivo delivery of the AAV to a human is believed to be in the range of from about 20 to about 50 ml of saline solution containing from about $1\times10^{10}$ to about $1\times10^{50}$ functional AAV/ml solution. The dosage may be adjusted to balance the therapeutic benefit against any side effects. In an embodiment herein, the AAV dose is generally in the range of concentrations of from about $1\times10^5$ to $1\times10^{50}$ genomes AAV, from about $1\times10^8$ to $1\times10^{20}$ genomes AAV, from about $1\times10^{10}$ to about $1\times10^{16}$ genomes, or about $1\times10^{11}$ to about $1\times10^{16}$ genomes AAV. A human dosage may be about $1\times10^{13}$ genomes AAV. Such concentrations may be delivered in from about 0.001 ml to about 100 ml, about 0.05 to about 50 ml, or about 10 to about 25 ml of a carrier solution. In a preferred embodiment, AAV is used with a titer of about $2\times10^{13}$ viral genomes/milliliter, and each of the striatal hemispheres of a mouse receives one 500 nanoliter injection. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In another embodiment effectively activating a cellular immune response for a neoplasia vaccine or immunogenic composition can be achieved by expressing the relevant neoantigens in a vaccine or immunogenic composition in a non-pathogenic microorganism. Well-known examples of such microorganisms are *Mycobacterium bovis* BCG, *Salmonella* and *Pseudomona* (See, U.S. Pat. No. 6,991,797, hereby incorporated by reference in its entirety).

In another embodiment a Poxvirus is used in the neoplasia vaccine or immunogenic composition. These include orthopoxvirus, avipox, vaccinia, MVA, NYVAC, canarypox, ALVAC, fowlpox, TROVAC, etc. (see e.g., Verardi et al., Hum Vaccin Immunother. 2012 July; 8(7):961-70; and Moss, Vaccine. 2013; 31(39): 4220-4222). Poxvirus expression vectors were described in 1982 and quickly became widely used for vaccine development as well as research in numerous fields. Advantages of the vectors include simple construction, ability to accommodate large amounts of foreign DNA and high expression levels.

In another embodiment the vaccinia virus is used in the neoplasia vaccine or immunogenic composition to express a neoantigen. (Rolph et al., Recombinant viruses as vaccines and immunological tools. Curr Opin Immunol 9:517-524, 1997). The recombinant vaccinia virus is able to replicate within the cytoplasm of the infected host cell and the polypeptide of interest can therefore induce an immune response. Moreover, Poxviruses have been widely used as vaccine or immunogenic composition vectors because of their ability to target encoded antigens for processing by the major histocompatibility complex class I pathway by directly infecting immune cells, in particular antigen-presenting cells, but also due to their ability to self-adjuvant.

In another embodiment ALVAC is used as a vector in a neoplasia vaccine or immunogenic composition. ALVAC is a canarypox virus that can be modified to express foreign transgenes and has been used as a method for vaccination against both prokaryotic and eukaryotic antigens (Horig H, Lee D S, Conkright W, et al. Phase I clinical trial of a recombinant canarypoxvirus (ALVAC) vaccine expressing human carcinoembryonic antigen and the B7.1 co-stimulatory molecule. Cancer Immunol Immunother 2000; 49:504-14; von Mehren M, Arlen P, Tsang K Y, et al. Pilot study of a dual gene recombinant avipox vaccine containing both carcinoembryonic antigen (CEA) and B7.1 transgenes in patients with recurrent CEA-expressing adenocarcinomas. Clin Cancer Res 2000; 6:2219-28; Musey L, Ding Y, Elizaga M, et al. HIV-1 vaccination administered intramuscularly can induce both systemic and mucosal T cell immunity in HIV-1-uninfected individuals. J Immunol 2003; 171:1094-101; Paoletti E. Applications of pox virus vectors to vaccination: an update. Proc Natl Acad Sci USA 1996; 93:11349-53; U.S. Pat. No. 7,255,862). In a phase I clinical trial, an ALVAC virus expressing the tumor antigen CEA showed an excellent safety profile and resulted in increased CEA-specific T-cell responses in selected patients; objective clinical responses, however, were not observed (Marshall J L, Hawkins M J, Tsang K Y, et al. Phase I study in cancer patients of a replication-defective avipox recombinant vaccine that expresses human carcinoembryonic antigen. J Clin Oncol 1999; 17:332-7).

In another embodiment a Modified Vaccinia Ankara (MVA) virus may be used as a viral vector for a neoantigen vaccine or immunogenic composition. MVA is a member of the Orthopoxvirus family and has been generated by about 570 serial passages on chicken embryo fibroblasts of the Ankara strain of Vaccinia virus (CVA) (for review see Mayr, A., et al., Infection 3, 6-14, 1975). As a consequence of these passages, the resulting MVA virus contains 31 kilobases less genomic information compared to CVA, and is highly host-cell restricted (Meyer, H. et al., J. Gen. Virol. 72, 1031-1038, 1991). MVA is characterized by its extreme attenuation, namely, by a diminished virulence or infectious ability, but still holds an excellent immunogenicity. When tested in a variety of animal models, MVA was proven to be avirulent, even in immuno-suppressed individuals. Moreover, MVA-BN®-HER2 is a candidate immunotherapy designed for the treatment of HER-2-positive breast cancer and is currently in clinical trials. (Mandl et al., Cancer Immunol Immunother. January 2012; 61(1): 19-29). Methods to make and use recombinant MVA has been described (e.g., see U.S. Pat. Nos. 8,309,098 and 5,185,146 hereby incorporated in its entirety).

In another embodiment the modified Copenhagen strain of vaccinia virus, NYVAC and NYVAC variations are used as a vector (see U.S. Pat. No. 7,255,862; PCT WO 95/30018; U.S. Pat. Nos. 5,364,773 and 5,494,807, hereby incorporated by reference in its entirety).

In one embodiment recombinant viral particles of the vaccine or immunogenic composition are administered to patients in need thereof. Dosages of expressed neoantigen can range from a few to a few hundred micrograms, e.g., 5 to 500 .mu.g. The vaccine or immunogenic composition can be administered in any suitable amount to achieve expression at these dosage levels. The viral particles can be administered to a patient in need thereof or transfected into cells in an amount of about at least 103-5 pfu; thus, the viral particles are preferably administered to a patient in need thereof or infected or transfected into cells in at least about $10^4$ pfu to about $10^6$ pfu; however, a patient in need thereof can be administered at least about $10^8$ pfu such that a more preferred amount for administration can be at least about $10^7$ pfu to about $10^9$ pfu. Doses as to NYVAC are applicable as to ALVAC, MVA, MVA-BN, and avipoxes, such as canarypox and fowlpox.

Vaccine or Immunogenic Composition Adjuvant

Effective vaccine or immunogenic compositions advantageously include a strong adjuvant to initiate an immune response. As described herein, poly-ICLC, an agonist of TLR3 and the RNA helicase-domains of MDA5 and RIG3, has shown several desirable properties for a vaccine or immunogenic composition adjuvant. These properties include the induction of local and systemic activation of immune cells in vivo, production of stimulatory chemokines and cytokines, and stimulation of antigen-presentation by DCs. Furthermore, poly-ICLC can induce durable CD4+ and CD8+ responses in humans. Importantly, striking similarities in the upregulation of transcriptional and signal transduction pathways were seen in subjects vaccinated with poly-ICLC and in volunteers who had received the highly effective, replication-competent yellow fever vaccine. Furthermore, >90% of ovarian carcinoma patients immunized with poly-ICLC in combination with a NY-ESO-1 peptide vaccine (in addition to Montanide) showed induction of CD4+ and CD8+ T cell, as well as antibody responses to the peptide in a recent phase 1 study. At the same time, poly-ICLC has been extensively tested in more than 25 clinical trials to date and exhibited a relatively benign toxicity profile. In addition to a powerful and specific immunogen the neoantigen peptides may be combined with an adjuvant (e.g., poly-ICLC) or another anti-neoplastic agent. Without being bound by theory, these neoantigens are expected to bypass central thymic tolerance (thus allowing stronger anti-tumor T cell response), while reducing the potential for autoimmunity (e.g., by avoiding targeting of normal self-antigens). An effective immune response advantageously includes a strong adjuvant to activate the immune system (Speiser and Romero, Molecularly defined vaccines for cancer immunotherapy, and protective T cell immunity Seminars in Immunol 22:144 (2010)). For example, Toll-like receptors (TLRs) have emerged as powerful sensors of microbial and viral pathogen "danger signals", effectively inducing the innate immune system, and in turn, the adaptive immune system (Bhardwaj and Gnjatic, TLR AGONISTS: Are They Good Adjuvants? Cancer J. 16:382-391 (2010)). Among the TLR agonists, poly-ICLC (a synthetic double-stranded RNA mimic) is one of the most potent activators of myeloid-derived dendritic cells. In a human volunteer study, poly-ICLC has been shown to be safe and to induce a gene expression profile in peripheral blood cells comparable to that induced by one of the most potent live attenuated viral vaccines, the yellow fever vaccine YF-17D (Caskey et al, Synthetic double-stranded RNA induces innate immune responses similar to a live viral vaccine in humans J Exp Med 208:2357 (2011)). In a preferred embodiment Hiltonol®, a GMP preparation of poly-ICLC prepared by Oncovir, Inc, is utilized as the adjuvant. In other embodiments, other adjuvants described herein are envisioned. For instance oil-in-water, water-in-oil or multiphasic W/O/W; see, e.g., U.S. Pat. No. 7,608,279 and Aucouturier et al, Vaccine 19 (2001), 2666-2672, and documents cited therein.

Checkpoint Inhibitors

The present invention features methods of treating or preventing a neoplasia comprising the steps of administering to a subject a neoplasia vaccine or immunogenic composition, as described herein, and at least one checkpoint inhibitor. Accordingly, 1, 2, 3, 4, 5, or more checkpoint inhibitors may be administered. In certain exemplary embodiments, one checkpoint inhibitor is administered. In other exemplary embodiments, 2 checkpoint inhibitors are administered.

Page et al. (Annu. Rev. Med. 2014.65) summarizes published trials investigating checkpoint modulators in solid tumors. Mullard, A. (Nature Reviews, Drug Discovery. Vol. 12, July 2013) provides a review of checkpoint inhibitors. A summary table of exemplary checkpoint inhibitors is provided herein.

| Drug | Lead company | Most advanced indicatons | Phase |
|---|---|---|---|
| Anti-PD1 | | | |
| Nivolumab | Bristol-Myers Squibb | Renal cell cancer, melanoma, NSCLC | III |
| Lambrolizumab | Merck & Co. | Melanoma | II |
| Pidilizumab* | CureTech | Colorectal cancer, melanoma, DLBCL | II |
| AMP-224* | GlaxoSmithKline | Solid tumours | I |
| Anti-PDL1 | | | |
| MEDI-4736 | AstraZeneca | Solid tumours | I |
| MPDL3280A | Roche | Melanoma, solid tumours | I |

Anti-CTLA4 Antibodies

Cytotoxic T-lymphocyte-associated antigen (CTLA-4), also known as CD152, is a co-inhibitory molecule that functions to regulate T-cell activation.

CTLA4 was initially identified as negative regulator on the surface of T-cells that was upregulated shortly after initiation of a de novo immune response or stimulation of an existing response in order to dampen the subsequent immune T-cell response and prevent auto-immunity or uncontrolled inflammation. Thus, the magnitude of the developing immune response has been closely tied to CTLA4 action. In certain embodiments, the anti-CTLA4 antibody is Ipilumumab or Tremelimumab.

Checkpoint inhibitors function by modulating the immune system's endogenous mechanisms of T cell regulation. Ipilimumab (YERVOY, Bristol-Meyers Squibb, New York, N.Y.)—is a monoclonal antibody and is the first such checkpoint inhibitor to be approved by the US Food and Drug Administration (FDA)—has become standard treatment for metastatic melanoma (Hodi et al., N. Engl. J. Med. 363:711-23. 2010; Robert et al., N. Engl. J. Med. 364:2517-26. 2011). Ipilimumab binds and blocks inhibitory signaling mediated by the T cell surface co-inhibitory molecule cytotoxic T lymphocyte antigen 4 (CTLA-4). Because the mechanism of action is not specific to one tumor type, and because a wealth of preclinical data supports the role of tumor immune surveillance across multiple malignancies (Andre et al., Clin. Cancer Res. 19:28-33. 2013; May et al. Clin. Cancer Res. 17:5233-38. 2011), Ipilumumab is being investigated as a treatment for patients with prostate, lung, renal, and breast cancer, among other tumor types. Ipilimumab works by activating the immune system by targeting CTLA-4.

Another CTLA-4-blocking antibody, Tremelimumab, continues to be investigated in clinical trials and has also demonstrated durable responses in patients with melanoma (Kirkwood et al., Clin. Cancer Res. 16:1042-48. 2010; Ribas et al. J. Clin. Oncol. 31:616-22, 2013).

Accordingly, the present invention features in exemplary embodiments, novel combinations of a neoplasia vaccine or immunogenic composition and one or more anti-CTLA4 antibodies. The invention also features in other exemplary embodiments, novel combinations of a neoplasia vaccine or immunogenic composition, Ipilimumab and/or Nivolumab and one or more anti-CTLA4 antibodies.

Inhibitors of Programmed Cell Death-1 Pathway

Whereas CTLA-4 serves to regulate early T cell activation, Programmed Death-1 (PD-1) signaling functions in part to regulate T cell activation in peripheral tissues. The PD-1 receptor refers to an immunoinhibitory receptor belonging to the CD28 family. PD-1 is expressed on a number of cell types including T regs, activated B cells, and natural killer (NK) cells, and is expressed predominantly on previously activated T cells in vivo, and binds to two ligands, PD-L1 and PD-L2. PD1's endogenous ligands, PD-L1 and PD-L2, are expressed in activated immune cells as well as nonhematopoietic cells, including tumor cells. PD-1 as used herein is meant to include human PD-1 (hPD-1), variants, isoforms, and species homologs of hPD-1, and analogs having at least one common epitope with hPD-1. The complete hPD-1 sequence can be found under GENBANK Accession No. U64863. Programmed Death Ligand-1 (PD-L1" is one of two cell surface glycoprotein ligands for PD-1 (the other being PD-L2) that downregulate T cell activation and cytokine secretion upon binding to PD-1. PD-L1 as used herein includes human PD-L1 (hPD-L1), variants, isoforms, and species homologs of hPD-L1, and analogs having at least one common epitope with hPD-L1. The complete hPD-L1 sequence can be found under GENBANK Accession No. Q9NZQ7. Tumors have been demonstrated to escape immune surveillance by expressing PD-L1/L2, thereby suppressing tumor-infiltrating lymphocytes via PD-1/PD-L1,2 interactions (Dong et al. Nat. Med. 8:793-800. 2002). Inhibition of these interactions with therapeutic antibodies has been shown to enhance T cell response and stimulate antitumor activity (Freeman et al. J. Exp. Med. 192:1027-34.2000).

The Abs of the invention include, but are not limited to, all of the anti-PD-1 and anti-PD-L1 Abs disclosed in U.S. Pat. Nos. 8,008,449 and 7,943,743, respectively. Other anti-PD-1 mAbs have been described in, for example, U.S. Pat. Nos. 7,488,802 and 8,168,757, and anti-PD-L1 mAbs have been described in, for example, U.S. Pat. Nos. 7,635,757 and 8,217,149, and U.S. Publication No. 2009/0317368. U.S. Pat. No. 8,008,449 exemplifies seven anti-PD-1 HuMAbs: 17D8, 2D3, 4H1, 5C4 (also referred to herein as nivolumab or BMS-936558), 4A11, 7D3 and 5F4.

In some embodiments, the anti-PD-1 antibody is nivolumab. Alternative names for Nivolumab include MDX-1106, MDX-1106-04, ONO-4538, BMS-936558. In some embodiments, the anti-PD-1 antibody is Nivolumab (CAS Registry Number: 946414-94-4).

Nivolumab is a fully human IgG4 blocking monoclonal antibody against PD-1 (Topaliam et al., N. Engl. J. Med. 366:2443-54. 2012). Nivolumab specifically blocks PD-1, which can overcome immune resistance. The ligands for PD-1 have been identified as PD-L1 (B7-H1), which is expressed on all hemopoietic cells and many nonhemopoietic tissues, and PD-L2 (B7-DC), whose expression is restricted primarily to dendritic cells and macrophages (Dong, H. et al. 1999. Nat. Med. 5:1365; Freeman, G. J. et al. 2000. J. Exp. Med. 192:1027; Latchman, Y. et al. 2001. Nat. Immunol. 2:261; Tseng, S. Y. et al. 2001. J. Exp. Med. 193:839). PD-L1 is overexpressed in many cancers and is often associated with poor prognosis (Okazaki T et al., Intern. Immun. 2007 19(7):813) (Thompson R H et al., Cancer Res 2006, 66(7):3381). Interestingly, the majority of tumor infiltrating T lymphocytes predominantly express PD-1, in contrast to T lymphocytes in normal tissues and peripheral blood T lymphocytes indicating that up-regulation of PD-1 on tumor-reactive T cells can contribute to impaired antitumor immune responses (Blood 2009 1 14(8): 1537). Specifically, since tumor cells express PD-L1, an immunosuppressive PD-1 ligand, inhibition of the interaction between PD-1 and PD-L1 can enhance T-cell responses in vitro and mediate preclinical antitumor activity.

A number of clinical trials (Phase I, II and III) involving Nivolumab have been conducted or are on-going (see clinicaltrials.gov/ct2/results?term=nivolumab&pg=1, accessed on Dec. 20, 2013). For example, in a phase I dose escalation trial, nivolumab was safe, and objective responses were 16-31% across tumor types, with most responses being durable for >1 year (Topaliam et al., Presented at Annu. Meet. Am. Soc. Clin. Oncol., Chicago, May 31-Jun. 4, 2013). In another study, the safety and clinical activity of nivolumab (anti-PD-1, BMS-936558, ONO-4538) in combination with ipilimumab in patients with advanced melanoma was investigated (Wolchok, J Clin Oncol 31, 2013 (suppl; abstr 9012 2013 ASCO Annual Meeting).

Two anti-PD-L1 inhibitory antibodies, MPDL3280A (Genentech, South San Francisco, Calif.) and BMS-936559 (Bristol Meyers Squibb, New York, N.Y.), have undergone clinical investigation. Like nivolumab and MK-3475, these antibodies are thought to function principally by blocking PD-1/PD-L1 signaling. Unlike PD-1 antibodies, PD-L1 antibodies spare potential interactions between PD-L2 and PD-1, but additionally block interactions between PD-L1 and CD80 (Park et al., 2010. Blood 116:1291-98). MPDL3280A has been evaluated in multiple tumor types, with safety and preliminary efficacy identified in melanoma; renal cell carcinoma; non-small cell lung carcinoma (NSCLC); and colorectal, gastric, and head/neck squamous cell carcinoma (Herbst et al. resented at Annu. Meet. Am. Soc. Clin. Oncol., Chicago, May 31-Jun. 4, 2013). Similarly, BMS-936559 was shown to be safe and clinically active across multiple tumor types in a phase I trial. MEDI-4736 is another PD-L1-blocking antibody currently in clinical development (NCT01693562).

In addition to CTLA-4 and PD-1/PD-L1, numerous other immunomodulatory targets have been identified preclinically, many with corresponding therapeutic antibodies that are being investigated in clinical trials. Page et al. (Annu. Rev. Med. 2014.65) details targets of antibody immune modulators in FIG. 1, incorporated by reference herein.

The present invention features in exemplary aspects, novel combinations of a neoplasia vaccine or immunogenic composition and one or more inhibitors of the PD-1 pathway. In preferred embodiments, the inhibitor of the PD-1 pathway is an anti-PD1 antibody, for example Nivolumab.

The present invention also features in other exemplary aspects, novel combinations of a neoplasia vaccine or immunogenic composition and Nivolumab and/or one or more anti-CTLA4 antibodies.

Indications

Examples of cancers and cancer conditions that can be treated with the combination therapy of this document include, but are not limited to a patient in need thereof that has been diagnosed as having cancer, or at risk of developing cancer. The subject may have a solid tumor such as breast, ovarian, prostate, lung, kidney, gastric, colon, testicular, head and neck, pancreas, brain, melanoma, and other tumors of tissue organs and hematological tumors, such as lymphomas and leukemias, including acute myelogenous leukemia, chronic myelogenous leukemia, chronic lymphocytic leukemia, T cell lymphocytic leukemia, and B cell lymphomas, tumors of the brain and central nervous system (e.g., tumors of the meninges, brain, spinal cord, cranial nerves and other parts of the CNS, such as glioblastomas or medulla blastomas); head and/or neck cancer, breast tumors, tumors of the circulatory system (e.g., heart, mediastinum and pleura, and other intrathoracic organs, vascular tumors, and tumor-associated vascular tissue); tumors of the blood and lymphatic system (e.g., Hodgkin's disease, Non-Hodgkin's disease lymphoma, Burkitt's lymphoma, AIDS-related lymphomas, malignant immunoproliferative diseases, multiple myeloma, and malignant plasma cell neoplasms, lymphoid leukemia, myeloid leukemia, acute or chronic lymphocytic leukemia, monocytic leukemia, other leukemias of specific cell type, leukemia of unspecified cell type, unspecified malignant neoplasms of lymphoid, hematopoietic and related tissues, such as diffuse large cell lymphoma, T-cell lymphoma or cutaneous T-cell lymphoma); tumors of the excretory system (e.g., kidney, renal pelvis, ureter, bladder, and other urinary organs); tumors of the gastrointestinal tract (e.g., esophagus, stomach, small intestine, colon, colorectal, rectosigmoid junction, rectum, anus, and anal canal); tumors involving the liver and intrahepatic bile ducts, gall bladder, and other parts of the biliary tract, pancreas, and other digestive organs; tumors of the oral cavity (e.g., lip, tongue, gum, floor of mouth, palate, parotid gland, salivary glands, tonsil, oropharynx, nasopharynx, puriform sinus, hypopharynx, and other sites of the oral cavity); tumors of the reproductive system (e.g., vulva, vagina, Cervix uteri, uterus, ovary, and other sites associated with female genital organs, placenta, penis, prostate, testis, and other sites associated with male genital organs); tumors of the respiratory tract (e.g., nasal cavity, middle ear, accessory sinuses, larynx, trachea, bronchus and lung, such as small cell lung cancer and non-small cell lung cancer); tumors of the skeletal system (e.g., bone and articular cartilage of limbs, bone articular cartilage and other sites); tumors of the skin (e.g., malignant melanoma of the skin, non-melanoma skin cancer, basal cell carcinoma of skin, squamous cell carcinoma of skin, mesothelioma, Kaposi's sarcoma); and tumors involving other tissues including peripheral nerves and autonomic nervous system, connective and soft tissue, retroperitoneum and peritoneum, eye, thyroid, adrenal gland, and other endocrine glands and related structures, secondary and unspecified malignant neoplasms of lymph nodes, secondary malignant neoplasm of respiratory and digestive systems and secondary malignant neoplasm of other sites.

Of special interest is the treatment of Non-Hodgkin's Lymphoma (NHL), clear cell Renal Cell Carcinoma (ccRCC), metastatic melanoma, sarcoma, leukemia or a cancer of the bladder, colon, brain, breast, head and neck, endometrium, lung, ovary, pancreas or prostate. In certain embodiments, the melanoma is high risk melanoma.

Cancers that can be treated using this combination therapy may include among others cases which are refractory to treatment with other chemotherapeutics. The term "refractory, as used herein refers to a cancer (and/or metastases thereof), which shows no or only weak antiproliferative response (e.g., no or only weak inhibition of tumor growth) after treatment with another chemotherapeutic agent. These are cancers that cannot be treated satisfactorily with other chemotherapeutics. Refractory cancers encompass not only (i) cancers where one or more chemotherapeutics have already failed during treatment of a patient, but also (ii) cancers that can be shown to be refractory by other means, e.g., biopsy and culture in the presence of chemotherapeutics.

The combination therapy described herein is also applicable to the treatment of patients in need thereof who have not been previously treated.

The combination therapy described herein is also applicable where the subject has no detectable neoplasia but is at high risk for disease recurrence.

Also of special interest is the treatment of patients in need thereof s who have undergone Autologous Hematopoietic Stem Cell Transplant (AHSCT), and in particular patients who demonstrate residual disease after undergoing AHSCT. The post-AHSCT setting is characterized by a low volume of residual disease, the infusion of immune cells to a situation of homeostatic expansion, and the absence of any standard relapse-delaying therapy. These features provide a unique opportunity to use the claimed neoplastic vaccine or immunogenic composition and checkpoint inhibitor compositions to delay disease relapse.

Pharmaceutical Compositions/Methods of Delivery

The present invention is also directed to pharmaceutical compositions comprising an effective amount of one or more compounds according to the present invention (including a pharmaceutically acceptable salt, thereof), optionally in combination with a pharmaceutically acceptable carrier, excipient or additive.

When administered as a combination, the therapeutic agents (i.e. the neoplasia vaccine or immunogenic composition and one or more checkpoint inhibitors) can be formulated as separate compositions that are given at the same time or different times, or the therapeutic agents can be given as a single composition.

The compositions may be administered once daily, twice daily, once every two days, once every three days, once every four days, once every five days, once every six days, once every seven days, once every two weeks, once every three weeks, once every four weeks, once every two months, once every six months, or once per year. The dosing interval can be adjusted according to the needs of individual patients. For longer intervals of administration, extended release or depot formulations can be used.

The compositions of the invention can be used to treat diseases and disease conditions that are acute, and may also be used for treatment of chronic conditions. In particular, the compositions of the invention are used in methods to treat or prevent a neoplasia.

In certain embodiments, the compounds of the invention are administered for time periods exceeding two weeks, three weeks, one month, two months, three months, four months, five months, six months, one year, two years, three years, four years, or five years, ten years, or fifteen years; or for example, any time period range in days, months or years in which the low end of the range is any time period between 14 days and 15 years and the upper end of the range is between 15 days and 20 years (e.g., 4 weeks and 15 years, 6 months and 20 years). In some cases, it may be advantageous for the compounds of the invention to be administered for the remainder of the patient's life. In preferred embodiments, the patient is monitored to check the progression of the disease or disorder, and the dose is adjusted accordingly. In preferred embodiments, treatment according to the invention is effective for at least two weeks, three weeks, one month, two months, three months, four months, five months, six months, one year, two years, three years, four years, or five years, ten years, fifteen years, twenty years, or for the remainder of the subject's life.

As described herein, in certain embodiments, administration of the checkpoint inhibitor is initiated before initiation of administration of the neoplasia vaccine or immunogenic composition. In other embodiments, administration of the checkpoint inhibitor is initiated after initiation of administration of the neoplasia vaccine or immunogenic composition. In still other embodiments, administration of the checkpoint inhibitor is initiated simultaneously with the initiation of administration of the neoplasia vaccine or immunogenic composition.

Administration of the checkpoint inhibitor may continue every 2, 3, 4, 5, 6, 7, 8 or more weeks after the first administration of the checkpoint inhibitor. It is understood that week 1 is meant to include days 1-7, week 2 is meant to include days 8-14, week 3 is meant to include days 15-21 and week 4 is meant to include days 22-28. When dosing is described as being on weekly intervals it means approximately 7 days apart although in any given week the day can be one or more days before or after the scheduled day In certain embodiments, administration of the checkpoint inhibitor is withheld during the week prior to administration of the neoplasia vaccine or immunogenic composition. In other embodiments, administration of the checkpoint inhibitor is withheld during administration of the neoplasia vaccine or immunogenic composition.

Surgical resection uses surgery to remove abnormal tissue in cancer, such as mediastinal, neurogenic, or germ cell tumors, or thymoma. In certain embodiments, administration of the checkpoint inhibitor is initiated following tumor resection. In other embodiments, administration of the neoplasia vaccine or immunogenic composition is initiated 1, 2, 3, 4, 5, 6, 7, 8, 9, 10, 11, 12, 13, 14, 15 or more weeks after tumor resection. Preferably, administration of the neoplasia vaccine or immunogenic composition is initiated 4, 5, 6, 7, 8, 9, 10, 11 or 12 weeks after tumor resection.

Prime/boost regimens refer to the successive administrations of a vaccine or immunogenic or immunological compositions. In certain embodiments, administration of the neoplasia vaccine or immunogenic composition is in a prime/boost dosing regimen, for example administration of the neoplasia vaccine or immunogenic composition at weeks 1, 2, 3 or 4 as a prime and administration of the neoplasia vaccine or immunogenic composition is at months 2, 3 or 4 as a boost. In another embodiment heterologous prime-boost strategies are used to ellicit a greater cytotoxic T-cell response (see Schneider et al., Induction of CD8+ T cells using heterologous prime-boost immunisation strategies, Immunological Reviews Volume 170, Issue 1, pages 29-38, August 1999). In another embodiment DNA encoding neoantigens is used to prime followed by a protein boost. In another embodiment protein is used to prime followed by boosting with a virus encoding the neoantigen. In another embodiment a virus encoding the neoantigen is used to prime and another virus is used to boost. In another embodiment protein is used to prime and DNA is used to boost. In a preferred embodiment a DNA vaccine or immunogenic composition is used to prime a T-cell response and a recombinant viral vaccine or immunogenic composition is used to boost the response. In another preferred embodiment a viral vaccine or immunogenic composition is coadministered with a protein or DNA vaccine or immunogenic composition to act as an adjuvant for the protein or DNA vaccine or immunogenic composition. The patient can then be boosted with either the viral vaccine or immunogenic composition, protein, or DNA vaccine or immunogenic composition (see Hutchings et al., Combination of protein and viral vaccines induces potent cellular and humoral immune responses and enhanced protection from murine malaria challenge. Infect Immun. 2007 December; 75(12): 5819-26. Epub 2007 Oct. 1).

The pharmaceutical compositions can be processed in accordance with conventional methods of pharmacy to produce medicinal agents for administration to patients in need thereof, including humans and other mammals.

Modifications of the neoantigenic peptides can affect the solubility, bioavailability and rate of metabolism of the peptides, thus providing control over the delivery of the active species. Solubility can be assessed by preparing the neoantigenic peptide and testing according to known methods well within the routine practitioner's skill in the art.

It has been found that a pharmaceutical composition comprising succinic acid or a pharmaceutically acceptable salt thereof (succinate) can provide improved solubility for the neoantigenic peptides. Thus, in one aspect, the invention provides a pharmaceutical composition comprising: at least one neoantigenic peptide or a pharmaceutically acceptable salt thereof; a pH modifier (such as a base, such as a dicarboxylate or tricarboxylate salt, for example, a pharmaceutically acceptable salt of succinic acid or citric acid); and a pharmaceutically acceptable carrier. Such pharmaceutical compositions can be prepared by combining a solution comprising at least one neoantigenic peptide with a base, such as a dicarboxylate or tricarboxylate salt, such as a pharmaceutically acceptable salt of succinic acid or citric acid (such as sodium succinate), or by combining a solution comprising at least one neoantigenic peptide with a solution comprising a base, such as a dicarboxylate or tricarboxylate salt, such as a pharmaceutically acceptable salt of succinic acid or citric acid (including, e.g., a succinate buffer solution). In certain embodiments, the pharmaceutical composition comprises sodium succinate. In certain embodiments, the pH modifier (such as citrate or succinate) is present in the composition at a concentration from about 1 mM to about 10 mM, and, in certain embodiments, at a concentration from about 1.5 mM to about 7.5 mM, or about 2.0 to about 6.0 mM, or about 3.75 to about 5.0 mM.

In certain embodiments of the pharmaceutical composition the pharmaceutically acceptable carrier comprises water. In certain embodiments, the pharmaceutically acceptable carrier further comprises dextrose. In certain embodiments, the pharmaceutically acceptable carrier further comprises dimethylsulfoxide. In certain embodiments, the pharmaceutical composition further comprises an immunomodulator or adjuvant. In certain embodiments, the immunomodulator or adjuvant is selected from the group consisting of poly-ICLC, 1018 ISS, aluminum salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PEPTEL, vector system, PLGA microparticles, resiquimod, SRL172, Virosomes and other Virus-like particles, YF-17D, VEGF trap, R848, beta-glucan, Pam3Cys, and Aquila's QS21 stimulon. In certain embodiments, the immunomodulator or adjuvant comprises poly-ICLC.

Xanthenone derivatives such as, for example, Vadimezan or AsA404 (also known as 5,6-dimethylxanthenone-4-acetic acid (DMXAA)), may also be used as adjuvants according to embodiments of the invention. Alternatively, such derivatives may also be administered in parallel to the vaccine or immunogenic composition of the invention, for example via systemic or intratumoral delivery, to stimulate immunity at the tumor site. Without being bound by theory, it is believed that such xanthenone derivatives act by stimulating interferon (IFN) production via the stimulator of IFN gene ISTING) receptor (see e.g., Conlon et al. (2013) Mouse, but not Human STING, Binds and Signals in Response to the Vascular Disrupting Agent 5,6-Dimethylxanthenone-4-Acetic Acid, Journal of Immunology, 190: 5216-25 and Kim et al. (2013) Anticancer Flavonoids are Mouse-Selective STING Agonists, 8:1396-1401).

The vaccine or immunological composition may also include an adjuvant compound chosen from the acrylic or methacrylic polymers and the copolymers of maleic anhydride and an alkenyl derivative. It is in particular a polymer of acrylic or methacrylic acid cross-linked with a polyalkenyl ether of a sugar or polyalcohol (carbomer), in particular cross-linked with an allyl sucrose or with allylpentaerythritol. It may also be a copolymer of maleic anhydride and ethylene cross-linked, for example, with divinyl ether (see U.S. Pat. No. 6,713,068 hereby incorporated by reference in its entirety).

In certain embodiments, the pH modifier can stabilize the adjuvant or immunomodulator as described herein.

In certain embodiments, a pharmaceutical composition comprises: one to five peptides, dimethylsulfoxide (DMSO), dextrose, water, succinate, poly I:poly C, poly-L-lysine, carboxymethylcellulose, and chloride. In certain embodiments, each of the one to five peptides is present at a concentration of 300 µg/ml. In certain embodiments, the pharmaceutical composition comprises ≤3% DMSO by volume. In certain embodiments, the pharmaceutical composition comprises 3.6-3.7% dextrose in water. In certain embodiments, the pharmaceutical composition comprises 3.6-3.7 mM succinate (e.g., as sodium succinate). In certain embodiments, the pharmaceutical composition comprises 0.5 mg/ml poly I:poly C. In certain embodiments, the pharmaceutical composition comprises 0.375 mg/ml poly-L-Lysine. In certain embodiments, the pharmaceutical composition comprises 1.25 mg/ml sodium carboxymethylcellulose. In certain embodiments, the pharmaceutical composition comprises 0.225% sodium chloride.

Pharmaceutical compositions comprise the herein-described tumor specific neoantigenic peptides in a therapeutically effective amount for treating diseases and conditions (e.g., a neoplasia/tumor), which have been described herein, optionally in combination with a pharmaceutically acceptable additive, carrier and/or excipient. One of ordinary skill in the art from this disclosure and the knowledge in the art will recognize that a therapeutically effective amount of one of more compounds according to the present invention may vary with the condition to be treated, its severity, the treatment regimen to be employed, the pharmacokinetics of the agent used, as well as the patient (animal or human) treated.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., ocular, oral, topical or parenteral, including gels, creams ointments, lotions and time released implantable preparations, among numerous others. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

The active compound is included in the pharmaceutically acceptable carrier or diluent in an amount sufficient to deliver to a patient a therapeutically effective amount for the desired indication, without causing serious toxic effects in the patient treated.

Oral compositions generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid or corn starch; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material herein discussed, a liquid carrier such as a fatty oil. In addition, dosage unit forms can contain various other materials which modify the physical form of the dosage unit, for example, coatings of sugar, shellac, or enteric agents.

Formulations of the present invention suitable for oral administration may be presented as discrete units such as capsules, cachets or tablets each containing a predetermined amount of the active ingredient; as a powder or granules; as a solution or a suspension in an aqueous liquid or a nonaqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein.

Methods of formulating such slow or controlled release compositions of pharmaceutically active ingredients, are known in the art and described in several issued US Patents, some of which include, but are not limited to, U.S. Pat. Nos. 3,870,790; 4,226,859; 4,369,172; 4,842,866 and 5,705,190, the disclosures of which are incorporated herein by reference in their entireties. Coatings can be used for delivery of compounds to the intestine (see, e.g., U.S. Pat. Nos. 6,638,534, 5,541,171, 5,217,720, and 6,569,457, and references cited therein).

The active compound or pharmaceutically acceptable salt thereof may also be administered as a component of an elixir, suspension, syrup, wafer, chewing gum or the like. A syrup may contain, in addition to the active compounds, sucrose or fructose as a sweetening agent and certain preservatives, dyes and colorings and flavors.

Solutions or suspensions used for ocular, parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose.

In certain embodiments, the pharmaceutically acceptable carrier is an aqueous solvent, i.e., a solvent comprising water, optionally with additional co-solvents. Exemplary pharmaceutically acceptable carriers include water, buffer solutions in water (such as phosphate-buffered saline (PBS), and 5% dextrose in water (DSW). In certain embodiments, the aqueous solvent further comprises dimethyl sulfoxide (DMSO), e.g., in an amount of about 1-4%, or 1-3%. In certain embodiments, the pharmaceutically acceptable carrier is isotonic (i.e., has substantially the same osmotic pressure as a body fluid such as plasma).

In one embodiment, the active compounds are prepared with carriers that protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid, and polylactic-co-glycolic acid (PLGA). Methods for preparation of such formulations are within the ambit of the skilled artisan in view of this disclosure and the knowledge in the art.

A skilled artisan from this disclosure and the knowledge in the art recognizes that in addition to tablets, other dosage forms can be formulated to provide slow or controlled release of the active ingredient. Such dosage forms include, but are not limited to, capsules, granulations and gel-caps.

Liposomal suspensions may also be pharmaceutically acceptable carriers. These may be prepared according to methods known to those skilled in the art. For example, liposomal formulations may be prepared by dissolving appropriate lipid(s) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension. Other methods of preparation well known by those of ordinary skill may also be used in this aspect of the present invention.

The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations and compositions suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

The parenteral preparation can be enclosed in ampoules, disposable syringes or multiple dose vials made of glass or plastic. If administered intravenously, preferred carriers include, for example, physiological saline or phosphate buffered saline (PBS).

For parenteral formulations, the carrier usually comprises sterile water or aqueous sodium chloride solution, though other ingredients including those which aid dispersion may be included. Of course, where sterile water is to be used and maintained as sterile, the compositions and carriers are also sterilized. Injectable suspensions may also be prepared, in which case appropriate liquid carriers, suspending agents and the like may be employed.

Formulations suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Administration of the active compound may range from continuous (intravenous drip) to several oral administrations per day (for example, Q.I.D.) and may include oral, topical, eye or ocular, parenteral, intramuscular, intravenous, subcutaneous, transdermal (which may include a penetration enhancement agent), buccal and suppository administration, among other routes of administration, including through an eye or ocular route.

The neoplasia vaccine or immunogenic composition and the at least one checkpoint inhibitor, and any additional agents, may be administered by injection, orally, parenterally, by inhalation spray, rectally, vaginally, or topically in dosage unit formulations containing conventional pharmaceutically acceptable carriers, adjuvants, and vehicles. The term parenteral as used herein includes, into a lymph node or nodes, subcutaneous, intravenous, intramuscular, intrasternal, infusion techniques, intraperitoneally, eye or ocular, intravitreal, intrabuccal, transdermal, intranasal, into the brain, including intracranial and intradural, into the joints, including ankles, knees, hips, shoulders, elbows, wrists, directly into tumors, and the like, and in suppository form.

In certain embodiments, the vaccine or immunogenic composition or the one of more checkpoint inhibitors are administered intravenously or subcutaneously.

Application of the subject therapeutics may be local, so as to be administered at the site of interest. In certain embodiments, the checkpoint inhibitor is administered subcutaneously near the site of administration of the neoplasia vaccine or immunogenic composition, for example within about 1, 2, 3, 4, 5, 6, 7, 8, 9, 10 cm of the site of vaccine or immunogenic composition administration, and preferably within 5 cm of the site of administration of the neoplasia vaccine or immunogenic composition. It is to be understood by one skilled in the art administering the compositions that the concentration of the checkpoint inhibitor administered to the subject may be changed based on the location of administration. For example, if the checkpoint inhibitor is administered near the site of administration of the neoplasia vaccine or immunogenic composition, then the concentration of the checkpoint inhibitor may be decreased.

Various techniques can be used for providing the subject compositions at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way.

The tumor specific neoantigenic peptides may be administered through a device suitable for the controlled and sustained release of a composition effective in obtaining a desired local or systemic physiological or pharmacological effect. The method includes positioning the sustained released drug delivery system at an area wherein release of the agent is desired and allowing the agent to pass through the device to the desired area of treatment.

The tumor specific neoantigenic peptides may be utilized in combination with at least one known other therapeutic agent, or a pharmaceutically acceptable salt of said agent. Examples of known therapeutic agents which can be used for combination therapy include, but are not limited to, corticosteroids (e.g., cortisone, prednisone, dexamethasone), non-steroidal anti-inflammatory drugs (NSAIDS) (e.g., ibuprofen, celecoxib, aspirin, indomethicin, naproxen), alkylating agents such as busulfan, cis-platin, mitomycin C, and carboplatin; antimitotic agents such as colchicine, vinblastine, paclitaxel, and docetaxel; topo I inhibitors such as camptothecin and topotecan; topo II inhibitors such as doxorubicin and etoposide; and/or RNA/DNA antimetabolites such as 5-azacytidine, 5-fluorouracil and methotrexate; DNA antimetabolites such as 5-fluoro-2'-deoxy-uridine, ara-C, hydroxyurea and thioguanine; antibodies such as HERCEPTIN and RITUXAN.

It should be understood that in addition to the ingredients particularly mentioned herein, the formulations of the present invention may include other agents conventional in the art having regard to the type of formulation in question, for example, those suitable for oral administration may include flavoring agents.

Pharmaceutically acceptable salt forms may be the preferred chemical form of compounds according to the present invention for inclusion in pharmaceutical compositions according to the present invention.

The present compounds or their derivatives, including prodrug forms of these agents, can be provided in the form of pharmaceutically acceptable salts. As used herein, the term pharmaceutically acceptable salts or complexes refers to appropriate salts or complexes of the active compounds according to the present invention which retain the desired biological activity of the parent compound and exhibit limited toxicological effects to normal cells. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, and polyglutamic acid, among others; (b) base addition salts formed with metal cations such as zinc, calcium, sodium, potassium, and the like, among numerous others.

The compounds herein are commercially available or can be synthesized. As can be appreciated by the skilled artisan, further methods of synthesizing the compounds of the formulae herein is evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, 2nd. Ed., Wiley-VCH Publishers (1999); T. W. Greene and P. G. M. Wuts, Protective Groups in Organic Synthesis, 3rd. Ed., John Wiley and Sons (1999); L. Fieser and M. Fieser, Fieser and Fieser's Reagents for Organic Synthesis, John Wiley and Sons (1999); and L. Paquette, ed., Encyclopedia of Reagents for Organic Synthesis, John Wiley and Sons (1995), and subsequent editions thereof.

Dosage

When the agents described herein are administered as pharmaceuticals to humans or animals, they can be given per se or as a pharmaceutical composition containing active ingredient in combination with a pharmaceutically acceptable carrier, excipient, or diluent.

Actual dosage levels and time course of administration of the active ingredients in the pharmaceutical compositions of the invention can be varied so as to obtain an amount of the active ingredient which is effective to achieve the desired therapeutic response for a particular patient, composition, and mode of administration, without being toxic to the patient. Generally, agents or pharmaceutical compositions of the invention are administered in an amount sufficient to reduce or eliminate symptoms associated with viral infection and/or autoimmune disease.

A preferred dose of an agent is the maximum that a patient can tolerate and not develop serious or unacceptable side effects.

Determination of an effective amount is well within the capability of those skilled in the art, especially in light of the detailed disclosure provided herein. Generally, an efficacious or effective amount of an agent is determined by first administering a low dose of the agent(s) and then incrementally increasing the administered dose or dosages until a desired effect (e.g., reduce or eliminate symptoms associated with viral infection or autoimmune disease) is observed in the treated subject, with minimal or acceptable toxic side effects. Applicable methods for determining an appropriate dose and dosing schedule for administration of a pharmaceutical composition of the present invention are described, for example, in Goodman and Gilman's The Pharmacological Basis of Therapeutics, Goodman et al., eds., 11th Edition, McGraw-Hill 2005, and Remington: The Science and Practice of Pharmacy, 20th and 21st Editions, Gennaro and University of the Sciences in Philadelphia, Eds., Lippencott Williams & Wilkins (2003 and 2005), each of which is hereby incorporated by reference.

Preferred unit dosage formulations are those containing a daily dose or unit, daily sub-dose, as herein discussed, or an appropriate fraction thereof, of the administered ingredient.

The dosage regimen for treating a disorder or a disease with the tumor specific neoantigenic peptides of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods.

The amounts and dosage regimens administered to a subject can depend on a number of factors, such as the mode of administration, the nature of the condition being treated, the body weight of the subject being treated and the judgment of the prescribing physician; all such factors being within the ambit of the skilled artisan from this disclosure and the knowledge in the art.

The amount of compound included within therapeutically active formulations according to the present invention is an effective amount for treating the disease or condition.

In general, a therapeutically effective amount of the present preferred compound in dosage form usually ranges from slightly less than about 0.025 mg/kg/day to about 2.5 g/kg/day, preferably about 0.1 mg/kg/day to about 100 mg/kg/day of the patient or considerably more, depending upon the compound used, the condition or infection treated and the route of administration, although exceptions to this dosage range may be contemplated by the present invention. In its most preferred form, compounds according to the present invention are administered in amounts ranging from about 1 mg/kg/day to about 100 mg/kg/day. The dosage of the compound can depend on the condition being treated, the particular compound, and other clinical factors such as weight and condition of the patient and the route of administration of the compound. It is to be understood that the present invention has application for both human and veterinary use.

According to certain exemplary embodiments, the vaccine or immunogenic composition is administered at a dose of about 10 µg-1 mg per neoantigenic peptide. According to certain exemplary embodiments, the vaccine or immunogenic composition is administered at an average weekly dose level of about 10 µg-2000 µg per neoantigenic peptide. According to certain exemplary embodiments, the checkpoint inhibitor is administered at a dose of about 0.1-10 mg/kg. According to certain exemplary embodiments, the anti-CTLA4 antibody is administered at a dose of about 1 mg/kg-3 mg/kg. For example, in certain exemplary embodiments, Nivolumab isgin dosing at the standard single agent dosing level of 3 mg/kg. When the one or more checkpoint inhibitors are administered at the site of administration of the vaccine or immunogenic composition, the inhibitor is preferably administered at a dose of about 0.1-1 mg per site of administration of the neoplasia vaccine or immunogenic composition.

Preferred embodiments use the concentrations and timings used in clinical trials for checkpoint inhibitors, alone or in combination with a neoantigen vaccine or immunogenic composition. Topalian, et al. N Engl J Med 2012; 366:2443-2454 describes a phase 1 study that assessed the safety, antitumor activity, and pharmacokinetics of BMS-936558, a fully human IgG4-blocking monoclonal antibody directed against PD-1, in patients in need thereof with selected advanced solid tumors. The antibody was administered as an intravenous infusion every 2 weeks of each 8-week treatment cycle. Response was assessed after each treatment cycle. Patients received treatment for up to 2 years (12 cycles). Patients with advanced melanoma, non-small-cell lung cancer, renal-cell cancer, castration-resistant prostate cancer, or colorectal cancer were enrolled. Cohorts of three to six patients per dose level were enrolled sequentially at doses of 1.0, 3.0, or 10.0 mg per kilogram of body weight. Initially, five expansion cohorts of approximately 16 patients each were enrolled at doses of 10.0 mg per kilogram for melanoma, non-small-cell lung cancer, renal-cell cancer, castration-resistant prostate cancer, and colorectal cancer. On the basis of initial signals of activity, additional expansion cohorts of approximately 16 patients each were enrolled for melanoma (at a dose of 1.0 or 3.0 mg per kilogram, followed by cohorts randomly assigned to 0.1, 0.3, or 1.0 mg per kilogram), lung cancer (patients with the squamous or nonsquamous subtype, randomly assigned to a dose of 1.0, 3.0, or 10.0 mg per kilogram), and renal-cell cancer (at a dose of 1.0 mg per kilogram).

Wolchok, et al. N Engl J Med 2013; 369:122-133, describes a clinical trial using Nivolumab plus Ipilimumab in advanced melanoma. In the study patients were administered intravenous doses of nivolumab and ipilimumab every 3 weeks for 4 doses, followed by nivolumab alone every 3 weeks for 4 doses. The combined treatment was subsequently administered every 12 weeks for up to 8 doses. In a sequenced regimen, patients previously treated with ipilimumab received nivolumab every 2 weeks for up to 48 doses. The maximum doses that were associated with an acceptable level of adverse events were nivolumab at a dose of 1 mg per kilogram of body weight and ipilimumab at a dose of 3 mg per kilogram.

Wolchok et al., Clin. Cancer Res. 15, 7412; 2009 describes a phase II clinical trial program with ipilimumab. Patients were treated with induction therapy (ipilimumab 10 mg/kg every 3 wk×4) followed by maintenance therapy in eligible patients (ipilimumab 10 mg/kg every 12 wk, beginning at week 24).

Hamid et al., N Engl J Med 2013; 369:134-144, describes safety and tumor responses with Lambrolizumab (Anti-PD-1) in melanoma. Patients with advanced melanoma were administered lambrolizumab intravenously at a dose of 10 mg per kilogram of body weight every 2 or 3 weeks or 2 mg per kilogram every 3 weeks. Patients included both those who had received prior treatment with the immune checkpoint inhibitor ipilimumab and those who had not.

Spigel et al., J Clin Oncol 31, 2013 (suppl; abstr 8008) describe a phase I trial for MPDL3280A, a human monoclonal Ab containing an engineered Fc-domain designed to optimize efficacy and safety, targeting PD-L1. Patients with squamous or nonsquamous NSCLC received MPDL3280A by IV at doses between 1-20 mg/kg for up to 1 y.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

The invention provides for pharmaceutical compositions containing at least one tumor specific neoantigen described herein. In embodiments, the pharmaceutical compositions contain a pharmaceutically acceptable carrier, excipient, or diluent, which includes any pharmaceutical agent that does not itself induce the production of an immune response harmful to a subject receiving the composition, and which may be administered without undue toxicity. As used herein, the term "pharmaceutically acceptable" means being approved by a regulatory agency of the Federal or a state government or listed in the U.S. Pharmacopia, European Pharmacopia or other generally recognized pharmacopia for use in mammals, and more particularly in humans. These compositions can be useful for treating and/or preventing viral infection and/or autoimmune disease.

A thorough discussion of pharmaceutically acceptable carriers, diluents, and other excipients is presented in Remington's Pharmaceutical Sciences (17th ed., Mack Publishing Company) and Remington: The Science and Practice of Pharmacy (21st ed., Lippincott Williams & Wilkins), which are hereby incorporated by reference. The formulation of the pharmaceutical composition should suit the mode of administration. In embodiments, the pharmaceutical composition is suitable for administration to humans, and can be sterile, non-particulate and/or non-pyrogenic.

Pharmaceutically acceptable carriers, excipients, or diluents include, but are not limited, to saline, buffered saline, dextrose, water, glycerol, ethanol, sterile isotonic aqueous buffer, and combinations thereof.

Wetting agents, emulsifiers and lubricants, such as sodium lauryl sulfate and magnesium stearate, as well as coloring agents, release agents, coating agents, sweetening, flavoring and perfuming agents, preservatives, and antioxidants can also be present in the compositions.

Examples of pharmaceutically-acceptable antioxidants include, but are not limited to: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In embodiments, the pharmaceutical composition is provided in a solid form, such as a lyophilized powder suitable for reconstitution, a liquid solution, suspension, emulsion, tablet, pill, capsule, sustained release formulation, or powder.

In embodiments, the pharmaceutical composition is supplied in liquid form, for example, in a sealed container indicating the quantity and concentration of the active ingredient in the pharmaceutical composition. In related embodiments, the liquid form of the pharmaceutical composition is supplied in a hermetically sealed container.

Methods for formulating the pharmaceutical compositions of the present invention are conventional and well known in the art (see Remington and Remington's). One of skill in the art can readily formulate a pharmaceutical composition having the desired characteristics (e.g., route of administration, biosafety, and release profile).

Methods for preparing the pharmaceutical compositions include the step of bringing into association the active ingredient with a pharmaceutically acceptable carrier and, optionally, one or more accessory ingredients. The pharmaceutical compositions can be prepared by uniformly and intimately bringing into association the active ingredient with liquid carriers, or finely divided solid carriers, or both, and then, if necessary, shaping the product. Additional methodology for preparing the pharmaceutical compositions, including the preparation of multilayer dosage forms, are described in Ansel's Pharmaceutical Dosage Forms and Drug Delivery Systems (9th ed., Lippincott Williams & Wilkins), which is hereby incorporated by reference.

Pharmaceutical compositions suitable for oral administration can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound(s) described herein, a derivative thereof, or a pharmaceutically acceptable salt or prodrug thereof as the active ingredient(s). The active ingredient can also be administered as a bolus, electuary, or paste.

In solid dosage forms for oral administration (e.g., capsules, tablets, pills, dragees, powders, granules and the like), the active ingredient is mixed with one or more pharmaceutically acceptable carriers, excipients, or diluents, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions can also comprise buffering agents. Solid compositions of a similar type can also be prepared using fillers in soft and hard-filled gelatin capsules, and excipients such as lactose or milk sugars, as well as high molecular weight polyethylene glycols and the like.

A tablet can be made by compression or molding, optionally with one or more accessory ingredients. Compressed tablets can be prepared using binders (for example, gelatin or hydroxypropylmethyl cellulose), lubricants, inert diluents, preservatives, disintegrants (for example, sodium starch glycolate or cross-linked sodium carboxymethyl cellulose), surface-actives, and/or dispersing agents. Molded tablets can be made by molding in a suitable machine a mixture of the powdered active ingredient moistened with an inert liquid diluent.

The tablets and other solid dosage forms, such as dragees, capsules, pills, and granules, can optionally be scored or prepared with coatings and shells, such as enteric coatings and other coatings well known in the art.

In some embodiments, in order to prolong the effect of an active ingredient, it is desirable to slow the absorption of the compound from subcutaneous or intramuscular injection. This can be accomplished by the use of a liquid suspension of crystalline or amorphous material having poor water solubility. The rate of absorption of the active ingredient then depends upon its rate of dissolution which, in turn, can depend upon crystal size and crystalline form. Alternatively, delayed absorption of a parenterally-administered active ingredient is accomplished by dissolving or suspending the compound in an oil vehicle. In addition, prolonged absorption of the injectable pharmaceutical form can be brought about by the inclusion of agents that delay absorption such as aluminum monostearate and gelatin.

Controlled release parenteral compositions can be in form of aqueous suspensions, microspheres, microcapsules, magnetic microspheres, oil solutions, oil suspensions, emulsions, or the active ingredient can be incorporated in biocompatible carrier(s), liposomes, nanoparticles, implants or infusion devices.

Materials for use in the preparation of microspheres and/or microcapsules include biodegradable/bioerodible polymers such as polyglactin, poly-(isobutyl cyanoacrylate), poly(2-hydroxyethyl-L-glutamine) and poly(lactic acid).

Biocompatible carriers which can be used when formulating a controlled release parenteral formulation include carbohydrates such as dextrans, proteins such as albumin, lipoproteins or antibodies.

Materials for use in implants can be non-biodegradable, e.g., polydimethylsiloxane, or biodegradable such as, e.g., poly(caprolactone), poly(lactic acid), poly(glycolic acid) or poly(ortho esters).

In embodiments, the active ingredient(s) are administered by aerosol. This is accomplished by preparing an aqueous aerosol, liposomal preparation, or solid particles containing the compound. A nonaqueous (e.g., fluorocarbon propellant) suspension can be used. The pharmaceutical composition can also be administered using a sonic nebulizer, which would minimize exposing the agent to shear, which can result in degradation of the compound.

Ordinarily, an aqueous aerosol is made by formulating an aqueous solution or suspension of the active ingredient(s) together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Dosage forms for topical or transdermal administration of an active ingredient(s) includes powders, sprays, ointments, pastes, creams, lotions, gels, solutions, patches and inhalants. The active ingredient(s) can be mixed under sterile conditions with a pharmaceutically acceptable carrier, and with any preservatives, buffers, or propellants as appropriate.

Transdermal patches suitable for use in the present invention are disclosed in Transdermal Drug Delivery: Developmental Issues and Research Initiatives (Marcel Dekker Inc., 1989) and U.S. Pat. Nos. 4,743,249, 4,906,169, 5,198,223, 4,816,540, 5,422,119, 5,023,084, which are hereby incorporated by reference. The transdermal patch can also be any transdermal patch well known in the art, including transscrotal patches. Pharmaceutical compositions in such transdermal patches can contain one or more absorption enhancers or skin permeation enhancers well known in the art (see, e.g., U.S. Pat. Nos. 4,379,454 and 4,973,468, which are hereby incorporated by reference). Transdermal therapeutic systems for use in the present invention can be based on iontophoresis, diffusion, or a combination of these two effects.

Transdermal patches have the added advantage of providing controlled delivery of active ingredient(s) to the body. Such dosage forms can be made by dissolving or dispersing the active ingredient(s) in a proper medium. Absorption enhancers can also be used to increase the flux of the active ingredient across the skin. The rate of such flux can be controlled by either providing a rate controlling membrane or dispersing the active ingredient(s) in a polymer matrix or gel.

Such pharmaceutical compositions can be in the form of creams, ointments, lotions, liniments, gels, hydrogels, solutions, suspensions, sticks, sprays, pastes, plasters and other kinds of transdermal drug delivery systems. The compositions can also include pharmaceutically acceptable carriers or excipients such as emulsifying agents, antioxidants, buffering agents, preservatives, humectants, penetration enhancers, chelating agents, gel-forming agents, ointment bases, perfumes, and skin protective agents.

Examples of emulsifying agents include, but are not limited to, naturally occurring gums, e.g. gum acacia or gum tragacanth, naturally occurring phosphatides, e.g. soybean lecithin and sorbitan monooleate derivatives.

Examples of antioxidants include, but are not limited to, butylated hydroxy anisole (BHA), ascorbic acid and derivatives thereof, tocopherol and derivatives thereof, and cysteine.

Examples of preservatives include, but are not limited to, parabens, such as methyl or propyl p-hydroxybenzoate and benzalkonium chloride.

Examples of humectants include, but are not limited to, glycerin, propylene glycol, sorbitol and urea.

Examples of penetration enhancers include, but are not limited to, propylene glycol, DMSO, triethanolamine, N,N-dimethylacetamide, N,N-dimethylformamide, 2-pyrrolidone and derivatives thereof, tetrahydrofurfuryl alcohol, propylene glycol, diethylene glycol monoethyl or monomethyl ether with propylene glycol monolaurate or methyl laurate, eucalyptol, lecithin, TRANSCUTOL, and AZONE.

Examples of chelating agents include, but are not limited to, sodium EDTA, citric acid and phosphoric acid.

Examples of gel forming agents include, but are not limited to, Carbopol, cellulose derivatives, bentonite, alginates, gelatin and polyvinylpyrrolidone.

In addition to the active ingredient(s), the ointments, pastes, creams, and gels of the present invention can contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain excipients such as lactose, talc, silicic acid, aluminum hydroxide, calcium silicates and polyamide powder, or mixtures of these substances. Sprays can additionally contain customary propellants, such as chlorofluorohydrocarbons, and volatile unsubstituted hydrocarbons, such as butane and propane.

Injectable depot forms are made by forming microencapsule matrices of compound(s) of the invention in biodegradable polymers such as polylactide-polyglycolide. Depending on the ratio of compound to polymer, and the nature of the particular polymer employed, the rate of compound release can be controlled. Examples of other biodegradable polymers include poly(orthoesters) and poly(anhydrides). Depot injectable formulations are also prepared by entrapping the drug in liposomes or microemulsions which are compatible with body tissue.

Subcutaneous implants are well known in the art and are suitable for use in the present invention. Subcutaneous implantation methods are preferably non-irritating and mechanically resilient. The implants can be of matrix type, of reservoir type, or hybrids thereof. In matrix type devices, the carrier material can be porous or non-porous, solid or semi-solid, and permeable or impermeable to the active compound or compounds. The carrier material can be biodegradable or may slowly erode after administration. In some instances, the matrix is non-degradable but instead relies on the diffusion of the active compound through the matrix for the carrier material to degrade. Alternative subcutaneous implant methods utilize reservoir devices where the active compound or compounds are surrounded by a rate controlling membrane, e.g., a membrane independent of component concentration (possessing zero-order kinetics). Devices consisting of a matrix surrounded by a rate controlling membrane also suitable for use.

Both reservoir and matrix type devices can contain materials such as polydimethylsiloxane, such as SILASTIC, or other silicone rubbers. Matrix materials can be insoluble polypropylene, polyethylene, polyvinyl chloride, ethylvinyl acetate, polystyrene and polymethacrylate, as well as glycerol esters of the glycerol palmitostearate, glycerol stearate, and glycerol behenate type. Materials can be hydrophobic or hydrophilic polymers and optionally contain solubilizing agents.

Subcutaneous implant devices can be slow-release capsules made with any suitable polymer, e.g., as described in U.S. Pat. Nos. 5,035,891 and 4,210,644, which are hereby incorporated by reference.

In general, at least four different approaches are applicable in order to provide rate control over the release and transdermal permeation of a drug compound. These approaches are: membrane-moderated systems, adhesive diffusion-controlled systems, matrix dispersion-type systems and microreservoir systems. It is appreciated that a controlled release percutaneous and/or topical composition can be obtained by using a suitable mixture of these approaches.

In a membrane-moderated system, the active ingredient is present in a reservoir which is totally encapsulated in a shallow compartment molded from a drug-impermeable laminate, such as a metallic plastic laminate, and a rate-controlling polymeric membrane such as a microporous or a non-porous polymeric membrane, e.g., ethylene-vinyl acetate copolymer. The active ingredient is released through the rate controlling polymeric membrane. In the drug reservoir, the active ingredient can either be dispersed in a solid polymer matrix or suspended in an unleachable, viscous liquid medium such as silicone fluid. On the external surface of the polymeric membrane, a thin layer of an adhesive polymer is applied to achieve an intimate contact of the transdermal system with the skin surface. The adhesive polymer is preferably a polymer which is hypoallergenic and compatible with the active drug substance.

In an adhesive diffusion-controlled system, a reservoir of the active ingredient is formed by directly dispersing the active ingredient in an adhesive polymer and then by, e.g., solvent casting, spreading the adhesive containing the active ingredient onto a flat sheet of substantially drug-impermeable metallic plastic backing to form a thin drug reservoir layer.

A matrix dispersion-type system is characterized in that a reservoir of the active ingredient is formed by substantially homogeneously dispersing the active ingredient in a hydrophilic or lipophilic polymer matrix. The drug-containing polymer is then molded into disc with a substantially well-defined surface area and controlled thickness. The adhesive polymer is spread along the circumference to form a strip of adhesive around the disc.

A microreservoir system can be considered as a combination of the reservoir and matrix dispersion type systems. In this case, the reservoir of the active substance is formed by first suspending the drug solids in an aqueous solution of water-soluble polymer and then dispersing the drug suspension in a lipophilic polymer to form a multiplicity of unleachable, microscopic spheres of drug reservoirs.

Any of the herein-described controlled release, extended release, and sustained release compositions can be formulated to release the active ingredient in about 30 minutes to about 1 week, in about 30 minutes to about 72 hours, in about 30 minutes to 24 hours, in about 30 minutes to 12 hours, in about 30 minutes to 6 hours, in about 30 minutes to 4 hours, and in about 3 hours to 10 hours. In embodiments, an effective concentration of the active ingredient(s) is sustained in a subject for 4 hours, 6 hours, 8 hours, 10 hours, 12 hours, 16 hours, 24 hours, 48 hours, 72 hours, or more after administration of the pharmaceutical compositions to the subject.

Vaccine or Immunogenic Compositions

The present invention is directed to methods of combination treatment. The combination treatment comprises at least an immunogenic composition, e.g., a neoplasia vaccine or immunogenic composition capable of raising a specific T-cell response. The neoplasia vaccine or immunogenic composition comprises neoantigenic peptides and/or neoantigenic polypeptides corresponding to tumor specific neoantigens identified by the methods described herein. The combination treatment also comprises at least one checkpoint inhibitor. In particular, the present invention is directed to methods of treating or preventing a neoplasia comprising the steps of administering to a subject (a) a neoplasia vaccine or immunogenic composition, and (b) at least one checkpoint inhibitor.

A suitable neoplasia vaccine or immunogenic composition can preferably contain a plurality of tumor specific neoantigenic peptides. In an embodiment, the vaccine or immunogenic composition can include between 1 and 100 sets of peptides, more preferably between 1 and 50 such peptides, even more preferably between 10 and 30 sets peptides, even more preferably between 15 and 25 peptides. According to another preferred embodiment, the vaccine or immunogenic composition can include at least one peptides, more preferably 2, 3, 4, or 5 peptides, In certain embodiments, the vaccine or immunogenic composition can comprise 5, 6, 7, 8, 9, 10, 11, 12, 13, 14, 15, 16, 17, 18, 19, 20, 21, 22, 23, 24, 25, 26, 27, 28, 29, or 30 different peptides.

The optimum amount of each peptide to be included in the vaccine or immunogenic composition and the optimum dosing regimen can be determined by one skilled in the art without undue experimentation. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c, i.d., i.p., i.m., and i.v. Preferred methods of DNA injection include i.d., i.m., s.c, i.p. and i.v. For example, doses of between 1 and 500 mg 50 µg and 1.5 mg, preferably 10 µg to 500 µg, of peptide or DNA may be given and can depend from the respective peptide or DNA. Doses of this range were successfully used in previous trials (Brunsvig P F, et al., Cancer Immunol Immunother. 2006; 55(12): 1553-1564; M. Staehler, et al., ASCO meeting 2007; Abstract No 3017). Other methods of administration of the vaccine or immunogenic composition are known to those skilled in the art.

In one embodiment of the present invention the different tumor specific neoantigenic peptides and/or polypeptides are selected for use in the neoplasia vaccine or immunogenic composition so as to maximize the likelihood of generating an immune attack against the neoplasia/tumor of the patient. Without being bound by theory, it is believed that the inclusion of a diversity of tumor specific neoantigenic peptides can generate a broad scale immune attack against a neoplasia/tumor. In one embodiment, the selected tumor specific neoantigenic peptides/polypeptides are encoded by missense mutations. In a second embodiment, the selected tumor specific neoantigenic peptides/polypeptides are encoded by a combination of missense mutations and neoORF mutations. In a third embodiment, the selected tumor specific neoantigenic peptides/polypeptides are encoded by neoORF mutations.

In one embodiment in which the selected tumor specific neoantigenic peptides/polypeptides are encoded by missense mutations, the peptides and/or polypeptides are chosen based on their capability to associate with the particular MHC molecules of the patient. Peptides/polypeptides derived from neoORF mutations can also be selected on the basis of their capability to associate with the particular MHC molecules of the patient, but can also be selected even if not predicted to associate with the particular MHC molecules of the patient.

The vaccine or immunogenic composition is capable of raising a specific cytotoxic T-cells response and/or a specific helper T-cell response.

The vaccine or immunogenic composition can further comprise an adjuvant and/or a carrier. Examples of useful adjuvants and carriers are given herein. The peptides and/or polypeptides in the composition can be associated with a carrier such as, e.g., a protein or an antigen-presenting cell such as e.g. a dendritic cell (DC) capable of presenting the peptide to a T-cell.

Adjuvants are any substance whose admixture into the vaccine or immunogenic composition increases or otherwise modifies the immune response to the mutant peptide. Carriers are scaffold structures, for example a polypeptide or a polysaccharide, to which the neoantigenic peptides, is capable of being associated. Optionally, adjuvants are conjugated covalently or non-covalently to the peptides or polypeptides of the invention.

The ability of an adjuvant to increase the immune response to an antigen is typically manifested by a significant increase in immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th2 response into a primarily cellular, or Th1 response.

Suitable adjuvants include, but are not limited to 1018 ISS, aluminum salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PEPTEL, vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Several immunological adjuvants (e.g., MF59) specific for dendritic cells and their preparation have been described previously (Dupuis M, et al., Cell Immunol. 1998; 186(1): 18-27; Allison A C; Dev Biol Stand. 1998; 92:3-11). Also cytokines may be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6):414-418).

Toll like receptors (TLRs) may also be used as adjuvants, and are important members of the family of pattern recognition receptors (PRRs) which recognize conserved motifs shared by many micro-organisms, termed "pathogen-associated molecular patterns" (PAMPS). Recognition of these "danger signals" activates multiple elements of the innate and adaptive immune system. TLRs are expressed by cells of the innate and adaptive immune systems such as dendritic cells (DCs), macrophages, T and B cells, mast cells, and granulocytes and are localized in different cellular compartments, such as the plasma membrane, lysosomes, endosomes, and endolysosomes. Different TLRs recognize distinct PAMPS. For example, TLR4 is activated by LPS contained in bacterial cell walls, TLR9 is activated by unmethylated bacterial or viral CpG DNA, and TLR3 is activated by double stranded RNA. TLR ligand binding leads to the activation of one or more intracellular signaling pathways, ultimately resulting in the production of many key molecules associated with inflammation and immunity (particularly the transcription factor NF-κB and the Type-I interferons). TLR mediated DC activation leads to enhanced DC activation, phagocytosis, upregulation of activation and co-stimulation markers such as CD80, CD83, and CD86, expression of CCR7 allowing migration of DC to draining lymph nodes and facilitating antigen presentation to T cells, as well as increased secretion of cytokines such as type I interferons, IL-12, and IL-6. All of these downstream events are critical for the induction of an adaptive immune response.

Among the most promising cancer vaccine or immunogenic composition adjuvants currently in clinical development are the TLR9 agonist CpG and the synthetic double-stranded RNA (dsRNA) TLR3 ligand poly-ICLC. In preclinical studies poly-ICLC appears to be the most potent TLR adjuvant when compared to LPS and CpG due to its induction of pro-inflammatory cytokines and lack of stimulation of IL-10, as well as maintenance of high levels of co-stimulatory molecules in DCsl. Furthermore, poly-ICLC was recently directly compared to CpG in non-human primates (rhesus macaques) as adjuvant for a protein vaccine or immunogenic composition consisting of human papillomavirus (HPV)16 capsomers (Stahl-Hennig C, Eisenblatter M, Jasny E, et al. Synthetic double-stranded RNAs are adjuvants for the induction of T helper 1 and humoral immune responses to human papillomavirus in rhesus macaques. PLoS pathogens. April 2009; 5(4)).

CpG immuno stimulatory oligonucleotides have also been reported to enhance the effects of adjuvants in a vaccine or immunogenic composition setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly, it enhances dendritic cell maturation and differentiation, resulting in enhanced activation of Th1 cells and strong cytotoxic T-lymphocyte (CTL) generation, even in the absence of CD4 T-cell help. The Th1 bias induced by TLR9 stimulation is maintained even in the presence of vaccine adjuvants such as alum or incomplete Freund's adjuvant (IFA) that normally promote a Th2 bias. CpG oligonucleotides show even greater adjuvant activity when formulated or co-administered with other adjuvants or in formulations such as microparticles, nano particles, lipid emulsions or similar formulations, which are especially necessary for inducing a strong response when the antigen is relatively weak. They also accelerate the immune response and enabled the antigen doses to be reduced by approximately two orders of magnitude, with comparable antibody responses to the full-dose vaccine without CpG in some experiments (Arthur M. Krieg, Nature Reviews, Drug Discovery, 5, June 2006, 471-484). U.S. Pat. No. 6,406,705 B1 describes the combined use of CpG oligonucleotides, non-nucleic acid adjuvants and an antigen to induce an antigen-specific immune response. A commercially available CpG TLR9 antagonist is dSLIM (double Stem Loop Immunomodulator) by Mologen (Berlin, GERMANY), which is a preferred component of the pharmaceutical composition of the present invention. Other TLR binding molecules such as RNA binding TLR 7, TLR 8 and/or TLR 9 may also be used.

Other examples of useful adjuvants include, but are not limited to, chemically modified CpGs (e.g. CpR, Idera), Poly(I:C)(e.g. polyi:CI2U), non-CpG bacterial DNA or RNA as well as immunoactive small molecules and antibodies such as cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab, and SC58175, which may act therapeutically and/or as an adjuvant. The amounts and concentrations of adjuvants and additives useful in the context of the present invention can readily be determined by the skilled artisan without undue experimentation. Additional adjuvants include colony-stimulating factors, such as Granulocyte Macrophage Colony Stimulating Factor (GM-CSF, sargramostim).

Poly-ICLC is a synthetically prepared double-stranded RNA consisting of polyI and polyC strands of average length of about 5000 nucleotides, which has been stabilized to thermal denaturation and hydrolysis by serum nucleases by the addition of polylysine and carboxymethylcellulose. The compound activates TLR3 and the RNA helicase-domain of MDA5, both members of the PAMP family, leading to DC and natural killer (NK) cell activation and production of a "natural mix" of type I interferons, cytokines, and chemokines. Furthermore, poly-ICLC exerts a more direct, broad host-targeted anti-infectious and possibly antitumor effect mediated by the two IFN-inducible nuclear enzyme systems, the 2'5'-OAS and the P1/eIF2a kinase, also known as the PKR (4-6), as well as RIG-I helicase and MDA5.

In rodents and non-human primates, poly-ICLC was shown to enhance T cell responses to viral antigens, cross-priming, and the induction of tumor-, virus-, and autoantigen-specific CD8+ T-cells. In a recent study in non-human primates, poly-ICLC was found to be essential for the generation of antibody responses and T-cell immunity to DC targeted or non-targeted HIV Gag p24 protein, emphasizing its effectiveness as a vaccine adjuvant.

In human subjects, transcriptional analysis of serial whole blood samples revealed similar gene expression profiles among the 8 healthy human volunteers receiving one single s.c. administration of poly-ICLC and differential expression of up to 212 genes between these 8 subjects versus 4 subjects receiving placebo. Remarkably, comparison of the poly-ICLC gene expression data to previous data from volunteers immunized with the highly effective yellow fever vaccine YF17D showed that a large number of transcriptional and signal transduction canonical pathways, including those of the innate immune system, were similarly upregulated at peak time points.

More recently, an immunologic analysis was reported on patients with ovarian, fallopian tube, and primary peritoneal cancer in second or third complete clinical remission who were treated on a phase 1 study of subcutaneous vaccination with synthetic overlapping long peptides (OLP) from the cancer testis antigen NY-ESO-1 alone or with Montanide-ISA-51, or with 1.4 mg poly-ICLC and Montanide. The generation of NY-ESO-1-specific CD4+ and CD8+ T-cell and antibody responses were markedly enhanced with the addition of poly-ICLC and Montanide compared to OLP alone or OLP and Montanide.

A vaccine or immunogenic composition according to the present invention may comprise more than one different adjuvant. Furthermore, the invention encompasses a therapeutic composition comprising any adjuvant substance including any of those herein discussed. It is also contemplated that the peptide or polypeptide, and the adjuvant can be administered separately in any appropriate sequence.

A carrier may be present independently of an adjuvant. The carrier may be covalently linked to the antigen. A carrier can also be added to the antigen by inserting DNA encoding the carrier in frame with DNA encoding the antigen. The function of a carrier can for example be to confer stability, to increase the biological activity, or to increase serum half-life. Extension of the half-life can help to reduce the number of applications and to lower doses, thus are beneficial for therapeutic but also economic reasons. Furthermore, a carrier may aid presenting peptides to T-cells. The carrier may be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier may be a physiologically acceptable carrier acceptable to humans and safe. However, tetanus toxoid and/or diptheria toxoid are suitable carriers in one embodiment of the invention. Alternatively, the carrier may be dextrans for example sepharose.

Cytotoxic T-cells (CTLs) recognize an antigen in the form of a peptide bound to an MHC molecule rather than the intact foreign antigen itself. The MHC molecule itself is located at the cell surface of an antigen presenting cell. Thus, an activation of CTLs is only possible if a trimeric complex of peptide antigen, MHC molecule, and APC is present. Correspondingly, it may enhance the immune response if not only the peptide is used for activation of CTLs, but if additionally APCs with the respective MHC molecule are added. Therefore, in some embodiments the vaccine or immunogenic composition according to the present invention additionally contains at least one antigen presenting cell. [002%] The antigen-presenting cell (or stimulator cell) typically has an MHC class I or II molecule on its surface, and in one embodiment is substantially incapable of itself loading the MHC class I or II molecule with the selected antigen. As is described in more detail herein, the MHC class I or II molecule may readily be loaded with the selected antigen in vitro.

CD8+ cell activity may be augmented through the use of CD4+ cells. The identification of CD4 T+ cell epitopes for tumor antigens has attracted interest because many immune based therapies against cancer may be more effective if both CD8+ and CD4+ T lymphocytes are used to target a patient's tumor. CD4+ cells are capable of enhancing CD8 T cell responses. Many studies in animal models have clearly demonstrated better results when both CD4+ and CD8+ T cells participate in anti-tumor responses (see e.g., Nishimura et al. (1999) Distinct role of antigen-specific T helper type 1 (TH1) and Th2 cells in tumor eradication in vivo. J Ex Med 190:617-27). Universal CD4+ T cell epitopes have been identified that are applicable to developing therapies against different types of cancer (see e.g., Kobayashi et al. (2008) Current Opinion in Immunology 20:221-27). For example, an HLA-DR restricted helper peptide from tetanus toxoid was used in melanoma vaccines to activate CD4+ T cells non-specifically (see e.g., Slingluff et al. (2007) Immunologic and Clinical Outcomes of a Randomized Phase II Trial of Two Multipeptide Vaccines for Melanoma in the Adjuvant Setting, Clinical Cancer Research 13(21):6386-95). It is contemplated within the scope of the invention that such CD4+ cells may be applicable at three levels that vary in their tumor specificity: 1) a broad level in which universal CD4+ epitopes (e.g., tetanus toxoid) may be used to augment CD8+ cells; 2) an intermediate level in which native, tumor-associated CD4+ epitopes may be used to augment CD8+ cells; and 3) a patient specific level in which neoantigen CD4+ epitopes may be used to augment CD8+ cells in a patient specific manner.

CD8+ cell immunity may also be generated with neoantigen loaded dendritic cell (DC) vaccine. DCs are potent antigen-presenting cells that initiate T cell immunity and can be used as cancer vaccines when loaded with one or more peptides of interest, for example, by direct peptide injection. For example, patients that were newly diagnosed with metastatic melanoma were shown to be immunized against 3 HLA-A*020l-restricted gp100 melanoma antigen-derived peptides with autologous peptide pulsed CD40L/IFN-g-activated mature DCs via an IL-12p70-producing patient DC vaccine (see e.g., Carreno et al (2013) L-12p70-producing patient DC vaccine elicits Tca-polarized immunity, Journal of Clinical Investigation, 123(8):3383-94 and Ali et al. (2009) In situ regulation of DC subsets and T cells mediates tumor regression in mice, Cancer Immunotherapy, 1(8):1-10). It is contemplated within the scope of the invention that neoantigen loaded DCs may be prepared using the synthetic TLR 3 agonist Polyinosinic-Polycytidylic Acid-poly-L-lysine Carboxymethylcellulose (Poly-ICLC) to stimulate the DCs. Poly-ICLC is a potent individual maturation stimulus for human DCs as assessed by an upregulation of CD83 and CD86, induction of interleukin-12 (IL-12), tumor necrosis factor (TNF), interferon gamma-induced protein 10 (IP-10), interleukin 1 (IL-1), and type I interferons (IFN), and minimal interleukin 10 (IL-10) production. DCs may be differentiated from frozen peripheral blood mononuclear cells (PBMCs) obtained by leukapheresis, while PBMCs may be isolated by Ficoll gradient centrifugation and frozen in aliquots.

Illustratively, the following 7 day activation protocol may be used. Day 1-PBMCs are thawed and plated onto tissue culture flasks to select for monocytes which adhere to the plastic surface after 1-2 hr incubation at 37° C. in the tissue culture incubator. After incubation, the lymphocytes are washed off and the adherent monocytes are cultured for 5 days in the presence of interleukin-4 (IL-4) and granulocyte macrophage-colony stimulating factor (GM-CSF) to differentiate to immature DCs. On Day 6, immature DCs are pulsed with the keyhole limpet hemocyanin (KLH) protein which serves as a control for the quality of the vaccine and may boost the immunogenicity of the vaccine. The DCs are stimulated to mature, loaded with peptide antigens, and incubated overnight. On Day 7, the cells are washed, and frozen in 1 ml aliquots containing 4-20×10(6) cells using a controlled-rate freezer. Lot release testing for the batches of DCs may be performed to meet minimum specifications before the DCs are injected into patients (see e.g., Sabado et al. (2013) Preparation of tumor antigen-loaded mature dendritic cells for immunotherapy, J. Vis Exp. August 1; (78). doi: 10.3791/50085).

A DC vaccine may be incorporated into a scaffold system to facilitate delivery to a patient. Therapeutic treatment of a patients neoplasia with a DC vaccine may utilize a biomaterial system that releases factors that recruit host dendritic cells into the device, differentiates the resident, immature DCs by locally presenting adjuvants (e.g., danger signals) while releasing antigen, and promotes the release of activated, antigen loaded DCs to the lymph nodes (or desired site of action) where the DCs may interact with T cells to generate a potent cytotoxic T lymphocyte response to the cancer neoantigens. Implantable biomaterials may be used to generate a potent cytotoxic T lymphocyte response against a neoplasia in a patient specific manner. The biomaterial-resident dendritic cells may then be activated by exposing them to danger signals mimicking infection, in concert with release of antigen from the biomaterial. The activated dendritic cells then migrate from the biomaterials to lymph nodes to induce a cytotoxic T effector response. This approach has previously been demonstrated to lead to regression of established melanoma in preclinical studies using a lysate prepared from tumor biopsies (see e.g., Ali et al. (2209) In situ regulation of DC subsets and T cells mediates tumor regression in mice, Cancer Immunotherapy 1(8):1-10; Ali et al. (2009) Infection-mimicking materials to program dendritic cells in situ. Nat Mater 8:151-8), and such a vaccine is currently being tested in a Phase I clinical trial recently initiated at the Dana-Farber Cancer Institute. This approach has also been shown to lead to regression of glioblastoma, as well as the induction of a potent memory response to prevent relapse, using the C6 rat glioma model.24 in the current proposal. The ability of such an implantable, biomatrix vaccine delivery scaffold to amplify and sustain tumor specific dendritic cell activation may lead to more robust anti-tumor immunosensitization than can be achieved by traditional subcutaneous or intra-nodal vaccine administrations.

Preferably, the antigen presenting cells are dendritic cells. Suitably, the dendritic cells are autologous dendritic cells that are pulsed with the neoantigenic peptide. The peptide may be any suitable peptide that gives rise to an appropriate T-cell response. T-cell therapy using autologous dendritic cells pulsed with peptides from a tumor associated antigen is disclosed in Murphy et al. (1996) The Prostate 29, 371-380 and Tjua et al. (1997) The Prostate 32, 272-278.

Thus, in one embodiment of the present invention the vaccine or immunogenic composition containing at least one antigen presenting cell is pulsed or loaded with one or more peptides of the present invention. Alternatively, peripheral blood mononuclear cells (PBMCs) isolated from a patient may be loaded with peptides ex vivo and injected back into the patient. As an alternative the antigen presenting cell comprises an expression construct encoding a peptide of the present invention. The polynucleotide may be any suitable polynucleotide and it is preferred that it is capable of transducing the dendritic cell, thus resulting in the presentation of a peptide and induction of immunity.

The inventive pharmaceutical composition may be compiled so that the selection, number and/or amount of peptides present in the composition is/are tissue, cancer, and/or patient-specific. For instance, the exact selection of peptides can be guided by expression patterns of the parent proteins in a given tissue to avoid side effects. The selection may be dependent on the specific type of cancer, the status of the disease, earlier treatment regimens, the immune status of the patient, and, of course, the HLA-haplotype of the patient. Furthermore, the vaccine or immunogenic composition according to the invention can contain individualized components, according to personal needs of the particular patient. Examples include varying the amounts of peptides according to the expression of the related neoantigen in the particular patient, unwanted side-effects due to personal allergies or other treatments, and adjustments for secondary treatments following a first round or scheme of treatment.

Pharmaceutical compositions comprising the peptide of the invention may be administered to an individual already suffering from cancer. In therapeutic applications, compositions are administered to a patient in an amount sufficient to elicit an effective CTL response to the tumor antigen and to cure or at least partially arrest symptoms and/or complications. An amount adequate to accomplish this is defined as "therapeutically effective dose." Amounts effective for this use can depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 µg to about 50,000 µg of peptide for a 70 kg patient, followed by boosting dosages or from about 1.0 µg to about 10,000 µg of peptide pursuant to a boosting regimen over weeks to months depending upon the patient's response and condition and possibly by measuring specific CTL activity in the patient's blood. It should be kept in mind that the peptide and compositions of the present invention may generally be employed in serious disease states, that is, life-threatening or potentially life threatening situations, especially when the cancer has metastasized. For therapeutic use, administration should begin as soon as possible after the detection or surgical removal of tumors. This is followed by boosting doses until at least symptoms are substantially abated and for a period thereafter.

The pharmaceutical compositions (e.g., vaccine compositions) for therapeutic treatment are intended for parenteral, topical, nasal, oral or local administration. Preferably, the pharmaceutical compositions are administered parenterally, e.g., intravenously, subcutaneously, intradermally, or intramuscularly. The compositions may be administered at the site of surgical excision to induce a local immune response to the tumor. The invention provides compositions for parenteral administration which comprise a solution of the peptides and vaccine or immunogenic compositions are dissolved or suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

A liposome suspension containing a peptide may be administered intravenously, locally, topically, etc. in a dose which varies according to, inter alia, the manner of administration, the peptide being delivered, and the stage of the disease being treated. For targeting to the immune cells, a ligand, such as, e.g., antibodies or fragments thereof specific for cell surface determinants of the desired immune system cells, can be incorporated into the liposome.

For solid compositions, conventional or nanoparticle nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, the immunogenic peptides are preferably supplied in finely divided form along with a surfactant and propellant. Typical percentages of peptides are 0.01%-20% by weight, preferably 1%-10%. The surfactant can, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included as desired, as with, e.g., lecithin for intranasal delivery.

The peptides and polypeptides of the invention can be readily synthesized chemically utilizing reagents that are free of contaminating bacterial or animal substances (Merrifield R B: Solid phase peptide synthesis. I. The synthesis of a tetrapeptide. J. Am. Chem. Soc. 85:2149-54, 1963).

The peptides and polypeptides of the invention can also be expressed by a vector, e.g., a nucleic acid molecule as herein-discussed, e.g., RNA or a DNA plasmid, a viral vector such as a poxvirus, e.g., orthopox virus, avipox virus, or adenovirus, AAV or lentivirus. This approach involves the use of a vector to express nucleotide sequences that encode the peptide of the invention. Upon introduction into an acutely or chronically infected host or into a noninfected host, the vector expresses the immunogenic peptide, and thereby elicits a host CTL response.

For therapeutic or immunization purposes, nucleic acids encoding the peptide of the invention and optionally one or more of the peptides described herein can also be administered to the patient. A number of methods are conveniently used to deliver the nucleic acids to the patient. For instance, the nucleic acid can be delivered directly, as "naked DNA". This approach is described, for instance, in Wolff et al., Science 247: 1465-1468 (1990) as well as U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles. Generally, a plasmid for a vaccine or immunological composition can comprise DNA encoding an antigen (e.g., one or more neoantigens) operatively linked to regulatory sequences which control expression or expression and secretion of the antigen from a host cell, e.g., a mammalian cell; for instance, from upstream to downstream, DNA for a promoter, such as a mammalian virus promoter (e.g., a CMV promoter such as an hCMV or mCMV promoter, e.g., an early-intermediate promoter, or an SV40 promoter—see documents cited or incorporated herein for useful promoters), DNA for a eukaryotic leader peptide for secretion (e.g., tissue plasminogen activator), DNA for the neoantigen(s), and DNA encoding a terminator (e.g., the 3' UTR transcriptional terminator from the gene encoding Bovine Growth Hormone or bGH polyA). A composition can contain more than one plasmid or vector, whereby each vector contains and expresses a different neoantigen. Mention is also made of Wasmoen U.S. Pat. No. 5,849,303, and Dale U.S. Pat. No. 5,811,104, whose text may be useful. DNA or DNA plasmid formulations can be formulated with or inside cationic lipids; and, as to cationic lipids, as well as adjuvants, mention is also made of Loosmore U.S. Patent Application 2003/0104008. Also, teachings in Audonnet U.S. Pat. Nos. 6,228,846 and 6,159,477 may be relied upon for DNA plasmid teachings that can be employed in constructing and using DNA plasmids that contain and express in vivo.

The nucleic acids can also be delivered complexed to cationic compounds, such as cationic lipids. Lipid-mediated gene delivery methods are described, for instance, in WO1996/18372; WO 1993/24640; Mannino & Gould-Fogerite, BioTechniques 6(7): 682-691 (1988); U.S. Pat. No. 5,279,833; WO 1991/06309; and Feigner et al., Proc. Natl. Acad. Sci. USA 84: 7413-7414 (1987).

RNA encoding the peptide of interest (e.g., mRNA) can also be used for delivery (see, e.g., Kiken et al, 2011; Su et al, 2011; see also U.S. Pat. No. 8,278,036; Halabi et al. J Clin Oncol (2003) 21:1232-1237; Petsch et al, Nature Biotechnology 2012 Dec. 7; 30(12):1210-6).

Information concerning poxviruses that may be used in the practice of the invention, such as Chordopoxvirinae subfamily poxviruses (poxviruses of vertebrates), for instance, orthopoxviruses and avipoxviruses, e.g., vaccinia virus (e.g., Wyeth Strain, WR Strain (e.g., ATCC® VR-1354), Copenhagen Strain, NYVAC, NYVAC.1, NYVAC.2, MVA, MVA-BN), canarypox virus (e.g., Wheatley C93 Strain, ALVAC), fowlpox virus (e.g., FP9 Strain, Webster Strain, TROVAC), dovepox, pigeonpox, quailpox, and raccoon pox, inter alia, synthetic or non-naturally occurring recombinants thereof, uses thereof, and methods for making and using such recombinants may be found in scientific and patent literature, such as:

U.S. Pat. Nos. 4,603,112, 4,769,330, 5,110,587, 5,174,993, 5,364,773, 5,762,938, 5,494,807, 5,766,597, 7,767,449, 6,780,407, 6,537,594, 6,265,189, 6,214,353, 6,130,066, 6,004,777, 5,990,091, 5,942,235, 5,833,975, 5,766,597, 5,756,101, 7,045,313, 6,780,417, 8,470,598, 8,372,622, 8,268,329, 8,268,325, 8,236,560, 8,163,293, 7,964,398, 7,964,396, 7,964,395, 7,939,086, 7,923,017, 7,897,156, 7,892,533, 7,628,980, 7,459,270, 7,445,924, 7,384,644, 7,335,364, 7,189,536, 7,097,842, 6,913,752, 6,761,893, 6,682,743, 5,770,212, 5,766,882, and 5,989,562, and Panicali, D. Proc. Natl. Acad. Sci. 1982; 79; 4927-493, Panicali D. Proc. Natl. Acad. Sci. 1983; 80(17): 5364-8, Mackett, M. Proc. Natl. Acad. Sci. 1982; 79: 7415-7419, Smith G L. Proc. Natl. Acad. Sci. 1983; 80(23): 7155-9, Smith G L. Nature 1983; 302: 490-5, Sullivan V J. Gen. Vir. 1987; 68: 2587-98, Perkus M Journal of Leukocyte Biology 1995; 58:1-13, Yilma T D. Vaccine 1989; 7: 484-485, Brochier B. Nature 1991; 354: 520-22, Wiktor, T J. Proc. Natl Acd. Sci. 1984; 81: 7194-8, Rupprecht, C E. Proc. Natl Acd. Sci. 1986; 83: 7947-50, Poulet, H Vaccine 2007; 25(July): 5606-12, Weyer J. Vaccine 2009; 27(November): 7198-201, Buller, R M Nature 1985; 317(6040): 813-5, Buller R M. J. Virol. 1988; 62(3):866-74, Flexner, C. Nature 1987; 330(6145): 259-62, Shida, H. J. Virol. 1988; 62(12): 4474-80, Kotwal, G J. J. Virol. 1989; 63(2): 600-6, Child, S J. Virology 1990; 174(2): 625-9, Mayr A. Zentralbl Bakteriol 1978; 167(5,6): 375-9, Antoine G. Virology. 1998; 244(2): 365-96, Wyatt, L S. Virology 1998; 251(2): 334-42, Sancho, M C. J. Virol. 2002; 76(16); 8313-34, Gallego-Gomez, J C. J. Virol. 2003; 77(19); 10606-22), Goebel S J. Virology 1990; (a,b) 179: 247-66, Tartaglia, J. Virol. 1992; 188(1): 217-32, Najera J L. J. Virol. 2006; 80(12): 603347, Najera, J L. J. Virol. 2006; 80: 6033-6047, Gomez, C E. J. Gen. Virol. 2007; 88: 2473-78, Mooij, P. Jour. Of Virol. 2008; 82: 2975-2988, Gomez, C E. Curr. Gene Ther. 2011; 11: 189-217, Cox, W. Virology 1993; 195: 845-50, Perkus, M. Jour. Of Leukocyte Biology 1995; 58: 1-13, Blanchard T J. J Gen Virology 1998; 79(5): 1159-67, Amara R. Science 2001; 292: 69-74, Hel, Z., J. Immunol. 2001; 167: 7180-9, Gherardi M M. J. Virol. 2003; 77: 7048-57, Didierlaurent, A. Vaccine 2004; 22: 3395-3403, Bissht H. Proc. Nat. Aca. Sci. 2004; 101: 6641-46, McCurdy L H. Clin. Inf. Dis 2004; 38: 1749-53, Earl P L. Nature 2004; 428: 182-85, Chen Z. J. Virol. 2005; 79: 2678-2688, Najera J L. J. Virol. 2006; 80(12): 6033-47, Nam J H. Acta. Virol. 2007; 51: 125-30, Antonis A F. Vaccine 2007; 25: 4818-4827, B Weyer J. Vaccine 2007; 25: 4213-22, Ferrier-Rembert A. Vaccine 2008; 26(14): 1794-804, Corbett M. Proc. Natl. Acad. Sci. 2008; 105(6): 2046-51, Kaufman H L., J. Clin. Oncol. 2004; 22: 2122-32, Amato, R J. Clin.

Cancer Res. 2008; 14(22): 7504-10, Dreicer R. Invest New Drugs 2009; 27(4): 379-86, Kantoff P W. J. Clin. Oncol. 2010, 28, 1099-1105, Amato R J. J. Clin. Can. Res. 2010; 16(22): 5539-47, Kim, D W. Hum. Vaccine. 2010; 6: 784-791, Oudard, S. Cancer Immunol. Immunother. 2011; 60: 261-71, Wyatt, L S. Aids Res. Hum. Retroviruses. 2004; 20: 645-53, Gomez, C E. Virus Research 2004; 105: 11-22, Webster, D P. Proc. Natl. Acad. Sci. 2005; 102: 4836-4, Huang, X. Vaccine 2007; 25: 8874-84, Gomez, C E. Vaccine 2007a; 25: 2863-85, Esteban M. Hum. Vaccine 2009; 5: 867-871, Gomez, C E. Curr. Gene therapy 2008; 8(2): 97-120, Whelan, K T. Plos one 2009; 4(6): 5934, Scriba, T J. Eur. Jour. Immuno. 2010; 40(1): 279-90, Corbett, M. Proc. Natl. Acad. Sci. 2008; 105: 2046-2051, Midgley, C M. J. Gen. Virol. 2008; 89: 2992-97, Von Krempelhuber, A. Vaccine 2010; 28: 1209-16, Perreau, M. J. Of Virol. 2011; October: 9854-62, Pantaleo, G. Curr Opin HIV-AIDS. 2010; 5: 391-396, each of which is incorporated herein by reference.

As to adenovirus vectors useful in the practice of the invention, mention is made of U.S. Pat. No. 6,955,808. The adenovirus vector used can be selected from the group consisting of the Ad5, Ad35, Ad11, C6, and C7 vectors. The sequence of the Adenovirus 5 ("Ad5") genome has been published. (Chroboczek, J., Bieber, F., and Jacrot, B. (1992) The Sequence of the Genome of Adenovirus Type 5 and Its Comparison with the Genome of Adenovirus Type 2, Virology 186, 280-285; the contents if which is hereby incorporated by reference). Ad35 vectors are described in U.S. Pat. Nos. 6,974,695, 6,913,922, and 6,869,794. Ad11 vectors are described in U.S. Pat. No. 6,913,922. C6 adenovirus vectors are described in U.S. Pat. Nos. 6,780,407; 6,537,594; 6,309, 647; 6,265,189; 6,156,567; 6,090,393; 5,942,235 and 5,833, 975. C7 vectors are described in U.S. Pat. No. 6,277,558. Adenovirus vectors that are E1-defective or deleted, E3-defective or deleted, and/or E4-defective or deleted may also be used. Certain adenoviruses having mutations in the E1 region have improved safety margin because E1-defective adenovirus mutants are replication-defective in non-permissive cells, or, at the very least, are highly attenuated. Adenoviruses having mutations in the E3 region may have enhanced the immunogenicity by disrupting the mechanism whereby adenovirus down-regulates MHC class I molecules. Adenoviruses having E4 mutations may have reduced immunogenicity of the adenovirus vector because of suppression of late gene expression. Such vectors may be particularly useful when repeated re-vaccination utilizing the same vector is desired. Adenovirus vectors that are deleted or mutated in E1, E3, E4, E1 and E3, and E1 and E4 can be used in accordance with the present invention. Furthermore, "gutless" adenovirus vectors, in which all viral genes are deleted, can also be used in accordance with the present invention. Such vectors require a helper virus for their replication and require a special human 293 cell line expressing both E1a and Cre, a condition that does not exist in natural environment. Such "gutless" vectors are non-immunogenic and thus the vectors may be inoculated multiple times for re-vaccination. The "gutless" adenovirus vectors can be used for insertion of heterologous inserts/genes such as the transgenes of the present invention, and can even be used for co-delivery of a large number of heterologous inserts/genes.

As to lentivirus vector systems useful in the practice of the invention, mention is made of U.S. Pat. Nos. 6,428,953, 6,165,782, 6,013,516, 5,994,136, 6,312,682, and 7,198,784, and documents cited therein.

With regard to AAV vectors useful in the practice of the invention, mention is made of U.S. Pat. Nos. 5,658,785, 7,115,391, 7,172,893, 6,953,690, 6,936,466, 6,924,128, 6,893,865, 6,793,926, 6,537,540, 6,475,769 and 6,258,595, and documents cited therein.

Another vector is BCG (Bacille Calmette Guerin). BCG vectors are described in Stover et al. (Nature 351:456-460 (1991)). A wide variety of other vectors useful for therapeutic administration or immunization of the peptides of the invention, e.g., *Salmonella typhi* vectors and the like, is apparent to those skilled in the art from the description herein.

Vectors can be administered so as to have in vivo expression and response akin to doses and/or responses elicited by antigen administration A preferred means of administering nucleic acids encoding the peptide of the invention uses minigene constructs encoding multiple epitopes. To create a DNA sequence encoding the selected CTL epitopes (minigene) for expression in human cells, the amino acid sequences of the epitopes are reverse translated. A human codon usage table is used to guide the codon choice for each amino acid. These epitope-encoding DNA sequences are directly adjoined, creating a continuous polypeptide sequence. To optimize expression and/or immunogenicity, additional elements can be incorporated into the minigene design. Examples of amino acid sequence that could be reverse translated and included in the minigene sequence include: helper T lymphocyte, epitopes, a leader (signal) sequence, and an endoplasmic reticulum retention signal. In addition, MHC presentation of CTL epitopes may be improved by including synthetic (e.g. poly-alanine) or naturally-occurring flanking sequences adjacent to the CTL epitopes.

The minigene sequence is converted to DNA by assembling oligonucleotides that encode the plus and minus strands of the minigene. Overlapping oligonucleotides (30-100 bases long) are synthesized, phosphorylated, purified and annealed under appropriate conditions using well known techniques. The ends of the oligonucleotides are joined using T4 DNA ligase. This synthetic minigene, encoding the CTL epitope polypeptide, can then cloned into a desired expression vector.

Standard regulatory sequences well known to those of skill in the art are included in the vector to ensure expression in the target cells. Several vector elements are required: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences can also be considered for increasing minigene expression. It has recently been proposed that immuno stimulatory sequences (ISSs or CpGs) play a role in the immunogenicity of DNA' vaccines. These sequences could be included in the vector, outside the minigene coding sequence, if found to enhance immunogenicity.

In some embodiments, a bicistronic expression vector, to allow production of the minigene-encoded epitopes and a second protein included to enhance or decrease immunogenicity can be used. Examples of proteins or polypeptides that could beneficially enhance the immune response if co-expressed include cytokines (e.g., IL2, IL12, GM-CSF), cytokine-inducing molecules (e.g. LeIF) or costimulatory molecules. Helper (HTL) epitopes could be joined to intracellular targeting signals and expressed separately from the CTL epitopes. This would allow direction of the HTL epitopes to a cell compartment different than the CTL epitopes. If required, this could facilitate more efficient entry of HTL epitopes into the MHC class II pathway, thereby improving CTL induction. In contrast to CTL induction, specifically decreasing the immune response by co-expression of immunosuppressive molecules (e.g. TGF-β) may be beneficial in certain diseases.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

Purified plasmid DNA can be prepared for injection using a variety of formulations. The simplest of these is reconstitution of lyophilized DNA in sterile phosphate-buffer saline (PBS). A variety of methods have been described, and new techniques may become available. As noted herein, nucleic acids are conveniently formulated with cationic lipids. In addition, glycolipids, fusogenic liposomes, peptides and compounds referred to collectively as protective, interactive, non-condensing (PINC) could also be complexed to purified plasmid DNA to influence variables such as stability, intramuscular dispersion, or trafficking to specific organs or cell types.

Target cell sensitization can be used as a functional assay for expression and MHC class I presentation of minigene-encoded CTL epitopes. The plasmid DNA is introduced into a mammalian cell line that is suitable as a target for standard CTL chromium release assays. The transfection method used is dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 labeled and used as target cells for epitope-specific CTL lines. Cytolysis, detected by 51 Cr release, indicates production of MHC presentation of mini gene-encoded CTL epitopes.

In vivo immunogenicity is a second approach for functional testing of minigene DNA formulations. Transgenic mice expressing appropriate human MHC molecules are immunized with the DNA product. The dose and route of administration are formulation dependent (e.g. IM for DNA in PBS, IP for lipid-complexed DNA). Twenty-one days after immunization, splenocytes are harvested and restimulated for 1 week in the presence of peptides encoding each epitope being tested. These effector cells (CTLs) are assayed for cytolysis of peptide-loaded, chromium-51 labeled target cells using standard techniques. Lysis of target cells sensitized by MHC loading of peptides corresponding to minigene-encoded epitopes demonstrates DNA vaccine function for in vivo induction of CTLs.

Peptides may be used to elicit CTL ex vivo, as well. The resulting CTL, can be used to treat chronic tumors in patients in need thereof that do not respond to other conventional forms of therapy, or does not respond to a peptide vaccine approach of therapy. Ex vivo CTL responses to a particular tumor antigen are induced by incubating in tissue culture the patient's CTL precursor cells (CTLp) together with a source of antigen-presenting cells (APC) and the appropriate peptide. After an appropriate incubation time (typically 1-4 weeks), in which the CTLp are activated and mature and expand into effector CTL, the cells are infused back into the patient, where they destroy their specific target cell (i.e., a tumor cell). In order to optimize the in vitro conditions for the generation of specific cytotoxic T cells, the culture of stimulator cells are maintained in an appropriate serum-free medium.

Prior to incubation of the stimulator cells with the cells to be activated, e.g., precursor CD8+ cells, an amount of antigenic peptide is added to the stimulator cell culture, of sufficient quantity to become loaded onto the human Class I molecules to be expressed on the surface of the stimulator cells. In the present invention, a sufficient amount of peptide is an amount that allows about 200, and preferably 200 or more, human Class I MHC molecules loaded with peptide to be expressed on the surface of each stimulator cell. Preferably, the stimulator cells are incubated with >2 µg/ml peptide. For example, the stimulator cells are incubates with >3, 4, 5, 10, 15, or more µg/ml peptide.

Resting or precursor CD8+ cells are then incubated in culture with the appropriate stimulator cells for a time period sufficient to activate the CD8+ cells. Preferably, the CD8+ cells are activated in an antigen-specific manner. The ratio of resting or precursor CD8+ (effector) cells to stimulator cells may vary from individual to individual and may further depend upon variables such as the amenability of an individual's lymphocytes to culturing conditions and the nature and severity of the disease condition or other condition for which the within-described treatment modality is used. Preferably, however, the lymphocyte:stimulator cell ratio is in the range of about 30:1 to 300:1. The effector/stimulator culture may be maintained for as long a time as is necessary to stimulate a therapeutically useable or effective number of CD8+ cells.

The induction of CTL in vitro requires the specific recognition of peptides that are bound to allele specific MHC class I molecules on APC. The number of specific MHC/peptide complexes per APC is crucial for the stimulation of CTL, particularly in primary immune responses. While small amounts of peptide/MHC complexes per cell are sufficient to render a cell susceptible to lysis by CTL, or to stimulate a secondary CTL response, the successful activation of a CTL precursor (pCTL) during primary response requires a significantly higher number of MHC/peptide complexes. Peptide loading of empty major histocompatability complex molecules on cells allows the induction of primary cytotoxic T lymphocyte responses.

Since mutant cell lines do not exist for every human MHC allele, it is advantageous to use a technique to remove endogenous MHC-associated peptides from the surface of APC, followed by loading the resulting empty MHC molecules with the immunogenic peptides of interest. The use of non-transformed (non-tumorigenic), noninfected cells, and preferably, autologous cells of patients as APC is desirable for the design of CTL induction protocols directed towards development of ex vivo CTL therapies. This application discloses methods for stripping the endogenous MHC-associated peptides from the surface of APC followed by the loading of desired peptides.

A stable MHC class I molecule is a trimeric complex formed of the following elements: 1) a peptide usually of 8-10 residues, 2) a transmembrane heavy polymorphic protein chain which bears the peptide-binding site in its a1 and a2 domains, and 3) a non-covalently associated non-polymorphic light chain, p2microglobuiin. Removing the bound peptides and/or dissociating the p2microglobulin from the complex renders the MHC class I molecules nonfunctional and unstable, resulting in rapid degradation. All MHC class I molecules isolated from PBMCs have endogenous peptides bound to them. Therefore, the first step is to remove all endogenous peptides bound to MHC class I molecules on the APC without causing their degradation before exogenous peptides can be added to them.

Two possible ways to free up MHC class I molecules of bound peptides include lowering the culture temperature from 37° C. to 26° C. overnight to destabilize p2microglobulin and stripping the endogenous peptides from the cell using a mild acid treatment. The methods release previously bound peptides into the extracellular environment allowing new exogenous peptides to bind to the empty class I molecules. The cold-temperature incubation method enables exogenous peptides to bind efficiently to the MHC complex, but requires an overnight incubation at 26° C. which may slow the cell's metabolic rate. It is also likely that cells not actively synthesizing MHC molecules (e.g., resting PBMC) would not produce high amounts of empty surface MHC molecules by the cold temperature procedure.

Harsh acid stripping involves extraction of the peptides with trifluoroacetic acid, pH 2, or acid denaturation of the immunoaffinity purified class I-peptide complexes. These methods are not feasible for CTL induction, since it is important to remove the endogenous peptides while preserving APC viability and an optimal metabolic state which is critical for antigen presentation. Mild acid solutions of pH 3 such as glycine or citrate-phosphate buffers have been used to identify endogenous peptides and to identify tumor associated T cell epitopes. The treatment is especially effective, in that only the MHC class I molecules are destabilized (and associated peptides released), while other surface antigens remain intact, including MHC class II molecules. Most importantly, treatment of cells with the mild acid solutions do not affect the cell's viability or metabolic state. The mild acid treatment is rapid since the stripping of the endogenous peptides occurs in two minutes at 4° C. and the APC is ready to perform its function after the appropriate peptides are loaded. The technique is utilized herein to make peptide-specific APCs for the generation of primary antigen-specific CTL. The resulting APC are efficient in inducing peptide-specific CD8+ CTL.

Activated CD8+ cells may be effectively separated from the stimulator cells using one of a variety of known methods. For example, monoclonal antibodies specific for the stimulator cells, for the peptides loaded onto the stimulator cells, or for the CD8+ cells (or a segment thereof) may be utilized to bind their appropriate complementary ligand. Antibody-tagged molecules may then be extracted from the stimulator-effector cell admixture via appropriate means, e.g., via well-known immunoprecipitation or immunoassay methods.

Effective, cytotoxic amounts of the activated CD8+ cells can vary between in vitro and in vivo uses, as well as with the amount and type of cells that are the ultimate target of these killer cells. The amount can also vary depending on the condition of the patient and should be determined via consideration of all appropriate factors by the practitioner. Preferably, however, about $1 \times 10^6$ to about $1 \times 10^{12}$, more preferably about $1 \times 10^8$ to about $1 \times 10^{11}$, and even more preferably, about $1 \times 10^9$ to about $1 \times 10^{10}$ activated CD8+ cells are utilized for adult humans, compared to about $5 \times 10^6$-$5 \times 10^7$ cells used in mice.

Preferably, as discussed herein, the activated CD8+ cells are harvested from the cell culture prior to administration of the CD8+ cells to the individual being treated. It is important to note, however, that unlike other present and proposed treatment modalities, the present method uses a cell culture system that is not tumorigenic. Therefore, if complete separation of stimulator cells and activated CD8+ cells are not achieved, there is no inherent danger known to be associated with the administration of a small number of stimulator cells, whereas administration of mammalian tumor-promoting cells may be extremely hazardous.

Methods of re-introducing cellular components are known in the art and include procedures such as those exemplified in U.S. Pat. No. 4,844,893 to Honsik, et al. and U.S. Pat. No. 4,690,915 to Rosenberg. For example, administration of activated CD8+ cells via intravenous infusion is appropriate.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Wei, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments are discussed in the sections that follow.

Therapeutic Methods

The present invention provides methods of inducing a neoplasia/tumor specific immune response in a subject, vaccinating against a neoplasia/tumor, treating and or alleviating a symptom of cancer in a subject by administering the subject a neoplasia vaccine or a neoantigenic peptide or composition of the invention and at least one checkpoint inhibitor.

In particular, the present invention is directed to methods of treating or preventing a neoplasia comprising the steps of administering to a subject (a) a neoplasia vaccine or immunogenic composition, and (b) at least one checkpoint inhibitor.

According to the invention, the herein-described neoplasia vaccine or immunogenic composition may be used for a patient that has been diagnosed as having cancer, or at risk of developing cancer.

The described combination of the invention is administered in an amount sufficient to induce a CTL response.

Additional Therapies

The tumor specific neoantigen peptides and pharmaceutical compositions described herein can also be administered in further combination with another agent, for example a therapeutic agent. In certain embodiments, the additional agents can be, but are not limited to, chemotherapeutic agents, anti-angiogenesis agents and agents that reduce immune-suppression.

The neoplasia vaccine or immunogenic composition and one or more checkpoint inhibitors can be administered before, during, or after administration of the additional agent. In embodiments, the neoplasia vaccine or immunogenic composition and/or one or more checkpoint inhibitors are administered before the first administration of the additional agent. In other embodiments, the neoplasia vaccine or immunogenic composition and/or one or more checkpoint inhibitors are administered after the first administration of the additional therapeutic agent (e.g., 1, 2, 3, 4, 5, 6, 7, 8, 9, 10, 11, 12, 13, 14 days or more). In embodiments, the neoplasia vaccine or immunogenic composition and one or more checkpoint inhibitors are administered simultaneously with the first administration of the additional therapeutic agent.

The therapeutic agent is for example, a chemotherapeutic or biotherapeutic agent, radiation, or immunotherapy. Any suitable therapeutic treatment for a particular cancer may be administered. Examples of chemotherapeutic and biotherapeutic agents include, but are not limited to, an angiogenesis inhibitor, such ashydroxy angiostatin K1-3, DL-α-Difluoromethyl-ornithine, endostatin, fumagillin, genistein, minocycline, staurosporine, and thalidomide; a DNA intercaltor/cross-linker, such as Bleomycin, Carboplatin, Carmustine, Chlorambucil, Cyclophosphamide, cis-Diammineplatinum (I) dichloride (Cisplatin), Melphalan, Mitoxantrone, and Oxaliplatin; a DNA synthesis inhibitor, such as (±)-Amethopterin (Methotrexate), 3-Amino-1,2,4-benzotriazine 1,4-dioxide, Aminopterin, Cytosine β-D-arabinofuranoside, 5-Fluoro-5'-deoxyuridine, 5-Fluorouracil, Ganciclovir, Hydroxyurea, and Mitomycin C; a DNA-RNA transcription regulator, such as Actinomycin D, Daunorubicin, Doxorubicin, Homoharringtonine, and Idarubicin; an enzyme inhibitor, such as S(+)-Camptothecin, Curcumin, (−)-Deguelin, 5,6-Dichlorobenzimidazole 1-β-D-ribofuranoside, Etoposide, Formestane, Fostriecin, Hispidin, 2-Imino-1-imidazoli-dineacetic acid (Cyclocreatine), Mevinolin, Trichostatin A, Tyrphostin AG 34, and Tyrphostin AG 879; a gene regulator, such as 5-Aza-2'-deoxycytidine, 5-Azacytidine, Cholecalciferol (Vitamin D3), 4-Hydroxytamoxifen, Melatonin, Mifepristone, Raloxifene, all trans-Retinal (Vitamin A aldehyde), Retinoic acid all trans (Vitamin A acid), 9-cis-Retinoic Acid, 13-cis-Retinoic acid, Retinol (Vitamin A), Tamoxifen, and Troglitazone; a microtubule inhibitor, such as Colchicine, docetaxel, Dolastatin 15, Nocodazole, Paclitaxel, Podophyllotoxin, Rhizoxin, Vinblastine, Vincristine, Vindesine, and Vinorelbine (Navelbine); and an unclassified therapeutic agent, such as 17-(Allylamino)-17-demethoxygeldanamycin, 4-Amino-1,8-naphthalimide, Apigenin, Brefeldin A, Cimetidine, Dichloromethylene-diphosphonic acid, Leuprolide (Leuprorelin), Luteinizing Hormone-Releasing Hormone, Pifithrin-α, Rapamycin, Sex hormone-binding globulin, Thapsigargin, and Urinary trypsin inhibitor fragment (Bikunin). The therapeutic agent may be altretamine, amifostine, asparaginase, capecitabine, cladribine, cisapride, cytarabine, dacarbazine (DTIC), dactinomycin, dronabinol, epoetin alpha, filgrastim, fludarabine, gemcitabine, granisetron, ifosfamide, irinotecan, lansoprazole, levamisole, leucovorin, megestrol, mesna, metoclopramide, mitotane, omeprazole, ondansetron, pilocarpine, prochloroperazine, or topotecan hydrochloride. The therapeutic agent may be a monoclonal antibody such as rituximab (Rituxan®), alemtuzumab (Campath®), Bevacizumab (Avastin®), Cetuximab (Erbitux®), panitumumab (Vectibix®), and trastuzumab (Herceptin®), Vemurafenib (Zelboraf®) imatinib mesylate (Gleevec®), erlotinib (Tarceva®), gefitinib (Iressa®), Vismodegib (Erivedge™), 90Y-ibritumomab tiuxetan, 131I-tositumomab, ado-trastuzumab emtansine, lapatinib (Tykerb®), pertuzumab (Perjeta™), ado-trastuzumab emtansine (Kadcyla™), regorafenib (Stivarga®), sunitinib (Sutent®), Denosumab (Xgeva®), sorafenib (Nexavar®), pazopanib (Votrient®), axitinib (Inlyta®), dasatinib (Sprycel®), nilotinib (Tasigna®), bosutinib (Bosulif®), ofatumumab (Arzerra®), obinutuzumab (Gazyva™), ibrutinib (Imbruvicam™), idelalisib (Zydelig®), crizotinib (Xalkori®), erlotinib (Tarceva®), afatinib dimaleate (Gilotrif®), ceritinib (LDK378/Zykadia), Tositumomab and 131I-tositumomab (Bexxar®), ibritumomab tiuxetan (Zevalin®), brentuximab vedotin (Adcetris®), bortezomib (Velcade®), siltuximab (Sylvant™), trametinib (Mekinist®), dabrafenib (Tafinlar®), pembrolizumab (Keytruda®), carfilzomib (Kyprolis®), Ramucirumab (Cyramza™), Cabozantinib (Cometriq™), vandetanib (Caprelsa®), Optionally, the therapeutic agent is a neoantigen. The therapeutic agent may be a cytokine such as interferons (INFs), interleukins (ILs), or hematopoietic growth factors. The therapeutic agent may be INF-α, IL-2, Aldesleukin, IL-2, Erythropoietin, Granulocyte-macrophage colony-stimulating factor (GM-CSF) or granulocyte colony-stimulating factor. The therapeutic agent may be a targeted therapy such as toremifene (Fareston®), fulvestrant (Faslodex®), anastrozole (Arimidex®), exemestane (Aromasin®), letrozole (Femara®), ziv-aflibercept (Zaltrap®), Alitretinoin (Panretin®), temsirolimus (Torisel®), Tretinoin (Vesanoid®), denileukin diftitox (Ontak®), vorinostat (Zolinza®), romidepsin (Istodax®), bexarotene (Targretin®), pralatrexate (Folotyn®), lenaliomide (Revlimid®), belinostat (Beleodaq™), lenaliomide (Revlimid®), pomalidomide (Pomalyst®), Cabazitaxel (Jevtana®), enzalutamide (Xtandi®), abiraterone acetate (Zytiga®), radium 223 chloride (Xofigo®), or everolimus (Afinitor®). Additionally, the therapeutic agent may be an epigenetic targeted drug such as HDAC inhibitors, kinase inhibitors, DNA methyltransferase inhibitors, histone demethylase inhibitors, or histone methylation inhibitors. The epigenetic drugs may be Azacitidine (Vidaza), Decitabine (Dacogen), Vorinostat (Zolinza), Romidepsin (Istodax), or Ruxolitinib (Jakafi). For prostate cancer treatment, a preferred chemotherapeutic agent with which anti-CTLA-4 can be combined is paclitaxel (TAXOL).

In certain embodiments, the one or more additional agents are one or more anti-glucocorticoid-induced tumor necrosis factor family receptor (GITR) agonistic antibodies. GITR is a costimulatory molecule for T lymphocytes, modulates innate and adaptive immune system and has been found to participate in a variety of immune responses and inflammatory processes. GITR was originally described by Nocentini et al. after being cloned from dexamethasone-treated murine T cell hybridomas (Nocentini et al. Proc Natl Acad Sci USA 94:6216-6221.1997). Unlike CD28 and CTLA-4, GITR has a very low basal expression on naive CD4+ and CD8+ T cells (Ronchetti et al. Eur J Immunol 34:613-622. 2004). The observation that GITR stimulation has immunostimulatory effects in vitro and induced autoimmunity in vivo prompted the investigation of the antitumor potency of triggering this pathway. A review of Modulation Of Ctla 4 And Gitr For Cancer Immunotherapy can be found in Cancer Immunology and Immunotherapy (Avogadri et al. Current Topics in Microbiology and Immunology 344. 2011). Other agents that can contribute to relief of immune suppression include checkpoint inhibitors targeted at another member of the CD28/CTLA4 Ig superfamily such as BTLA, LAG3, ICOS, PDL1 or KIR (Page et a, Annual Review of Medicine 65:27 (2014)). In further additional embodiments, the checkpoint inhibitor is targeted at a member of the TNFR superfamily such as CD40, OX40, CD137, GITR, CD27 or TIM-3. In some cases targeting a checkpoint inhibitor is accomplished with an inhibitory antibody or similar molecule. In other cases, it is accomplished with an agonist for the target; examples of this class include the stimulatory targets OX40 and GITR.

In certain embodiments, the one or more additional agents are synergistic in that they increase immunogenicity after treatment. In one embodiment the additional agent allows for lower toxicity and/or lower discomfort due to lower doses of the additional therapeutic agents or any components of the combination therapy described herein. In another embodiment the additional agent results in longer lifespan due to increased effectiveness of the combination therapy described herein. Chemotherapeutic treatments that enhance the immunological response in a patient have been reviewed (Zitvogel et al., Immunological aspects of cancer chemotherapy. Nat Rev Immunol. 2008 January; 8(1):59-73). Additionally, chemotherapeutic agents can be administered safely with immunotherapy without inhibiting vaccine specific T-cell responses (Perez et al., A new era in anticancer peptide vaccines. Cancer May 2010). In one embodiment the additional agent is administered to increase the efficacy of the combination therapy described herein. In one embodiment the additional agent is a chemotherapy treatment. In one embodiment low doses of chemotherapy potentiate delayed-type hypersensitivity (DTH) responses. In one embodiment the chemotherapy agent targets regulatory T-cells. In one embodiment cyclophosphamide is the therapeutic agent. In one embodiment cyclophosphamide is administered prior to vaccination. In one embodiment cyclophosphamide is administered as a single dose before vaccination (Walter et al., Multipeptide immune response to cancer vaccine IMA901 after single-dose cyclophosphamide associates with longer patient survival. Nature Medicine; 18:8 2012). In another embodiment, cyclophosphamide is administered according to a metronomic program, where a daily dose is administered for one month (Ghiringhelli et al., Metronomic cyclophosphamide regimen selectively depletes CD4+CD25+ regulatory T cells and restores T and NK effector functions in end stage cancer patients. Cancer Immunol Immunother 2007 56:641-648). In another embodiment taxanes are administered before vaccination to enhance T-cell and NK-cell functions (Zitvogel et al., 2008). In another embodiment a low dose of a chemotherapeutic agent is administered with the combination therapy described herein. In one embodiment the chemotherapeutic agent is estramustine. In one embodiment the cancer is hormone resistant prostate cancer. A ≥50% decrease in serum prostate specific antigen (PSA) was seen in 8.7% of advanced hormone refractory prostate cancer patients by personalized vaccination alone, whereas such a decrease was seen in 54% of patients when the personalized vaccination was combined with a low dose of estramustine (Itoh et al., Personalized peptide vaccines: A new therapeutic modality for cancer. Cancer Sci 2006; 97: 970-976). In another embodiment glucocorticoids are not administered with or before the combination therapy described herein (Zitvogel et al., 2008). In another embodiment glucocorticoids are administered after the combination therapy described herein. In another embodiment Gemcitabine is administered before, simultaneously, or after the combination therapy described herein to enhance the frequency of tumor specific CTL precursors (Zitvogel et al., 2008). In another embodiment 5-fluorouracil is administered with the combination therapy described herein as synergistic effects were seen with a peptide based vaccine (Zitvogel et al., 2008). In another embodiment an inhibitor of Braf, such as Vemurafenib, is used as an additional agent. Braf inhibition has been shown to be associated with an increase in melanoma antigen expression and T-cell infiltrate and a decrease in immunosuppressive cytokines in tumors of treated patients (Frederick et al., BRAF inhibition is associated with enhanced melanoma antigen expression and a more favorable tumor microenvironment in patients with metastatic melanoma. Clin Cancer Res. 2013; 19:1225-1231). In another embodiment an inhibitor of tyrosine kinases is used as an additional agent. In one embodiment the tyrosine kinase inhibitor is used before vaccination with the combination therapy described herein. In one embodiment the tyrosine kinase inhibitor is used simultaneously with the combination therapy described herein. In another embodiment the tyrosine kinase inhibitor is used to create a more immune permissive environment. In another embodiment the tyrosine kinase inhibitor is sunitinib or imatinib mesylate. It has previously been shown that favorable outcomes could be achieved with sequential administration of continuous daily dosing of sunitinib and recombinant vaccine (Farsaci et al., Consequence of dose scheduling of sunitinib on host immune response elements and vaccine combination therapy. Int J Cancer; 130: 1948-1959). Sunitinib has also been shown to reverse type-1 immune suppression using a daily dose of 50 mg/day (Finke et al., Sunitinib Reverses Type-1 Immune Suppression and Decreases T-Regulatory Cells in Renal Cell Carcinoma Patients. Clin Cancer Res 2008; 14(20)). In another embodiment targeted therapies are administered in combination with the combination therapy described herein. Doses of targeted therapies has been described previously (Alvarez, Present and future evolution of advanced breast cancer therapy. Breast Cancer Research 2010, 12(Suppl 2):S1). In another embodiment temozolomide is administered with the combination therapy described herein. In one embodiment temozolomide is administered at 200 mg/day for 5 days every fourth week of a combination therapy with the combination therapy described herein. Results of a similar strategy have been shown to have low toxicity (Kyte et al., Telomerase Peptide Vaccination Combined with Temozolomide: A Clinical Trial in Stage IV Melanoma Patients. Clin Cancer Res; 17(13) 2011). In another embodiment the combination therapy is administered with an additional therapeutic agent that results in lymphopenia. In one embodiment the additional agent is temozolomide. An immune response can still be induced under these conditions (Sampson et al., Greater chemotherapy-induced lymphopenia enhances tumor-specific immune responses that eliminate EGFRvIII-expressing tumor cells in patients with glioblastoma. Neuro-Oncology 13(3):324-333, 2011).

Figure 2:
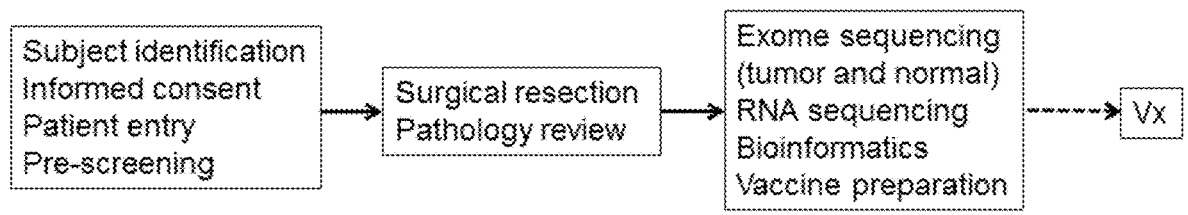
FIG. 2 shows a flow process for pre-treatment steps for generating a cancer vaccine or immunogenic composition for a melanoma patient.

The herein-described compositions and methods may be used on patients in need thereof with any cancer according to the general flow process shown in FIG. 2. Patients in need thereof may receive a series of priming vaccinations with a mixture of personalized tumor-specific peptides. Additionally, over a 4 week period the priming may be followed by two boosts during a maintenance phase. All vaccinations are subcutaneously delivered. The vaccine or immunogenic composition is evaluated for safety, tolerability, immune response and clinical effect in patients and for feasibility of producing vaccine or immunogenic composition and successfully initiating vaccination within an appropriate time frame. The first cohort can consist of 5 patients, and after safety is adequately demonstrated, an additional cohort of 10 patients may be enrolled. Peripheral blood is extensively monitored for peptide-specific T-cell responses and patients are followed for up to two years to assess disease recurrence.

Administering Combination Therapy Consistent with Standard of Care

In another aspect, the combination therapy described herein provides selecting the appropriate point to administer the combination therapy in relation to and within the standard of care for the cancer being treated for a patient in need thereof. The studies described herein show that the combination therapy can be effectively administered even within the standard of care that includes surgery, radiation, or chemotherapy. The standards of care for the most common cancers can be found on the website of National Cancer Institute (http://www.cancer.gov/cancertopics). The standard of care is the current treatment that is accepted by medical experts as a proper treatment for a certain type of disease and that is widely used by healthcare professionals. Standard or care is also called best practice, standard medical care, and standard therapy. Standards of Care for cancer generally include surgery, lymph node removal, radiation, chemotherapy, targeted therapies, antibodies targeting the tumor, and immunotherapy. Immunotherapy can include checkpoint blockers (CBP), chimeric antigen receptors (CARs), and adoptive T-cell therapy. The combination therapy described herein can be incorporated within the standard of care. The combination therapy described herein may also be administered where the standard of care has changed due to advances in medicine.

Incorporation of the combination therapy described herein may depend on a treatment step in the standard of care that can lead to activation of the immune system. Treatment steps that can activate and function synergistically with the combination therapy have been described herein. The therapy can be advantageously administered simultaneously or after a treatment that activates the immune system.

Incorporation of the combination therapy described herein may depend on a treatment step in the standard of care that causes the immune system to be suppressed. Such treatment steps may include irradiation, high doses of alkylating agents and/or methotrexate, steroids such as glucosteroids, surgery, such as to remove the lymph nodes, imatinib mesylate, high doses of TNF, and taxanes (Zitvogel et al., 2008). The combination therapy may be administered before such steps or may be administered after.

In one embodiment the combination therapy may be administered after bone marrow transplants and peripheral blood stem cell transplantation. Bone marrow transplantation and peripheral blood stem cell transplantation are procedures that restore stem cells that were destroyed by high doses of chemotherapy and/or radiation therapy. After being treated with high-dose anticancer drugs and/or radiation, the patient receives harvested stem cells, which travel to the bone marrow and begin to produce new blood cells. A "mini-transplant" uses lower, less toxic doses of chemotherapy and/or radiation to prepare the patient for transplant. A "tandem transplant" involves two sequential courses of high-dose chemotherapy and stem cell transplant. In autologous transplants, patients receive their own stem cells. In syngeneic transplants, patients receive stem cells from their identical twin. In allogeneic transplants, patients receive stem cells from their brother, sister, or parent. A person who is not related to the patient (an unrelated donor) also may be used. In some types of leukemia, the graft-versus-tumor (GVT) effect that occurs after allogeneic BMT and PBSCT is crucial to the effectiveness of the treatment. GVT occurs when white blood cells from the donor (the graft) identify the cancer cells that remain in the patient's body after the chemotherapy and/or radiation therapy (the tumor) as foreign and attack them. Immunotherapy with the combination therapy described herein can take advantage of this by vaccinating after a transplant. Additionally, the transferred cells may be presented with neoantigens of the combination therapy described herein before transplantation.

In one embodiment the combination therapy is administered to a patient in need thereof with a cancer that requires surgery. In one embodiment the combination therapy described herein is administered to a patient in need thereof in a cancer where the standard of care is primarily surgery followed by treatment to remove possible micro-metastases, such as breast cancer. Breast cancer is commonly treated by various combinations of surgery, radiation therapy, chemotherapy, and hormone therapy based on the stage and grade of the cancer. Adjuvant therapy for breast cancer is any treatment given after primary therapy to increase the chance of long-term survival. Neoadjuvant therapy is treatment given before primary therapy. Adjuvant therapy for breast cancer is any treatment given after primary therapy to increase the chance of long-term disease-free survival. Primary therapy is the main treatment used to reduce or eliminate the cancer. Primary therapy for breast cancer usually includes surgery, a mastectomy (removal of the breast) or a lumpectomy (surgery to remove the tumor and a small amount of normal tissue around it; a type of breast-conserving surgery). During either type of surgery, one or more nearby lymph nodes are also removed to see if cancer cells have spread to the lymphatic system. When a woman has breast-conserving surgery, primary therapy almost always includes radiation therapy. Even in early-stage breast cancer, cells may break away from the primary tumor and spread to other parts of the body (metastasize). Therefore, doctors give adjuvant therapy to kill any cancer cells that may have spread, even if they cannot be detected by imaging or laboratory tests.

In one embodiment the combination therapy is administered consistent with the standard of care for Ductal carcinoma in situ (DCIS). The standard of care for this breast cancer type is:

1. Breast-conserving surgery and radiation therapy with or without tamoxifen.
2. Total mastectomy with or without tamoxifen.
3. Breast-conserving surgery without radiation therapy.

The combination therapy may be administered before breast conserving surgery or total mastectomy to shrink the tumor before surgery. In another embodiment the combination therapy can be administered as an adjuvant therapy to remove any remaining cancer cells.

In another embodiment patients diagnosed with stage I, II, IIIA, and Operable IIIC breast cancer are treated with the combination therapy as described herein. The standard of care for this breast cancer type is:

1. Local-regional treatment:
    Breast-conserving therapy (lumpectomy, breast radiation, and surgical staging of the axilla).
    Modified radical mastectomy (removal of the entire breast with level I-II axillary dissection) with or without breast reconstruction.
    Sentinel node biopsy.
2. Adjuvant radiation therapy postmastectomy in axillary node-positive tumors:
    For one to three nodes: unclear role for regional radiation (infra/supraclavicular nodes, internal mammary nodes, axillary nodes, and chest wall).

For more than four nodes or extranodal involvement: regional radiation is advised.

3. Adjuvant systemic therapy

In one embodiment the combination therapy is administered as a neoadjuvant therapy to shrink the tumor. In another embodiment the combination is administered as an adjuvant systemic therapy.

In another embodiment patients diagnosed with inoperable stage IIIB or IIIC or inflammatory breast cancer are treated with the combination therapy as described herein. The standard of care for this breast cancer type is:
1. Multimodality therapy delivered with curative intent is the standard of care for patients with clinical stage IB disease.
2. Initial surgery is generally limited to biopsy to permit the determination of histology, estrogen-receptor (ER) and progesterone-receptor (PR) levels, and human epidermal growth factor receptor 2 (HER2/neu) overexpression. Initial treatment with anthracycline-based chemotherapy and/or taxane-based therapy is standard. For patients who respond to neoadjuvant chemotherapy, local therapy may consist of total mastectomy with axillary lymph node dissection followed by postoperative radiation therapy to the chest wall and regional lymphatics. Breast-conserving therapy can be considered in patients with a good partial or complete response to neoadjuvant chemotherapy. Subsequent systemic therapy may consist of further chemotherapy. Hormone therapy should be administered to patients whose tumors are ER-positive or unknown. All patients should be considered candidates for clinical trials to evaluate the most appropriate fashion in which to administer the various components of multimodality regimens.

In one embodiment the combination therapy is administered as part of the various components of multimodality regimens. In another embodiment the combination therapy is administered before, simultaneously with, or after the multimodality regimens. In another embodiment the combination therapy is administered based on synergism between the modalities. In another embodiment the combination therapy is administered after treatment with anthracycline-based chemotherapy and/or taxane-based therapy (Zitvogel et al., 2008). Treatment after administering the combination therapy may negatively affect dividing effector T-cells. The combination therapy may also be administered after radiation.

In another embodiment the combination therapy described herein is used in the treatment in a cancer where the standard of care is primarily not surgery and is primarily based on systemic treatments, such as Chronic Lymphocytic Leukemia (CLL).

In another embodiment patients diagnosed with stage I, II, III, and IV Chronic Lymphocytic Leukemia are treated with the combination therapy as described herein. The standard of care for this cancer type is:
1. Observation in asymptomatic or minimally affected patients
2. Rituximab
3. Ofatumomab
4. Oral alkylating agents with or without corticosteroids
5. Fludarabine, 2-chlorodeoxyadenosine, or pentostatin
6. Bendamustine
7. Lenalidomide
8. Combination chemotherapy.
   combination chemotherapy regimens include the following:
   Fludarabine plus cyclophosphamide plus rituximab.
   Fludarabine plus rituximab as seen in the CLB-9712 and CLB-9011 trials.
   Fludarabine plus cyclophosphamide versus fludarabine plus cyclophosphamide plus rituximab.
   Pentostatin plus cyclophosphamide plus rituximab as seen in the MAYO-MC0183 trial, for example.
   Ofatumumab plus fludarabine plus cyclophosphamide.
   CVP: cyclophosphamide plus vincristine plus prednisone.
   CHOP: cyclophosphamide plus doxorubicin plus vincristine plus prednisone.
   Fludarabine plus cyclophosphamide versus fludarabine as seen in the E2997 trial [NCT00003764] and the LRF-CLL4 trial, for example.
   Fludarabine plus chlorambucil as seen in the CLB-9011 trial, for example.
9. Involved-field radiation therapy.
10. Alemtuzumab
11. Bone marrow and peripheral stem cell transplantations are under clinical evaluation.
12. Ibrutinib In one embodiment the combination therapy is administered before, simultaneously with or after treatment with Rituximab or Ofatumomab. As these are monoclonal antibodies that target B-cells, treatment with the combination therapy may be synergistic. In another embodiment the combination therapy is administered after treatment with oral alkylating agents with or without corticosteroids, and Fludarabine, 2-chlorodeoxyadenosine, or pentostatin, as these treatments may negatively affect the immune system if administered before. In one embodiment bendamustine is administered with the combination therapy in low doses based on the results for prostate cancer described herein. In one embodiment the combination therapy is administered after treatment with bendamustine.

Vaccine or Immunogenic Composition Kits and Co-Packaging

In an aspect, the invention provides kits containing any one or more of the elements discussed herein to allow administration of the combination therapy. Elements may be provided individually or in combinations, and may be provided in any suitable container, such as a vial, a bottle, or a tube. In some embodiments, the kit includes instructions in one or more languages, for example in more than one language. In some embodiments, a kit comprises one or more reagents for use in a process utilizing one or more of the elements described herein. Reagents may be provided in any suitable container. For example, a kit may provide one or more delivery or storage buffers. Reagents may be provided in a form that is usable in a particular process, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more of the vectors, proteins and/or one or more of the polynucleotides described herein. The kit may advantageously allow the provision of all elements of the systems of the invention. Kits can involve vector(s) and/or particle(s) and/or nanoparticle(s) containing or encoding RNA(s) for 1-50 or more neoantigen mutations to be administered to an animal, mammal, primate, rodent, etc., with such a kit including instructions for administering to such a eukaryote; and such a kit can optionally include any of the anti-cancer agents described herein. The kit may include any of the components above (e.g. vector(s) and/or particle(s) and/or nanoparticle(s) containing or encoding RNA(s) for 1-50 or more neoantigen mutations, neoantigen proteins or peptides, checkpoint inhibitors) as well as instructions for use with any of the methods of the present invention.

In one embodiment the kit contains at least one vial with an immunogenic composition or vaccine and at least one vial with an anticancer agent. In one embodiment kits may comprise ready to use components that are mixed and ready to administer. In one aspect a kit contains a ready to use immunogenic or vaccine composition and a ready to use anti-cancer agent. The ready to use immunogenic or vaccine composition may comprise separate vials containing different pools of immunogenic compositions. The immunogenic compositions may comprise one vial containing a viral vector or DNA plasmid and the other vial may comprise immunogenic protein. The ready to use anticancer agent may comprise a cocktail of anticancer agents or a single anticancer agent. Separate vials may contain different anti-cancer agents. In another embodiment a kit may contain a ready to use anti-cancer agent and an immunogenic composition or vaccine in a ready to be reconstituted form. The immunogenic or vaccine composition may be freeze dried or lyophilized. The kit may comprise a separate vial with a reconstitution buffer that can be added to the lyophilized composition so that it is ready to be administered. The buffer may advantageously comprise an adjuvant or emulsion according to the present invention. In another embodiment the kit may comprise a ready to reconstitute anti-cancer agent and a ready to reconstitute immunogenic composition or vaccine. In this aspect both may be lyophilized. In this aspect separate reconstitution buffers for each may be included in the kit. The buffer may advantageously comprise an adjuvant or emulsion according to the present invention. In another embodiment the kit may comprise single vials containing a dose of immunogenic composition and anti-cancer agent that are administered together. In another aspect multiple vials are included so that one vial is administered according to a treatment timeline. One vial may only contain the anti-cancer agent for one dose of treatment, another may contain both the anti-cancer agent and immunogenic composition for another dose of treatment, and one vial may only contain the immunogenic composition for yet another dose. In a further aspect the vials are labeled for their proper administration to a patient in need thereof. The immunogen or anti-cancer agents of any embodiment may be in a lyophilized form, a dried form or in aqueous solution as described herein. The immunogen may be a live attenuated virus, protein, or nucleic acid as described herein.

In one embodiment the anticancer agent is one that enhances the immune system to enhance the effectiveness of the immunogenic composition or vaccine. In a preferred embodiment the anti-cancer agent is a checkpoint inhibitor. In another embodiment the kit contains multiple vials of immunogenic compositions and anti-cancer agents to be administered at different time intervals along a treatment plan. In another embodiment the kit may comprise separate vials for an immunogenic composition for use in priming an immune response and another immunogenic composition to be used for boosting. In one aspect the priming immunogenic composition could be DNA or a viral vector and the boosting immunogenic composition may be protein. Either composition may be lyophilized or ready for administering. In another embodiment different cocktails of anti-cancer agents containing at least one anti-cancer agent are included in different vials for administration in a treatment plan.

Although the present invention and its advantages have been described in detail, it should be understood that various changes, substitutions and alterations can be made herein without departing from the spirit and scope of the invention as defined in the appended claims.

The present invention is further illustrated in the following Examples which are given for illustration purposes only and are not intended to limit the invention in any way.

EXAMPLES

Example 1

Cancer Vaccine Testing Protocol

The herein-described compositions and methods may be tested on 15 patients with high-risk melanoma (fully resected stages IIIB, IIC and IVM1a,b) according to the general flow process shown in FIG. 2. Patients may receive a series of priming vaccinations with a mixture of personalized tumor-specific peptides and poly-ICLC over a 4 week period followed by two boosts during a maintenance phase. All vaccinations are subcutaneously delivered. The vaccine or immunogenic composition is evaluated for safety, tolerability, immune response and clinical effect in patients and for feasibility of producing vaccine or immunogenic composition and successfully initiating vaccination within an appropriate time frame. The first cohort can consist of 5 patients, and after safety is adequately demonstrated, an additional cohort of 10 patients may be enrolled. Peripheral blood is extensively monitored for peptide-specific T-cell responses and patients are followed for up to two years to assess disease recurrence.

As described herein, there is a large body of evidence in both animals and humans that mutated epitopes are effective in inducing an immune response and that cases of spontaneous tumor regression or long term survival correlate with CD8+ T-cell responses to mutated epitopes (Buckwalter and Srivastava PK. "It is the antigen(s), stupid" and other lessons from over a decade of vaccitherapy of human cancer. Seminars in immunology 20:296-300 (2008); Karanikas et al, High frequency of cytolytic T lymphocytes directed against a tumor-specific mutated antigen detectable with HLA tetramers in the blood of a lung carcinoma patient with long survival. Cancer Res. 61:3718-3724 (2001); Lennerz et al, The response of autologous T cells to a human melanoma is dominated by mutated neoantigens. Proc Natl Acad Sci USA. 102:16013 (2005)) and that "immunoediting" can be tracked to alterations in expression of dominant mutated antigens in mice and man (Matsushita et al, Cancer exome analysis reveals a T-cell-dependent mechanism of cancer immunoediting Nature 482:400 (2012); DuPage et al, Expression of tumor-specific antigens underlies cancer immunoediting Nature 482:405 (2012); and Sampson et al, Immunologic escape after prolonged progression-free survival with epidermal growth factor receptor variant III peptide vaccination in patients with newly diagnosed glioblastoma J Clin Oncol. 28:4722-4729 (2010)).

Next-generation sequencing can now rapidly reveal the presence of discrete mutations such as coding mutations in individual tumors, most commonly single amino acid changes (e.g., missense mutations) and less frequently novel stretches of amino acids generated by frame-shift insertions/deletions/gene fusions, read-through mutations in stop codons, and translation of improperly spliced introns (e.g., neoORFs). NeoORFs are particularly valuable as immunogens because the entirety of their sequence is completely novel to the immune system and so are analogous to a viral or bacterial foreign antigen. Thus, neoORFs: (1) are highly specific to the tumor (i.e. there is no expression in any normal cells); (2) can bypass central tolerance, thereby increasing the precursor frequency of neoantigen-specific CTLs. For example, the power of utilizing analogous foreign sequences in a therapeutic anti-cancer vaccine was recently demonstrated with peptides derived from human papilloma virus (HPV). ~50% of the 19 patients with pre-neoplastic, viral-induced disease who received 3-4 vaccinations of a mix of HPV peptides derived from the viral oncogenes E6 and E7 maintained a complete response for ≥24 months (Kenter et a, Vaccination against HPV-16 Oncoproteins for Vulvar Intraepithelial Neoplasia NEJM 361:1838 (2009)).

Sequencing technology has revealed that each tumor contains multiple, patient-specific mutations that alter the protein coding content of a gene. Such mutations create altered proteins, ranging from single amino acid changes (caused by missense mutations) to addition of long regions of novel amino acid sequence due to frame shifts, read-through of termination codons or translation of intron regions (novel open reading frame mutations; neoORFs). These mutated proteins are valuable targets for the host's immune response to the tumor as, unlike native proteins, they are not subject to the immune-dampening effects of self-tolerance. Therefore, mutated proteins are more likely to be immunogenic and are also more specific for the tumor cells compared to normal cells of the patient.

Utilizing recently improved algorithms for predicting which missense mutations create strong binding peptides to the patient's cognate MHC molecules, a set of peptides representative of optimal mutated epitopes (both neoORF and missense) for each patient is identified and prioritized and up to 20 or more peptides are prepared for immunization (Zhang et al, Machine learning competition in immunology—Prediction of HLA class I binding peptides J Immunol Methods 374:1 (2011); Lundegaard et al Prediction of epitopes using neural network based methods J Immunol Methods 374:26 (2011)). Peptides ~20-35 amino acids in length is synthesized because such "long" peptides undergo efficient internalization, processing and cross-presentation in professional antigen-presenting cells such as dendritic cells, and have been shown to induce CTLs in humans (Melief and van der Burg, Immunotherapy of established (pre) malignant disease by synthetic long peptide vaccines Nature Rev Cancer 8:351 (2008)).

In addition to a powerful and specific immunogen, an effective immune response advantageously includes a strong adjuvant to activate the immune system (Speiser and Romero, Molecularly defined vaccines for cancer immunotherapy, and protective T cell immunity Seminars in Immunol 22:144 (2010)). For example, Toll-like receptors (TLRs) have emerged as powerful sensors of microbial and viral pathogen "danger signals", effectively inducing the innate immune system, and in turn, the adaptive immune system (Bhardwaj and Gnjatic, TLR AGONISTS: Are They Good Adjuvants? Cancer J. 16:382-391 (2010)). Among the TLR agonists, poly-ICLC (a synthetic double-stranded RNA mimic) is one of the most potent activators of myeloid-derived dendritic cells. In a human volunteer study, poly-ICLC has been shown to be safe and to induce a gene expression profile in peripheral blood cells comparable to that induced by one of the most potent live attenuated viral vaccines, the yellow fever vaccine YF-17D (Caskey et al, Synthetic double-stranded RNA induces innate immune responses similar to a live viral vaccine in humans J Exp Med 208:2357 (2011)). Hiltonol®, a GMP preparation of poly-ICLC prepared by Oncovir, Inc, is utilized as the adjuvant.

Example 2

Target Patient Population

Patients with stage IIIB, IIC and IVM1a,b, melanoma have a significant risk of disease recurrence and death, even with complete surgical resection of disease (Balch et al, Final Version of 2009 AJCC Melanoma Staging and Classification J Clin Oncol 27:6199-6206 (2009)). An available systemic adjuvant therapy for this patient population is interferon-α (IFNα) which provides a measurable but marginal benefit and is associated with significant, frequently dose-limiting toxicity (Kirkwood et al, Interferon alfa-2b Adjuvant Therapy of High-Risk Resected Cutaneous Melanoma: The Eastern Cooperative Oncology Group Trial EST 1684 J Clin Oncol 14:7-17 (1996); Kirkwood et al, High- and Low-dose Interferon Alpha-2b in High-Risk Melanoma: First Analysis of Intergroup Trial E1690/S9111/C9190 J Clin Oncol 18:2444-2458 (2000)). These patients are not immuno-compromised by previous cancer-directed therapy or by active cancer and thus represent an excellent patient population in which to assess the safety and immunological impact of the vaccine. Finally, current standard of care for these patients does not mandate any treatment following surgery, thus allowing for the 8-10 week window for vaccine preparation.

The target population is cutaneous melanoma patients with clinically detectable, histologically confirmed nodal (local or distant) or in transit metastasis, who have been fully resected and are free of disease (most of stage IIIB (because of the need to have adequate tumor tissue for sequencing and cell line development, patients with ulcerated primary tumor but micrometastatic lymph nodes (Tl-4b, N1a or N2a) is excluded), all of stage IIIC, and stage IVM1a, b). These may be patients at first diagnosis or at disease recurrence after previous diagnosis of an earlier stage melanoma.

Tumor harvest: Patients can undergo complete resection of their primary melanoma (if not already removed) and all regional metastatic disease with the intent of rendering them free of melanoma. After adequate tumor for pathological assessment has been harvested, remaining tumor tissue is placed in sterile media in a sterile container and prepared for disaggregation. Portions of the tumor tissue is used for whole-exome and transcriptome sequencing and cell line generation and any remaining tumor is frozen.

Normal tissue harvest: A normal tissue sample (blood or sputum sample) is taken for whole exome sequencing.

Patients with clinically evident locoregional metastatic disease or fully resectable distant nodal, cutaneous or lung metastatic disease (but absence of unresectable distant or visceral metastatic disease) is identified and enrolled on the study. Entry of patients prior to surgery is necessary in order to acquire fresh tumor tissue for melanoma cell line development (to generate target cells for in vitro cytotoxicity assays as part of the immune monitoring plan).

Example 3

Dose and Schedule

Figure 3:
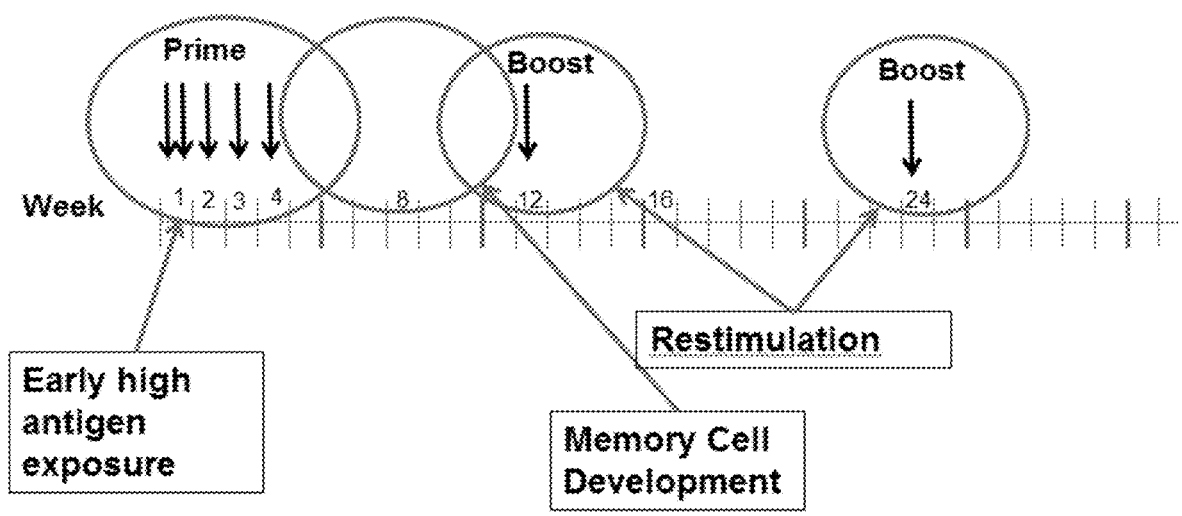
FIG. 3 illustrates an immunization schedule based on a prime boost strategy according to an exemplary embodiment of the present invention.

For patients who have met all pre-treatment criteria, vaccine administration can commence as soon as possible after the study drug has arrived and has met incoming specifications. For each patient, there is four separate study drugs, each containing 5 of 20 patient-specific peptides. Immunizations may generally proceed according to the schedule shown in FIG. 3.

Patients are treated in an outpatient clinic. Immunization on each treatment day can consist of four 1 ml subcutaneous injections, each into a separate extremity in order to target different regions of the lymphatic system to reduce antigenic competition. If the patient has undergone complete axillary or inguinal lymph node dissection, vaccines are administered into the right or left midriff as an alternative. Each injection can consist of 1 of the 4 study drugs for that patient and the same study drug is injected into the same extremity for each cycle. The composition of each 1 ml injection is:

0.75 ml study drug containing 300 sg each of 5 patient-specific peptides 0.25 ml (0.5 mg) of 2 mg/ml poly-ICLC (Hiltonol®)

During the induction/priming phase, patients are immunized on days 1, 4, 8, 15 and 22. In the maintenance phase, patients can receive booster doses at weeks 12 and 24.

Blood samples may be obtained at multiple time points: pre- (baseline; two samples on different days); day 15 during priming vaccination; four weeks after the induction/priming vaccination (week 8); pre- (week 12) and post- (week 16) first boost; pre- (week 24) and post-(week 28) second boost 50-150 ml blood is collected for each sample (except week 16). The primary immunological endpoint is at week 16, and hence patients can undergo leukapheresis (unless otherwise indicated based on patient and physician assessment).

Example 4

Immune Monitoring

The immunization strategy is a "prime-boost" approach, involving an initial series of closely spaced immunizations to induce an immune response followed by a period of rest to allow memory T-cells to be established. This is followed by a booster immunization, and the T-cell response 4 weeks after this boost is expected to generate the strongest response and is the primary immunological endpoint. Global immunological response is initially monitored using peripheral blood mononuclear cells from this time point in an 18 hr ex vivo ELISPOT assay, stimulating with a pool of overlapping 15mer peptides (11 as overlap) comprising all the immunizing epitopes. Pre-vaccination samples are evaluated to establish the baseline response to this peptide pool. As warranted, additional PBMC samples are evaluated to examine the kinetics of the immune response to the total peptide mix. For patients demonstrating responses significantly above baseline, the pool of all 15mers are de-convoluted to determine which particular immunizing peptide(s) were immunogenic. In addition, a number of additional assays are conducted on a case-by-case basis for appropriate samples:

The entire 15mer pool or sub-pools are used as stimulating peptides for intracellular cytokine staining assays to identify and quantify antigen-specific CD4+, CD8+, central memory and effector memory populations Similarly, these pools are used to evaluate the pattern of cytokines secreted by these cells to determine the TH1 vs TH2 phenotype Extracellular cytokine staining and flow cytometry of unstimulated cells are used to quantify Treg and myeloid-derived suppressor cells (MDSC).

Figure 4:
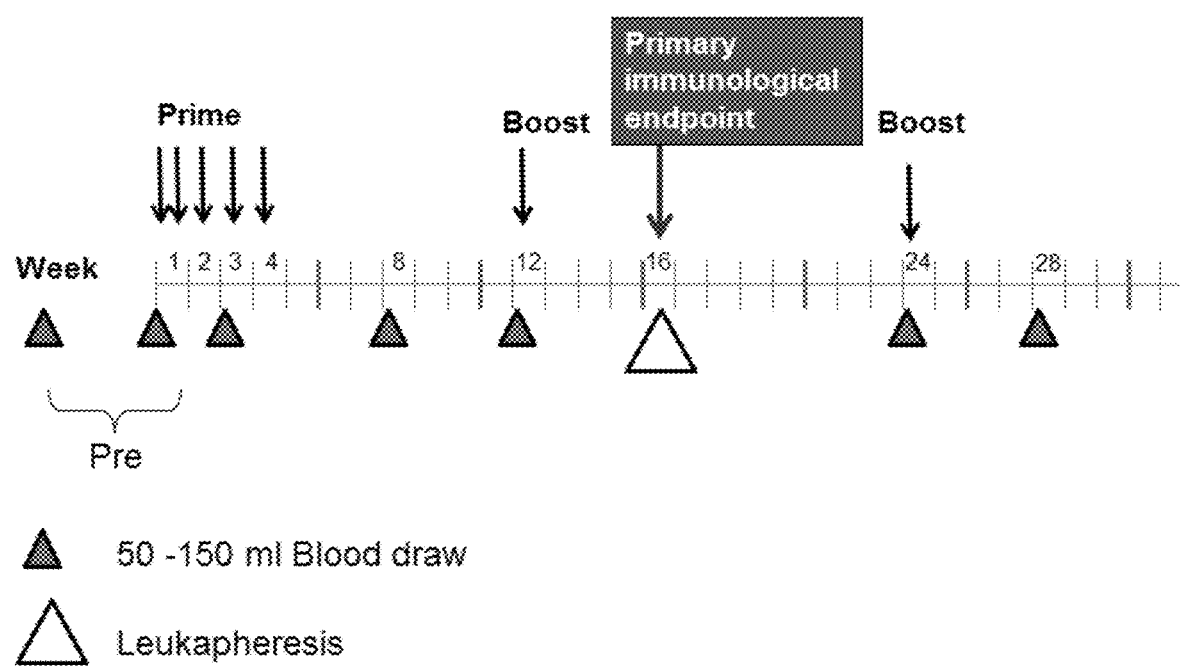
FIG. 4 shows a time line indicating the primary immunological endpoint according to an exemplary aspect of the invention.

If a melanoma cell line is successfully established from a responding patient and the activating epitope can be identified, T-cell cytotoxicity assays are conducted using the mutant and corresponding wild type peptide PBMC from the primary immunological endpoint is evaluated for "epitope spreading" by using known melanoma tumor associated antigens as stimulants and by using several additional identified mutated epitopes that were not selected to be among the immunogens, as shown in FIG. 4.

Immuno-histochemistry of the tumor sample is conducted to quantify CD4+, CD8+, MDSC, and Treg infiltrating populations.

Example 5

Clinical Efficacy in Patients with Metastatic Disease

Figure 5:
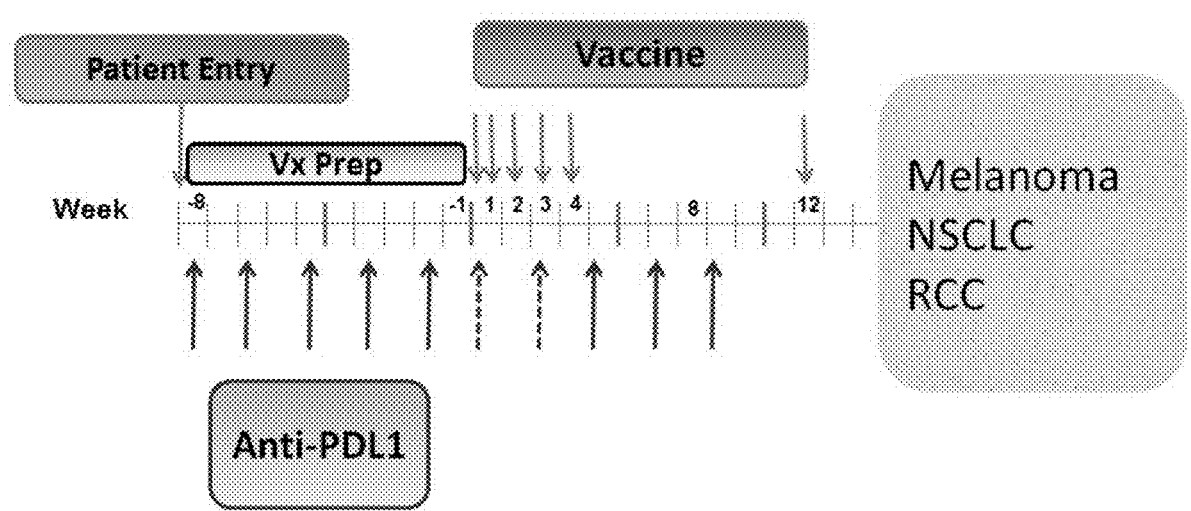
FIG. 5 illustrates a time line for administering a co-therapy with checkpoint blockade antibodies to evaluate the combination of relief of local immune suppression coupled with the stimulation of new immunity according to an exemplary embodiment of the invention. As shown in the scheme, patients who enter as appropriate candidates for checkpoint blockade therapy, e.g., anti-PDL1 as shown here, may be entered and immediately treated with antibody, while the vaccine or immunogenic composition is being prepared. Patients may then be vaccinated. Checkpoint blockade antibody dosing can be continued or possibly deferred while the priming phase of vaccination occurs.

Vaccine treatment of patients with metastatic disease is complicated by their need for an effective therapy for the active cancer and the consequent absence of an off treatment time window for vaccine preparation. Furthermore, these cancer treatments may compromise the patient's immune system, possibly impeding the induction of an immune response. With these considerations in mind, settings may be chosen where timing of vaccine preparation fits temporally with other standard care approaches for the particular patient population and/or where such standard care is demonstrably compatible with an immunotherapeutic approach. There are two types of settings that may be pursued:

1. Combination with checkpoint blockade: Checkpoint blockade antibodies have emerged as an effective immunotherapy for metastatic melanoma (Hodi et al, Improved Survival with Ipilimumab in Patients with Metastatic Melanoma NEJM 363:711-723 (2010)) and are being actively pursued in other disease settings including non-small cell lung cancer (NSCLC) and renal cell carcinoma (Topalian et al, Safety, Activity, and Immune Correlates of Anti-PD-1 Antibody in Cancer NEJM 366:2443-2454 (2012); Brahmer et al, Safety and Activity of Anti-PD-L1 Antibody in Patients with Advanced Cancer NEJM 366:2455-2465(2012)). Although the mechanism of action is not proven, both reversal of relief from local immunosuppression and enhancement of an immune response are possible explanations. Integrating a powerful vaccine to initiate an immune response with checkpoint blockade antibodies may provide synergies, as observed in multiple animal studies (van Elsas et al Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation J Exp Med 190:35-366 (1999); Li et al, Anti-programmed death-1 synergizes with granulocyte macrophage colony-stimulating factor-secreting tumor cell immunotherapy providing therapeutic benefit to mice with established tumors Clin Cancer Res 15:1623-1634 (2009); Pardoll, D. M. The blockade of immune checkpoints in cancer immunotherapy Nature Reviews Cancer 12:252-264 (2012); Curran et al. PD-1 and CTLA-4 combination blockade expands infiltrating T cells and reduces regulatory T and myeloid cells within B16 melanoma tumors. Proc Natl Acad Sci USA. 2010 Mar. 2; 107(9):4275-80; Curran et al. Tumor vaccines expressing flt3 ligand synergize with ctla-4 blockade to reject preimplanted tumors. Cancer Res. 2009 Oct. 1; 69(19):7747-55). Patients can be immediately started on checkpoint blockade therapy while vaccine is being prepared and once prepared, the vaccine dosing can be integrated with antibody therapy, as illustrated in FIG. 5; and
2. Combination with standard treatment regimens exhibiting beneficial immune properties.
   a) Renal cell carcinoma (RCC) patients who present with metastatic disease typically undergo surgical de-bulking followed by systemic treatment, which is commonly with one of the approved tyrosine kinase inhibitors (TKI) such as sunitinib, pazopanib and sorafenib. Of the approved TKIs, sunitinib has been shown to increase TH1 responsiveness and decrease Treg and myeloid-derived suppressor cells (Finke et al, Sunitinib reverses Type-1 immune suppression and decreases T-regulatory cells in renal cell carcinoma patients Clin Can Res 14:6674-6682 (2008); Terme et al, VEGFA-VEGFR pathway blockade inhibits tumor-induced regulatory T cell proliferation in colorectal cancer (Cancer Research Author Manuscript published Online (2102)). The ability to immediately treat patients with an approved therapy that does not compromise the immune system provides the needed window to prepare the vaccine and could provide synergy with a vaccine therapy. In addition, cyclophosphamide (CTX) has been implicated in multiple animal and human studies to have an inhibitory effect on Treg cells and a single dose of CTX prior to a vaccine has been recently shown to improve survival in RCC patients who responded to the vaccine (Walter et al, Multipeptide immune response to a cancer vaccine IMA901 after single-dose cyclophosphamide associates with longer patient survival Nature Medicine 18:1254-1260 (2012)). Both of these immune-synergistic approaches have been utilized in a recently completed phase 3 study of a native peptide vaccine in RCC (ClinicalTrials.gov, NCT01265901 IMA901 in Patients Receiving Sunitinib for Advanced/Metastatic Renal Cell Carcinoma);
   b) Alternatively, standard treatment of glioblastoma (GBM) involves surgery, recovery and follow-up radiation and low dose temozolomide (TMZ) followed by a four week rest period before initiating standard dose TMZ. This standard treatment provides a window for vaccine preparation followed by initiation of vaccination prior to starting standard dose TMZ. Interestingly, in a study in metastatic melanoma, peptide vaccination during standard dose TMZ treatment increased the measured immune responsiveness compared to vaccination alone, suggesting additional synergistic benefit (Kyte et al, Telomerase peptide vaccination combined with temozolomide: a clinical trial in stage IV melanoma patients Clin Cancer Res 17:4568 (2011)).

Example 6

Neoantigen Preparation

Following surgical resection of the tumor, a portion of the tumor tissue and a blood sample is transferred immediately to the facility where it is assigned a unique identification code for further tracking. The tumor tissue is disaggregated with collagenase and separate portions are frozen for nucleic acid (DNA and RNA) extraction. The blood sample is immediately transferred to a facility for nucleic acid extraction. DNA and/or RNA extracted from the tumor tissue is used for whole-exome sequencing (e.g., by using the Illumina HiSeq platform) and to determine HLA typing information. It is contemplated within the scope of the invention that missense or neoORF neoantigenic peptides may be directly identified by protein-based techniques (e.g., mass spectrometry).

Bioinformatics analysis are conducted as follows. Sequence analysis of the Exome and RNA-SEQ fast Q files leverage existing bioinformatic pipelines that have been used and validated extensively in large-scale projects such as the TCGA for many patient samples (e.g., Chapman et al, 2011, Stransky et al, 2011, Berger et al, 2012). There are two sequential categories of analyses: data processing and cancer genome analysis.

Data processing pipeline: The Picard data processing pipeline (picard.sourceforge.net/) was developed by the Sequencing Platform. Raw data extracted from (e.g., Illumina) sequencers for each tumor and normal sample is subjected to the following processes using various modules in the Picard pipeline:

(i) Data conversion: Raw Illumina data is converted to the standard BAM format and basic QC metrics pertaining to the distribution of bases exceeding different quality thresholds are generated.

(ii) Alignment: The Burrows-Wheeler Alignment Tool (BWA) is used to align read pairs to the human genome (hg19).

(iii) Mark Duplicates: PCR and optical duplicates are identified based on read pair mapping positions and marked in the final BAM file.

(iv) Indel Realignment: Reads that align to known insertion and deletion polymorphic sites in the genome is examined and those sites where the log odds (LOD) score for improvement upon realignment is at least 0.4 is corrected.

(v) Quality Recalibration: Original base quality scores reported by the Illumina pipeline is recalibrated based on the read-cycle, the lane, the flow cell tile, the base in question and the preceding base. The recalibration assumes that all mismatches in non-dbSNP positions are due to errors which enable recalibration of the probability of error in each category of interest as the fraction of mismatches amongst the total number of observations.

(vi) Quality Control: The final BAM file is processed to generate extensive QC metrics including read quality by cycle, distribution of quality scores, summary of alignment and the insert size distribution. Data that fails quality QC is blacklisted.

(vii) Identity Verification: Orthogonally collected sample genotype data at ~100 known SNP positions are checked against the sequence data to confirm the identity of the sample. A LOD score of ≥10 is used as a threshold for confirmation of identity. Data that fails identity QC is blacklisted.

(viii) Data Aggregation: All data from the same sample is merged and the mark duplicates step is repeated. Novel target regions containing putative short insertions and deletion regions are identified and the indel realignment step is performed at these loci.

(ix) Local realignment around putative indels in aggregated data: Novel target regions containing putative short insertions and deletions are identified and a local realignment step is performed at these loci (e.g., using the GATK RealignerTargetCreator and IndelRealigner modules) to ensure consistency and correctness of indel calls.

(x) Quality Control on Aggregated Data: QC metrics such as alignment summary and insert size distribution is recomputed. Additionally a set of metrics that evaluate the rate of oxidative damage in the early steps of the library constructions process caused by acoustic shearing of DNA in the presence of reactive contaminants from the extraction process are generated.

The output of Picard is a bam file (Li et al, 2009) (see, e.g., http://samtools.sourceforge.net/SAM1.pdf) that stores the base sequences, quality scores, and alignment details for all reads for the given sample.

Cancer Mutation Detection Pipeline: Tumor and matched normal bam files from the Picard pipeline is analyzed as described herein:

1. Quality Control
    (i). The Capseg program is applied to tumor and matched normal exome samples to get the copy number profiles. The CopyNumberQC tool can then be used to manually inspect the generated profiles and assess tumor/normal sample mix-ups. Normal samples that have noisy profiles as well as cases where the tumor sample has lower copy number variation than the corresponding normal is flagged and tracked through the data generation and analysis pipelines to check for mix-ups.
    (ii). Tumor purity and ploidy is estimated by the ABSOLUTE tool 15 based on Capseg-generated copy number profiles. Very noisy profiles might result from sequencing of highly degraded samples. No tumor purity and ploidy estimates would be possible in such cases and the corresponding sample is flagged.
    (iii). ContEst (Cibulskis et al, 2011) is used to determine the level of cross-sample contamination in samples. Samples with greater than 4% contamination is discarded.
2. Identification of somatic single nucleotide variations (SSNVs) Somatic base pair substitutions are identified by analyzing tumor and matched normal bams from a patient using a Bayesian statistical framework called muTect (Cibulskis et al, 2013). In the preprocessing step, reads with a preponderance of low quality bases or mismatches to the genome are filtered out. Mutect then computes two log-odds (LOD) scores which encapsulate confidence in presence and absence of the variant in the tumor and normal samples respectively. In the post-processing stage candidate mutations are filtered by six filters to account for artifacts of capture, sequencing and alignment:
    (i) Proximal gap: removes false positives that arise due to the presence of misaligned indels in the vicinity of the event. Samples with 3 reads with insertions or deletions in a 11-bp window around the candidate mutation are rejected.
    (ii) Poor mapping: discards false positives that arise by virtue of ambiguous placement of reads in the genome. Rejects candidates if ≥50% reads in tumor and normal samples have mapping quality zero or if there are no reads harboring the mutant allele with mapping quality 220.
    (iii) Trialleleic sites: discards sites that are heterozygous in the normal since these have a tendency to generate many false positives.
    (iv) Strand bias: removes false positives caused by context-specific sequencing errors where a large fraction of reads harboring the mutation have the same orientation. Rejects candidates where the strand-specific LOD is <2 where the sensitivity to pass that threshold is ≥90%.
    (v) Clustered position: rejects false positives due to alignment errors characterized by the alternative allele occurring at a fixed distance from the start or end of the read alignment. Rejects if the median distance from the start and end of the reads are ≤10 which implies that the mutation is at the start or end of the alignment, or if the median absolute deviation of the distances are ≤3 which implies that the mutations are clustered.
    (vi) Observed in control: discards false positives in the tumor where there is evidence of occurrence of the alternate allele in the normal sample beyond what is expected by random sequencing errors. Rejects if there are ≥2 reads containing the alternate allele in the normal sample or if they are in ≥3% of the reads, and if the sum of their quality scores are >20.
    In addition to these 6 filters, candidates are compared against a panel of normal samples and those that are found to be present as germline variants in two or more normal samples are rejected. The final set of mutations can then be annotated with the Oncotator tool by several fields including genomic region, codon, cDNA and protein changes.
3. Identification of somatic small insertions and deletions
    The local realignment output described herein (see "Local realignment around putative indels in aggregated data", supra) is used to predict candidate somatic and germline indels based on assessment of reads supporting the variant exclusively in tumor or both in tumor and normal bams respectively. Further filtering based on number and distribution of mismatches and base quality scores are done (McKenna et al, 2010, DePristo et al, 2011). All indels are manually inspected using the Integrated Genomics Viewer (Robinson et al, 2011) (www.broadinstitute.org/igv) to ensure high-fidelity calls.
4. Gene fusion detection
    The first step in the gene fusion detection pipeline is alignment of tumor RNA-Seq reads to a library of known gene sequences following by mapping of this alignment to genomic coordinates. The genomic mapping helps collapse multiple read pairs that map to different transcript variants that share exons to common genomic locations. The DNA aligned barn file is queried for read pairs where the two mates map to two different coding regions that are either on different chromosomes or at least 1 MB apart if on the same chromosome. It can also be required that the pair ends aligned in their respective genes be in the direction consistent with coding→coding 5'→3' direction of the (putative) fusion mRNA transcript. A list of gene pairs where there are at least two such 'chimeric' read pairs are enumerated as the initial putative event list subject to further refinement. Next, all unaligned reads are extracted from the original barn file, with the additional constraint that their mates were originally aligned and map into one of the genes in the gene pairs obtained as described herein. An attempt can then be made to align all such originally unaligned reads to the custom "reference" built of all possible exon-exon junctions (full length, boundary-to-boundary, in coding 5'→3' direction) between the discovered gene pairs. If one such originally unaligned read maps (uniquely) onto a junction between an exon of gene X and an exon of gene Y, and its mate was indeed mapped to one of the genes X or Y, then such a read is marked as a "fusion" read. Gene fusion events are called in cases where there is at least one fusion read in correct relative orientation to its mate, without excessive number of mismatches around the exon:exon junction and with a coverage of at least 10 bp in either gene. Gene fusions between highly homologous genes (ex. HLA family) are likely spurious and is filtered out.

5. Estimation of clonality

Bioinformatic analysis may be used to estimate clonality of mutations. For example, the ABSOLUTE algorithm (Carter et al, 2012, Landau et al, 2013) may be used to estimate tumor purity, ploidy, absolute copy numbers and clonality of mutations. Probability density distributions of allelic fractions of each mutation is generated followed by conversion to cancer cell fractions (CCFs) of the mutations. Mutations are classified as clonal or subclonal based on whether the posterior probability of their CCF exceeds 0.95 is greater or lesser than 0.5 respectively.

6. Quantification of expression

The TopHat suite (Langmead et al, 2009) is used to align RNA-Seq reads for the tumor and matched normal bams to the hg19 genome. The quality of RNA-Seq data is assessed by the RNA-SeQC (DeLuca et al., 2012) package. The RSEM tool (Li et al., 2011) can then be used to estimate gene and isoform expression levels. The generated reads per kilobase per million and tau estimates are used to prioritize neoantigens identified in each patient as described elsewhere.

7. Validation of mutations in RNA-Seq

8. Confirmation of the somatic mutations identified by analysis of whole exome data as described herein (including single nucleotide variations, small insertions and deletions and gene fusions) are assessed by examining the corresponding RNA-Seq tumor BAM file of the patient. For each variant locus, a power calculation based on the beta-binomial distribution is performed to ensure that there is at least 95% power to detect it in the RNA-Seq data. A capture identified mutation is considered validated if there are at least 2 reads harboring the mutation for adequately powered sites.

Selection of Tumor-Specific Mutation-Containing Epitopes: All missense mutations and neoORFs are analyzed for the presence of mutation-containing epitopes using the neural-network based algorithm netMHC, provided and maintained by the Center for Biological Sequence Analysis, Technical University of Denmark, Netherlands. This family of algorithms were rated the top epitope prediction algorithms based on a competition recently completed among a series of related approaches (ref). The algorithms were trained using an artificial neural network based approach on 69 different human HLA A and B alleles covering 99% of the HLA-A alleles and 87% of the HLA-B alleles found in the Caucasian population, the major ethnic group in the target patient population in the local area. The most up-do-date version is utilized (v2.4).

The accuracy of the algorithms were evaluated by conducting predictions from mutations found in CLL patients for whom the HLA allotypes were known. The included allotypes were A0101, A0201, A0310, A1101, A2402, A6801, B0702, B0801, B1501. Predictions were made for all 9mer and 10 mer peptides spanning each mutation using netMHCpan in mid-2011. Based on these predictions, seventy-four (74) 9mer peptides and sixty-three (63) 10mer peptides, most with predicted affinities below 500 nM, were synthesized and the binding affinity was measured using a competitive binding assay (Sette).

The predictions for these peptides were repeated in March 2013 using each of the most up to date versions of the netMHC servers (netMHCpan, netMHC and netMHCcons). These three algorithms were the top rated algorithms among a group of 20 used in a competition in 2012 (Zhang et al). The observed binding affinities were then evaluated with respect to each of the new predictions. For each set of predicted and observed values, the % of correct predictions for each range is given, as well as the number of samples. The definition for each range is as follows:

0-150: Predicted to have an affinity equal to or lower than 150 nM and measured to have an affinity equal to or lower than 150 nM.

0-150*: Predicted to have an affinity equal to or lower than 150 nM and measured to have an affinity equal to or lower than 500 nM.

151-500 nM: Predicted to have an affinity greater than 150 nM but equal to or lower than 500 nM and measured to have an affinity equal to or below 500 nM.

FN (>500 nM): False Negatives—Predicted to have an affinity greater than 500 nM but measured to have an affinity equal to or below 500 nM.

For 9mer peptides (Table 1), there was little difference between the algorithms, with the slightly higher value for the 151-500 nM range for netMHC cons not judged to be significant because of the low number of samples.

TABLE 1

| Range (nM) | 9mer PAN | 9mer netMHC | 9mer CONS |
|---|---|---|---|
| 0-150 | 76% | 78% | 76% |
|  | (33) | (37) | (34) |
| 0-150* | 91% | 89% | 88% |
|  | (33) | (37) | (34) |
| 151-500 | 50% | 50% | 62% |
|  | (28) | (14) | (13) |
| FN (>500) | 38% | 39% | 41% |
|  | (13) | (23) | (27) |

For 10mer peptides (Table 2), again there was little difference between the algorithms except that netMHC produced significantly more false positives than netMHCpan or netMMHCcons. However, the precision of the 10mer predictions are slightly lower in the 0-150 nM and 0-150* nM ranges and significantly lower in the 151-500 nM range, compared to the 9mers.

TABLE 2

| Range (nM) | 10mer PAN | 10mer netMHC | 10mer CONS |
|---|---|---|---|
| 0-150 | 53% | 50% | 59% |
|  | (19) | (16) | (17) |
| 0-150* | 68% | 69% | 76% |
|  | (19) | (16) | (17) |
| 151-500 | 35% | 42% | 35% |
|  | (26) | (12) | (23) |
| FN (>500) | 11% | 23% | 13% |
|  | (18) | (35) | (23) |

For 10mers, only predictions in the 0-150 nM range is utilized due to the lower than 50% precision for binders in the 151-500 nM range.

The number of samples for any individual HLA allele was too small to draw any conclusions regarding accuracy of the prediction algorithm for different alleles. Data from the largest available subset (0-150* nM; 9mer) is shown in Table 3 as an example.

TABLE 3

| Allele | Fraction correct |
|---|---|
| A0101 | 2/2 |
| A0201 | 9/11 |
| A0301 | 5/5 |
| A1101 | 4/4 |
| A2402 | 0/0 |
| A6801 | 3/4 |
| B0702 | 4/4 |
| B0801 | 1/2 |
| B1501 | 2/2 |

Only predictions for HLA A and B alleles are utilized as there is little available data on which to judge accuracy of predictions for HLA C alleles (Zhang et al).

An evaluation of melanoma sequence information and peptide binding predictions was conducted using information from the TCGA database. Information for 220 melanomas from different patients revealed that on average there were approximately 450 missense and 5 neoORFs per patient. 20 patients were selected at random and the predicted binding affinities were calculated for all the missense and neoORF mutations using netMHC (Lundegaard et al Prediction of epitopes using neural network based methods J Immunol Methods 374:26 (2011)). As the HLA allotypes were unknown for these patients, the number of predicted binding peptides per allotype were adjusted based on the frequency of that allotype (Bone Marrow Registry dataset for the expected affected dominant population in the geographic area [Caucasian for melanoma]) to generate a predicted number of actionable mutant epitopes per patient. For each of these mutant epitopes (MUT), the corresponding native (NAT) epitope binding was also predicted.

Utilizing the Prioritization Described Herein:

90% (18 of 20) of patients were predicted to have at least 20 peptides appropriate for vaccination;

For nearly a quarter of the patients, neoORF peptides could constitute half to all of the 20 peptides;

For just over half of the patients, only peptides in categories 1 and 2 would be used;

For 80% of the patients, only peptides in categories 1, 2, and 3 would be utilized.

Thus, there is a sufficient number of mutations in melanoma to expect a high proportion of patients to generate an adequate number of immunogenic peptides.

Example 7

Peptide Production and Formulation

GMP neoantigenic peptides for immunization is prepared by chemical synthesis Merrifield R B: Solid phase peptide synthesis. I. The synthesis of a tetrapeptide. J. Am. Chem. Soc. 85:2149-54, 1963) in accordance with FDA regulations. Three development runs have been conducted of 20 ~20-30mer peptides each. Each run was conducted in the same facility and utilized the same equipment as is used for the GMP runs, utilizing draft GMP batch records. Each run successfully produced >50 mg of each peptide, which were tested by all currently planned release tests (e.g., Appearance, Identify by MS, Purity by RP-HPLC, Content by Elemental Nitrogen, and TFA content by RP-HPLC) and met the targeted specification where appropriate. The products were also produced within the timeframe anticipated for this part of the process (approximately 4 weeks). The lyophilized bulk peptides were placed on a long term stability study and is evaluated at various time points up to 12 months.

Material from these runs has been used to test the planned dissolution and mixing approach. Briefly, each peptide is dissolved at high concentration (50 mg/ml) in 100% DMSO and diluted to 2 mg/ml in an aqueous solvent. Initially, it was anticipated that PBS would be used as a diluent, however, a salting out of a small number of peptides caused a visible cloudiness. D5W (5% dextrose in water) was shown to be much more effective; 37 of 40 peptides were successfully diluted to a clear solution. The only problematic peptides are very hydrophobic peptides.

Table 4 shows the results of solubility evaluations of 60 potential neoantigen peptides, sorted based on the calculated fraction of hydrophobic amino acids. As shown, almost all peptides with a hydrophobic fraction lower than 0.4 are soluble in DMSO/DSW, but a number of peptides with a hydrophobic fraction greater than or equal to 0.4 were not soluble in DMSO/D5W (indicated by "*" in the column labeled "Solubility in DMSO/D5W"). A number of these can be solubilized by addition of succinate (indicated by "**" in the column "Solubility in DMSO/D5W/Succinate"). 3 of 4 of these peptides had hydrophobic fractions between 0.4 and 0.43. Four peptides became less soluble upon addition of succinate; 3 of 4 of these peptides had a hydrophobic fraction greater than or equal to 0.45.

TABLE 4

| ID | SEQUENCES | SEQ ID NO: | Solubility in DMSO | Solubility In DMSO/D5W | pH of peptides in DMSO/D5W | Solubility DMSO/D5W/ Succinate | pH of peptides in DMSO/D5W/ 5 mM S. Succinate spike | pH of peptides in DMSO/D5W/ 5 mM Succinate and Hiltonol | Hydrophobicity | Hydrophillic | Approx. Isoelectric Point |
|---|---|---|---|---|---|---|---|---|---|---|---|
| CS6 715 | PPYPYSSP SLVLPTEP HTPKSLQQ PGLPS | 1 | Y | | 4.11 | | | | 0.17 | 0.10 | 7.86 |
| C56 722 | NPEKYKA KSRSPGSP VVEGTGSP PKWQIGE QEF | 2 | | | | | | | 0.18 | 0.27 | 9.45 |

TABLE 4-continued

| ID | SEQUENCES | SEQ ID NO: | Solubility in DMSO | Solubility In DMSO/D5W | pH of peptides in DMSO/D5W | Solubility DMSO/D5W/ S. Succinate | pH of peptides in DMSO/D5W/ 5 mM S. Succinate spike | pH of peptides in DMSO/D5W/ 5 mM Succinate and Hiltonol | Hydrophobicity | Hydrophillic | Approx. Isoelectric Point |
|---|---|---|---|---|---|---|---|---|---|---|---|
| CS6 725 | GTYLQGT ASALSQSQ ERPPSVNR VPPSSPSS QE | 3 | | Y | 3.95 | | | | 0.18 | 0.12 | 7.03 |
| CS7 416 | AESAQRQ GPNGGGE QSANEF | 4 | | Y | 3.91 | Y | 6.31 | 6.54 | 0.20 | 0.20 | 3.73 |
| CS6 710 | EPDQEAV QSSTYKDC NTLHLPTE RFSPVR | 5 | | Y | 3.65 | | | | 0.21 | 0.31 | 4.71 |
| CS6 712 | LKDSNSW PPSNKRGF DTEDAHK SNATPVP | 6 | | | | | | | 0.21 | 0.31 | 7.95 |
| CS6 781 | GASRRSSA SQGAGSL GLSEEKTL RSGGGP | 7 | | Y | | | | | 0.21 | 0.21 | 11.26 |
| CS6 718 | KKEKAEK LEKERQR HISKPLLG GPFSLTTH TGE | 8 | | Y | | | | | 0.21 | 0.45 | 10.31 |
| CS6 720 | SPTEPSTK LPGFDSCG NTEIAERK IKRIYGGF K | 9 | | Y | | | | | 0.21 | 0.30 | 9.48 |
| CS6 723 | ECGKAFTR GSQLTQH QGIHISEKS FEYKECGI D | 10 | | Y | 3.68 | | | | 0.21 | 0.33 | 6.14 |
| CS6 708 | SHVEKAHI TAESAQR QGPNGGG EQSANEF | 11 | | Y | | | | | 0.24 | 0.28 | 5.25 |
| CS6 721 | PIERVKKN LLKKEYN VSDDSMK LGGNNTSE KAD | 12 | | Y | | | | | 0.24 | 0.39 | 9.33 |
| CS6 916 | HKSIGQPK LSTHPFLC PKPQKMN TSLGQHLT L | 13 | | Y | | | | | 0.25 | 0.22 | 10.64 |
| CS7 417 | AESAQRQ GPLGGGE QSANEF | 14 | | Y | 3.82 | Y | 6.28 | 6.5 | 0.25 | 0.20 | 3.73 |
| CS6 717 | KPKKVAG AATPKKSI KRTPKKV KKPATAA GTKK | 15 | | Y | 4.65 | | | | 0.27 | 0.39 | 12.18 |

TABLE 4-continued

| ID | SEQUENCES | SEQ ID NO: | Solubility in DMSO | Solubility In DMSO/D5W | pH of peptides in DMSO/D5W | Solubility DMSO/D5W/ Succinate | pH of peptides in DMSO/D5W/ 5 mM S. Succinate spike | pH of peptides in DMSO/D5W/ 5 mM Succinate and Hiltonol | Hydro-phobicity | Hydro-phillic | Approx. Iso-electric Point |
|---|---|---|---|---|---|---|---|---|---|---|---|
| CS6 719 | SKLPYPVA KSGKRAL ARGPAPTE KTPHSGA QLG | 16 | | Y | 3.94 | | | | 0.27 | 0.24 | 11.1 |
| CS6 925 | EQGPWQS EGQTWRA AGGRVPV PCPAAGPG | 17 | | Y | | | | | 0.28 | 0.14 | 6.14 |
| CS6 915 | SGARIGAP PPHATATS SSSFMPGT WGREDL | 18 | | Y | | | | | 0.30 | 0.17 | 8.02 |
| CS6 919 | KLAWRGR ISSSGCPS MTSPPSPM FGMTLHT | 19 | | Y | 4.38 | Y | 6.74 | 6.99 | 0.30 | 0.13 | 11.38 |
| CS6 726 | DSAVDKG HPNRSALS LTPGLRIG PSGIPQAG LG | 20 | | Y | | | | | 0.30 | 0.18 | 10.26 |
| CS7 409 | LLTDRNTS GTTFTLLG VSDYPELQ VP | 21 | | Y | 3.86 | Y | 6.32 | 6.62 | 0.31 | 0.15 | 3.59 |
| CS6 709 | LTDLPGRI RVAPQQN DLDSPQQI LSISNAE | | X | | | NT | | | 0.31 | 0.21 | 3.91 |
| CS7 414 | KGASLDA GWGSPRW TTTRMTSA SAGRSTRA | 23 | | Y | 3.81 | Y | 6.71 | 6.99 | 0.31 | 0.21 | 12.5 |
| CS6 917 | FRLIWRSV KNGKSSRE QELSWNC SHQVPSLG A | 24 | | Y | | | | | 0.31 | 0.25 | 10.67 |
| CS6 938 | GKSRGQQ AQDRARH AAGAAPA RPLGALRE Q | 25 | | Y | | | | | 0.33 | 0.30 | 12.31 |
| CS7 408 | LLTDRNTS GTTFTLLG VSDYPELQ VPIPQAGL G | 26 | | Y | 3.89 | Y | 6.31 | 6.75 | 0.33 | 0.12 | 3.59 |
| CS6 711 | RGLHSQG LGRGRIA MAQTAGV LRSLEQEE | 27 | | Y | 3.82 | | | | 0.34 | 0.28 | 10.92 |
| CS6 716 | PQLAGGG GSGAPGE HPLLPGGA PLPAGLF | 28 | | Y | | | | | 0.34 | 0.07 | 5.08 |

TABLE 4-continued

| ID | SEQUENCES | SEQ ID NO: | Solubility in DMSO | Solubility In DMSO/ D5W | pH of peptides in DMSO/D5W | Solubility DMSO/D5W/ Succinate | pH of peptides in DMSO/D5W/ 5 mM S. Succinate spike | pH of peptides in DMSO/D5W/ 5 mM Succinate and Hiltonol | Hydro-phobicity | Hydro-phillic | Approx. Iso-electric Point |
|---|---|---|---|---|---|---|---|---|---|---|---|
| CS6 926 | TWAGHVS TALARPLG APWAEPG SCGPGTN | 29 | | Y | | | | | 0.34 | 0.10 | 7.05 |
| CS7 431 | KKNITNLS RLVVRPDT DAVY | 30 | | Y | 3.8 | Y | 6.45 | 6.69 | 0.35 | 0.30 | 10.29 |
| CS7 432 | WDGPPEN DMLLKEIC GSLIP | 31 | | Y | 3.72 | Y | 6.22 | 6.45 | 0.35 | 0.25 | 3.43 |
| CS6 930 | LAASGLH GSAWLVP GEQPVSGP HHGKQPA GV | 32 | | Y | | | | | 0.35 | 0.16 | 8.17 |
| CS6 729 | PIQVFYTK QPQNDYL HVALVSV FQIHQEAP SSQ | 33 | | Y | 3.87 | | | | 0.36 | 0.15 | 6.15 |
| CS6 931 | VAGLAAS GLHGSAW LVPGEQPV SGPHHGK Q | 34 | | Y | 3.80 | Y | 6.42 | 6.66 | 0.37 | 0.17 | 8.17 |
| CS6 934 | SKRGVGA KTLLLPDP FLFWPCLE GTRRSL | 35 | | Y | 3.86 | Y | 6.57 | 6.79 | 0.38 | 0.24 | 10.67 |
| CS6 936 | SYKKLPLL IFPSHRRA PLLSATGD RGFSV | 36 | | Y | | | | | 0.38 | 0.24 | 11.48 |
| CS6 914 | GLLSDGSG LGQITWAS AEHLQRP GAGAELA | 37 | | Y | | | | | 0.40 | 0.17 | 4.4 |
| CS6 932 | DLCICPRS HRGAFQL LPSALLVR VLEGSDS | 38 | | Y | | | | | 0.40 | 0.23 | 6.9 |
| CS6 935 | DASDFLPD TQLFPHFT ELLLPLDP LEGSSV | 39 | | N | | Y | | | 0.40 | 0.23 | 3.2 |
| CS6 943 | DMAWRR NSRLYWLI KMVEQW QEQHLPSL SS | 40 | | Y | | | | | 0.40 | 0.27 | 9.79 |
| CS7 428 | LSVPFTCG VNFGDSIE DLEI | 41 | | N | n/a | Y | n/a | n/a | 0.40 | 0.20 | 2.75 |
| CS7 430 | PLMQTEL HQLVPEA DPEEMA | 42 | | Y | 3.95 | Y | 6.23 | 6.37 | 0.40 | 0.30 | 3.35 |

TABLE 4-continued

| ID | SEQUENCES | SEQ ID NO: | Solubility in DMSO | Solubility In DMSO/ D5W | pH of peptides in DMSO/D5W | Solubility DMSO/D5W/ Succinate | pH of peptides in DMSO/D5W/ 5 mM S. Succinate spike | pH of peptides in DMSO/D5W/ 5 mM Succinate and Hiltonol | Hydro-phobicity | Hydro-phillic | Approx. Iso-electric Point |
|---|---|---|---|---|---|---|---|---|---|---|---|
| CS6918 | EDLHLLSVPCPSYKKLPLLIFPSHRRAPLLSA | 43 | | Y | | | | | 0.41 | 0.25 | 9.67 |
| CS6941 | AHRQGEKQHLLPVFSRLALRLPWRHSVQL | 44 | | Y | 3.92 | Y | 6.49 | 6.78 | 0.41 | 0.31 | 12.5 |
| CS7410 | ALSLTPGLRIGPSGLFLVFLAESAVDKGHPNRS | 45 | | Y | 3.99 | Y | 6.46 | 6.88 | 0.42 | 0.18 | 10.26 |
| CS7411 | DSAVDKGHPNRSALSLTPGLRIGPSGLFLVFLA | 46 | | Y | 3.87 | Y | 6.53 | 6.94 | 0.42 | 0.18 | 10.26 |
| CS7412 | LRVFIGNIAVNHAPVSLRPGLGLPPGAPPGTVP | 47 | | Y | 4.24 | N | 6.61 | 6.96 | 0.42 | 0.09 | 12.49 |
| CS7438 | LPVFIGNIAVNHAPVSLRPGLGLPPGAPPGTVP | 48 | | Y | 4.24 | Y | 6.78 | 6.96 | 0.42 | 0.06 | 11.18 |
| CS6942 | VSWGKKVQPIDSILADWNEDIEAFEMMEKD | 49 | | N | | Y | | | 0.43 | 0.37 | 3.68 |
| CS7415 | GTKALQLHSIAGRWPRMEPWVVESMSLGVP | 50 | | Y | 3.91 | Y | 6.61 | 6.81 | 0.43 | 0.20 | 10.26 |
| CS6937 | SGQPAPEETVLFLGLLHGLLLILRRLRGG | 51 | | Y | 3.87 | N | 6.51 | 6.76 | 0.45 | 0.21 | 10.98 |
| CS7418 | YLLPKTAVVLRCPALRVRKP | 52 | | Y | 3.98 | Y | 6.76 | 6.96 | 0.45 | 0.25 | 11.48 |
| CS7420 | IGALNPKRAAFFAEHYESWE | 53 | | Y | 3.84 | N | 6.38 | 6.56 | 0.45 | 0.30 | 5.38 |
| CS7425 | SYDSVIRELLQKPNVRVVVL | 54 | X | Y | 3.78 | N | 6.44 | 6.65 | 0.45 | 0.25 | 9.79 |
| CS7427 | VEQGHVRVGPDVVTHPAFLV | 55 | | Y | 3.72 | Y | 6.34 | 6.52 | 0.45 | 0.25 | 6.15 |
| C56927 | APALGPGAASVASRCGLDPALAPGGSHMLRA | 56 | | Y | | | | | 0.45 | 0.13 | 8.99 |

TABLE 4-continued

| ID | SEQUENCES | SEQ ID NO: | Solubility in DMSO | Solubility In DMSO/D5W | pH of peptides in DMSO/D5W | Solubility DMSO/D5W/ Succinate | pH of peptides in DMSO/D5W/ 5 mM S. Succinate spike | pH of peptides in DMSO/D5W/ 5 mM Succinate and Hiltonol | Hydrophobicity | Hydrophillic | Approx. Isoelectric Point |
|---|---|---|---|---|---|---|---|---|---|---|---|
| CS6783 | LLTDRNTSGTTFTLLGVSDYPELQVPLFLVFLA | 57 | | N | 3.96 | Y | | | 0.45 | 0.12 | 3.59 |
| CS6933 | EEGLLPEVFGAGVPLALCPAVPSAAKPHRPRVL | 58 | | Y | | | | | 0.45 | 0.21 | 7.05 |
| CS7413 | VQLSIQDVIRRARLSTVPTAQRVALRSGWI | 59 | | Y | 3.9 | Y | 6.73 | 7.02 | 0.47 | 0.20 | 12.68 |
| CS6730 | LPVFIGNIAVNHAPVSLRPGLGLPPGAPPLVVP | 60 | | Y | 4.20 | | | | 0.48 | 0.06 | 11.18 |

The predicted biochemical properties of planned immunizing peptides are evaluated and synthesis plans may be altered accordingly (using a shorter peptide, shifting the region to be synthesized in the N- or C-terminal direction around the predicted epitope, or potentially utilizing an alternate peptide) in order to limit the number of peptides with a high hydrophobic fraction.

Ten separate peptides in DMSO/D5W were subjected to two freeze/thaw cycles and showed full recovery. Two individual peptides were dissolved in DMSO/D5W and placed on stability at two temperatures (−20° C. and −80° C.). These peptides were evaluated (RP-HPLC and pH and visual inspection) for up to 24 weeks. Both peptides are stable for up to 24 weeks; the percent impurities detected by the RP-HPLC assay did not change significantly for either peptide when stored at either −20° C. or −80° C. Any small changes appear to be due to assay variability as no trends were noted to be evaluated.

Figure 6:
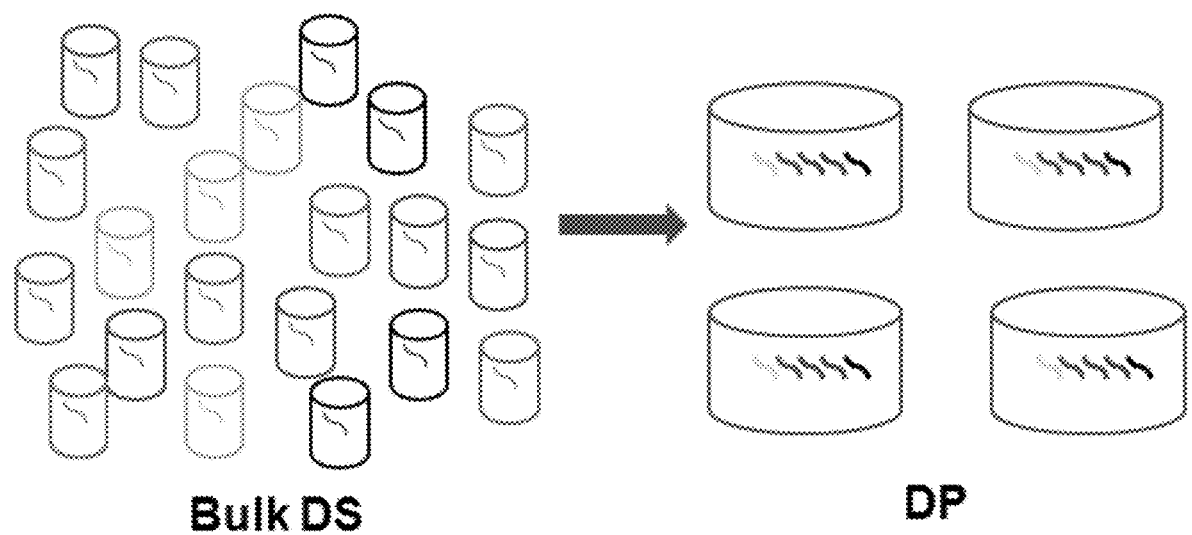
FIG. 6 shows a schematic depicting drug product processing of individual neoantigenic peptides into pools of 4 subgroups according to an exemplary embodiment of the invention.
Figure 7:
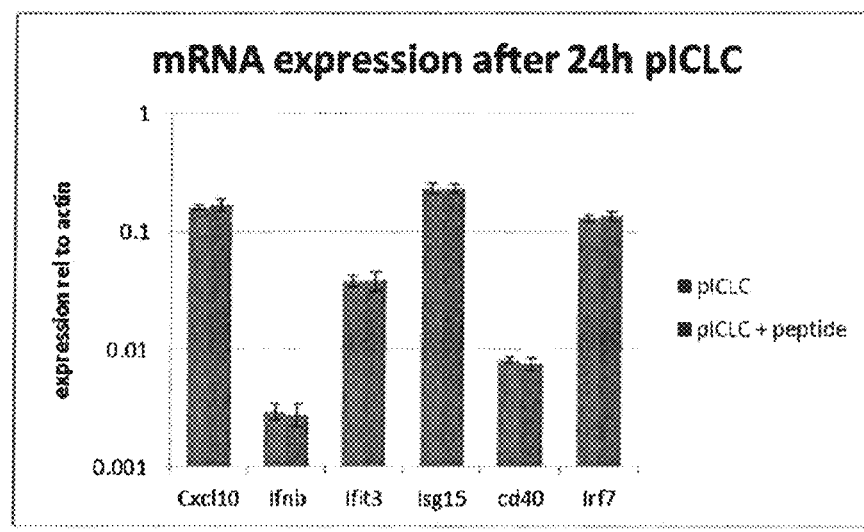
FIG. 7 shows the results of quantitative PCR to assess the levels of induction of a number of key immune markers after stimulation of mouse dendritic cells using a neoantigenic formulation.

As shown in FIG. 6, the design of the dosage form process are to prepare 4 pools of patient-specific peptides consisting of 5 peptides each. A RP-HPLC assay has been prepared and qualified to evaluate these peptide mixes. This assay achieves good resolution of multiple peptides within a single mix and can also be used to quantitate individual peptides.

Membrane filtration (0.2 μm pore size) is used to reduce bioburden and conduct final filter sterilization. Four different appropriately sized filter types were initially evaluated and the Pall, PES filter (#4612) was selected. To date, 4 different mixtures of 5 different peptides each have been prepared and individually filtered sequentially through two PES filters. Recovery of each individual peptide was evaluated utilizing the RP-HPLC assay. For 18 of the 20 peptides, the recovery after two filtrations was >90%. For two highly hydrophobic peptides, the recovery was below 60% when evaluated at small scale but were nearly fully recovered (87 and 97%) at scale. As stated herein, approaches are undertaken to limit the hydrophobic nature of the sequences selected.

A peptide pool (Pool 4) consisting of five peptides was prepared by dissolution in DMSO, dilution with D5W/Succinate (5 mM) to 2 mg/ml and pooling to a final peptide concentration of 400 μg per ml and a final DMSO concentration of 4%. After preparation, peptides were filtered with a 25 mm Pall PES filter (Cat #4612) and dispensed into Nunc Cryo vials (#375418) in one ml aliquots. Samples were analyzed at time zero and at 2 and 4 weeks to date. Additional samples are analyzed at 8 and 24 weeks. At −80° C., no significant change in the HPLC profiles or impurity profile of the peptide Pool 4 was observed at the four-week time point. Through the 4 week time point, visual observation and pH for the peptide pool did not change.

Example 8

Peptide Synthesis

GMP peptides are synthesized by standard solid phase synthetic peptide chemistry (e.g., using CS 536 XT peptide synthesizers) and purified by RP-HPLC. Each individual peptide is analyzed by a variety of qualified assays to assess appearance (visual), purity (RP-HPLC), identity (by mass spectrometry), quantity (elemental nitrogen), and trifluoroacetate counterion (RP-HPLC) and released.

The personalized neoantigen peptides may be comprised of up to 20 distinct peptides unique to each patient. Each peptide may be a linear polymer of ~20-~30 L-amino acids joined by standard peptide bonds. The amino terminus may be a primary amine (NH2-) and the carboxy terminus is a carbonyl group (—COOH). The standard 20 amino acids commonly found in mammalian cells are utilized (alanine, arginine, asparagine, aspartic acid, cysteine, glutamine, glutamic acid, glycine, histidine, isoleucine, leucine lysine, methionine, phenylalanine, proline, serine, threonine, tryptophan, tyrosine, valine). The molecular weight of each peptide varies based on its length and sequence and is calculated for each peptide.

Fmoc (9-fluorenylmethoyloxycarbnyl)-N-terminal protected amino acids are utilized for all synthesis reactions. The side chains of the amino acids are protected by 2,2,4,6,7-pentamethyl-dihydrobenzofuran-5-sulfonyl (Pbf), triphenylmethyl (Trt), t-butyloxycarbonyl (Boc) or t-butyl ether (tBu) group as appropriate. All bulk amino acids are dissolved in dimethylformamide (DMF). Condensation utilizes the following two catalyst combinations in separate reactions:

Diisopylcarbodiimide/1-Hydroxybenzotriazole (DIC/HOBT)
Diisoprolyethylamine/2-(1H-Benzotriazol-1-yl)-1,1,3,3-tetramethyluronium hexafluorophosphate (DIEA/HBTU)

Each amino acid is coupled twice in order to ensure high level of incorporation. The first coupling utilizes DIC/HOBT for 2-6 hours and the second coupling utilizes DIEA/HBTU for 1-2 hours. Each of the two couplings are monitored by UV absorbance and the resin is washed extensively with DMF in between coupling cycles to improve efficiency. After two cycles of coupling, calculated coupling efficiency must be at least 95% to continue to the next cycle. Further synthesis of any peptides that do not meet that minimal coupling efficiency is stopped.

After all amino acids have been coupled, the resin is washed twice with DMF and subsequently three times with methanol. The resin is then vacuum dried briefly while still in the reaction vessel and then transferred to a new, tared vessel for vacuum drying (greater than 12 hours) until it is freely flowing. The mass of crude peptide synthesized is determined by weighing the vessel containing dried resin, subtracting the mass of the tared vessel and adjusting for the resin mass. Expected mass yields range from 60%-90%. Any synthesis that failed to produce at least 200 mg crude peptide is terminated. The dried resin may be stored at 4° C. for up to 28 days prior to initiation of cleavage.

The cleavage reaction is conducted in a single room. Prior to transfer of the set of patient-specific dried resins from the synthesis room to the cleavage room, the cleavage room is fully qualified by QA for synthesis of a new GMP product. Qualification includes line clearance inspection, verification of GMP suite cleaning, staging of all required materials and glassware, verification of equipment suitability and labeling, and verification that all required personnel are properly trained and qualified to conduct the work and are properly gowned and free of apparent illness.

Room readiness operations initiates with verification of the equipment to be used (rotary evaporator, vacuum pump, balance) and inspection of documentation indicating that the equipment has been properly cleaned and calibrated (if appropriate). A complete list of all raw materials (TFA, triisopropylsilane (TIS) and 1,2-ethanedithiol) required is issued by QA and manufacturing identifies lot number to be utilized, retest or expiration date and quantity of material dispensed for each day's reactions.

Cleavage of the peptide chain from the resin and cleavage of the side chain protecting groups are accomplished under acidic conditions (95% TFA) in the presence of 2% triisopropylsilane (TIS) and 1% 1,2-ethanedithiol as scavengers of acid-generated free-radicals for 3 to 4 hours at room temperature.

Resin is separated from free crude peptide by filtration. The final solution of released and de-protected peptide undergoes precipitation with ether and the precipitate is freeze-dried for 12 hours. The yield of released crude peptide is determined by weighing the freeze-dried powder and calculating the ratio of released peptide/resin-bound peptide. Expected yields of crude peptide are 200 mg to 1000 mg. Any cleavage reaction that fails to yield at least 200 mg crude peptide is terminated. The crude peptide is then transferred to the purification suite.

The purification is conducted in a single room. Prior to transfer of the set of dried crude peptide from the cleavage room to the purification room, the purification room is fully qualified by Quality Assurance for synthesis of a new GMP product. Qualification includes line clearance inspection, verification of GMP suite cleaning, staging of all required materials and glassware, verification of equipment suitability and labeling, and verification that all required personnel are properly trained and qualified to conduct the work and are properly gowned and free of apparent illness.

Room readiness operations initiates with verification of the equipment to be used (preparative Reverse-Phase High-Performance Liquid Chromatography [RP-HPLC], balance, analytical Liquid Chromatography/Mass Spectrometer (LC/MS), lyophilizer, balance) and inspection of documentation indicating that the equipment has been properly cleaned and calibrated (if appropriate). A complete list of all raw materials (trifluoroacetic acid [TFA], acetonitrile [ACN], water) required is issued by QA and Manufacturing identifies lot number to be utilized, retest or expiration date and quantity of material dispensed for each day's reactions.

Purification is initiated by dissolving no more than 200 mg of the freeze-dried released peptide in ACN. The sample is then further diluted with water to 5%-10% ACN. TFA is added to a final concentration of 0.1%. One C-18 RP-HPLC column (10 cm×250 cm) is freshly packed prior to the initiation of each set of patient specific peptides. Columns are extensively washed with 5% acetonitrile containing 0.1% TFA prior to loading patient peptide. Maximum amount of peptide loaded onto a single column is 200 mgs. Columns are monitored by UV observance at 220 nm. Following loading of single peptide, the sample is allowed to enter the column and column is washed with 5% acetonitrile/0.1% TFA. A 10%-50% gradient of acetonitrile with 0.1% TFA is used to elute the peptide. Fractions is collected (50 ml each) beginning at the point UV observance is at 20% above baseline. Fractions continue to be collected until no further UV absorbing material is eluting from the column or the gradient is complete. Typically, the main elution peak is separated into 4 to 8 fractions.

Each individual fraction is assessed by analytical LC/MS. Analytical conditions chosen is based on the percent acetonitrile associated with the peak eluted product. Fractions with the expected mass and purity greater than or equal to 95% is pooled as peptide product. Typically 2 to 4 fractions meet this pooling requirement. The pooled peptide is placed into a tared jar for freeze-drying and freeze-dried for 24 to 72 hours. The mass of lyophilized peptide is determined by determining the mass of the jar containing freeze-dried peptide and subtracting the mass of the tared jar.

Portions of the freeze-dried peptide is transferred to quality control for analysis and disposition. The remaining is stored at −20° C. prior to further processing.

Any peptides for which none of the fractions meet the requirement of 95% purity is discarded. No reprocessing of RP-HPLC fractions can occur. If sufficient unpurified freeze-dried and cleaved peptide is available, a second sample of the peptide may be purified over the column, adjusting the gradient conditions to improve purity of the eluted peptide.

The column can then be stripped of any remaining peptide by washing extensively with 4 column volumes of 100% ACN/0.1% TFA and then re-equilibrated with 5% ACN/0.1% TFA prior to loading the next peptide.

Peptides for an individual patient is sequentially processed over the same column. No more than 25 peptides are processed over a single column.

Unit operations for drug substance manufacturing thus constitute:
Synthesis:
Condensation, wash and re-condensation for each amino acid
Resin washing and vacuum drying
Transfer to the cleavage suite
Cleavage:
Acid cleavage from the resin
Separation of released peptide from the resin and peptide precipitation
Transfer to the purification suite
Purification:
Dissolution in acetonitrile and RP-HPLC purification
Freeze-drying of peak fractions for 24 to 72 hours
Removal of aliquots for QC testing and storage of remaining lyophilized product.

Personalized neoantigen peptides may be supplied as a box containing 2 ml Nunc Cryo vials with color-coded caps, each vial containing approximately 1.5 ml of a frozen DMSO/D5W solution containing up to 5 peptides at a concentration of 400 ug/ml. There may be 10-15 vials for each of the four groups of peptides. The vials are to be stored at −80° C. until use. Ongoing stability studies support the storage temperature and time.

Storage and Stability: The personalized neoantigen peptides are stored frozen at −80° C. The thawed, sterile filtered, in process intermediates and the final mixture of personalized neoantigen peptides and poly-ICLC can be kept at room temperature but should be used within 4 hours.

Compatibility: The personalized neoantigen peptides are mixed with ⅓ volume poly-ICLC just prior to use.

Example 9

NeoVax. A Neoplasia Vaccine, and Nivolumab in Preventing Relapse Following Autologous Stem-Cell Transplantation in Non-Hodgkin's Lymphoma (NHL).

Three exemplary dosing regimens are provided herein. The first two are focused on improving the activity of Nivolumab, a fully human IgG4 monoclonal antibody developed for the treatment of cancer that acts by blocking ligand activation of the programmed cell death 1 (PCD1) receptor on activated T cells, by evaluating the combination of the novel personalized neoantigen vaccine (also referred to herein as "NeoVax," and disclosed in U.S. Provisional Application 61/869,721, 61/809,406 and 61/913,127, incorporated by reference in their entireties herein), and Nivolumab. The third dosing regimen focuses on improving the safety and activity profile of Ipilimumab, a monoclonal antibody directed against cytotoxic T-lymphocyte-associated antigen-4 (CTLA4), either alone or in combination with Nivolumab by reducing Ipilimumab overall exposure, enabled by a focusing of Ipilimumab co-therapy to the time-frame of the developing the immune response to NeoVax. This reduced exposure is enabled by the combination with an effective vaccine and can be achieved by either reducing the dose of Ipilimumab or lengthening the period between doses or by delivering Ipilimumab subcutaneously near to the vaccination site and temporally coincident with vaccination. Each is explained in more detail herein.

Autologous Hematopoietic Stem Cell Transplant (AHSCT) is an effective option for patients suffering relapse after initial induction therapy but long term remission and cures are rarely observed. Recently, based on the observed expression of programmed cell death 1 ligand (PDL1) on the surface of diffuse large B-cell lymphoma (DLBCL) and primary mediastinal large B-cell lymphoma (PMLBCL), a study of anti-PD1 antibody (pidilizumab) treatment following AHSCT was conducted (Armand et al. Journal of Clinical Oncology 31:4199 (2013)); incorporated by reference in its entirety herein). That study showed encouraging indications of beneficial activity including improved progression free survival in anti-PD1 treated patients compared to other recent clinical trials, changes in immune cell populations consistent with effective reversal of PD-1 mediated suppression, and an increase in survival of CD4+, CD54RO+ memory cells. Nevertheless, improved therapies are needed, particularly for patients who demonstrate residual disease after AHSCT.

While anti-PD1 therapy may help relieve local immune suppression and over-come T-cell exhaustion or anergy, limitations on the number and specificity of the existing T-cell population may prevent maximal impact of this effect. Hence, combining anti-PD1 therapy with an immune stimulating approach, such as a cancer vaccine, may allow anti-PD1 to demonstrate maximal clinical benefit.

NeoVax (a neoplasia vaccine) is a novel personalized cancer vaccine utilizing the exquisitely tumor-specific neoantigens created by the personal mutations found in each patient's tumor (Hacohen et al Cancer Immunology Research 1:11 (2013); Heemskerk et al. EMBO Journal 32:194 (2013); both incorporated by reference herein). These mutations, because they result in peptides that are distinct from "self"-peptides, create epitopes that are expected to escape the immune dampening effects of central tolerance. NeoVax vaccine therapy is being developed to create stronger and more durable responses than those characteristic of the multiple native antigen ("Tumor Associated Antigens; TAAs) which have clinically proven ineffective to date alone, or in combination with checkpoint blockade inhibition. NeoVax product is disclosed in disclosed in U.S. Provisional Application 61/869,721, 61/809, 406 and 61/913,127, incorporated by reference in their entireties herein, and utilizes multiple (~20) long peptides as immunogens, each representing separate target epitopes, and poly-ICLC as adjuvant. Long peptides and polyICLC represent the "best in class" delivery system and immune adjuvant respectively. The first-in-human clinical study with NeoVax is described on ClinicalTrials.gov (NCT 01970358).

Combining an effective immune stimulating agent with the relief of immune suppression would be expected to improve clinical outcome. The post-AHSCT setting is characterized by a low volume of residual disease, the infusion of immune cells to a situation of homeostatic expansion, and the absence of any standard relapse-delaying therapy. These features provide a unique opportunity to test the impact of a checkpoint inhibitor, such a Nivolumab, plus NeoVax therapy to delay disease relapse.

Figure 8:
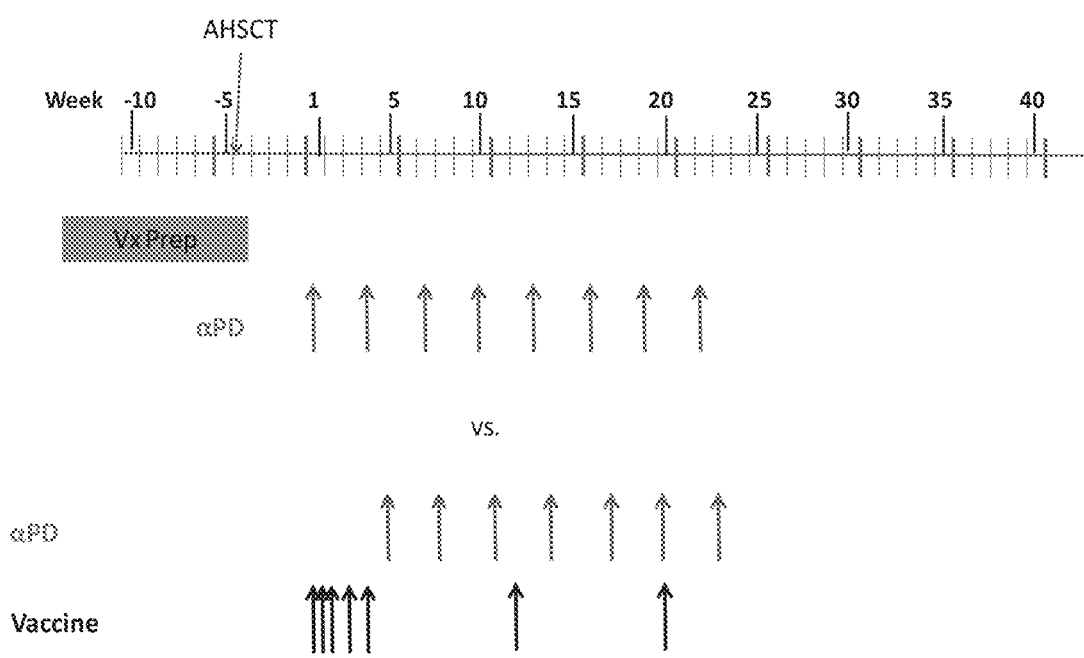
FIG. 8 is a schematic outline of study 1: Nivolumab vs Nivolumab and NeoVax following AHSCT in Non-Hodgkin's Lymphoma.

An exploratory two arm study is carried out to compare treatment with Nivolumab alone vs Nivolumab and NeoVax in a small number of patients to evaluate safety and to monitor the impact of treatment on Progression Free Survival (PFS) and, for any patients with measurable disease at the time of confirmatory screening, for Objective Response Rate (ORR). Patients are consented prior to initiation of pre-transplant conditioning in order to collect and sequence tumor tissue for vaccine preparation and is randomized at time of a confirmatory CT screening (approximately 4 weeks prior to of initiation of therapy). Fifteen patients are included in each agent arm. The results are compared to comparable patients receiving no additional post-AHSCT at this institution(s). An outline of the study is shown in FIG. 8.

Therapy can initiate 4 weeks after AHSCT. The schedule for the individual arms are as follows:
Nivolumablhi1
  Nivolumab: Vx on days 1, 4, 8, 15, 22 (Weeks 1, 2, 3 and 4; "Priming") and boosts at weeks 11 and 19. Nivolumab (3 mg/kg) beginning at week 5 and continuing each 3 weeks thereafter with a last dose at week 23.

Patients on the vaccine alone arm with progressive disease may, at the discretion of the investigator and the PI, begin receiving Nivolumab at about 3 weeks to attempt rescue.

CT scans are conducted every 4 months after initiation of therapy (with confirmatory PET scans at the discretion of the treating physician) with a final CT scan at 16 months after initiation of therapy. All patients receiving NeoVax is evaluated for immune responses to the immunizing peptides.

This study can provide additional safety information in this setting but most importantly extend and improve, with NeoVax, the encouraging results observed already with pidilizumab in this setting.

Example 10

NeoVax and Nivolumab in Metastatic Clear Cell Renal Cell Carcinoma and Melanoma.

Clear cell Renal Cell Carcinoma (ccRCC) and metastatic melanoma are both tumor types that have been shown to be responsive to immune modulating therapies, including cytokines, vaccines and inhibition of checkpoint blockade. Multiple immune modulating therapies have been approved for both diseases, including Ipilimumab for metastatic melanoma. Nivolumab has been evaluated as a single agent in non-blinded, non-randomized Phase I/II trial with encouraging results in both diseases and multiple pivotal studies are currently underway utilizing Nivolumab alone or Nivolumab and Ipilimumab combinations.

Despite this success of checkpoint blockade, there are still many patients who do not respond or do not respond robustly and the lack of coincident targeted immune stimulation with an effective vaccine may prevent the maximal impact of such therapy. Checkpoint blockade therapy alone may help relieve local immune suppression and over-come T-cell exhaustion or anergy, but may be limited by the number and specificity of the existing T-cell population—those T cells arising from the normal physiological presentation of the evolving tumor to the host immune system. Indeed, in many animal studies, including the studies supporting the initial development of Ipilimumab, anti-CTLA4 treatment alone was only mildly effective but was considerably more effective when combined with a vaccine.

Combining an effective vaccine with the relief of immune suppression may qualitatively broaden the repertoire of T cell targets as well as strengthen the activity of extant and newly induced T cells and could thus significantly improve clinical outcomes.

Figure 9:
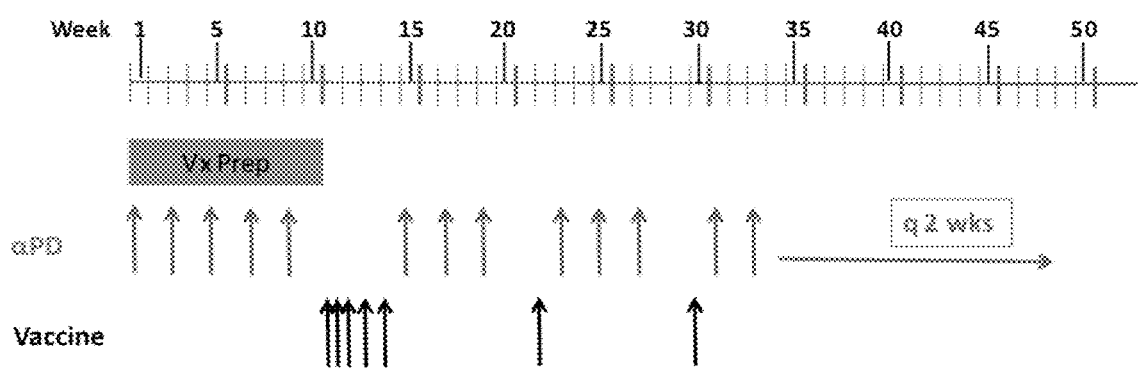
FIG. 9 is a schematic outline of study 2: Nivolumab and NeoVax in metastatic melanoma and metastatic RCC.

Separate studies are carried out combining NeoVax with Nivolumab in previously untreated metastatic melanoma patients (with a surgically accessible tumor for sequence analysis) and in previously untreated metastatic clear cell Renal Cell Carcinoma patients who have a resectable primary tumor in place. An outline of the studies are shown in FIG. 9. Each study is a two-arm study comparing Nivolumab alone to Nivolumab+NeoVax. Patients are consented prior to surgery. Patients are evaluated for Objective Response Rate (ORR), Progression Free Survival (PFS) and Overall Survival (OS). Nivolumab isgin dosing at the standard single agent dosing level of 3 mg/kg as soon as acceptable following surgical tumor removal and continue each 2 weeks until documented progression, discontinuation due to toxicity or withdrawal of consent. NeoVax therapy can initiate approximately 8 weeks after tumor resection is administered on days 1, 4, 8, 15, and 22 (Weeks 1, 2, 3 and 4; "Priming Phase") and on weeks 11 and 19 ("boosts"). Nivolumab is withheld during the period of priming vaccinations. 15 patients are included in each arm.

Upon initial indication of progressive disease, patients may, at the discretion of the investigator, continue on therapy or on the protocol until confirmation or not of disease progression (which must be resolved within 6 weeks of initial indication).

CT scans are conducted every 4 months after initiation of therapy (with confirmatory PET scans at the discretion of the treating physician) with a final CT scan at 24 months after initiation of therapy. All patients receiving NeoVax is evaluated for immune responses to the immunizing peptides.

An effective vaccine provides the opportunity to considerably improve the clinical outcome of Nivolumab therapy by increasing the breadth of T-cell responses and NeoVax is a first-in-class vaccine focused on neoantigens, a class of highly personal-tumor specific epitopes not subject to the immune dampening effects of self-tolerance. Reciprocally, checkpoint blockade inhibition during vaccination may increase the breadth and immune response level to NeoVax. These exploratory studies are done in disease settings different than the ongoing pivotal studies (prior to failure with Ipilimumab for Melanoma and prior to systemic anti-VEGF targeted therapy for RCC) allowing collection of safety and efficacy data of Nivolumab alone in these settings.

Example 11

Reduced Dose/Schedule Ipilimumab in Combination with NeoVax in High Risk Melanoma (without Nivolumab) and Metastatic Melanoma (with Systemic Nivolumab).

CTLA4 was initially identified as negative regulator on the surface of T-cells that was upregulated shortly after initiation of a de novo immune response or stimulation of an existing response in order to dampen the subsequent immune T-cell response and prevent auto-immunity or uncontrolled inflammation. Thus, the magnitude of the developing immune response has been closely tied to CTLA4 action. Therapy with anti-CTLA4 antibodies, such as Ipilimumab, was expected to increase the anti-cancer response by blocking the negative regulatory signal and allowing more extensive T-cell expansion. Although many animal and human correlative studies have suggested other possible mechanisms of action, the clinical responses observed with Ipilimumab are consistent with such a hypothesis and recently it was shown that antigen-specific T-cells to a personal neoantigen in a patient treated with Ipilimumab were observed prior to Ipilimumab therapy and increased following therapy (van Rooij et al, Journal of Clinical Oncology 31:e439 (2013)).

Many studies in animals have shown that combining anti-CTLA4 treatment with a vaccine enhances, sometimes dramatically, the anti-cancer effect and anecdotal information in humans suggests the same (Hodi et al, PNAS USA 105:3005-3010, 2008; Hodi et al., PNAS USA 100:4712-7; Le et al, J Immunother 36:382-9, 2013). This may depend critically on the antigen as the most dramatic effects of the combination in animals and the effects in humans are typically observed with complex vaccines such as autologous cellular vaccines and were not observed with a standard individual tumor associated antigen (such as gp100 for melanoma). Autologous tumor cell vaccines contain both neoantigens and tumor associated antigens (Hodi et al, 2008 and 2003). In the study of Le et al. (2013), a mixture of two pancreatic allogeneic tumor cell lines was used as the immunogen. Although it is unlikely there was any overlap of almost all neoantigens between the cell lines and the patients, pancreatic cancer is characterized by frequent K-ras mutations at position 12 which can be immunogenic for multiple HLA types (Weden et al., Int J Cancer 128: 1120-8, 2011).

Nivolumab, an anti-Programmed Death Receptor 1 (PD1) antibody, may have a distinct mechanism of action. The ligand for PD1, PDL1, is often over-expressed on tumor cells in the native tumor micro-environment and is an inhibitory ligand, causing T-cell anergy/exhaustion of tumor infiltrating lymphocytes. It seemed likely therefore that a combination of anti-CTLA4 and anti-PD1 antibodies may yield greater positive results because they have different mechanisms of action and this has been observed in animals (Duraiswamy et al, Cancer Res; 73(12) and possibly in humans (Wolchok J D et al., N Engl J Med, 2013). Unfortunately, the combination therapy appears to be more toxic both in the initial report and in ongoing clinical evaluation (Wolchok, 2013).

One approach to reducing the apparent toxicity while maintaining or increasing efficacy of the combination therapy would be to add in an effective vaccine to the therapeutic regimen (to directly generate effective de novo T cell responses to additional antigens) and simultaneously reduce the total exposure to checkpoint blockade antibodies. Although the two CPB Abs have not been compared side-by-side, in general anti-CTLA4 appears to generate a higher toxicity profile than anti-PD1, consistent with the effects observed in knock-out mice. Given that CTLA4 has a clear role in the de novo immune response, this would suggest that limiting anti-CTLA4 exposure to the time frame of antigen exposure may achieve both toxicity reduction and maintenance of efficacy.

Figure 10A:
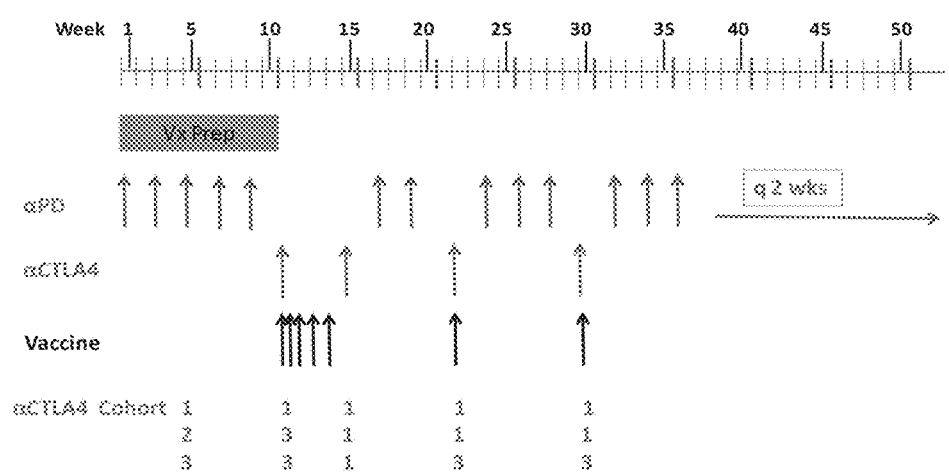
FIG. 10A-D are schematics of four studies. (A) Study 3a shows dose escalation of reduced intensity intravenous Ipilimumab in metastatic melanoma. (B) Study 3b shows dose escalation of sub-cutaneous Ipilimumab (Local) in metastatic melanoma. (C) Study 3c shows dose escalation of reduced intensity intravenous Ipilimumab in high-risk Melanoma. (D) Study 3d shows dose escalation of sub-cutaneous Ipilimumab (Local) in high-risk melanoma.
Figure 10B:
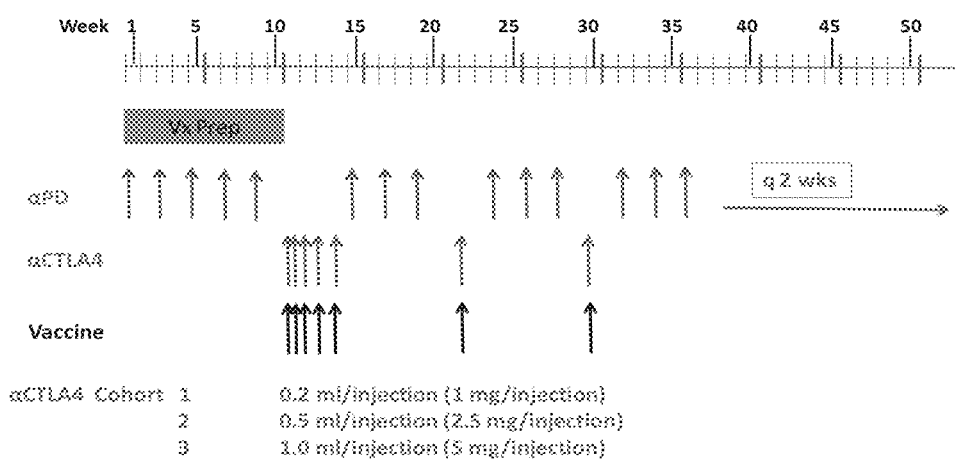
Figure 10C:
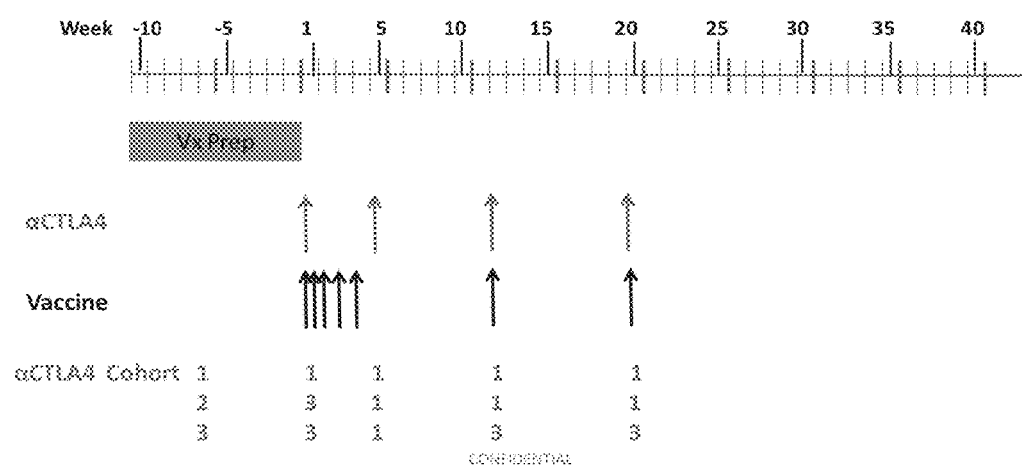
Figure 10D:
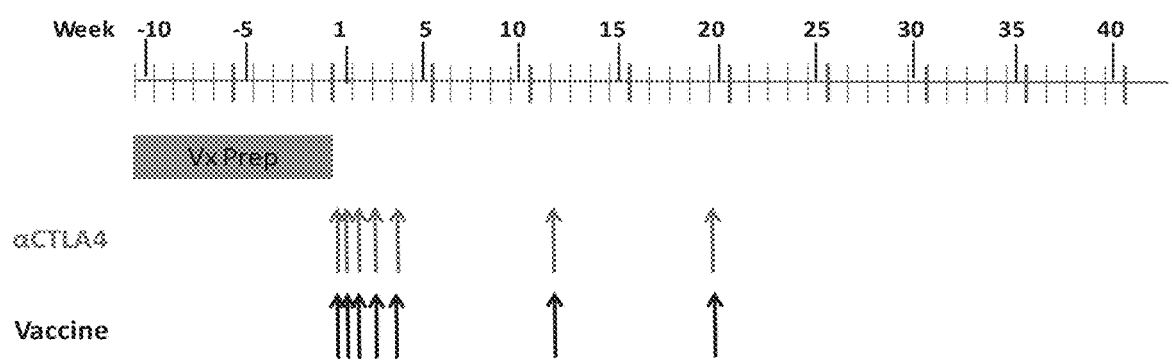

Described herein are four exploratory studies in melanoma patients. Studies 3A and 3B, outlined in FIGS. 10A and 10B, are in metastatic disease and utilize both Ipilimumab and Nivolumab. Studies 3C and 3D, outlined in FIGS. 10C and 10D, mirror 3A and 3B except that the setting is high-risk disease and do not utilize Nivolumab.

The first study (3A) is a 3 cohort dose escalating (dose escalating for Ipilimumab only) study in metastatic melanoma patients. Patients are consented prior to surgery. Five patients can initially be included in each cohort. In each cohort, patients can receive Nivolumab beginning just after surgical excision (for tumor sequencing) at 3 mg/kg (the dose being evaluated in all Nivolumab alone phase 3 studies) each 2 weeks until NeoVax has been prepared. Nivolumab is with-held during the priming vaccination phase and during the weeks prior to or during the boost when Ipilimumab is being given. NeoVax therapy can initiate approximately 8 weeks after tumor resection and is administered on days 1, 4, 8, 15, and 22 (Weeks 1, 2, 3 and 4; "Priming Phase") and on weeks 11 and 19 ("boosts"). Nivolumab is resumed in the week following the last priming dose and in the week following each boost. In the first cohort, patients can receive Ipilimumab at the start of the priming cycle, one week after the 5th priming dose and prior to each boost, all at a dose of 1 mg/kg. The next cohort can increase the dose associated with the start of priming vaccination to 3 mg/kg (the therapeutically approved level) and the dose associated with the end of priming and the boosts can remain at 1 mg/kg. For the third cohort, the start of priming dose and the dose associated with each boost is at 3 mg/kg. (See graphic view of the schedule herein). The maximal exposure to Ipilimumab can thus be three 3 mg/kg doses and one 1 mg/kg dose spread over 19 weeks, about 2.5-fold lower than the approved regimen (four 3 mg/kg doses spread over 10 weeks). Two expansion cohorts (five patients each) is added at the highest dose level judged to have a toxicity profile comparable to that observed with Nivolumab alone and at the next highest dose level (if the overall toxicity profile is acceptable). For each cohort, the quantitative and qualitative features of the immune response to the neoantigens are evaluated. Patients are followed for Objective Response Rate (ORR), Progression Free Survival (PFS) and Overall Survival (OS).

The second study (3B) is of similar design to study 3A except that Ipilimumab is delivered via subcutaneous injection near to (within 2 cm) each vaccination site with each vaccination in order to focus anti-CTLA4 activity on the vaccine draining lymph nodes and limit systemic effects. Nivolumab is delivered as described herein. There is three dose escalation cohorts. The first cohort can inject 0.2 ml of 5 mg/ml Ipilimumab at each vaccination site with each vaccination. The second cohort can increase the volume to 0.5 ml and the third cohort to 1.0 ml. The maximal exposure to Ipilimumab is 140 mg over 19 weeks (about 11-fold lower than 840 mg [for a 70 kg patient] spread over 10 weeks for the approved regimen). Two expansion cohorts (five patients each) is added at the highest dose level judged to have a toxicity profile comparable to that observed with Nivolumab alone and at the next highest dose level (if there is one and the overall toxicity profile is acceptable). Patients are evaluated as described herein.

The third and the fourth study, described herein, essentially mirror the 1st and 2nd except that each is in high risk disease and does not utilize Nivolumab.

The third study (3C) is a 3 cohort dose escalating (Ipilimumab only) study in high risk (Stage IIIB, IIIC and fully resected IV) melanoma or surgically resected ccRCC patients. Patients are consented prior to surgery. Five patients can initially be included in each cohort. NeoVax therapy can initiate approximately 8 weeks after tumor resection and is administered on days 1, 4, 8, 15, and 22 (Weeks 1, 2, 3 and 4; "Priming Phase") and on weeks 11 and 19 ("boosts"). In the first cohort, patients can receive Ipilimumab at the start of the priming cycle, one week after the 5th priming dose and prior to each boost, all at a dose of 1 mg/kg. The next cohort can increase the dose associated with the start of priming vaccination to 3 mg/kg (the therapeutically approved level) and the dose associated with the end of priming and the boosts can remain at 1 mg/kg. For the third cohort, the start of priming dose and the dose associated with each boost is at 3 mg/kg. (See graphic view of the schedule herein). The maximal exposure to Ipilimumab can thus be three 3 mg/kg doses and one 1 mg/kg dose spread over 19 weeks, about 2.5-fold lower than the approved regimen (four 3 mg/kg doses spread over 10 weeks). One expansion cohorts (ten patients) is added at the highest dose level judged to have an acceptable toxicity profile consistent with adjuvant therapy and the recurrence risk profile. For each cohort, the quantitative and qualitative features of the immune response to the neoantigens are evaluated. Patients are followed for Recurrence Free Survival (RFS) for up to two years as in protocol 13-240.

The fourth study (3D) is of similar design to Study 3B except that Ipilimumab is delivered via subcutaneous injection near to (within 1 cm) each vaccination site with each vaccination in order to focus anti-CTLA4 activity on the vaccine draining lymph nodes and limit systemic effects. There is three dose escalation cohorts. The first cohort can inject 0.2 ml of 5 mg/ml Ipilimumab at each vaccination site with each vaccination. The second cohort can increase the volume to 0.5 ml and the third cohort to 1.0 ml. The maximal exposure to Ipilimumab is 140 mg over 19 weeks (about 11-fold lower than 840 mg [for a 70 kg patient] spread over 10 weeks for the approved regimen). One expansion cohorts (ten patients) is added at the highest dose level judged to have an acceptable toxicity profile consistent with adjuvant therapy and the recurrence risk profile. For each cohort, the quantitative and qualitative features of the immune response to the neoantigens are evaluated. Patients are followed for Recurrence Free Survival (RFS) for up to two years as in protocol 13-240.

The exciting results of the combination of Ipilimumab and Nivolumab is tempered by increased toxicity. Although potentially manageable by appropriate monitoring and response (to be confirmed in larger studies), the underlying biology of the molecules and the observations that have accumulated from animal and some human studies would suggest that coupling an effective vaccine with Ipilimumab may allow a reduced Ipilimumab overall exposure while maintaining or increasing efficacy. NeoVax is a paradigm shifting vaccine that has the potential for generating significantly stronger and more specific immune responses and to synergize with Ipilimumab. These studies provide the opportunity to maintain or increase efficacy while reducing toxicity. In addition, extending the reduced intensity concept may allow effective and setting-appropriate expansion of Ipilimumab to high risk disease.

Example 12

Phase I Study Design Combining NeoVax, a Personalized NeoAntigen Cancer Vaccine, with Ipilimumab to Treat High-Risk Renal Cell Carcinoma Sequencing technology has revealed that each tumor contains multiple, patient-specific mutations that alter the protein coding content of a gene.[1] Such mutations create altered proteins, ranging from single amino acid changes (caused by missense mutations) to addition of long regions of novel amino acid sequence due to frame shifts, read-through of termination codons or translation of intron regions (novel open reading frame mutations; neoORFs). These mutated proteins are valuable targets for the host's immune response to the tumor as, unlike native proteins, they are not subject to the immune-dampening effects of self-tolerance. Therefore, mutated proteins are more likely to be immunogenic and are also more specific for the tumor cells compared to normal cells of the patient.[2]

There have been multiple reports indicating that missense mutations or neoORFs in animal tumors induce strong CD8+ cytotoxic T lymphocyte (CTL) reactions, in some cases leading to prevention or eradication of disease.[3-6] More recently Matsushita and colleagues demonstrated that a single amino acid change in a normal murine structural protein (spectrin-β2) was the dominant target for immune attack against a methylcholanthrene-induced transplantable tumor, defining whether the tumor would survive or not following transplantation.[7] Furthermore, spectrin-β2 expression was also dramatically reduced in escape variants, providing a clear mechanistic example of the immunoediting hypothesis. At the same time, DuPage and colleagues made a similar observation using a small immunogenic neoORF in the mouse (ovalbumin peptide).[8] Both of these studies indicate that the immuno-edited neoantigen is therefore sufficient as the target of an effective anti-tumor response.

Correspondingly, many human studies of spontaneous regression and long-term survival have shown that powerful CD8+ T cell responses against mutated epitopes correlate with good clinical responses 9 These studies began with the first identification of human immunogenic neoantigens[10,11] and the seminal study by Lennerz demonstrating the strength and durability of neoantigen response compared to native protein responses[12], and now have included the observations of an increase in neoantigen-specific CD8+ T cells in a patient responding to anti-CTLA-4 therapy[13] and tumor regression following infusion of a tumor infiltrating lymphocyte (TIL) population highly enriched in a neoantigen directed CD4+ T cell.[14] These observations were made in multiple cancer types for multiple HLA alleles and have been widely observed in tumor infiltrating T cell populations[15,16]. Most of the CD8+ T cell responses show a high degree of specificity toward the mutated missense epitope compared to the native epitope, represent a high proportion of circulating T cells, and result in cells that are more abundant and active than CD8+ T cell responses in the same patients directed toward over-expressed native antigens.

Thus, in animals and in humans, immune responses to both discrete, mutated antigens (such as missense mutations) and expansive novel antigens (neoORFs) are observationally correlated with regression and long-term remission. Extending that correlation among a large set (n=468) of patients found in the Cancer Genome Atlas (TCGA) database, a recent meta-analysis of six tumor types revealed a significant survival advantage (hazard ratio=0.53; p=0.002) for patients with at least one predicted immunogenic neoepitope compared to patients with no predicted immunogenic epitopes.[17]

Three studies in humans have directly assessed the immunotherapeutic potential of mutated antigens. First, follicular lymphoma is characterized by uncontrolled growth of a B cell expressing rearranged immunoglobulin. Purification of that rearranged immunoglobulin and use as a vaccine may improve disease-free survival.[18] The induced CD8+ T cells showed reactivity to the rearranged, mutated portion of the immunoglobulin molecule (the idiotype) and not the germline framework.[19] Second, a mix of peptides corresponding to the oncogenic proteins of HPV (a neoORF for humans) has been shown to result in significant remission of premalignant lesions induced by HPV.[20,22] Finally, immunization with a synthetic version of an in-frame junctional deletion variant of the epidermal growth factor receptor (EGFRviii) in two studies in glioblastoma patients, a population known to frequently contain this mutation, provided encouraging phase 2 results.[23,24] Importantly, in both studies, evaluation of tumors in patients with tumor recurrence showed that the recurrent tumors almost uniformly (20 of 23) lost expression of EGFRviii. This was interpreted as clear evidence of immunoediting due to immune pressure against an immunogenic neoantigen in humans.

Most cancer vaccines employing peptides as immunogens have utilized "short" peptides. These peptides are typically 9-10 amino acids in length and capable of direct binding to the HLA molecule on the surface of HLA-expressing cells. "Long" peptides, about 20-30 amino acids in length, have recently been shown to produce a more robust and more durable immune response[20,21]. Long peptides require internalization, processing and cross-presentation in order to bind to HLA molecules; these functions only occur in professional antigen-presenting cells, such as dendritic cells, which can induce strong T cell responses.

Many studies in humans have demonstrated the safety of peptide vaccines. These include studies with multiple short peptides[25] as well as multiple long peptides, including neoORFs. In particular, four studies have been conducted with a mixture of 10 overlapping long peptides derived from p53[26-30] and five separate studies with a mixture of 13 long peptides derived from the oncogenic proteins of HPV.[20-22,31,32] In these studies, no toxicity higher than grade 2 was observed and most adverse events were of limited duration and severity. Additionally, many heterologous antigen preparations have been tested in humans. Such preparations include irradiated cell vaccines,[33,34] tumor cell lysates[35] and shed tumor cell line antigens.[36] These heterogeneous vaccines contain mutated antigens, in the form of intact proteins, partially degraded intracellular protein, and peptides found on the surface bound to MHC I. Moreover, they contain over-expressed and selectively-expressed molecules as well as many additional native proteins. In addition, purified heat shock protein (HSP) 96 peptide complexes have been used as antigen; such complexes also contain many mutated peptides.[37] None of these studies have reported significant safety issues directly attributable to the immunogens of the vaccines.

Toll like receptors (TLRs) are important members of the family of pattern recognition receptors (PRRs) which recognize conserved motifs shared by many micro-organisms, termed "pathogen-associated molecular patterns" (PAMPS). Recognition of these "danger signals" activates multiple elements of the innate and adaptive immune system. TLRs are expressed by cells of the innate and adaptive immune systems such as dendritic cells (DCs), macrophages, T and B cells, mast cells, and granulocytes and are localized in different cellular compartments, such as the plasma membrane, lysosomes, endosomes, and endolysosomes[38]. Different TLRs recognize distinct PAMPS. For example, TLR4 is activated by LPS contained in bacterial cell walls, TLR9 is activated by unmethylated bacterial or viral CpG DNA, and TLR3 is activated by double stranded RNA[39]. TLR ligand binding leads to the activation of one or more intracellular signaling pathways, ultimately resulting in the production of many key molecules associated with inflammation and immunity (particularly the transcription factor NF-κB and the Type-I interferons).

TLR mediated DC activation leads to enhanced DC activation, phagocytosis, upregulation of activation and co-stimulation markers such as CD80, CD83, and CD86, expression of CCR7 allowing migration of DC to draining lymph nodes and facilitating antigen presentation to T cells, as well as increased secretion of cytokines such as type I interferons, IL-12, and IL-6. All of these downstream events are critical for the induction of an adaptive immune response.

Among the most promising cancer vaccine adjuvants currently in clinical development are the TLR9 agonist CpG and the synthetic double-stranded RNA (dsRNA) TLR3 ligand poly-ICLC. In preclinical studies poly-ICLC appears to be the most potent TLR adjuvant when compared to LPS and CpG due to its induction of pro-inflammatory cytokines and lack of stimulation of IL-10, as well as maintenance of high levels of co-stimulatory molecules in DCs40. Furthermore, poly-ICLC was recently directly compared to CpG in non-human primates (rhesus macaques) as adjuvant for a protein vaccine consisting of human papillomavirus (HPV) 16 capsomers. Poly-ICLC was found to be much more effective in inducing HPV specific Th1 immune responses[41].

Poly-ICLC is a synthetically prepared double-stranded RNA consisting of polyI and polyC strands of average length of about 5000 nucleotides, which has been stabilized to thermal denaturation and hydrolysis by serum nucleases by the addition of polylysine and carboxymethylcellulose. The compound activates TLR3 and the RNA helicase-domains of MDA5 and RIG3, both members of the PAMP family, leading to DC and natural killer (NK) cell activation and production of a "natural mix" of type I interferons, cytokines, and chemokines. Furthermore, poly-ICLC exerts a more direct, broad host-targeted anti-infectious and possibly anti-tumor effect mediated by the two IFN-inducible nuclear enzyme systems, the 2'5'-OAS and the P1/eIF2a kinase, also known as the PKR (4-6), as well as RIG-I helicase and MDA5.

In rodents and non-human primates, poly-ICLC was shown to enhance T cell responses to viral antigens[42-45], cross-priming, and the induction of tumor-, virus-, and autoantigen-specific CD8+ T-cells[46-48]. In a recent study in non-human primates, poly-ICLC was found to be essential for the generation of antibody responses and T-cell immunity to DC targeted or non-targeted HIV Gag p24 protein, emphasizing its effectiveness as a vaccine adjuvant.

In human subjects, transcriptional analysis of serial whole blood samples revealed similar gene expression profiles among 8 healthy human volunteers receiving one single s.c. administration of poly-ICLC and differential expression of up to 212 genes between these 8 subjects versus 4 subjects receiving placebo[49]. Remarkably, comparison of the poly-ICLC gene expression data to previous data from volunteers immunized with the highly effective yellow fever vaccine YF17D50 showed that a large number of transcriptional and signal transduction canonical pathways, including those of the innate immune system, were similarly upregulated at peak time points.

Two studies of poly-ICLC in conjunction with long peptides have been published. An immunologic analysis was reported on patients with ovarian, fallopian tube, and primary peritoneal cancer in second or third complete clinical remission who were treated on a phase 1 study of subcutaneous vaccination with synthetic overlapping long peptides (OLP) from the cancer testis antigen NY-ESO-1 alone or with Montanide-ISA-51, or with 1.4 mg poly-ICLC and Montanide. The generation of NY-ESO-1-specific CD4+ and CD8+ T-cell and antibody responses were markedly enhanced with the addition of poly-ICLC and Montanide compared to OLP alone or OLP and Montanide.[51] In a second human study, poly-ICLC was combined with a MUC1 synthetic long peptide in patients with pre-malignant adenomas. Robust antibody responses were detected in nearly half the patients which inversely correlated with the pre-existing circulating myeloid derived suppressor cell level.[52]

Poly-ICLC has also been utilized as an adjuvant for immunization with minimal epitope-loaded patient-derived dendritic cells. Both CD4+ and CD8+ T cell responses to multiple peptides were observed in the majority of patients.[53]

Poly-ICLC is the TLR3 agonist formulation most extensively tested in patients with infectious diseases and in subjects with a variety of different tumor types. Prior to the availability of recombinant interferon, poly-ICLC was used clinically at high doses ≥6 mg/m2 (about 170 μg/kg) in patients with a variety of solid tumors and leukemia.$_{53}$ Fever, often above 40° C., was a common adverse event and the primary dose-limiting factor. Other common adverse events were flu-like symptoms (nausea, vomiting, arthralgia. myalgia and fatigue) and hypotension, thrombocytopenia and leukopenia. Once recombinant interferon became clinically available, the need to pursue high dose poly-ICLC was eliminated, and it became recognized that lower doses (10-50 gig/kg) were highly effective at stimulating host defense and as an immune adjuvant.

By now, more than 400 patients with malignant gliomas have been entered on 7 clinical trials using low dose (1-2 mg total dose) poly-ICLC either as monotherapy or in conjunction with chemotherapy, radiation, or vaccine (Table 5). Furthermore, patients with various other solid tumors (prostate, colorectal, pancreatic, hepatocellular, breast, and ovarian cancers), in addition to patients with HIV/AIDS and multiple sclerosis have been treated on more than 10 additional clinical phase I and phase II studies. Overall, the drug has been well-tolerated across all studies and spectrum of diseases.

TABLE 5

Clinical Trials with Low-Dose poly-ICLC

| Protocol Title | Phase | Protocol Location | Indication | Status | Patients N | Active | Year of initation | Dosing Schedule |
|---|---|---|---|---|---|---|---|---|
| Long-term IM poly-ICLC in Malignant Glioma-an Open Pilot Study | III | Walter Reed | Malignant Glioma | Closed | 67 | 0 | 1996 | IM 10-50 μg/kg 1-3 × week |
| Poly-ICLC in Recurrent Malignant Brain Tumors, an Open Label Study | III | MCV | Recurrent Glioma | Closed | 99 | 0 | 2000 | IM 20 μg/kg 3 × week |
| Poly-ICLC in Malignant Pediatric Brain Tumors | III | L.A. Childrens Hosp | Pediatric Glioma | Closed | 46 | 0 | 2002 | IM 20 μg/kg 2 × week |
| Poly-ICLC plus Radiation in Glioblastoma | II | NABTC 2001-05 | New Glioblastoma | Closed | 31 | 0 | 2006 | IM 20 μg/kg 3 × week |
| Poly-ICLC in Recurrent Anaplastic Glioma | II | NABTC 2001-06 | Recurrent Anaplastic Glioma | Closed | 55 | 6 | 2006 | IM 20 μg/kg 3 × week |
| Poly-ICLC plus Temodar in Newly Diagnosed Glioblastoma | II | NABTT 2005-01 | New Glioblastoma | Closed | 97 | 24 | 2006 | IM 20 μg/kg 3 × week |
| Pilot Study of MUC1 Vaccine plus poly-ICLC in Advanced Prostate Cancer | III | UPMC05-086 | Advanced Prostate Cancer | Open | 25 | 15 | 2006 | IM 25 μg/kg 2 × week |
| Poly-ICLC plus Dendritic Cell vaccine in Recurrent Gliomas | I | UPMC | Recurrent malignant gliomas | Open | 25 | 20 | 2007 | IM 20 mcg/kg |
| Poly-ICLC plus HSP-HPVE7 Vaccine in Cervical Dysplasia | I | Nventa | Cervical Dysplasia | Closed | 24 | 5 | 2007 | .05-2 mg |
| IntraTumoral poly-ICLC plus Radiation and TACE in Liver Cancer | I | UMDNJ | Hepatoma, Metastatic pancreatic cancer | Open | 31 | 1 | 2007 | .25-2 mg |
| A Randomized Controlled Phase I dose escalation trial of Nasal Hiltonol in normal volunteers. | I | NIAID, NIH: | Normal volunteers | Closed | 56 | 0 | 2009 | .25-4 mg IN |

TABLE 5-continued

Clinical Trials with Low-Dose poly-ICLC

| Protocol Title | Phase | Protocol Location | Indication | Status | Patients N | Active | Year of initation | Dosing Schedule |
|---|---|---|---|---|---|---|---|---|
| PSMA and TARP peptide with poly ICLC adjuvant in . . . Prostate Cancer. | I/II | Moffit Cancer Center | Prostate Cancer | Open | 30 | | 2009 | 1 mg |
| CDX 1307 vaccine with poly-ICLC in metastatic cancers | I | Various | Metastatic Cancers | Closed | 20 | | 2009 | 2 mg IM |
| Poly-ICLC with glioma associated peptide vaccine | I/II | UPMC | Grade II Gliomas | Open | 20 | | 2009 | 20 mcg/kg IM 2 × Wk |
| MUC1 Hundred-mer and poly-ICLC Vaccine for Triple-Negative Breast Cancer. | I/II | Case Western | Triple negative breast cancer | Open | 37 | | 2009 | 50 mg IM |
| MUC1 100-mer and poly-ICLC Vaccine for Colonic Polyposis | I/II | UPMC | Colonic Adenoma | Open | 45 | | 2009 | .5 mg SC |
| Hiltonol + NYESO1 Protein Vaccine in Ovarian Cancer | I/II | MSKCC, LICR | Ovarian Cancer | Closed | 28 | 0 | 2009 | 1.4 mg SC |

Clear cell renal cell carcinoma (ccRCC) is one of the ten most common cancers and the incidence is increasing. Between 20 and 30% of patients initially present with metastatic disease, which is generally incurable, whereas 30% of patients who undergo curative-intent nephrectomy experience recurrence with distant metastases. Targeted systemic agents such as inhibitors of vascular endothelial growth factor (VEGF) or mammalian target of rapamycin (mTOR) have provided significant clinical benefit for patients with metastatic disease, but tumor responses are not durable and most patients relapse and eventually succumb to the disease[54]. Combinations of existing therapeutic modalities are being investigated in these settings but are associated with significant toxicities and modest added activity. Effective adjuvant treatment of resected, high-risk patients with presumably micrometastatic, if any, disease burden is lacking. Innovative approaches are therefore necessary to achieve substantial improvement.

Perhaps more than any other therapeutic approach, immunotherapy has the potential for curative outcome by capturing the diversity and long-lasting memory of the immune system and its ability to destroy malignant tumor cells and prevent relapse. High dose interleukin-2 (HD-IL2) is used in patients with metastatic ccRCC based on a durable complete remission rate of 7%, but this therapy is only offered in select centers due to its significant toxicity and there is no established biomarker to predict for responses. Nevertheless, the results with HD-IL2 provide proof that "first generation" immunotherapy attempts can work in ccRCC.

Two immunotherapeutic approaches are being actively evaluated in ccRCC and other diseases—antigen-specific immunization (vaccination) and, more recently, non-specific immune stimulation via treatment with checkpoint blockade antibodies (CPB)[56-58]. Vaccines in ccRCC to date have provided hints of efficacy but tumor response rates and durability of tumor responses remain low,[59,60] most likely due to the lack of effective tumor-specific immune responses induced with these approaches. Historically, most cancer vaccines have utilized tumor-associated antigens (TAA), a class of native proteins, which are preferentially or selectively expressed on tumor cells, but can also be found on some normal cells. Native proteins generate relatively weak immune responses due to central tolerance (the naturally occurring phenomenon that prevents the immune system from recognizing self-antigens and thereby generating autoimmunity). Despite the relatively weak results achieved with TAA vaccination to date, several pivotal clinical studies are underway in ccRCC utilizing such native antigens, pointing to the demand for more effective therapies.

DNA sequencing, particularly next-generation sequencing technology, has revealed a genetic landscape of cancer that contains many protein coding mutations found uniquely in the tumor of an individual patient. These mutations include both single-amino acid missense mutations (the predominant type) and novel open reading frames created by frame-shift or read-through mutations (neoORFs) varying in length from 1 to up to 100's of amino acids. There is evidence in both animals and humans demonstrating that such mutated epitopes are effective at inducing an immune response. Importantly, strong CD8+ T cell responses against mutated epitopes have been found in patients with multiple tumor types who either had a spontaneous regression or a dramatic response after adoptive T cell transfer, suggesting that there may be an association with CD8+ T cell activity and good clinical responses[9]. Most of these CD8+ T cell responses showed very good specificity toward the mutated epitope compared to the native epitope, represented a high proportion of circulating T cells, and induced cells that were more abundant and active than CD8+ T cells in the same patients directed toward over-expressed native antigens.

Three studies in humans have directly assessed the immunotherapeutic potential of mutated antigens. Purified rearranged immunoglobulin expressed by malignant B cells in follicular lymphoma has been used as vaccine and has led to good clinical outcomes in some phase 2 and phase 3 studies (possibly dependent on amounts of residual disease)$_{61}$. More recently, a mix of peptides corresponding to the oncogenic proteins of HPV (directly analogous to the neoORF type of mutation) has been shown to result in significant remission of premalignant lesions induced by HPV$_{20-22}$. Finally, a mutated form of the epidermal growth factor receptor (EGFR) commonly found in glioblastoma patients has been used as an immunogen in multiple early clinical trials.$_{62}$ Interestingly, evidence for down-regulation of this mutated gene has been found, suggesting immune editing due to immune pressure induced by the vaccine.$_{24}$ Thus, in animals and in humans, immune responses to both discrete mutated antigens (such as missense mutations) and expansive novel antigen (neoORF) are observationally correlated with regression and long-term remission and, in three clinical studies, have been shown to control disease following therapeutic vaccination. The direct and comprehensive identification of the many mutated epitopes found in cancer genomes creates the opportunity to use this class of immunogen to improve the immune response and efficacy of cancer vaccines.

Ipilimumab, an anti-CTLA4 specific IgG1 monoclonal antibody, blocks a key regulatory pathway that dampens both de novo and memory T-cell responses following antigen activation and has been demonstrated to improve overall survival as monotherapy in patients with advanced melanoma$_{56}$. Furthermore, antibodies targeting the PD-1 pathway (another immune checkpoint) have demonstrated impressive anti-tumor activity in multiple cancer types$_{57,5858,63-65}$ and the combination of CTLA-4 and PD-1 pathway blockade showed apparent synergy in advanced melanoma$_{63,64}$ and most recently in ccRCC (Hammers et al, ASCO 2014 Abstract #4504). Despite this success, the lack of coincident immune stimulation with an effective vaccine may limit the maximal impact of such therapy.

Many studies in animals have shown that combining anti-CTLA4 treatment with a vaccine can substantially augment efficacy$_{66-68}$ and anecdotal information suggests a similar effect in humans$_{69,70}$. This potential synergy may depend critically on the antigen as the most dramatic effects of the combination in animals and the effects in humans have typically been observed with complex vaccines such as autologous cellular vaccines and not with an individual tumor-associated antigen (such as gp100 for melanoma). Autologous tumor cell vaccines 69 contain both neoantigens and tumor-associated antigens. NeoVax, by focusing the immune system on neoantigens, presumably the most immunogenic subset of possible antigens, is expected to strengthen and focus the immune response to the tumor, thereby generating more robust clinical activity. Reciprocally, checkpoint blockade during vaccination may increase the breadth and the magnitude of the response to NeoVax and increase memory cell formation. Recently, neoantigen-specific T-cells were observed in an Ipilimumab-treated patient prior to treatment initiation and increased following therapy$_{71}$.

An innovative aspect of the study is the route of delivery of Ipilimumab. There are real concerns regarding the toxicity profile of intravenously delivered Ipilimumab, the approved delivery route for metastatic disease. For this reason, the study design includes delivery of Ipilimumab "locally" by sub-cutaneous injection in proximity to the vaccination site during each vaccine dosing. Large proteins like Ipilimumab enter the circulation following sub-cutaneous injection by transit through the lymphatics and draining lymph nodes$_{72}$. Thus, it is expected that this approach can target Ipilimumab to the same draining lymph node as the vaccine and reduce systemic exposure, thereby both maximizing effectiveness and limiting systemic toxicity of Ipilimumab. Multiple animal studies have shown that localized dosing of anti-CTLA4 is effective. The modes of localized dosing have included: (i) local production of anti-CTLA4 from the irradiated tumor cell being used as vaccine$_{73}$, (ii) "in transit" delivery of anti-CTLA4 between the tumor (antigen source) and the local draining lymph node$_{74}$, and (iii) direct intra-tumoral injection of anti-CTLA4$_{75}$. Anti-tumor activity with localized administration from irradiated anti-CTLA4 expressing tumor cells was reduced compared to systemic administration, but it was equal or better with "in transit" delivery and with direct intra-tumoral injection. Of note, an abscopal effect was observed, wherein injection of anti-CTLA4 antibody near to or into a tumor on one flank of the animal resulted in elimination of the tumor on the opposite flank 74.75 indicating a systemic treatment effect.

Figure 11:
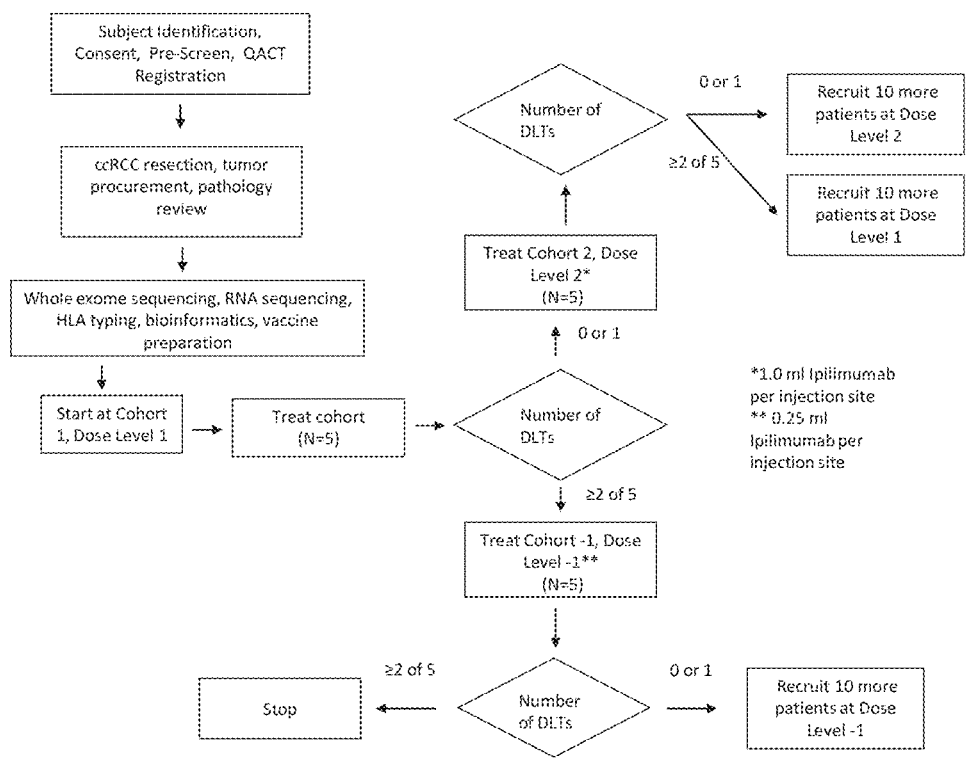
FIG. 11 illustrates a study scheme combining NeoVax and Ipilimumab to treat high-risk renal cell carcinoma.

Described herein is a study design combining a personalized neoantigen cancer vaccine with Ipilimumab to treat high-risk renal cell carcinoma (see FIG. 11). The study is an open label, phase I trial in which patients with clear ccRCC (both fully resected but high risk patients as well as patients with low or intermediate risk metastatic disease) is immunized with up to 20 peptides that are both specific to the participant's tumor cells (i.e.—not found in their normal cells) and unique to the participant (i.e.—"personal") and concurrently receive Ipilimumab in close proximity to the vaccine site. These peptides are encoded by missense mutations, in-frame gene fusions and novel open reading frame mutations (collectively known as "neoantigens") that have occurred within that participant's tumor cells and are identified through DNA and RNA sequencing. Up to 20 peptides at least ~20 amino acids in length is prepared for each participant and is administered together with the immune adjuvant polyinosinic-polycytidylic (poly-IC) stabilized with poly-L-lysine and carboxymethylcellulose (poly-ICLC)(Hiltonol®). Thus, the personalized NeoAntigen Cancer Vaccine consists of peptides+poly-ICLC and is termed "NeoVax". Ipilimumab is an antibody against CTLA4, a molecule on the surface of T cells that limits T cell expansion, and has been approved for the treatment of metastatic melanoma (Yervoy®). Ipilimumab is delivered via subcutaneous injection in proximity to each vaccination site in order to 1) direct anti-CTLA4 activity to the vaccine-draining lymph nodes and 2) limit systemic toxic effects. This approach is effective in animal tumor models and is expected to result in significantly reduced levels of systemic Ipilimumab compared to the approved dose/schedule in advanced melanoma (3 mg/kg q3wks for four doses).

Eligible patients are entered into the trial to undergo surgery with the intent to resect the primary kidney tumor or a metastatic site. Patients who have undergone surgery, fulfill eligibility criteria, and for whom sufficient tissue was obtained to prepare nucleic acid for sequencing can continue onto the treatment phase of the trial.

The study is conducted in two parts. In the first part (10 patients) the maximum tolerated dose (MTD) is identified from three possible dose levels. In the second part, 10 additional patients are enrolled at the MTD to extend the safety and activity analysis of the NeoVax cancer vaccine given in combination with locally administered ipilimumab.

Five patients are entered for the initial safety evaluation (Cohort 1). If none or only 1 patient experiences a DLT during the first 7 weeks of treatment of Cohort 1, 5 patients are entered to Cohort 2. If two or more patients in Cohort 1 experience dose limiting toxicity (DLT) during the first 7 weeks of treatment, then 5 patients are entered on Cohort-1.

If none or only 1 patient experiences a DLT on Cohort 2, then Dose Level 2 is the maximum tolerated dose (MTD) and an additional 10 patients are entered at that dose level to increase the likelihood of detecting serious toxicities, to complete biologic correlative endpoints and to gain preliminary experience with clinical tumor activity. If two or more patients in Cohort 2 experience dose limiting toxicity (DLT), then Dose Level 1 is the MTD and an additional 10 patients are treated at this dose.

If none or only 1 patient experiences a DLT on Cohort-1, then Dose Level-1 is the maximum tolerated dose (MTD) and an additional 10 patients are entered at that dose level. If two or more patients in Cohort 2 experience dose limiting toxicity (DLT), then the study is stopped.

GMP peptides are prepared by synthetic chemistry, purified by Reverse Phase High-Performance Liquid Chromatography (RP-HPLC), mixed in small groups and combined with the immune adjuvant poly-ICLC, a stabilized double-stranded RNA. The mixtures of peptides and poly-ICLC is used for vaccination with the intention to induce cellular immune responses directed at these patient/tumor specific mutations. Each participant can receive the full complement of peptides at each immunization.

The induction of a neoantigen-specific T cell response following vaccination with NeoVax and simultaneous treatment with locally delivered Ipilimumab is assessed by IFN-γ ELISPOT and/or tetramer analysis. Comparison is made between samples taken prior to vaccine administration and after vaccination, beginning 4 weeks after the last priming dose. Assays are conducted for all 10 patients in the expansion cohort only.

IFN-γ secretion occurs as a result of the recognition of cognate peptides or mitogenic stimuli by CD4+ and/or CD8+ T-cells. A multitude of different CD4+ and CD8+ determinants can be presented to T cells in vivo since the 20-30-mer peptides used for vaccination should undergo processing into smaller peptides by antigen presenting cells. Patients are evaluated using the predicted epitope short peptides as well as longer peptides which require proteasomal processing as stimulant in the IFN-γ ELISPOT assay. If warranted, the precise immunogenic peptide(s) is determined in follow-up analyses.

When feasible, HLA-tetramers are prepared for one or more epitopes and is used for cell staining and flow cytometry to independently evaluate the level of responding T cells.

In addition to the analysis of the magnitude and determinant mapping of the T cell response in peripheral blood, other aspects of the immune response induced by the vaccine are critical and is assessed. These evaluations are performed in patients who exhibit an ex vivo IFN-γ ELISPOT or tetramer response in the screening assay. They include the evaluation of T cell subsets (Th1 versus Th2, T effector versus memory cells), analysis of the presence and abundance of regulatory cells such as T regulatory cells or myeloid derived suppressor cells, and patient-specific tumor cell recognition. Finally, through targeted deep sequencing of the Vβ subfamily of the T cell receptor in peripheral blood samples collected before and after vaccination or in TIL populations, the global changes in TCR repertoire as well as changes in the abundance of individual T cell clones are determined.

After adequate tumor for pathological assessment has been harvested, remaining tumor tissue is placed in sterile media in a sterile container and transferred for immediate freezing or is used for disaggregation. Portions of the tumor tissue is used for whole-exome and transcriptome sequencing. If single cells are prepared, a cell line may be initiated. Additionally, tumor infiltrating lymphocyte is prepared from the single cell suspension. In the event that sequence analysis yields no results or sub-optimal results, tumor cell line cells may be used to prepare additional nucleic acid for sequencing. Peripheral blood mononuclear cells from a blood draw is utilized for a normal tissue sample.

Nucleic acid is extracted from the tissue samples and sequencing is conducted at the CLIA-certified laboratory at Broad Institute. For tumor and normal DNA samples, whole exome capture is conducted prior to sequencing on Illumina HiSeq. For tumor RNA, a cDNA library is prepared on poly-A selected RNA prior to sequencing on Illumina HiSeq. If the quantity or quality of DNA or RNA isolated from the tissue sample is inadequate for exome or cDNA library preparation and sequencing, then DNA or RNA may be extracted from the patient-specific tumor cell line (if generated).

Whole exome DNA sequence of tumor and normal tissue samples from the patient is used to identify the specific coding-sequence mutations that have occurred in the tumor of that participant. These mutations include both single-amino acid missense mutations (the predominant type of mutation) and novel open reading frames (neoORFs) varying in length from one up to hundreds of amino acids. A well-established algorithm (netMHCpan) is used to identify mutation-containing epitopes that are predicted to bind to the MHC class I molecules of each participant.[76] From this list of candidate mutations, 20-40 mutations are selected and prioritized for peptide preparation based on a pre-defined set of criteria including:

Type of mutation (missense vs neoORF)
Predicted binding potential of peptides encoded by the mutated region to the MHC class I alleles of the particular individual
Predicted binding potential of the corresponding native peptide
The likelihood that the mutation is directly or indirectly related to the tumorigenic phenotype (i.e. an "oncogenic driver" mutation or a mutation in a related biochemical pathway)
RNA expression
Biochemical properties of the full peptide (e.g. predicted poor solubility secondary to hydrophobic amino acid number or distribution and/or cysteine content).

Twenty to forty mutations for each participant is used to design peptides, each approximately 20-30 amino acids in length. Analysis of mutations is limited to comparison of normal and tumor sequence information for each participant.

GMP peptides are synthesized by standard solid phase synthetic peptide chemistry and purified by RP-HPLC. Each individual peptide is analyzed by a variety of qualified assays to assess appearance (visual), purity (RP-HPLC), identity (by mass spectrometry), quantity (elemental nitrogen), and trifluoro-acetate counterion (RP-HPLC) and released. This work is performed by CS Bio, Menlo Park, Calif. Synthesis are initiated with up to 25 peptides if possible so that additional peptides are immediately available for replacement of insoluble peptides if needed.

It is intended to immunize patients with as many peptides as possible, up to a maximum of 20. Peptides are mixed together in 4 pools of up to 5 peptides each. The selection criteria for each pool is based on the particular MHC allele to which the peptide is predicted to bind. Peptides predicted to bind to the same MHC allele is placed into separate pools whenever possible in order to limit antigenic competition. Some of the neoORF peptides may not be predicted to bind to any MHC allele of the patient. These peptides can still be utilized however, primarily because they are completely novel and therefore not subject to the immune-dampening effects of central tolerance, thus having a high probability of being immunogenic. NeoORF peptides also carry a dramatically reduced potential for autoimmunity as there is no equivalent molecule in any normal cell. In addition, there can be false negatives arising from the prediction algorithm and it is possible that the peptide can contain a HLA class II epitope (HLA class II epitopes are not reliably predicted based on current algorithms). All peptides not identified with a particular HLA allele is randomly assigned to the individual pools.

The peptide pools are prepared. The amounts of each peptide are predicated on a final dose of 300 μg of each peptide per injection. The peptide pools are prepared by dissolving appropriate quantities of each peptide individually at high concentration (approximately 50 mg/ml) in dimethyl sulfoxide (DMSO) and dilution with 5% dextrose in water (DSW)/5 mM succinate to a final concentration of 2 mg/ml. Any peptides that do not demonstrate clear solutions upon dilution is discarded and replaced with another peptide if available; if no additional peptides are available, D5W/succinate will be used. Equal quantities of each of 5 peptides can then be admixed, effectively diluting each peptide to a concentration of 400 μg/ml. The bioburden in the pooled peptides are reduced by filtration through a 0.2 μm sterilizing filter. The pooled and filtered bulk is filter sterilized in a laminar flow biosafety cabinet and aliquoted into 2 ml Nunc cryo individual dosing vials for storage. Each pool is tested by RP-HPLC for identity, residual solvents (by gas-chromatography), sterility and endotoxin. Individual dosing vials are stored frozen at −80° C.

The standard and approved 10 ml vial (5 mg Ipilimumab/ml) is utilized for this clinical study. No additional preparation is required.

Preparation of the final NeoVax product and syringes containing Ipilimumab is begun upon confirmation that the patient is medically cleared to undergo vaccine administration (confirmed arrival in the clinic, stable vital signs, no new acute medical issues or laboratory abnormalities potentially interfering with vaccine administration).

The final step in the preparation of NeoVax (mixing with poly-ICLC) is conducted on the day of the scheduled vaccine administration. For each patient, four distinct pools (labeled "A", "B", "C" and "D") of up to 5 synthetic peptides each can be prepared at the GMP peptide manufacturer and filter sterilized as described in detail and stored at −80° C.

On the day of immunization, the complete vaccine consisting of the peptide component(s) and poly-ICLC is prepared in a laminar flow biosafety cabinet. One vial each (A, B, C and D) is thawed at room temperature in a biosafety cabinet. 0.75 ml of each peptide pool is withdrawn from the vial into separate syringes. Separately, four 0.25 ml (0.5 mg) aliquots of poly-ICLC is withdrawn into separate syringes. The contents of each peptide-pool containing syringe can then be gently mixed with a 0.25 ml aliquot of poly-ICLC by syringe-to-syringe transfer. The entire one ml of the mixture is used for injection.

These four preparations are labeled "NeoVax A", "NeoVax B", "NeoVax C", "NeoVax D". The total dose of NeoVax can consist of the four 1 ml syringes each containing 1 ml of the peptide pool+poly-ICLC mixtures.

On each dosing day, a single 10 ml vial containing 5 mg/ml Ipilimumab is used to prepare 4 syringes, each containing 0.25 ml (Cohort-1), 0.5 ml (Cohort 1) or 1 ml (Cohort 2).

Figure 12:
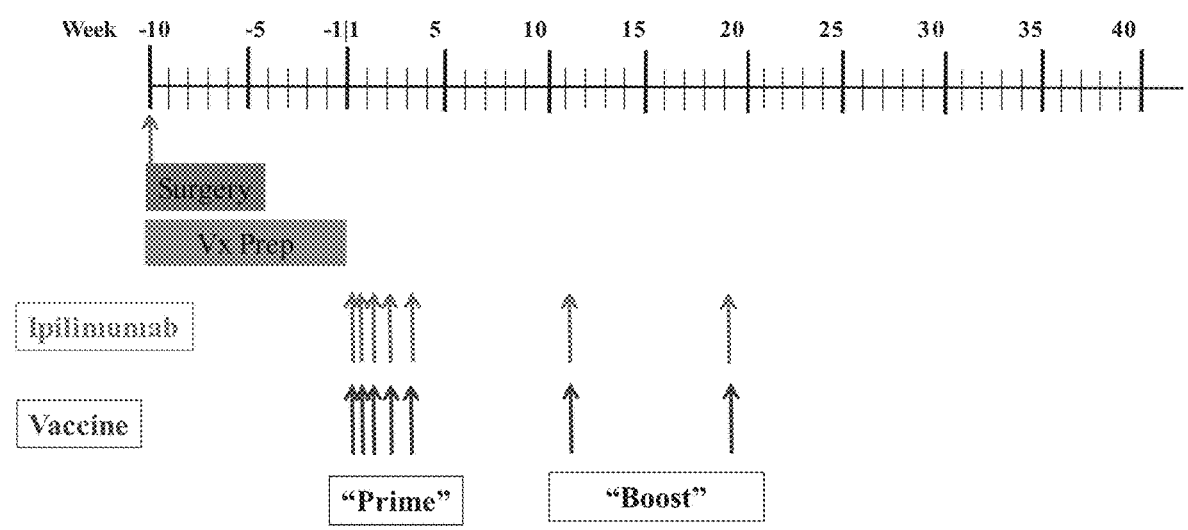
FIG. 12 illustrates a treatment scheme for a study combining NeoVax and Ipilimumab to treat high-risk renal cell carcinoma.

Vaccine is administered following a prime/boost schedule. Priming doses of vaccine is administered on days 1, 4, 8, 15, and 22 as shown herein and (FIG. 12). In the boost phase, vaccine is administered on days 78 (week 12) and 162 (week 20).

| | | | Treatment Description | | | |
|---|---|---|---|---|---|---|
| Agent | Treatment phase | Schedule | Allowable Treatment Admin Window | Pre-medications Precautions | Dose | Route |
| NeoVax (peptides + poly-ICLC) and Ipilimumab | Prime | Day 1 Days 4 and 8 Days 15 and 22 | N/A ±1 day ±3 days but at least 5 days must elapse between doses | none | Poly-ICLC: 4 × 0.5 mg (total dose 2 mg) Peptides: 4 × 300 μg per peptide Volume = 4 × 1 ml Ipilimumab 4 × 0.25 ml, 0.5 ml or 1.0 ml depending on the cohort | NeoVax s.c. injections into 4 different anatomic sites Ipilimumab s.c injection within 1 cm of each NeoVax injection |
| | Boost | Days 78 and 134 | ±7 days | | | |

Each of the 4 NeoVax and Ipilimumab syringes is assigned to one of four extremities. At each immunization, each NeoVax syringe is administered s.c. to the assigned extremity (i.e. NeoVax A is injected into left arm on day 1, 4, 8 etc., NeoVax B is injected into right arm on days 1, 4, 8 etc.). Alternative anatomical locations for patients who are status post complete axillary or inguinal lymph node dissection or other contraindications that prevent injections to a particular extremity are the left and right midriff, respectively.

Immediately following NeoVax administration at a respective extremity (or alternative anatomical location), Ipilimumab is injected within 1 cm of each NeoVax administration.

NeoVax and Ipilimumab may be administered within 1 day of the scheduled administration date for days 4 and 8, within 3 days of the scheduled administration date for days 15 and 22 (but must be at least 5 days apart) and within 7 days for days 78 and 162.

Five patients are entered for the initial safety evaluation (Cohort 1). If none or only 1 patient experiences a DLT during the first 7 weeks of treatment of Cohort 1, 5 patients are entered to Cohort 2. If two or more patients in Cohort 1 experience dose limiting toxicity (DLT) during the first 7 weeks of treatment, then 5 patients are entered on Cohort-1.

If none or only 1 patient experiences a DLT on Cohort 2, then Dose Level 2 is the maximum tolerated dose (MTD) and an additional 10 patients are entered at that dose level to increase the likelihood of detecting serious toxicities, to complete biologic correlative endpoints and to gain preliminary experience with clinical tumor activity. If two or more patients in Cohort 2 experience dose limiting toxicity (DLT), then Dose Level 1 is the MTD and an additional 10 patients are treated at this dose.

If none or only 1 patient experiences a DLT on Cohort-1, then Dose Level-1 is the maximum tolerated dose (MTD) and an additional 10 patients are entered at that dose level.

If two or more patients in Cohort 2 experience dose limiting toxicity (DLT), then the study is stopped.

Duration of therapy can depend on tolerability of the immunizations and evidence of disease recurrence. In the absence of treatment delays due to adverse events, treatment is given until the day 134 vaccination (the 2nd booster vaccination) or until one of the following criteria applies:
- Disease recurrence, if it is deemed by the treating investigator to be in the best interest of the patient to discontinue study treatment
- Intercurrent illness that prevents further administration of treatment
- Unacceptable adverse event(s)
- Patient demonstrates an inability or unwillingness to comply with protocol requirements
- Patient decides to withdraw from the study, or
- General or specific changes in the patient's condition which render the patient unacceptable for further treatment in the opinion of the treating investigator.

REFERENCES

1. Wood L D, Parsons D W, Jones S, et al. The genomic landscapes of human breast and colorectal cancers. Science. Nov. 16, 2007; 318(5853):1108-1113.
2. Hacohen N, Fritsch E F, Carter T A, Lander E S, Wu C J. Cancer Immunology at the Crossroads: Functional Genomics Getting Personal with Neoantigen-Based Therapeutic Cancer Vaccines. Cancer Immunology Research. 2013; 1:11-15.
3. Dubey P, Hendrickson R C, Meredith S C, et al. The immunodominant antigen of an ultraviolet-induced regressor tumor is generated by a somatic point mutation in the DEAD (SEQ ID NO: 62) box helicase p68. The Journal of experimental medicine. Feb. 17, 1997; 185(4): 695-705.
4. Zwaveling S, Ferreira Mota S C, Nouta J, et al. Established human papillomavirus type 16-expressing tumors are effectively eradicated following vaccination with long peptides. J Immunol. Jul. 1, 2002; 169(1):350-358.
5. Mandelboim O, Vadai E, Fridkin M, et al. Regression of established murine carcinoma metastases following vaccination with tumour-associated antigen peptides. Nature medicine. November 1995; 1(11):1179-1183.
6. Castle J C, Kreiter S, Diekmann J, et al. Exploiting the mutanome for tumor vaccination. Cancer research. Mar. 1, 2012; 72(5):1081-1091.
7. Matsushita H, Vesely M D, Koboldt D C, et al. Cancer exome analysis reveals a T-cell-dependent mechanism of cancer immunoediting. Nature. Feb. 16, 2012; 482(7385): 400-404.
8. DuPage M, Mazumdar C, Schmidt L M, Cheung A F, Jacks T. Expression of tumour-specific antigens underlies cancer immunoediting. Nature. Feb. 16, 2012; 482(7385): 405-409.
9. Fritsch E F, Rajasagi M, Ott P A, Brusic V, Hacohen N, Wu C J. HLA-Binding Properties of Tumor Neoepitopes in Himans. Ca Immunol Res. 2014.
10. Wolfel T, Hauer M, Schneider J, et al. A p16INK4a-insensitive CDK4 mutant targeted by cytolytic T lymphocytes in a human melanoma. Science. Sep. 1, 1995; 269(5228):1281-1284.
11. Coulie P G, Lehmann F, Lethe B, et al. A mutated intron sequence codes for an antigenic peptide recognized by cytolytic T lymphocytes on a human melanoma. Proc Natl Acad Sci USA. Aug. 15, 1995; 92(17):7976-7980.
12. Lennerz V, Fatho M, Gentilini C, et al. The response of autologous T cells to a human melanoma is dominated by mutated neoantigens. Proceedings of the National Academy of Sciences of the United States of America. Nov. 1, 2005; 102(44):16013-16018.
13. van Rooij N, van Buuren M M, Philips D, et al. Tumor exome analysis reveals neoantigen-specific T-cell reactivity in an ipilimumab-responsive melanoma. J Clin Oncol. Nov. 10, 2013; 31(32):e439-442.
14. Tran E, Turcotte S, Gros A, et al. Cancer immunotherapy based on mutation-specific CD4+ T cells in a patient with epithelial cancer. Science. May 9, 2014 2014; 344(6184): 641-645.
15. Gros A, Robbins P F, Yao X, et al. PD-1 identifies the patient-specific CD8+ tumor-reactive repertoire infiltrating human tumors. The Journal of clinical investigation. May 1, 2014; 124(5):2246-2259.
16. Robbins P F, Lu Y C, El-Gamil M, et al. Mining exomic sequencing data to identify mutated antigens recognized by adoptively transferred tumor-reactive T cells. Nature medicine. June 2013; 19(6):747-752.
17. Brown S D, Warren R L, Gibb E A, et al. Neoantigens predicted by tumor genome meta-analysis correlate with increased patient survival. Genome Res. May 2014; 24(5):743-750.
18. Schuster S J, Neelapu S S, Gause B L, et al. Vaccination with patient-specific tumor-derived antigen in first remission improves disease-free survival in follicular lymphoma. J Clin Oncol. Jul. 10, 2011; 29(20):2787-2794.
19. Baskar S, Kobrin C B, Kwak L W. Autologous lymphoma vaccines induce human T cell responses against multiple, unique epitopes. J Clin Invest. May 2004; 113 (10):1498-1510.
20. Welters M J, Kenter G G, Piersma S J, et al. Induction of tumor-specific CD4+ and CD8+ T-cell immunity in cervical cancer patients by a human papillomavirus type 16 E6 and E7 long peptides vaccine. Clinical cancer research: an official journal of the American Association for Cancer Research. Jan. 1, 2008; 14(1):178-187.
21. Kenter G G, Welters M J, Valentijn A R, et al. Phase I immunotherapeutic trial with long peptides spanning the E6 and E7 sequences of high-risk human papillomavirus 16 in end-stage cervical cancer patients shows low toxicity and robust immunogenicity. Clinical cancer research: an official journal of the American Association for Cancer Research. Jan. 1, 2008; 14(1):169-177.
22. Kenter G G, Welters M J, Valentijn A R, et al. Vaccination against HPV-16 oncoproteins for vulvar intraepithelial neoplasia. N Engl J Med. Nov. 5, 2009; 361(19): 1838-1847.
23. Sampson J H, Aldape K D, Archer G E, et al. Greater chemotherapy-induced lymphopenia enhances tumor-specific immune responses that eliminate EGFRvIII-expressing tumor cells in patients with glioblastoma. Neuro-oncology. March 2011; 13(3):324-333.
24. Sampson J H, Heimberger A B, Archer G E, et al. Immunologic escape after prolonged progression-free survival with epidermal growth factor receptor variant III peptide vaccination in patients with newly diagnosed glioblastoma. Journal of clinical oncology: official journal of the American Society of Clinical Oncology. Nov. 1, 2010; 28(31):4722-4729.
25. Slingluff C L, Jr., Petroni G R, Chianese-Bullock K A, et al. Randomized multicenter trial of the effects of melanoma-associated helper peptides and cyclophosphamide on the immunogenicity of a multipeptide melanoma vaccine. J Clin Oncol. Jul. 20, 2011; 29(21):2924-2932.
26. Leffers N, Lambeck A J, Gooden M J, et al. Immunization with a P53 synthetic long peptide vaccine induces P53-specific immune responses in ovarian cancer patients, a phase H trial. Int J Cancer. Nov. 1, 2009; 125(9):2104-2113.
27. Leffers N, Vermeij R, Hoogeboom B N, et al. Long-term clinical and immunological effects of p53-SLP® vaccine in patients with ovarian cancer. Int J Cancer. Jan. 1, 2012; 130(1):105-112.
28. Speetjens F M, Kuppen P J, Welters M J, et al. Induction of p53-specific immunity by a p53 synthetic long peptide vaccine in patients treated for metastatic colorectal cancer. Clin Cancer Res. Feb. 1, 2009; 15(3):1086-1095.
29. Vermeij R, Leffers N, Hoogeboom B N, et al. Potentiation of a p53-SLP vaccine by cyclophosphamide in ovarian cancer: a single-arm phase U study. Int J Cancer. Sep. 1, 2012; 131(5):E670-680.
30. Zeestraten E C, Speetjens F M, Welters M J, et al. Addition of interferon-alpha to the p53-SLP® vaccine results in increased production of interferon-gamma in vaccinated colorectal cancer patients: a phase I/II clinical trial. Int J Cancer. Apr. 1, 2013; 132(7):1581-1591.
31. van Poelgeest M I, Welters M J, van Esch E M, et al. HPV16 synthetic long peptide (HPV16-SLP) vaccination therapy of patients with advanced or recurrent HPV16-induced gynecological carcinoma, a phase II trial. J Transl Med. 2013; 11:88.
32. Welters M J, Kenter G G, de Vos van Steenwijk P J, et al. Success or failure of vaccination for HPV16-positive vulvar lesions correlates with kinetics and phenotype of induced T-cell responses. Proc Natl Acad Sci USA. Jun. 29, 2010; 107(26):11895-11899.
33. Soiffer R, Hodi F S, Haluska F, et al. Vaccination with irradiated, autologous melanoma cells engineered to secrete granulocyte-macrophage colony-stimulating factor by adenoviral-mediated gene transfer augments antitumor immunity in patients with metastatic melanoma. Journal of clinical oncology: official journal of the American Society of Clinical Oncology. Sep. 1, 2003; 21(17):3343-3350.
34. Morton D L, Hsueh E C, Essner R, et al. Prolonged survival of patients receiving active immunotherapy with Canvaxin therapeutic polyvalent vaccine after complete resection of melanoma metastatic to regional lymph nodes. Ann Surg. October 2002; 236(4):438-448; discussion 448-439.
35. Vaishampayan U, Abrams J, Darrah D, Jones V, Mitchell M S. Active immunotherapy of metastatic melanoma with allogeneic melanoma lysates and interferon alpha. Clin Cancer Res. December 2002; 8(12):3696-3701.
36. Bystryn J C, Zeleniuch-Jacquotte A, Oratz R, Shapiro R L, Harris M N, Roses D F. Double-blind trial of a polyvalent, shed-antigen, melanoma vaccine. Clin Cancer Res. July 2001; 7(7):1882-1887.
37. Testori A, Richards J, Whitman E, et al. Phase III comparison of vitespen, an autologous tumor-derived heat shock protein gp96 peptide complex vaccine, with physician's choice of treatment for stage IV melanoma: the C-100-21 Study Group. J Clin Oncol. Feb. 20, 2008; 26(6):955-962.
38. Kawai T, Akira S. TLR signaling. Seminars in immunology. February 2007; 19(1):24-32.
39. Adams S. Toll-like receptor agonists in cancer therapy. Immunotherapy. November 2009; 1(6):949-964.
40. Bogunovic D, Manches O, Godefroy E, et al. TLR4 engagement during TLR3-induced proinflammatory signaling in dendritic cells promotes IL-10-mediated suppression of antitumor immunity. Cancer Res. Aug. 15, 2011; 71(16):5467-5476.
41. Stahl-Hennig C, Eisenblatter M, Jasny E, et al. Synthetic double-stranded RNAs are adjuvants for the induction of T helper 1 and humoral immune responses to human papillomavirus in rhesus macaques. PLoS Pathog. April 2009; 5(4):e1000373.
42. Boscardin S B, Hafalla J C, Masilamani R F, et al. Antigen targeting to dendritic cells elicits long-lived T cell help for antibody responses. The Journal of experimental medicine. Mar. 20, 2006; 203(3):599-606.
43. Soares H, Waechter H, Glaichenhaus N, et al. A subset of dendritic cells induces CD4+ T cells to produce IFN-gamma by an IL-12-independent but CD70-dependent mechanism in vivo. The Journal of experimental medicine. May 14, 2007; 204(5):1095-1106.
44. Trumpfheller C, Caskey M, Nchinda G, et al. The microbial mimic poly IC induces durable and protective CD4+ T cell immunity together with a dendritic cell targeted vaccine. Proc Natl Acad Sci USA. Feb. 19, 2008; 105(7):2574-2579.
45. Trumpfheller C, Finke J S, Lopez C B, et al. Intensified and protective CD4+ T cell immunity in mice with anti-dendritic cell HIV gag fusion antibody vaccine. The Journal of experimental medicine. Mar. 20, 2006; 203(3):607-617.
46. Salem M L, Kadima A N, Cole D J, Gillanders W E. Defining the antigen-specific T-cell response to vaccination and poly(I:C)/TLR3 signaling: evidence of enhanced primary and memory CD8 T-cell responses and antitumor immunity. J Immunother. May-June 2005; 28(3):220-228.
47. Tough D F, Borrow P, Sprent J. Induction of bystander T cell proliferation by viruses and type I interferon in vivo. Science. Jun. 28, 1996; 272(5270):1947-1950.
48. Zhu X, Nishimura F, Sasaki K, et al. Toll like receptor-3 ligand poly-ICLC promotes the efficacy of peripheral vaccinations with tumor antigen-derived peptide epitopes in murine CNS tumor models. J Transl Med. 2007; 5:10.
49. Caskey M, Lefebvre F, Filali-Mouhim A, et al. Synthetic double-stranded RNA induces innate immune responses 50. Gaucher D, Therrien R, Kettaf N, et al. Yellow fever vaccine induces integrated multilineage and polyfunctional immune responses. The Journal of experimental medicine. Dec. 22, 2008; 205(13):3119-3131.
51. Sabbatini P. Tsuji T, Ferran L, et al. Phase I trial of overlapping long peptides from a tumor self-antigen and poly-ICLC shows rapid induction of integrated immune response in ovarian cancer patients. Clin Cancer Res. Dec. 1, 2012; 18(23):6497-6508.
52. Okada H, Kalinski P, Ueda R, et al. Induction of CD8+ T-cell responses against novel glioma-associated antigen peptides and clinical activity by vaccinations with {alpha}-type 1 polarized dendritic cells and polyinosinic-polycytidylic acid stabilized by lysine and carboxymethylcellulose in patients with recurrent malignant glioma. Journal of clinical oncology: official journal of the American Society of Clinical Oncology. Jan. 20, 2011; 29(3):330-336.
53. Robinson R A, DeVita V T, Levy H B, Baron S, Hubbard S P, Levine A S. A phase I-II trial of multiple-dose polyriboinosic-polyribocytidylic acid in patieonts with leukemia or solid tumors. J Natl Cancer Inst. September 1976; 57(3):599-602.
54. Rini B I, Powles T. Biology and treatment of advanced renal cell carcinoma: a global perspective. Semin Oncol. August 2013; 40(4):419-420.
55. McDermott D F, Atkins M B. Immune therapy for kidney cancer: a second dawn? Semin Oncol. August 2013; 40(4):492-498.
56. Hodi F S, O'Day S J, McDermott D F, et al. Improved survival with ipilimumab in patients with metastatic melanoma. N Engl J Med. 2010; 363(8):711-723.
57. Brahmer J R. Tykodi S S, Chow L Q, et al. Safety and activity of anti-PD-L1 antibody in patients with advanced cancer. N Engl J Med. Jun. 28, 2012; 366(26):2455-2465.
58. Topalian S L, Hodi F S, Brahmer J R, et al. Safety, activity, and immune correlates of anti-PD-1 antibody in cancer. N Engl J Med. Jun. 28, 2012; 366(26):2443-2454.
59. Rosenberg S A. Raising the bar: the curative potential of human cancer immunotherapy. Sci Transl Med. Mar. 28, 2012; 4(127):127ps128.
60. Klebanoff C A, Acquavella N, Yu Z, Restifo N P. Therapeutic cancer vaccines: are we there yet? Immunol Rev. January 2011; 239(1):27-44.
61. Kannan S, Neelapu S S. Vaccination strategies in follicular lymphoma. Curr Hematol Malig Rep. October 2009; 4(4):189-195.
62. Sampson J H, Aldape K D, Archer G E, et al. Greater chemotherapy-induced lymphopenia enhances tumor-specific immune responses that eliminate EGFRvIII-expressing tumor cells in patients with glioblastoma. Neuro Oncol. March 2011; 13(3):324-333.
63. Wolchok J D, Kluger H, Callahan M K, et al. Nivolumab plus ipilimumab in advanced melanoma. N Engl J Med. Jul. 11, 2013; 369(2):122-133.
64. Ott P A, Hodi F S, Robert C. CTLA-4 and PD-1/PD-L1 blockade: new immunotherapeutic modalities with durable clinical benefit in melanoma patients. Clin Cancer Res. Oct. 1, 2013; 19(19):5300-5309.
65. Topalian S L, Sznol M, McDermott D F, et al. Survival, durable tumor remission, and long-term safety in patients with advanced melanoma receiving nivolumab. J Clin Oncol. Apr. 1, 2014; 32(10):1020-1030.
66. Simpson T R, Li F, Montalvo-Ortiz W, et al. Fc-dependent depletion of tumor-infiltrating regulatory T cells co-defines the efficacy of anti-CTLA-4 therapy against melanoma. J Exp Med. Aug. 26, 2013; 210(9):1695-1710.
67. Quezada S A, Peggs K S, Curran M A, Allison J P. CTLA4 blockade and GM-CSF combination immunotherapy alters the intratumor balance of effector and regulatory T cells. J Clin Invest. July 2006; 116(7):1935-1945.
68. van Elsas A, Hurwitz A A, Allison J P. Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med. Aug. 2, 1999; 190(3):355-366.
69. Hodi F S, Butler M, Oble D A, et al. Immunologic and clinical effects of antibody blockade of cytotoxic T lymphocyte-associated antigen 4 in previously vaccinated cancer patients. Proc Natl Acad Sci USA. 2008; 105(8):3005-3010.
70. Le D T, Lutz E, Uram J N, et al. Evaluation of ipilimumab in combination with allogeneic pancreatic tumor cells transfected with a G M-CSF gene in previously treated pancreatic cancer. J Immunother. September 2013; 36(7):382-389.
71. Giannopoulos K, Dmoszynska A, Kowal M, et al. Peptide vaccination elicits leukemia-associated antigen-specific cytotoxic CD8+ T-cell responses in patients with chronic lymphocytic leukemia. Leukemia. April 2010; 24(4):798-805.
72. Richter W F B, S. G.; Morris, M. E. Mechanistic Determinants of Biotherapeutics Absorption Following SC Administration. The AAPS Journal. September 2012 2012; 15(3):559-568.
73. Simmons A D, Moskalenko M, Creson J, et al. Local secretion of anti-CTLA-4 enhances the therapeutic efficacy of a cancer immunotherapy with reduced evidence of systemic autoimmunity. Cancer Immunol Immunother. August 2008; 57(8):1263-1270.
74. Fransen M F, van der Sluis T C, Ossendorp F, Arens R, Melief C J. Controlled local delivery of CTLA-4 blocking antibody induces CD8+ T-cell-dependent tumor eradication and decreases risk of toxic side effects. Clin Cancer Res. Oct. 1, 2013; 19(19):5381-5389.
75. Marabelle A, Kohrt H, Sagiv-Barfi I, et al. Depleting tumor-specific Tregs at a single site eradicates disseminated tumors. J Clin Invest. Nov. 1, 2013; 123(11):4980.
76. Lundegaard C, Lund O, Nielsen M. Prediction of epitopes using neural network based methods. J Immunol Methods. Nov. 30, 2011; 374(1-2):26-34.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of treating melanoma, non-small cell lung cancer, bladder cancer, renal cell carcinoma, or non-Hodgkin's lymphoma (NHL) in a single human subject in need thereof comprising:
  (A) administering to the subject nivolumab or pembrolizumab at an interval of at least every two or three weeks for a period of 2-12 weeks;
  (B) following step (A), administering to the subject a composition at least once every week for a period of 14 weeks, wherein the subject is administered up to five doses of the composition during the period of 1-4 weeks, said composition comprising:
    (i) one or more polypeptides comprising at least two peptide sequences calculated by an HLA peptide binding analysis using a program implemented on a computer system to have a binding affinity to a protein encoded by an HLA allele of the single human subject with an $IC_{50}$ of less than 500 nM, or
    (ii) one or more polynucleotides encoding the one or more polypeptides of (B)(i);
      wherein the at least two peptide sequences are encoded by a plurality of cancer specific nucleic acid sequences that are identified as being specific to cancer cells of the single human subject based on a comparison of (i) whole genome or whole exome nucleic acid sequencing data from a nucleic acid sample of the human subject's cancer cells and (ii) whole genome or whole exome nucleic acid sequencing data from a nucleic acid sample of the human subject's non-cancer cells, wherein each of the cancer specific nucleic acid sequences of the plurality are present in the genome of cancer cells of the human subject but not in the genome of non-cancer cells of the human subject,
      wherein each of the at least two peptide sequences is present in different proteins expressed by the cancer cells;
      wherein each of the at least two peptide sequences comprises a cancer specific amino acid mutation that is not present in the proteins expressed by the non-cancer cells from the single human subject;
  (C) administering nivolumab or pembrolizumab at the start of step (B), or following step (B), every two or three weeks for a period of at least 13 weeks and up to 104 weeks; and
  (D) administering one or more doses of the composition of step (B) during the period of the at least 13 weeks and up to 104 weeks of step (C), wherein the composition of step (B) and nivolumab or pembrolizumab of step (C) are not administered to the single human subject on the same day.

2. The method of claim 1, wherein the composition of step (B) comprises at least five peptide sequences.

3. The method of claim 2, wherein the composition of step (B) is administered at a dose of from about 10 µg to 1 mg per peptide, or at an average weekly dose level of from about 10 µg to 2000 µg per peptide.

4. The method of claim 1, further comprising administering an immunomodulator or adjuvant.

5. The method of claim 4, wherein the immunomodulator or adjuvant is selected from the group consisting of poly(I:C), 1018 ISS, aluminum salts, Amplivax, AS15, BCG, CP-870,893, Cp.7909, CyaA, dSLIM, GM-CSF, IC30, IC31, Imiquimod, ImuFact IMP321, IS Patch, ISS, ISCO- MATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PEPTEL, vector system, PLGA microparticles, resiquimod, SRL172, Virosomes and other Virus-like particles, YF-17D, VEGF trap, R848, beta-glucan, Pam3Cys, acrylic or methacrylic polymers, copolymers of maleic anhydride and Aquila's QS21 stimulon.

6. The method of claim 1, wherein nivolumab is administered in steps (A) and (C).

7. The method of claim 1, wherein the melanoma is metastatic melanoma; or wherein the bladder cancer is bladder carcinoma, a cancer of the renal pelvis, or a cancer of the ureter.

8. The method of claim 1, wherein the subject is at high risk for disease recurrence, or has previously undergone autologous hematopoietic stem cell transplant (AHSCT).

9. The method of claim 1, wherein the administration of step (A) is initiated following tumor resection.

10. The method of claim 1, wherein the administration of the nivolumab or the pembrolizumab of step (C) continues every 2-8 or more weeks after a first administration in step (C).

11. The method of claim 1, wherein administration of the nivolumab or the pembrolizumab is withheld during a week prior to administration of the composition of step (B).

12. The method of claim 1, wherein the administration of the composition of step (B) is in a prime-boost dosing regimen, and/or the administration of the composition of step (B) is at weeks 1, 2, 3, 4, 5 or more as a prime, and/or the administration of the composition of step (B) in step (D) is at months 2, 3, 4 or 5 as a boost.

13. The method of claim 1, wherein the nivolumab or the pembrolizumab in step (A) or (C) is administered at a dose of from about 0.1 to 10 mg/kg.

14. The method of claim 1, wherein the administration in step (A) is intravenous, intradermal, or subcutaneous; the administration in step (B) or step (D) is intravenous, intradermal, or subcutaneous; and the administration in step (C) is intravenous, intradermal, or subcutaneous.

15. The method of claim 14, wherein the at least two peptides sequences or polynucleotides encoding the at least two peptide sequences are separated into up to four groupings to minimize the number of peptides binding to the same HLA allele in each grouping and each grouping is administered into a separate location of the subject.

16. The method of claim 1, wherein the nivolumab or the pembrolizumab of step (C) is administered subcutaneously within about 2 cm of a site of administration of the composition of step (B).

17. The method of claim 1, further comprising:
administering one or more additional agents selected from the group consisting of a chemotherapeutic agent, an anti-angiogenesis agent, an agent that reduces immune-suppression, and an agent that stimulates an immune response; or
administering an anti-glucocorticoid induced tumor necrosis factor family receptor (GITR) agonistic antibody; or
administering an anti-CTLA4 antibody subcutaneously within about 2 cm of a site of administration of the composition of step (B).

18. The method of claim 1, wherein the pembrolizumab is administered in steps (A) and (C).

19. The method of claim 18, wherein the method comprises administering carboplatin to the subject.

20. The method of claim 18, wherein the method comprises administering a DNA synthesis inhibitor or a DNA methyltransferase inhibitor to the subject.

21. The method of claim 18, wherein the method comprises administering (i) carboplatin and (ii) a DNA synthesis inhibitor or a DNA methyltransferase inhibitor to the subject.

22. The method of claim 1, wherein the administration of the composition of step (B) is initiated 1-15 weeks after tumor resection.

23. The method of claim 1, wherein the melanoma, non-small cell lung cancer, or bladder cancer is metastatic.

24. The method of claim 1, wherein the composition of step (B) is administered for at least two days and the nivolumab or the pembrolizumab of step (C) is administered for at least two days.

25. The method of claim 1, wherein the composition of step (B) is administered for at least five days and the nivolumab or the pembrolizumab of step (C) is administered for at least two days.

26. The method of claim 1, wherein the method further comprises administering nivolumab or the pembrolizumab on the same day the composition of step (B) is administered.

27. The method of claim 1, wherein the administration of the composition of step (B) is in a dosing regimen, and wherein the method comprises administering the nivolumab or pembrolizumab during the dosing regimen.

28. The method of claim 1, wherein step (B) comprises administering to the subject
(i) one dose of the composition on day 1 of week one,
(ii) one dose of the composition on day 4 of week 1,
(iii) one dose of the composition during week 2,
(iv) one dose of the composition during week 3, and
(v) one dose of the composition during week 4.

29. The method of claim 28, wherein the nivolumab or the pembrolizumab of step (C) is administered at the start of step (B) on either day 1 or day 4 of week 1.

30. The method of claim 28, wherein the nivolumab or the pembrolizumab of step (C) is administered on the same day as the dose for week 3.

31. The method of claim 1, wherein the nivolumab or the pembrolizumab of step (C) is not administered during step (B).

32. The method of claim 1, wherein the administration in step (D) is at 4 weeks or 8 weeks following step (B).

* * * * *